United States Patent
Rageot et al.

(10) Patent No.: US 11,878,972 B2
(45) Date of Patent: *Jan. 23, 2024

(54) TREATMENT OF NEUROLOGICAL DISORDERS

(71) Applicants: TORQUR AG, Basel (CH); UNIVERSITÄT BASEL, Basel (CH)

(72) Inventors: Denise Rageot, Saint-Louis (FR); Paul Hebeisen, Basel (CH); Florent Beaufils, Bartenheim (FR); Doriano Fabbro, Arlesheim (CH); Petra Hillmann-Wüllner, Oberengstringen (CH); Hoa Huu Phuc Nguyen, Tübingen (DE); Wolfgang Löscher, Hannover (DE); Claudia Brandt, Langenhagen (DE); Alexander Markus Sele, Basel (CH)

(73) Assignees: TORQUR AG, Basel (CH); UNIVERSITÄT BASEL, Basel (CH)

( * ) Notice: Subject to any disclaimer, the term of this patent is extended or adjusted under 35 U.S.C. 154(b) by 190 days.

This patent is subject to a terminal disclaimer.

(21) Appl. No.: 17/125,012

(22) Filed: Dec. 17, 2020

(65) Prior Publication Data

US 2022/0135551 A1 May 5, 2022

Related U.S. Application Data

(63) Continuation of application No. 16/301,729, filed as application No. PCT/EP2017/025136 on May 17, 2017, now abandoned.

(30) Foreign Application Priority Data

May 18, 2016 (EP) ..................................... 16170107

(51) Int. Cl.
  *C07D 413/14* (2006.01)
  *A61P 25/28* (2006.01)
  (Continued)

(52) U.S. Cl.
  CPC ............ *C07D 413/14* (2013.01); *A61K 31/53* (2013.01); *A61K 31/5377* (2013.01);
  (Continued)

(58) Field of Classification Search
  CPC ................................................ A61P 25/08–16
  See application file for complete search history.

(56) References Cited

U.S. PATENT DOCUMENTS

| | | |
|---|---|---|
| 8,022,205 B2 | 9/2011 | Shimma |
| 10,640,516 B2 | 5/2020 | Cmiljanovic et al. |
| 11,186,591 B2 * | 11/2021 | Cmiljanovic ........ C07D 491/18 |

FOREIGN PATENT DOCUMENTS

| | | |
|---|---|---|
| WO | 2007/084786 A1 | 7/2007 |
| WO | 2007/127175 A2 | 11/2007 |

(Continued)

OTHER PUBLICATIONS

Curatolo et al., "mTOR inhibitors as a new therapeutic option for epilepsy," Expert Rev. Neurother. Jun. 2013;13(6):627-38. PMID: 23739000. (Year: 2013).*

(Continued)

*Primary Examiner* — Theodore R. Howell
(74) *Attorney, Agent, or Firm* — MEDLER FERRO WOODHOUSE & MILLS PLLC

(57) ABSTRACT

The present invention is relates to a compound of formula (I),

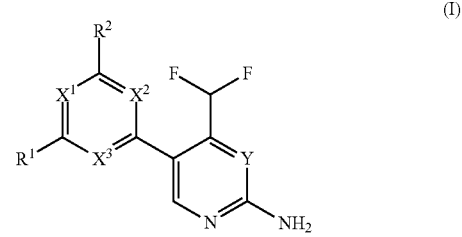

wherein
$X^1$, $X^2$ and $X^3$ are, independently of each other, N or CH; with the proviso that at least two of
$X^1$, $X^2$ and $X^3$ are N;
Y is N or CH;
$R^1$ and $R^2$ are independently of each other
(iii) a morpholinyl of formula (II)

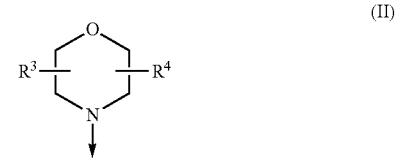

wherein the arrow denotes the bond in formula (I); and
wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxy$C_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —$CH_2$—O—$CH_2$—, —$CH_2$—NH—$CH_2$—, or any of the structures (Continued)

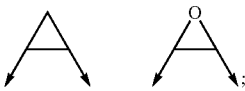

wherein the arrows denote the bonds in formula (II); or
(iv) a saturated 6-membered heterocyclic ring Z selected from thiomorpholinyl and piperazinyl, optionally substituted by 1 to 3 $R^7$; wherein $R^7$ is independently at each occurrence $C_1$-$C_3$alkyl optionally substituted with one or two OH, $C_1$-$C_2$fluoroalkyl, $C_1$-$C_2$alkoxy$C_1$-$C_3$alkyl, $C_3$-$C_6$cycloalkyl; or two R 7 substituents form together a bivalent residue —$R^8R^9$— selected from $C_1$-$C_3$alkylene optionally substituted with 1 to 4 F, —$CH_2$—O—$CH_2$— or —O—$CH_2CH_2$—O—;

with the proviso that at least one of $R^1$ and $R^2$ is a morpholinyl of formula II;

and prodrugs, metabolites, tautomers, solvates and pharmaceutically acceptable salts thereof, for use in the prevention or treatment of a neurological disorder in a subject.

20 Claims, 22 Drawing Sheets

(51) Int. Cl.
<table>
<tr><td>A61P 25/08</td><td>(2006.01)</td></tr>
<tr><td>C07D 417/14</td><td>(2006.01)</td></tr>
<tr><td>C07D 451/02</td><td>(2006.01)</td></tr>
<tr><td>C07D 451/14</td><td>(2006.01)</td></tr>
<tr><td>C07D 498/08</td><td>(2006.01)</td></tr>
<tr><td>C07D 519/00</td><td>(2006.01)</td></tr>
<tr><td>A61K 31/5386</td><td>(2006.01)</td></tr>
<tr><td>A61K 31/541</td><td>(2006.01)</td></tr>
<tr><td>A61K 31/5377</td><td>(2006.01)</td></tr>
<tr><td>A61K 31/53</td><td>(2006.01)</td></tr>
</table>

(52) U.S. Cl.
CPC ........ *A61K 31/5386* (2013.01); *A61K 31/541* (2013.01); *A61P 25/08* (2018.01); *A61P 25/28* (2018.01); *C07D 417/14* (2013.01); *C07D 451/02* (2013.01); *C07D 451/14* (2013.01); *C07D 498/08* (2013.01); *C07D 519/00* (2013.01)

(56) References Cited

FOREIGN PATENT DOCUMENTS

<table>
<tr><td>WO</td><td>2008/098058 A1</td><td>8/2008</td></tr>
<tr><td>WO</td><td>2009/143313 A1</td><td>11/2009</td></tr>
<tr><td>WO</td><td>2010/052569 A2</td><td>5/2010</td></tr>
<tr><td>WO</td><td>2015/049369 A1</td><td>4/2015</td></tr>
<tr><td>WO</td><td>2016/075130 A1</td><td>5/2016</td></tr>
<tr><td>WO</td><td>2017/198347 A1</td><td>11/2017</td></tr>
</table>

OTHER PUBLICATIONS

Ostendorf et al., "mTOR inhibition in epilepsy: rationale and clinical perspectives," CNS Drugs Feb. 2015;29(2):91-99. PMID: 25633849. (Year: 2015).*
Chong, Z. et al., "A Critical Kinase Cascade in Neurological Disorders: Pi 3-K, Akt, and mTOR," Future Neurol. 7(6): 733-748 (2012).
Curatolo, P. et al., "mTOR Inhibitors in Tuberous Sclerosis Complex," Curr Neuropharmacol. 10: 404-415 (2012).
Galanopoulou et al., "Finding a better drug for epilepsy: the mTOR pathway as an antiepileptogenic target," Epilepsia 53(7):1119-1130 (2012).
Krueger, D. A. et al., "Long-term Treatment of Epilepsy with Everolimus in Tuberous Sclerosis," Neurology 87: 2408-2415 (2016).
Laplante, M. et al., "mTOR Signaling in Growth Control and Disease," Cell 149(2): 274-293 (2012).
Meikle, L. et al., "Response of a Neuronal Model of Tuberous Sclerosis to Mammalian Target of Rapamycin (mTOR) Inhibitors: Effects on mTORC1 and Akt Signaling Lead to Improved Survival and Function," J Neurosci 28: 5422-5432 (2008).
Sadowski, K. et al., "Role of mTOR Inhibitors in Epilepsy Treatment," Pharmacol Rep 67(3): 636-646 (2015).
Wong, M. et al., "Mammalian Target of Rapamycin (mTOR) Pathways in Neurological Diseases," Biomed J 36(2): 40-50 (2013).
Zeng, L. H. et al., "Rapamycin Prevents Epilepsy in a Mouse Model of Tuberous Sclerosis Complex," Ann Neurol 63(4): 444-453 (2008).
The International Search Report issued in International Application No. PCT/EP2017/025136 dated Jul. 21, 2017.
Heras-Sandoval et al., "The Phosphatidylinositol 3-Kinase/mTor Pathway as a Therapeutic Target for Brain Aging and Neurodegeneration," Pharmaceuticals 4(8): 1070-1087 (2011).
Heras-Sandoval et al., "The role of PI3K/AKT/mTOR pathway in the modulation of autophagy and the clearance of protein aggregates in neurodegeneration," Cellular Signalling 26:2694-2701 (2014).

* cited by examiner

TREATMENT OF NEUROLOGICAL DISORDERS

The present invention relates to compositions for use in the prevention or treatment of a neurological disorder in a subject.

RELATED ART

The protein kinase mTOR (mammalian target of rapamycin) is an integrating factor in energy metabolism, differentiation, growth and survival of the cell. Additionally, mTOR has critical functions in brain-specific mechanisms such as synaptic plasticity, learning and cortical development (Wong, M., Biomed J, 2013. 36(2): p. 40-50). The mTOR signaling pathway is activated in many diseases. In particular, various neurological disorders such as Huntington's disease and epileptic seizures have been linked to the phosphatidylinositol-3-kinase (PI3K)/mTOR pathway.

So far available mTOR inhibitors such as rapamycin, a macrolide antibiotic with immunosuppressive and anti-inflammatory potency, and the closely related rapalogs bind allosterically to the FKBP binding pocket of mTORC1 (Laplante, M. and D. M. Sabatini, Cell, 2012. 149(2): p. 274-93.). Prominent downstream effectors of mTOR are S6 kinase (S6K), S6 ribosomal protein (S6rP) and 4E-binding protein (4E-BP). Inhibitory effects on mTORC2 appear negligible resulting in a partial inhibition of mTOR effects in neurological disorders. Furthermore, these compounds show undesirable physicochemical properties. A first generation of ATP site directed mTOR inhibitors like INK128 has been developed. These inhibitors inhibit mTORC1 and mTORC2 and block all the functions of mTOR but on the other hand, lack high target specificity which might result in lower tolerability. Additionally, a non-favorable PK profile limits penetration over the blood brain barrier and, therefore, target inhibition in the CNS, which is needed for treatment of CNS disorders.

Aggregation of proteins can lead to various diseases. Certain proteins are toxic in the central nervous system (CNS) despite the fact that they are ubiquitously expressed. These neurodegenerative diseases include disorders in which the pathological proteins may accumulate within the nucleus, as is the case with polyglutamine expansion diseases (such as Huntington's disease and spinocerebellar ataxias), disorders characterized by cytoplasmic inclusions (such as α-synuclein in Parkinson's disease), as well as disorders in which pathological proteins accumulate extracellularly (for example in prion diseases) or both intracellularly and extracellularly (for example, tau and amyloid-β (Aβ) in Alzheimer's disease) (Aguzzi, A. and T. O'Connor, Nat Rev Drug Discov, 2010. 9(3): p. 237-248).

Huntington's disease, an autosomal dominant disorder, involves relatively selective neurodegeneration in the basal ganglia and cortex, related to trinucleotide repeat expansion of polyglutamine on the huntingtin protein (HTT). Mutant huntingtin protein (mHTT) is not effectively cleared from neurons, leading to accumulation of toxic intracellular aggregates and associated neuronal death. Lowering levels of mHTT or transforming mHTT into less toxic species are the most promising strategies for development of effective therapies. Besides HTT gene silencing approaches, attempts to enhance clearance of the mHTT protein, particularly by autophagy, have been initiated (Nopoulos, P. C., Dialogues Clin Neurosci, 2016. 18(1): p. 91-98).

Autophagy is a cellular pathway through which damaged or pathological proteins and organelles are engulfed by a double-membrane autophagosome vesicle, which fuses with the lysosome, leading to cargo degradation (Nyfeler, B., et al., Methods Mol Biol, 2012. 821: p. 239-250.). Autophagy may play a key role in neurodegenerative proteinopathies, such as Huntington's disease, which are characterized by the accumulation of misfolded proteins. Impaired autophagy and protein aggregation have also been shown to be connected to other neurological disorders, like Alzheimer's and Parkinson's disease.

Activation of the mammalian target of rapamycin (mTOR) signaling pathway is known to reduce macroautophagy (Jung, C. H., et al., FEBS Lett, 2010. 584(7): p. 1287-95), and mHTT promotes mTOR signaling (Pryor, W. M., et al., Sci Signal, 2014. 7(349): p. ra103). In mouse models and human brains of Huntington's disease, mTOR has been shown to be sequestered in polyglutamine aggregates. Furthermore, mTOR inhibitors have been shown to enhance autophagy and consequently reduce mHTT accumulation and associated neuronal death in cellular and animal models of Huntington's disease (Ravikumar B. et al., Nat Genet, 2004. 36: p. 585-595; Floto R A et al., Autophagy, 2007. 3: p. 620-622). Allosteric mTOR inhibitors (e.g. rapamycin/rapalogs) mediate clearance of mHTT fragments and protect against mHTT-induced toxicity in non-neuronal cells by stimulating autophagy (Ravikumar, B. et al., Hum Mol Genet, 2002. 11(9): p. 1107-1117). However, recent studies showed that rapalogs are inefficient in preventing neurodegeneration in the R6/2 mouse HD model (Fox, J. H., et al., Mol Neurodegener, 2010. 5: p. 26).

Compared to allosteric mTOR inhibitors, catalytic ATP-site directed mTOR inhibitors were recently shown to be more potent at inducing autophagic flux and reducing mHTT accumulation in non-neuronal cells (Roscic, A., et al., J Neurochem, 2011. 119 (2): p. 398-407) as well as to reduce mHTT aggregate accumulation and toxicity, and prevented medium spiny neuron degeneration in corticostriatal brain slices of R6/2 mice (Proenca, C. C., et al., PLoS One, 2013. 8(7): p. e68357.). Unfortunately, currently available catalytic mTOR inhibitors lack sufficient brain penetration and might be too toxic for long-term, in vivo proof-of concept (PoC) studies.

The most advanced therapeutic approaches to date are based on HTT gene silencing using antisense oligonucleotides or siRNAs by central administration. In HD animal model these approaches have convincingly demonstrated a strong reduction in disease progression. Current key challenges of the antisense approach is its invasive central administration as well as whether these antisense molecule achieve sufficient spread in human brain.

Among the 50 million people with activated epilepsy worldwide, 30-40% are therapy resistant (Löscher, W. et al., Nat Rev Drug Discov, 2013. 12(10): p. 757-776.). Examples of current standard treatment are phenobarbital and levetiracetam. Phenobarbital is a first generation anti-seizure drug with a pronounced anticonvulsant efficacy but also with severe side effects like strong sedation in human patients and animal models. Levetiracetam belongs to the second generation anti-seizure drugs and is one of the most widely used drugs in the treatment of epilepsy.

Several genetic defects associated with elevated mTOR signaling (TORopathies) lead to epileptic seizures. TSC seizures are a form of epilepsy caused by an autosomal dominant inactivation mutation of TSC1 or TSC2 that induces constitutive mTOR activation resulting in the formation of benign tumors, mental retardation and seizures. In clinical studies, everolimus treatment decreased seizure frequency in patients with TSC and in patients with TSC-associated SEGA. Other "TORopathies" causing epilepsy are polyhydramnios, megalencephaly, symptomatic epilepsy syndrome, PMSE, focal cortical dysplasia (FCD) and "TORopathies" associated with PTEN mutations (Cardamone, M., et al., J Pediatr, 2014. 164(5): p. 1195-200; Sadowski, K., et al., Pharmacol Rep, 2015. 67(3): p. 636-46).

Epileptogenesis is the period between the occurrence of a pro-epileptic insult (e.g. brain injury or genetic defect) and the first spontaneous seizure. Many factors that are involved in different types of epileptogenesis have been described, and mTOR activation is one factor that has been observed in many types of epilepsies (Sadowski, K., K. Kotulska-Jozwiak, and S. Jozwiak, Pharmacol Rep, 2015. 67(3): p. 636-46.). All current seizure suppressing agents used act symptomatically and do not alter epileptogenesis. mTOR activation is involved in different processes during epileptogenesis: neuronal growth and formation of hypertrophic neural cells, inhibition of autophagy and neuroinflammation. Furthermore, there is data that indicates that the mTOR inhibitor rapamycin influences epileptogenesis and the number/strength of seizures in different animal models of epilepsy.

A major drawback of the current therapies is the limited ability or even inability of the reported mTOR or dual mTOR/PI3K inhibitors to cross the blood brain barrier (BBB), let alone the cytotoxic potential of the compounds of the state of the art, which makes the same of limited medical benefit for the treatment of neurological disorders.

SUMMARY OF THE INVENTION

It has now surprisingly been found that the compounds of the invention are useful for the treatment of neurological disorders. In particular, it has been found that the compounds of the present invention are specific inhibitors of mTOR or dual inhibitors of PI3K/mTOR and that they are able to penetrate the blood brain barrier, i.e. they have been found to inhibit the PI3K/mTOR pathway in the brain. In addition, the compounds of the invention have surprisingly been found to be non-cytotoxic and orally bioavailable. Notably, the compounds of the invention have surprisingly been found to induce autophagy in vitro and in vivo. Moreover, the compounds of the invention have been found to reduce formation of neurotoxic mutant huntingtin aggregates in vitro and to reduce electroshock induced seizures in mice.

Due to the proven efficacy in preclinical models, the well tolerated and blood brain barrier penetrating mTOR inhibitors of the present invention have the potential to be developed into clinical candidates for the treatment or prevention of neurological disorders, such as HD and epilepsy, which are so far devastating and often deadly diseases without any treatment options.

Thus, in a first aspect of the invention, there is provided a compound of formula (I),

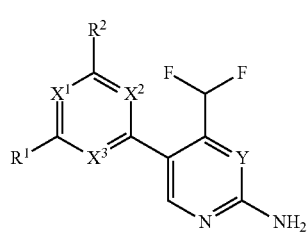

wherein
$X^1$, $X^2$ and $X^3$ are, independently of each other, N or CH;
  with the proviso that at least two of
  $X^1$, $X^2$ and $X^3$ are N;
Y is N or CH;
$R^1$ and $R^2$ are independently of each other
  (i) a morpholinyl of formula (II)

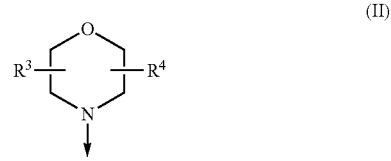

wherein the arrow denotes the bond in formula (I); and
wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —CH$_2$—O—CH$_2$—, —CH$_2$—NH—CH$_2$—, or any of the structures

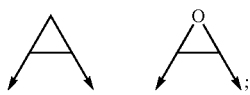

wherein the arrows denote the bonds in formula (II); or
  (ii) a saturated 6-membered heterocyclic ring Z selected from thiomorpholinyl and piperazinyl, optionally substituted by 1 to 3 $R^7$; wherein $R^7$ is independently at each occurrence $C_1$-$C_3$alkyl optionally substituted with one or two OH, $C_1$-$C_2$fluoroalkyl, $C_1$-$C_2$alkoxyC$_1$-$C_3$alkyl, $C_3$-$C_6$cycloalkyl; or two $R^7$ substituents form together a bivalent residue —$R^8R^9$— selected from $C_1$-$C_3$alkylene optionally substituted with 1 to 4 F, —CH$_2$—O—CH$_2$— or —O—CH$_2$CH$_2$—O—;

with the proviso that at least one of $R^1$ and $R^2$ is a morpholinyl of formula II;
and prodrugs, metabolites, tautomers, solvates and pharmaceutically acceptable salts thereof,
  for use in the prevention or treatment of a neurological disorder in a subject.

Further aspects and embodiments of the present invention will be become apparent as this description continues.

DESCRIPTION OF FIGURES

FIG. 4 C, D: MEST of pilocarpine treated, epileptic mice.
Pheno=Phenobarbital, LEV=Levetiracetam, Evero=Everolimus, Rapa=Rapamycin, Brackets: dose provided in mg/kg, pretreatment time in h, route of administration per oral (po) or intra peritoneal (ip). A, C: $CC_{50}$ in mA±standard error of the mean (SEM); B, D: Change of $CC_{50}$ in % to vehicle $CC_{50}$, ANOVA and post hoc Dunnett's test, * p<0.05

FIG. 5 A+B Lactate dehydrogenase (LDH) assay in A: STHdh$^{Q7/Q7}$. B: STHdh$^{Q111/Q111}$. Both, Cpd. 3 and Cpd. 8 reduced LDH production at time points between 24 h and 48 h; n=3-6

FIG. 5 C+D PrestoBlue assay detecting the mitochondrial activity of STHdh$^{Q7/Q7}$ and STHdh$^{Q111/Q111}$ at different time points after incubation with Cpd. 3, Cpd. 8 and reference compounds INK128 (100 nM) and rapamycin (400 nM). Compounds were well tolerated only leading to slight inhibition after 72 hours of incubation with 1230 nM of Cpd. 3. n=6-9 ANOVA * p<0.0005,  p<0.005, * p<0.05

FIG. 6 C+D: Induction of autophagy indicated by increase in $LC_3$-II. n=3 ANOVA * p<0.0005,  p<0.005, * p<0.05

FIG. 7 A+B: Filter trap assay of lysed HEK293 cell transfected with exon 1 of mHTT with a Q51 pre-treated with Cpd. 8 (130 nM, 1230 nM), cpd. 3 (400 nM), 1230 nM), INK128 (100 nM), rapamycin (400 nM) or DMSO control and Q19 extension treated with DMSO control. Treatment with mTOR inhibitors significantly reduced aggregate formation. n=3, ANOVA * p<0.0005,  p<0.005, * p<0.05

FIG. 7 C+D: Immuno staining of HEK293 cell transfected with exon 1 of mHTT with a Q51 pre-treated with Cpd. 8 (130 nM, 1230 nM), cpd. 3 (400 nM, 1230 nM), INK128 (100 nM), rapamycin (400 nM) or DMSO control. Aggregates were manually counted in 10000 cells per sample. ANOVA ** p<0.00005, * p<0.0005, ** p<0.005, * p<0.05

FIG. 10: IHC analysis of striata from R6/2 mice and one wt animal. Mice were treated with vehicle, Cpd. 3 and Cpd.8 for 11.5 weeks and striata were sectioned. After staining for mutHTT aggregates, number of aggregates was counted and area of aggregates was analyzed in 4 samples. While the number of mutHTT aggregates was unchanged, the area covered by these aggregates was significantly reduced after Cpd. 3 treatment indicating that mutHTT aggregates were smaller after treatment. (ANOVA, $p<0.05$)

DETAILED DESCRIPTION OF THE INVENTION

Figure 1A:
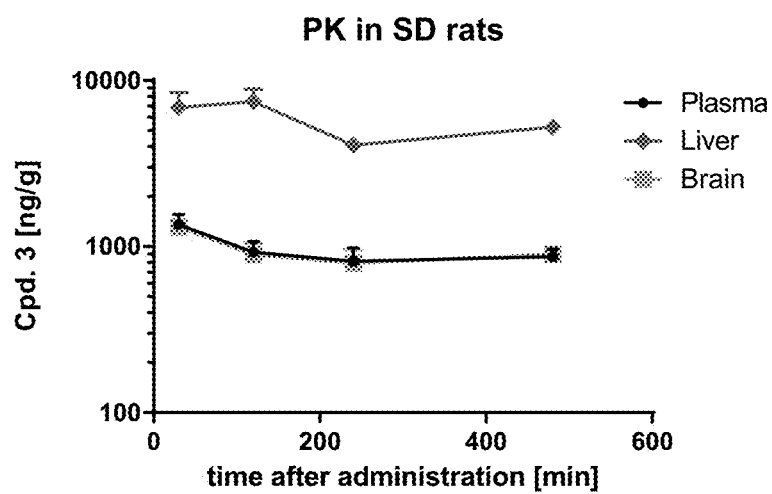
FIG. 1A: Pharmacokinetic analysis of Compound 3 ("Cpd. 3") levels in Sprague Dawley (SD) rats. After a single oral administration of Cpd. 3 (10 mg/kg), tissue samples were analyzed for compound levels at different time points by LC-MS. n=3

Reference will now be made in detail to the presented and further aspects and the presented and further embodiments of the invention, examples of which are illustrated in the accompanying structures and formulas. While the invention will be described in conjunction with the enumerated embodiments, it will be understood that they are not intended to limit the invention to those embodiments. One skilled in the art will recognize many methods and materials similar or equivalent to those described herein, which could be used in the practice of the present invention. The present invention is in no way limited to the methods and materials herein described.

Features, integers and characteristics, described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Unless defined otherwise, all technical and scientific terms used herein have the same meanings as commonly understood by one of ordinary skill in the art to which this invention belongs.

For the purposes of interpreting this specification, the following definitions will apply and whenever appropriate, terms used in the singular will also include the plural and vice versa. It is to be understood that the terminology used herein is for the purpose of describing particular embodiments only and is not intended to be limiting.

Definitions

The terms "comprising", "having", and "including" are to be construed as open-ended terms (i.e., meaning "including, but not limited to,") unless otherwise noted.

The terms "individual," "subject" or "patient" are used herein interchangeably. In a preferred embodiment, the subject is a human.

The terms "treatment"/"treating" as used herein include: (1) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (2) inhibiting the state, disorder or condition (e.g. arresting, reducing or delaying the development of the disease, or a relapse thereof in case of maintenance treatment, of at least one clinical or subclinical symptom thereof); and/or (3) relieving the condition (i.e. causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment. In one embodiment, the terms "treatment"/"treating" as used herein, refer to a therapeutic treatment. In another embodiment, the terms "treatment"/"treating" as used herein, refer to a prophylactic treatment.

The term "chiral" refers to molecules, which have the property of non-superimposability of the mirror image partner, while the term "achiral" refers to molecules, which are superimposable on their mirror image partner.

The term "stereoisomers" refers to compounds, which have identical chemical constitution, but differ with regard to the arrangement of the atoms or groups in space.

"Diastereomer" refers to a stereoisomer with two or more centers of chirality in which the compounds are not mirror images of one another. Diastereomers have different physical properties, e.g. melting points, boiling points, spectral properties, and chemical and biological reactivities. Mixtures of diastereomers may be separated under high resolution analytical procedures such as electrophoresis and chromatography.

"Enantiomers" refer to two stereoisomers of a compound which are non-superimposable mirror images of one another. Stereochemical definitions and conventions used herein generally follow S. P. Parker, Ed., *McRaw-Hiff Dictionary of Chemical Terms* (1984), McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric or a scalemic mixture. A 50:50 mixture of enantiomers is referred to as a racemic mixture or a racemate. The term "tautomer" or "tautomeric form" refers to structural isomers of different energies, which are interconvertible via a low energy barrier. For example, proton tautomers include interconversions via migration of a proton, such as keto-enol and imine-enamine isomerizations.

The phrase "pharmaceutically acceptable salt" as used herein, refers to pharmaceutically acceptable organic or inorganic salts of a compound of the invention, in particular acid addition salts. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate (mesylate), ethanesulfonate, benzenesulfonate, p-toluenesulfonate, and pamoate salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, dimethyl sulfoxide (DMSO), ethyl acetate, acetic acid, and ethanolamine. The term "hydrate" refers to the complex where the solvent molecule is water.

The term "protecting group" refers to a substituent that is commonly employed to block or protect a particular functionality during the reaction of other functional groups on the compound. For example, an "amino-protecting group" is a substituent attached to an amino group that blocks or protects the amino functionality in the compound. Suitable amino-protecting groups include acetyl, trifluoroacetyl, tert-butoxycarbonyl (BOC), benzyloxycarbonyl and 9-fluorenyl-methylenoxycarbonyl (Fmoc). For a general description of protecting groups and their use, see T. W. Greene, Protective Groups in Organic Synthesis, John Wiley & Sons, New York, 1991.

The terms "compound of this invention" and "compounds of the present invention" and "compounds of formula (I)" include stereoisomers, geometric isomers, tautomers, solvates, pharmaceutically acceptable salts, and solvates of the salts thereof.

The term "mammal" includes, but is not limited to, humans, mice, rats, guinea pigs, monkeys, dogs, cats, horses, cows, pigs, and sheep. The term "mammal", as used herein, preferably refers to humans.

The terms "Alzheimer's disease" and "morbus Alzheimer" are used herein interchangeably.

The term "neurological disorder" generally refers to a disorder affecting the nervous system, including the central nervous system and the peripheral nervous system. Neurological disorders, in particular central nervous system (CNS) disorders, encompass numerous afflictions, including inter alia neurodegenerative diseases, such as Huntington's disease and a large number of central nervous system dysfunctions, such as epilepsy.

The term "neurodegenerative disease" refers to a disease which is caused by damage to the central nervous system and can be identified by progressive dysfunction, degeneration and death of specific populations of neurons which are often synaptically interconnected. Neurodegeneration causes dysfunction of movement and/or mental function. Further, the term "neurodegenerative disease" as used herein describes neurodegenerative diseases which are associated with or caused by protein misfolding and/or aggregation. Exemplary neurodegenerative diseases include Huntington's disease, spinocerebellar ataxias, Parkinson's disease, morbus Alzheimer, amyotrophic lateral sclerosis (ALS), cystic fibrosis, familial amyloidotic polyneuropathy, spongiform encephalopathies, dementia with Lewy bodies, frontotemporal dementia with Parkinsonism, spinocerebellar ataxias, spinal and bulbar muscular atrophy, hereditary dentatorubral-pallidoluysian atrophy, familial British dementia, familial Danish dementia and prion disease.

The terms "epilepsy" as used herein refer to any chronic neurological disorder characterized by recurrent seizures. Each seizure may appear to be unprovoked or may be triggered or provoked by stress, anxiety, sleep deprivation, illness, chemical exposure (e.g., drug abuse or alcohol consumption), photic stimulation (e.g., a flashing/flickering light), and/or the like. The disorder may have a cause that is unknown ("idiopathic epilepsy") or may be caused, for example, by head trauma, a brain tumor, a genetic predisposition, an infection, a developmental defect, or any combination thereof, among others ("symptomatic epilepsy"). Exemplary types of epileptic seizures include partial or focal onset seizures, which are localized (at least initially) within the brain, and generalized seizures, which are distributed widely within the brain. Partial seizures may be further categorized as simple partial seizures, which do not affect consciousness, and complex partial seizures, which do affect consciousness. Generalized seizures, which produce a loss of consciousness, may include absence, atonic, clonic, myoclonic, tonic, and tonic-clonic seizures, among others. Epilepsy and/or an epileptic seizure may be diagnosed by any suitable technique or combination of techniques including electroencephalography (EEG), magnetoencephalography, magnetic resonance imaging (MRI), positron emission tomography (PET), single photon emission computed tomography (SPECT), or video-EEG, among others.

The term "seizure," as used herein, means a neurological event characterized by abnormal electrical activity in the brain that results in at least one clinical symptom. The electrical activity may be characterized by hypersynchrony, hyperactivity, and/or hyperexcitability of neurons in a portion or all of the brain. Exemplary symptoms produced by seizures may include sudden and involuntary muscle contraction (e.g., convulsions), numbness of a part or all of the body, memory loss, loss of consciousness, inability to concentrate, hallucinations, and/or the like. Seizures thus may affect motor, autonomic, cognitive, sensory (visual, auditory, olfactory, taste, feel), and/or emotional function, among others. Each seizure may be characterized either as an epileptic seizure, produced by epilepsy, or a non-epileptic seizure with any other cause.

As indicated above, classification of epilepsy as "symptomatic" indicates that a probable cause exists and a specific course of therapy to eliminate that cause may be tried, whereas classification as "idiopathic" indicates that no obvious cause can be found.

The term "TSC" relates to a form of epilepsy caused by an autosomal dominant inactivation mutation of TSC1 or TSC2 that induces constitutive mTOR activation resulting in the formation of benign tumors, mental retardation and seizures. Therefore, TSC is a model form of epilepsy to investigate effects of mTOR inhibitors on epileptogenesis and epileptic seizures. Subependymal giant cell astrocytomas (SEGAs) develop in 90% of patients with TSC. In the brain, disturbances of normal cellular development and function can lead to epilepsy and neurocognitive, behavioral, and psychiatric deficits. Epilepsy occurs in 80-90% of patients with TSC, and drug resistance is common (Curatolo, P., R. Moavero, and P. J. de Vries, The Lancet Neurology. 14(7): p. 733-745). Inhibition of mTOR with rapamycin has positive effects on behavior, reduces tumor formation and suppresses seizures in TSC mouse models. Early treatment with rapamycin prevents the development of epilepsy and premature death (Meikle, L., et al., J Neurosci, 2008. 28(21): p. 5422-5432). A brief treatment with rapamycin in adult mice rescued not only the synaptic plasticity, but also the behavioral deficits a heterozygous model of TSC (Ehninger, D., et al., Nat Med, 2008. 14(8): p. 843-848.). Furthermore, rapamycin treatment could reverse cellular abnormalities of neurons with TSC mutation (Goto, J., et al., Proceedings of the National Academy of Sciences, 2011. 108(45): p. E1070-E1079.).

Other "TORopathies", i.e. primary diseases that are due to upregulation of mTOR, causing epilepsy are polyhydramnios, megalencephaly, symptomatic epilepsy syndrome, PMSE, focal cortical dysplasia (FCD) and "TORopathies" associated with PTEN mutations.

The term "PMSE" refers to polyhydramnios, megalencephaly, and symptomatic epilepsy, a rare syndrome found in some Amish children characterized by an abnormally large brain, cognitive disability, and severe, treatment-resistant epilepsy.

The term "PTEN" refers to phosphatase and tensin homolog, a phosphatase that dephosphorylates the 3' phosphate of the inositol ring in PIP3. PTEN is a tumor suppressor that is commonly mutated in cancer, leading to increased signaling of the mTOR pathway. PTEN deletion in the CNS can be associated with seizures.

The term "epileptogenesis" refers to the period between the occurrence of a pro-epileptic insult (e.g. brain injury or genetic defect) and the first spontaneous seizure. "Epileptogenesis" is divided into primary epileptogenesis (until first seizure) and secondary epileptogenesis (progression of epilepsy after occurrence of a first seizure). The compounds of the invention may be used both during primary epileptogenesis and during secondary epileptogenesis (partial seizures) as well as in fully developed epileptic disorders (generalized seizures).

Treating epilepsy means, for example to suppress one or more seizures and/or to suppress seizure activity, i.e. to reduce the frequency of seizures; to reduce the severity, physical extent, and/or duration of at least one seizure; to substantially prevent at least one seizure; or to slow down/reduce/prohibit epileptogenesis; or any combination thereof. Seizure suppression for a particular subject may be measurable directly from the subject (e.g., if a seizure is in progress during treatment) and/or, more typically, may be a statistically predicted outcome based on results from controlled tests or clinical trials with a group of subjects.

The term "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

In case of epilepsy, the effective amount of the drug may reduce strength or number of seizures as well as events during epileptogenesis leading to development of epilepsy.

In the case of neurodegenerative diseases, the effective amount of the drug may reduce the amount of protein aggregates in neurons or other cells and in the CNS in general as well as associated cognitive, psychological and motor symptoms. For therapy of neurodegenerative diseases, efficacy can be measured, for example, by assessing the number of protein aggregates, cognitive and motor function.

The term "maximum tolerated dose" (MTD) refers to the highest dose of a drug or treatment that does not cause unacceptable side effects. Typically, the maximum tolerated dose is determined in the species that needs to be treated, e.g. in rodents or in humans during a clinical trial by testing increasing doses on different groups of a given species until the highest dose with acceptable side effects is found. The compounds of the present invention have been found to have a MTD within their therapeutic window (see Examples 3 and 4).

The term "prodrug" as used in this application refers to a precursor or derivative form of a compound of the invention that may have improved properties such as better solubility, reduced cytotoxicity or increased bioavailability compared to the parent compound or drug and is capable of being activated or converted into the more active parent form. The prodrugs of this invention include, but are not limited to, derivatives of the amino group connected to the pyridine or pyrimidine nucleus in which one or two hydrogens are replaced by a suitable substituent, or derivatives of the ring amino function if $R^2$ is piperazin-1-yl. Examples of such prodrugs are compounds acylated by an amino acid selected from the 20 most often occurring natural L-alpha-amino acids, acylated by a dipeptide such as L-Ala-L-Ala, by carbonic acid, sulfuric acid or phosphoric acid, as well as pharmaceutically acceptable salts thereof.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. In particular, compounds of formula (I) as defined hereinbefore, which are oxygenated or hydroxylated at any one position in the morpholine, piperazine or thiomorpholine ring $R^1$ and/or $R^2$ are considered metabolites. Further metabolites considered are thiomorpholine S-oxides and thiomorpholine S,S-dioxides. Accordingly, the invention is also directed to metabolites of compounds of the invention, including compounds produced by a process comprising contacting a compound of this invention with a mammal for a period of time sufficient to yield a metabolic product thereof.

In a first aspect, the present invention provides for a compound of formula (I),

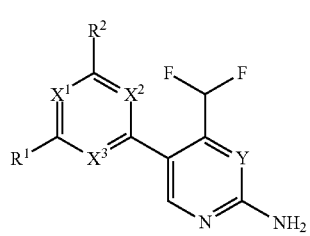
(I)

wherein

X¹, X² and X³ are, independently of each other, N or CH; with the proviso that at least two of X¹, X² and X³ are N;

Y is N or CH;

R¹ and R² are independently of each other (i) a morpholinyl of formula (II)

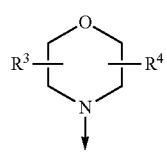
(II)

wherein the arrow denotes the bond in formula (I); and wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxy$C_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —CH₂—O—CH₂—, —CH₂—NH—CH₂—, or any of the structures

wherein the arrows denote the bonds in formula (II); or (ii) a saturated 6-membered heterocyclic ring Z selected from thiomorpholinyl and piperazinyl, optionally substituted by 1 to 3 $R^7$; wherein $R^7$ is independently at each occurrence $C_1$-$C_3$alkyl optionally substituted with one or two OH, $C_1$-$C_2$fluoroalkyl, $C_1$-$C_2$alkoxy$C_1$-$C_3$alkyl, $C_3$-$C_6$cycloalkyl; or two $R^7$ substituents form together a bivalent residue —$R^8R^9$— selected from $C_1$-$C_3$alkylene optionally substituted with 1 to 4 F, —CH₂—O—CH₂— or —O—CH₂CH₂—O—;

with the proviso that at least one of R¹ and R² is a morpholinyl of formula II;

and prodrugs, metabolites, tautomers, solvates and pharmaceutically acceptable salts thereof, for use in the prevention or treatment of a neurological disorder in a subject.

In another aspect, the invention provides for a compound of formula (I),

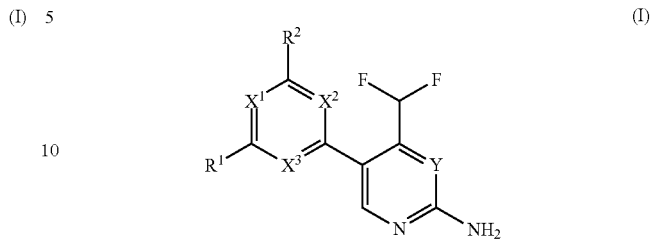
(I)

wherein

X¹, X² and X³ are, independently of each other, N or CH; with the proviso that at least two of X¹, X² and X³ are N; Y is N or CH;

R¹ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and R² is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, piperazin-1-yl, 4-methylpiperazin-1-yl, or 4-thiomorpholinyl.

Each alkyl moiety either alone or as part of a larger group such as alkoxy is a straight or branched chain and is preferably $C_1$-$C_3$alkyl, more preferably $C_1$-$C_2$alkyl. Examples include in particular methyl, ethyl, n-propyl and prop-2-yl (iso-propyl). Examples of an alkoxy include in particular methoxy, ethoxy, n-propoxy and iso-propoxy. As described herein, alkoxy may include further substituents such as halogen atoms leading to haloalkoxy moieties.

The term "alkoxyalkyl" refers to an R—O—R' moiety in which the R and R' groups are alkyl groups as defined herein. Examples include methoxymethyl, methoxyethyl, ethoxyethyl and methoxypropyl.

Each alkylene moiety is a straight or branched chain and is, particularly for example, —CH₂—, —CH₂—CH₂—, —CH(CH₃)—, —CH₂—CH₂—CH₂—, —CH(CH₃)—CH₂—, or —CH(CH₂CH₃)—, preferably —CH₂—, —CH₂—CH₂— or —CH(CH₃)—.

Each haloalkyl moiety either alone or as part of a larger group such as haloalkoxy is an alkyl group substituted by one or more of the same or different halogen atoms. Haloalkyl moieties include for example 1 to 5 halo substituents, or 1 to 3 halo substituents. Examples include in particular fluoromethyl, difluoromethyl, trifluoromethyl, chlorodifluoromethyl and 2,2,2-trifluoro-ethyl.

Each haloalkenyl moiety either alone or as part of a larger group such as haloalkenyloxy is an alkenyl group substituted by one or more of the same or different halogen atoms. Examples include 2-difluoro-vinyl and 1,2-dichloro-2-fluoro-vinyl. Haloalkenyl moieties include for example 1 to 5 halo substituents, or 1 to 3 halo substituents.

Each cycloalkyl moiety can be in mono- or bi-cyclic form, typically and preferably in mono-cyclic form, and preferably contains 3 to 6 carbon atoms. Preferred examples of monocyclic cycloalkyl groups include in particular cyclopropyl, cyclobutyl, cyclopentyl and cyclohexyl.

The term "heterocyclic ring" refers to a saturated or partially unsaturated carbocyclic ring containing one to three heteroatoms selected from nitrogen, oxygen and sulfur as ring members. Such rings do not contain adjacent oxygen atoms, adjacent sulfur atoms, or adjacent oxygen and sulfur atoms within the ring. Preferred examples include in particular tetrahydrofuranyl, pyrrolidinyl, pyrazolidinyl, imidazolidinyl, piperidinyl, piperazinyl, dioxanyl, morpholinyl, oxazolidinyl and isooxazolidinyl.

Where a group is said to be optionally substituted, preferably there are optionally 1-3 substituents, more preferably optionally 1-2 substituents.

Certain compounds of formula (I) may contain one or two or more centers of chirality and such compounds may be provided as pure enantiomers or pure diastereoisomers as well as mixtures thereof in any ratio. The compounds of the invention also include all tautomeric forms of the compounds of formula (I).

In a preferred embodiment, the present invention provides for the compound of formula (I) as defined herein and tautomers, solvates and pharmaceutically acceptable salts thereof In another preferred embodiment, the present invention provides for the compound of formula (I), wherein $X^1$, $X^2$ and $X^3$ are N.

In another preferred embodiment, (i) said $X^1$ and said $X^2$ are N, and said $X^3$ is CH; (ii) said $X^1$ and said $X^3$ are N, and said $X^2$ is CH; or (iii) said $X^2$ and said $X^3$ are N, and said $X^1$ is CH, and preferably tautomers, solvates and pharmaceutically acceptable salts thereof. In another embodiment, (i) said $X^1$ and said $X^2$ are N, and said $X^3$ is CH; or (ii) said $X^2$ and said $X^3$ are N, and said $X^1$ is CH, and preferably tautomers, solvates and pharmaceutically acceptable salts thereof. In another preferred embodiment, said $X^1$ and said $X^3$ are N, and said $X^2$ is CH; and preferably tautomers, solvates and pharmaceutically acceptable salts thereof.

In another preferred embodiment, said Y is N, and preferably tautomers, solvates and pharmaceutically acceptable salts thereof. In another preferred embodiment, said Y is CH, and preferably tautomers, solvates and pharmaceutically acceptable salts thereof.

In another preferred embodiment, said $R^1$ and said $R^2$ are independently of each other selected from

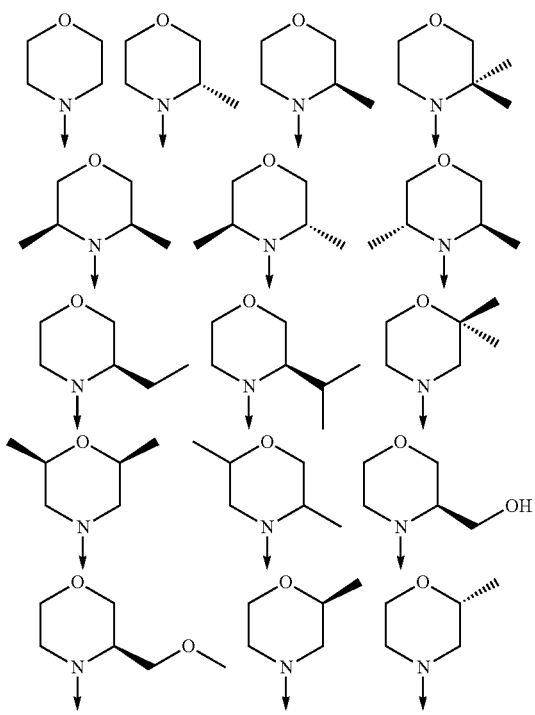

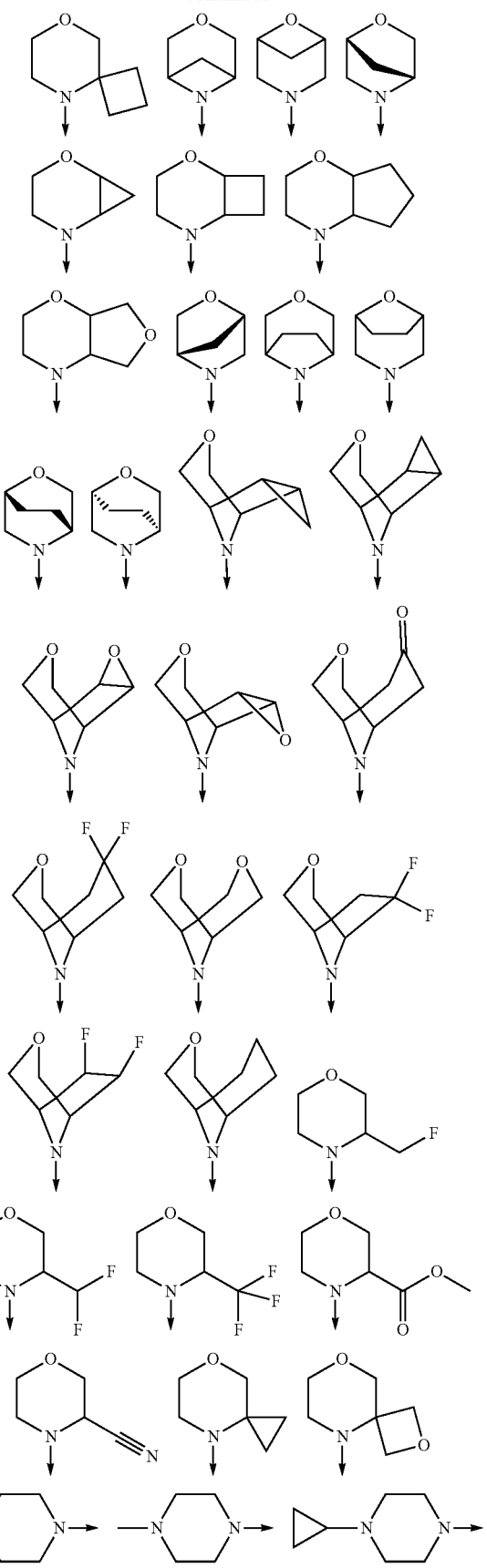

-continued

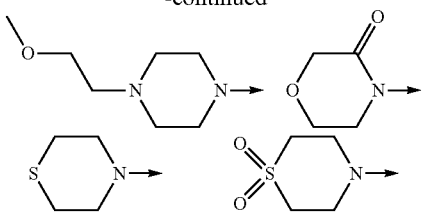

In another preferred embodiment, said R¹ and said R² are independently of each other selected from

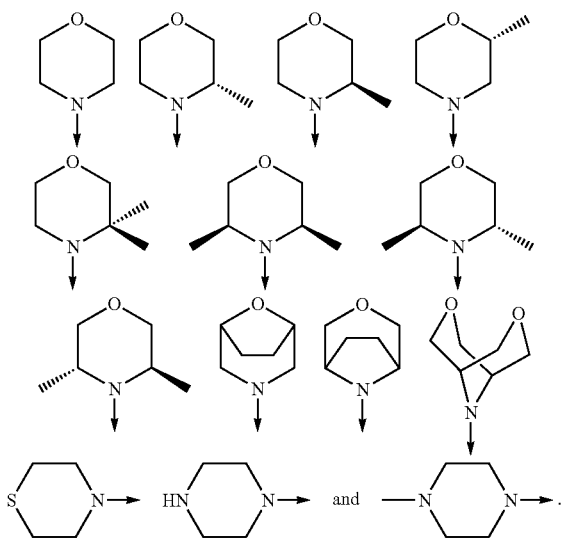

In another preferred embodiment, said R¹ and said R² are independently of each other selected from

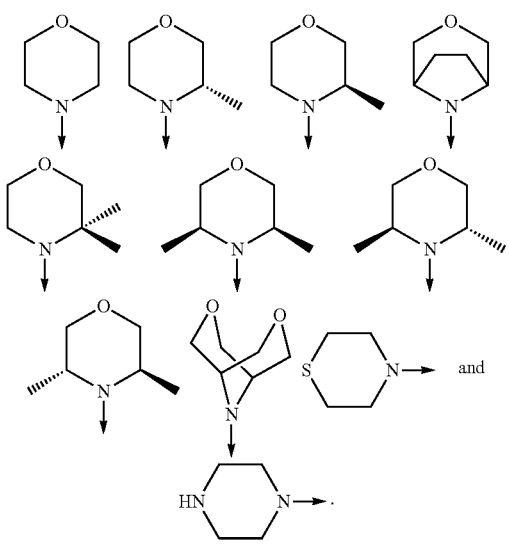

In another preferred embodiment, said compound is selected from
4-(difluoromethyl)-5-(4,6-dimorpholino-1,3,5-triazin-2-yl)pyridin-2-amine;
4-(difluoromethyl)-5-(4,6-dimorpholino-1,3,5-triazin-2-yl)pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
5-(4-(3-oxa-8-azabicyclo[3.2.1]octan-8-yl)-6-morpholino-1,3,5-triazin-2-yl)-4-(difluoromethyl)pyridin-2-amine;
5-(4-(3-oxa-8-azabicyclo[3.2.1]octan-8-yl)-6-morpholino-1,3,5-triazin-2-yl)-4-(difluoromethyl)pyrimidin-2-amine;
5-(4,6-bis((S)-3-methylmorpholino)-1,3,5-triazin-2-yl)-4-(difluoromethyl)pyridin-2-amine;
5-(4,6-bis((S)-3-methylmorpholino)-1,3,5-triazin-2-yl)-4-(difluoromethyl)pyrimidin-2-amine;
(S)-4-(difluoromethyl)-5-(4-(3-methylmorpholino)-6-morpholino-1,3,5-triazin-2-yl)pyridin-2-amine;
(S)-4-(difluoromethyl)-5-(4-(3-methylmorpholino)-6-morpholino-1,3,5-triazin-2-yl)pyrimidin-2-amine;
5-(4-(3-oxa-8-azabicyclo[3.2.1]octan-8-yl)-6-((S)-3-methylmorpholino)-1,3,5-triazin-2-yl)-4-(difluoromethyl)pyridin-2-amine;
5-(4-(3-oxa-8-azabicyclo[3.2.1]octan-8-yl)-6-((S)-3-methylmorpholino)-1,3,5-triazin-2-yl)-4-(difluoromethyl)pyrimidin-2-amine;
4-(difluoromethyl)-5-(4-morpholino-6-(piperazin-1-yl)-1,3,5-triazin-2-yl)pyridin-2-amine;
4-(difluoromethyl)-5-(4-morpholino-6-(piperazin-1-yl)-1,3,5-triazin-2-yl)pyrimidin-2-amine;
(S)-4-(difluoromethyl)-5-(4-(3-methylmorpholino)-6-(piperazin-1-yl)-1,3,5-triazin-2-yl)pyridin-2-amine;
(S)-4-(difluoromethyl)-5-(4-(3-methylmorpholino)-6-(piperazin-1-yl)-1,3,5-triazin-2-yl)pyrimidin-2-amine;
4-(difluoromethyl)-5-(2,6-dimorpholinopyrimidin-4-yl)pyridin-2-amine;
4'-(difluoromethyl)-2,6-dimorpholino-[4,5'-bipyrimidin]-2'-amine;
4-(difluoromethyl)-5-(4,6-dimorpholinopyrimidin-2-yl)pyridin-2-amine;
4'-(difluoromethyl)-4,6-dimorpholino-[2,5'-bipyrimidin]-2'-amine;
4-(difluoromethyl)-5-(4-morpholino-6-thiomorpholino-1,3,5-triazin-2-yl)pyridin-2-amine;
4-(difluoromethyl)-5-(4-morpholino-6-thiomorpholino-1,3,5-triazin-2-yl)pyrimidin-2-amine;
5-(6-(3-oxa-8-azabicyclo[3.2.1]octan-8-yl)-2-(3-oxa-8-azabicyclo[3.2.1]octan-8-yl)pyrimidin-4-yl)-4-(difluoromethyl)pyridin-2-amine;
5-(2-(3-oxa-8-azabicyclo[3.2.1]octan-8-yl)-6-morpholinopyrimidin-4-yl)-4-(difluoromethyl)pyridin-2-amine;
2-(3-oxa-8-azabicyclo[3.2.1]octan-8-yl)-4'-(difluoromethyl)-6-morpholino-[4,5'-bipyrimidin]-2'-amine;
5-(2,6-bis((S)-3-methylmorpholino)pyrimidin-4-yl)-4-(difluoromethyl)pyridin-2-amine;
4'-(difluoromethyl)-2,6-bis((S)-3-methylmorpholino)-[4,5'-bipyrimidin]-2'-amine;
(S)-4-(difluoromethyl)-5-(6-(3-methylmorpholino)-2-morpholinopyrimidin-4-yl)pyridin-2-amine;
(S)-4'-(difluoromethyl)-6-(3-methylmorpholino)-2-morpholino-[4,5'-bipyrimidin]-2'-amine;
5-(4-(8-Oxa-3-azabicyclo[3.2.1]octan-3-yl)-6-(8-oxa-3-azabicyclo[3.2.1]octan-3-yl)-1,3,5-triazin-2-yl)-4-(difluoromethyl)pyridin-2-amine;
5-[4,6-bis(2,2-dimethylmorpholin-4-yl)-1,3,5-triazin-2-yl]-4-(difluoromethyl)pyridin-2-amine;
(S)-4-(difluoromethyl)-5-(2-(3-methylmorpholino)-6-morpholinopyrimidin-4-yl)pyridin-2-amine;
(S)-4'-(difluoromethyl)-2-(3-methylmorpholino)-6-morpholino-[4,5'-bipyrimidin]-2'-amine; 4-(difluoromethyl)-

5-[4-[(2S,6R)-2,6-dimethylmorpholin-4-yl]-6-[(3R)-3-methylmorpholin-4-yl]-1,3,5-triazin-2-yl]pyridin-2-amine;

5-[4,6-bis[(2R,6S)-2,6-dimethylmorpholin-4-yl]-1,3,5-triazin-2-yl]4-(difluoromethyl)pyridin-2-amine;

5-[4,6-bis(3,7-dioxa-9-azabicyclo[3.3.1]nonan-9-yl)-1,3,5-triazin-2-yl]-4-(difluoromethyl)pyridin-2-amine;

4-(difluoromethyl)-5-[4-(3,7-dioxa-9-azabicyclo[3.3.1]nonan-9-yl)-6-(3-oxa-8-azabicyclo[3.2.1]octan-8-yl)-1,3,5-triazin-2-yl]pyridin-2-amine;

5-[4,6-bis(3,3-dimethylmorpholin-4-yl)-1,3,5-triazin-2-yl]-4-(difluoromethyl)pyridin-2-amine;

5-[4,6-bis[(3R,5S)-3,5-dimethylmorpholin-4-yl]-1,3,5-triazin-2-yl]-4-(difluoromethyl)pyridin-2-amine;

5-[4,6-bis[(3R)-3-methylmorpholin-4-yl]-1,3,5-triazin-2-yl]-4-(difluoromethyl)pyridin-2-amine;

4-(difluoromethyl)-5-[4-(3,3-dimethylmorpholin-4-yl)-6-morpholino-1,3,5-triazin-2-yl]pyridin-2-amine;

4-(difluoromethyl)-5-[4-[(3R,5S)-3,5-dimethylmorpholin-4-yl]-6-[(3R)-3-methylmorpholin-4-yl]-1,3,5-triazin-2-yl]pyridin-2-amine;

4-(difluoromethyl)-5-[4-(3,3-dimethylmorpholin-4-yl)-6-[(3R)-3-methylmorpholin-4-yl]-1,3,5-triazin-2-yl]pyridin-2-amine;

4-(difluoromethyl)-5-[4-[(3R)-3-(methoxymethyl)morpholin-4-yl]-6-[(3R)-3-methylmorpholin-4-yl]-1,3,5-triazin-2-yl]pyridin-2-amine;

4-(difluoromethyl)-5-[4-(3,7-dioxa-9-azabicyclo[3.3.1]nonan-9-yl)-6-[(3R)-3-methylmorpholin-4-yl]-1,3,5-triazin-2-yl]pyridin-2-amine;

4-(difluoromethyl)-5-[4-[(3R)-3-methylmorpholin-4-yl]-6-(3-oxa-6-azabicyclo[3.1.1]heptan-6-yl)-1,3,5-triazin-2-yl]pyridin-2-amine;

4-(difluoromethyl)-5-[4-[(3R)-3-methylmorpholin-4-yl]-6-(6-oxa-3-azabicyclo[3.1.1]heptan-3-yl)-1,3,5-triazin-2-yl]pyridin-2-amine;

4-(difluoromethyl)-5-[4-[(3R)-3-methylmorpholin-4-yl]-6-[(1R,4R)-2-oxa-5-azabicyclo[2.2.1]heptan-5-yl]-1,3,5-triazin-2-yl]pyridin-2-amine;

4-(difluoromethyl)-5-[4-[(3R)-3-methylmorpholin-4-yl]-6-[(1S,4S)-2-oxa-5-azabicyclo[2.2.1]heptan-5-yl]-1,3,5-triazin-2-yl]pyridin-2-amine;

5-[4,6-bis[(3R)-3-ethylmorpholin-4-yl]-1,3,5-triazin-2-yl]-4-(difluoromethyl)pyridin-2-amine;

5-[4,6-bis(8-oxa-5-azaspiro[3.5]nonan-5-yl)-1,3,5-triazin-2-yl]-4-(difluoromethyl)pyridin-2-amine;

5-[4,6-bis[(3R)-3-isopropylmorpholin-4-yl]-1,3,5-triazin-2-yl]-4-(difluoromethyl)pyridin-2-amine 4-(difluoromethyl)-5-[4-(3,3-dimethylmorpholin-4-yl)-6-[(3R,5S)-3,5-dimethylmorpholin-4-yl]-1,3,5-triazin-2-yl]pyridin-2-amine;

4-(difluoromethyl)-5-[4-(3,3-dimethylmorpholin-4-yl)-6-[(3R)-3-(methoxymethyl)morpholin-4-yl]-1,3,5-triazin-2-yl]pyridin-2-amine;

[(3R)-4-[4-[6-amino-4-(difluoromethyl)-3-pyridyl]-6-(3,3-dimethylmorpholin-4-yl)-1,3,5-triazin-2-yl]morpholin-3-yl]methanol;

4-(difluoromethyl)-5-[4-(3,3-dimethylmorpholin-4-yl)-6-(3,7-dioxa-9-azabicyclo[3.3.1]nonan-9-yl)-1,3,5-triazin-2-yl]pyridin-2-amine;

5-[4-(4-cyclopropylpiperazin-1-yl)-6-(3,3-dimethylmorpholin-4-yl)-1,3,5-triazin-2-yl]-4-(difluoromethyl)pyridin-2-amine;

4-(difluoromethyl)-5-[4-(3,3-dimethylmorpholin-4-yl)-6-[4-(2-methoxyethyl)piperazin-1-yl]-1,3,5-triazin-2-yl]pyridin-2-amine;

[(3R)-4-[4-[6-amino-4-(difluoromethyl)-3-pyridyl]-6-[(3R)-3-methylmorpholin-4-yl]-1,3,5-triazin-2-yl]morpholin-3-yl]methanol;

4-(difluoromethyl)-5-[4-[(3R,5R)-3,5-dimethylmorpholin-4-yl]-6-[(3R)-3-methylmorpholin-4-yl]-1,3,5-triazin-2-yl]pyridin-2-amine;

4-(difluoromethyl)-5-[4-[(3S,5S)-3,5-dimethylmorpholin-4-yl]-6-[(3R)-3-methylmorpholin-4-yl]-1,3,5-triazin-2-yl]pyridin-2-amine;

4-(difluoromethyl)-5-[4-morpholino-6-(3-oxa-9-azabicyclo[3.3.1]nonan-9-yl)-1,3,5-triazin-2-yl]pyridin-2-amine;

4-(difluoromethyl)-5-[4-(3,7-dioxa-9-azabicyclo[3.3.1]nonan-9-yl)-6-(3-oxa-9-azabicyclo[3.3.1]nonan-9-yl)-1,3,5-triazin-2-yl]pyridin-2-amine;

5-[4,6-bis[(3S,5S)-3,5-dimethylmorpholin-4-yl]-1,3,5-triazin-2-yl]-4-(difluoromethyl)pyridin-2-amine;

4-(difluoromethyl)-5-[4-(3,7-dioxa-9-azabicyclo[3.3.1]nonan-9-yl)-6-morpholino-1,3,5-triazin-2-yl]pyridin-2-amine;

4-(difluoromethyl)-5-[4-[(3S)-3-ethylmorpholin-4-yl]-6-[(3R)-3-methylmorpholin-4-yl]-1,3,5-triazin-2-yl]pyridin-2-amine;

4-(difluoromethyl)-5-[4-[(3R)-3-ethylmorpholin-4-yl]-6-[(3R)-3-methylmorpholin-4-yl]-1,3,5-triazin-2-yl]pyridin-2-amine;

4-(difluoromethyl)-5-[4-[(3R)-3-methylmorpholin-4-yl]-6-(8-oxa-5-azaspiro[3.5]nonan-5-yl)-1,3,5-triazin-2-yl]pyridin-2-amine.

In another preferred embodiment, said compound is selected from 4-(difluoromethyl)-5-(4,6-dimorpholino-1,3,5-triazin-2-yl)pyridin-2-amine;

4-(difluoromethyl)-5-(4,6-dimorpholino-1,3,5-triazin-2-yl)pyrimidin-2-amine;

5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;

5-(4-(3-oxa-8-azabicyclo[3.2.1]octan-8-yl)-6-morpholino-1,3,5-triazin-2-yl)-4-(difluoromethyl)pyridin-2-amine;

5-(4-(3-oxa-8-azabicyclo[3.2.1]octan-8-yl)-6-morpholino-1,3,5-triazin-2-yl)-4-(difluoromethyl)pyrimidin-2-amine;

5-(4,6-bis((S)-3-methylmorpholino)-1,3,5-triazin-2-yl)-4-(difluoromethyl)pyridin-2-amine;

5-(4,6-bis((S)-3-methylmorpholino)-1,3,5-triazin-2-yl)-4-(difluoromethyl)pyrimidin-2-amine;

(S)-4-(difluoromethyl)-5-(4-(3-methylmorpholino)-6-morpholino-1,3,5-triazin-2-yl)pyridin-2-amine;

(S)-4-(difluoromethyl)-5-(4-(3-methylmorpholino)-6-morpholino-1,3,5-triazin-2-yl)pyrimidin-2-amine;

5-(4-(3-oxa-8-azabicyclo[3.2.1]octan-8-yl)-6-((S)-3-methylmorpholino)-1,3,5-triazin-2-yl)-4-(difluoromethyl)pyridin-2-amine;

5-(4-(3-oxa-8-azabicyclo[3.2.1]octan-8-yl)-6-((S)-3-methylmorpholino)-1,3,5-triazin-2-yl)-4-(difluoromethyl)pyrimidin-2-amine;

4-(difluoromethyl)-5-(4-morpholino-6-(piperazin-1-yl)-1,3,5-triazin-2-yl)pyridin-2-amine;

4-(difluoromethyl)-5-(4-morpholino-6-(piperazin-1-yl)-1,3,5-triazin-2-yl)pyrimidin-2-amine;

(S)-4-(difluoromethyl)-5-(4-(3-methylmorpholino)-6-(piperazin-1-yl)-1,3,5-triazin-2-yl)pyridin-2-amine;

(S)-4-(difluoromethyl)-5-(4-(3-methylmorpholino)-6-(piperazin-1-yl)-1,3,5-triazin-2-yl)pyrimidin-2-amine;

4-(difluoromethyl)-5-(2,6-dimorpholinopyrimidin-4-yl)pyridin-2-amine;

4'-(difluoromethyl)-2,6-dimorpholino-[4,5'-bipyrimidin]-2'-amine;

4-(difluoromethyl)-5-(4,6-dimorpholinopyrimidin-2-yl)pyridin-2-amine;
4'-(difluoromethyl)-4,6-dimorpholino-[2,5'-bipyrimidin]-2'-amine;
4-(difluoromethyl)-5-(4-morpholino-6-thiomorpholino-1,3,5-triazin-2-yl)pyridin-2-amine;
4-(difluoromethyl)-5-(4-morpholino-6-thiomorpholino-1,3,5-triazin-2-yl)pyrimidin-2-amine;
5-(6-(3-oxa-8-azabicyclo[3.2.1]octan-8-yl)-2-(3-oxa-8-azabicyclo[3.2.1]octan-8-yl)pyrimidin-4-yl)-4-(difluoromethyl)pyridin-2-amine;
5-(2-(3-oxa-8-azabicyclo[3.2.1]octan-8-yl)-6-morpholinopyrimidin-4-yl)-4-(difluoromethyl)pyridin-2-amine;
2-(3-oxa-8-azabicyclo[3.2.1]octan-8-yl)-4'-(difluoromethyl)-6-morpholino-[4,5'-bipyrimidin]-2'-amine;
5-(2,6-bis((S)-3-methylmorpholino)pyrimidin-4-yl)-4-(difluoromethyl)pyridin-2-amine;
4'-(difluoromethyl)-2,6-bis((S)-3-methylmorpholino)-[4,5'-bipyrimidin]-2'-amine;
(S)-4-(difluoromethyl)-5-(6-(3-methylmorpholino)-2-morpholinopyrimidin-4-yl)pyridin-2-amine;
(S)-4'-(difluoromethyl)-6-(3-methylmorpholino)-2-morpholino-[4,5'-bipyrimidin]-2'-amine;
5-(4-(8-Oxa-3-azabicyclo[3.2.1]octan-3-yl)-6-(8-oxa-3-azabicyclo[3.2.1]octan-3-yl)-1,3,5-triazin-2-yl)-4-(difluoromethyl)pyridin-2-amine;
5-[4,6-bis(2,2-dimethylmorpholin-4-yl)-1,3,5-triazin-2-yl]-4-(difluoromethyl)pyridin-2-amine;
(S)-4-(difluoromethyl)-5-(2-(3-methylmorpholino)-6-morpholinopyrimidin-4-yl)pyridin-2-amine;
(S)-4'-(difluoromethyl)-2-(3-methylmorpholino)-6-morpholino-[4,5'-bipyrimidin]-2'-amine;
4-(difluoromethyl)-5-[4-[(2S,6R)-2,6-dimethylmorpholin-4-yl]-6-[(3R)-3-methylmorpholin-4-yl]-1,3,5-triazin-2-yl]pyridin-2-amine;
5-[4,6-bis[(2R,6S)-2,6-dimethylmorpholin-4-yl]-1,3,5-triazin-2-yl]-4-(difluoromethyl)pyridin-2-amine;
5-[4,6-bis(3,7-dioxa-9-azabicyclo[3.3.1]nonan-9-yl)-1,3,5-triazin-2-yl]-4-(difluoromethyl)pyridin-2-amine;
4-(difluoromethyl)-5-[4-(3,7-dioxa-9-azabicyclo[3.3.1]nonan-9-yl)-6-(3-oxa-8-azabicyclo[3.2.1]octan-8-yl)-1,3,5-triazin-2-yl]pyridin-2-amine;
5-[4,6-bis(3,3-dimethylmorpholin-4-yl)-1,3,5-triazin-2-yl]-4-(difluoromethyl)pyridin-2-amine;
5-[4,6-bis[(3R,5S)-3,5-dimethylmorpholin-4-yl]-1,3,5-triazin-2-yl]-4-(difluoromethyl)pyridin-2-amine;
5-[4,6-bis[(3R)-3-methylmorpholin-4-yl]-1,3,5-triazin-2-yl]-4-(difluoromethyl)pyridin-2-amine;
4-(difluoromethyl)-5-[4-(3,3-dimethylmorpholin-4-yl)-6-morpholino-1,3,5-triazin-2-yl]pyridin-2-amine;
4-(difluoromethyl)-5-[4-[(3R,5S)-3,5-dimethylmorpholin-4-yl]-6-[(3R)-3-methylmorpholin-4-yl]-1,3,5-triazin-2-yl]pyridin-2-amine;
4-(difluoromethyl)-5-[4-(3,3-dimethylmorpholin-4-yl)-6-[(3R)-3-methylmorpholin-4-yl]-1,3,5-triazin-2-yl]pyridin-2-amine;
4-(difluoromethyl)-5-[4-[(3R)-3-(methoxymethyl)morpholin-4-yl]-6-[(3R)-3-methylmorpholin-4-yl]-1,3,5-triazin-2-yl]pyridin-2-amine;
4-(difluoromethyl)-5-[4-(3,7-dioxa-9-azabicyclo[3.3.1]nonan-9-yl)-6-[(3R)-3-methylmorpholin-4-yl]-1,3,5-triazin-2-yl]pyridin-2-amine;
4-(difluoromethyl)-5-[4-(3,7-dioxa-9-azabicyclo[3.3.1]nonan-9-yl)-6-(3-oxa-9-azabicyclo[3.3.1]nonan-9-yl)-1,3,5-triazin-2-yl]pyridin-2-amine;
5-[4,6-bis[(3S,5S)-3,5-dimethylmorpholin-4-yl]-1,3,5-triazin-2-yl]-4-(difluoromethyl)pyridin-2-amine;
4-(difluoromethyl)-5-[4-(3,7-dioxa-9-azabicyclo[3.3.1]nonan-9-yl)-6-morpholino-1,3,5-triazin-2-yl]pyridin-2-amine;
4-(difluoromethyl)-5-[4-[(3S)-3-ethylmorpholin-4-yl]-6-[(3R)-3-methylmorpholin-4-yl]-1,3,5-triazin-2-yl]pyridin-2-amine;
4-(difluoromethyl)-5-[4-[(3R)-3-ethylmorpholin-4-yl]-6-[(3R)-3-methylmorpholin-4-yl]-1,3,5-triazin-2-yl]pyridin-2-amine;
4-(difluoromethyl)-5-[4-[(3R)-3-methylmorpholin-4-yl]-6-(8-oxa-5-azaspiro[3.5]nonan-5-yl)-1,3,5-triazin-2-yl]pyridin-2-amine;

In another preferred embodiment, said compound is selected from 4-(difluoromethyl)-5-(4,6-dimorpholino-1,3,5-triazin-2-yl)pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
5-(4-(3-oxa-8-azabicyclo[3.2.1]octan-8-yl)-6-morpholino-1,3,5-triazin-2-yl)-4-(difluoromethyl)pyridin-2-amine;
5-(4,6-bis((S)-3-methylmorpholino)-1,3,5-triazin-2-yl)-4-(difluoromethyl)pyrimidin-2-amine;
(S)-4-(difluoromethyl)-5-(4-(3-methylmorpholino)-6-morpholino-1,3,5-triazin-2-yl)pyridin-2-amine;
4-(difluoromethyl)-5-(4-morpholino-6-(piperazin-1-yl)-1,3,5-triazin-2-yl)pyrimidin-2-amine;
4-(difluoromethyl)-5-(4,6-dimorpholino-1,3,5-triazin-2-yl)pyridin-2-amine; and
(S)-4-(difluoromethyl)-5-(4-(3-methylmorpholino)-6-morpholino-1,3,5-triazin-2-yl)pyrimidin-2-amine;
5-[4,6-bis(3,7-dioxa-9-azabicyclo[3.3.1]nonan-9-yl)-1,3,5-triazin-2-yl]-4-(difluoromethyl)pyridin-2-amine;
4-(difluoromethyl)-5-[4-(3,7-dioxa-9-azabicyclo[3.3.1]nonan-9-yl)-6-(3-oxa-8-azabicyclo[3.2.1]octan-8-yl)-1,3,5-triazin-2-yl]pyridin-2-amine;
5-[4,6-bis(3,3-dimethylmorpholin-4-yl)-1,3,5-triazin-2-yl]-4-(difluoromethyl)pyridin-2-amine;
5-[4,6-bis[(3R,5S)-3,5-dimethylmorpholin-4-yl]-1,3,5-triazin-2-yl]-4-(difluoromethyl)pyridin-2-amine;
5-[4,6-bis[(3R)-3-methylmorpholin-4-yl]-1,3,5-triazin-2-yl]-4-(difluoromethyl)pyridin-2-amine;
4-(difluoromethyl)-5-[4-(3,3-dimethylmorpholin-4-yl)-6-morpholino-1,3,5-triazin-2-yl]pyridin-2-amine;
4-(difluoromethyl)-5-[4-[(3R,5S)-3,5-dimethylmorpholin-4-yl]-6-[(3R)-3-methylmorpholin-4-yl]-1,3,5-triazin-2-yl]pyridin-2-amine;
4-(difluoromethyl)-5-[4-(3,3-dimethylmorpholin-4-yl)-6-[(3R)-3-methylmorpholin-4-yl]-1,3,5-triazin-2-yl]pyridin-2-amine;
4-(difluoromethyl)-5-[4-[(3R)-3-(methoxymethyl)morpholin-4-yl]-6-[(3R)-3-methylmorpholin-4-yl]-1,3,5-triazin-2-yl]pyridin-2-amine;
4-(difluoromethyl)-5-[4-(3,7-dioxa-9-azabicyclo[3.3.1]nonan-9-yl)-6-[(3R)-3-methylmorpholin-4-yl]-1,3,5-triazin-2-yl]pyridin-2-amine;
4-(difluoromethyl)-5-[4-(3,7-dioxa-9-azabicyclo[3.3.1]nonan-9-yl)-6-(3-oxa-9-azabicyclo[3.3.1]nonan-9-yl)-1,3,5-triazin-2-yl]pyridin-2-amine;
5-[4,6-bis[(3S,5S)-3,5-dimethylmorpholin-4-yl]-1,3,5-triazin-2-yl]-4-(difluoromethyl)pyridin-2-amine;
4-(difluoromethyl)-5-[4-(3,7-dioxa-9-azabicyclo[3.3.1]nonan-9-yl)-6-morpholino-1,3,5-triazin-2-yl]pyridin-2-amine;
4-(difluoromethyl)-5-[4-[(3S)-3-ethylmorpholin-4-yl]-6-[(3R)-3-methylmorpholin-4-yl]-1,3,5-triazin-2-yl]pyridin-2-amine;

4-(difluoromethyl)-5-[4-[(3R)-3-ethylmorpholin-4-yl]-6-[(3R)-3-methylmorpholin-4-yl]-1,3,5-triazin-2-yl]pyridin-2-amine;

4-(difluoromethyl)-5-[4-[(3R)-3-methylmorpholin-4-yl]-6-(8-oxa-5-azaspiro[3.5]nonan-5-yl)-1,3,5-triazin-2-yl]pyridin-2-amine In another preferred embodiment, said compound is selected from 4-(difluoromethyl)-5-(4,6-dimorpholino-1,3,5-triazin-2-yl)pyrimidin-2-amine;

5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;

5-(4-(3-oxa-8-azabicyclo[3.2.1]octan-8-yl)-6-morpholino-1,3,5-triazin-2-yl)-4-(difluoromethyl)pyridin-2-amine;

5-(4,6-bis((S)-3-methylmorpholino)-1,3,5-triazin-2-yl)-4-(difluoromethyl)pyrimidin-2-amine;

(S)-4-(difluoromethyl)-5-(4-(3-methylmorpholino)-6-morpholino-1,3,5-triazin-2-yl)pyridin-2-amine;

4-(difluoromethyl)-5-(4-morpholino-6-(piperazin-1-yl)-1,3,5-triazin-2-yl)pyrimidin-2-amine;

4-(difluoromethyl)-5-(4,6-dimorpholino-1,3,5-triazin-2-yl)pyridin-2-amine; and (S)-4-(difluoromethyl)-5-(4-(3-methylmorpholino)-6-morpholino-1,3,5-triazin-2-yl)pyrimidin-2-amine;

In another preferred embodiment, said compound is selected from 4-(difluoromethyl)-5-(4,6-dimorpholino-1,3,5-triazin-2-yl)pyrimidin-2-amine;

5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;

(S)-4-(difluoromethyl)-5-(4-(3-methylmorpholino)-6-morpholino-1,3,5-triazin-2-yl)pyridin-2-amine;

and tautomers, solvates and pharmaceutically acceptable salts thereof.

In another very preferred embodiment, said compound is selected from 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; and (S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof.

In another very preferred embodiment, said compound is selected from 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; and (S)-4-(difluoromethyl)-5-(4-(3-methylmorpholino)-6-morpholino-1,3,5-triazin-2-yl)pyridin-2-amine.

In another very preferred embodiment, said compound of formula (I) is 4-(difluoromethyl)-5-(4,6-dimorpholino-1,3,5-triazin-2-yl)pyrimidin-2-amine.

In another very preferred embodiment, said compound of formula (I) is 4-(difluoromethyl)-5-(4,6-dimorpholino-1,3,5-triazin-2-yl)pyrimidin-2-amine; and tautomers, solvates and pharmaceutically acceptable salts thereof.

In another very preferred embodiment, said compound of formula (I) is 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine.

In another very preferred embodiment, said compound of formula (I) is 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; and tautomers, solvates and pharmaceutically acceptable salts thereof.

In another very preferred embodiment, said compound of formula (I) is (S)-4-(difluoromethyl)-5-(4-(3-methylmorpholino)-6-morpholino-1,3,5-triazin-2-yl)pyridin-2-amine.

In another very preferred embodiment, said compound of formula (I) is (S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof.

In another preferred embodiment, said $R^1$ and $R^2$ are independently of each other a morpholinyl of formula (II). In one preferred embodiment, said $R^1$ is equal to $R^2$. In another preferred embodiment, said $R^1$ is not equal to $R^2$.

In another preferred embodiment, said $R^1$ and $R^2$ are independently of each other a morpholinyl of formula (II) and said saturated 6-membered heterocyclic ring Z.

In another preferred embodiment, within said morpholinyl of formula (II)

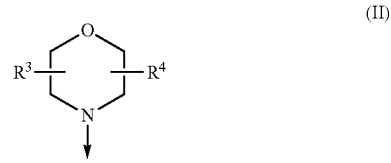

$R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxy$C_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —CH$_2$—O—CH$_2$—, —CH$_2$—NH—CH$_2$—, or any of the structures

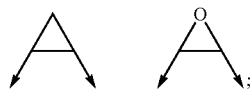

wherein the arrows denote the bonds in formula (II).

In the instance that R3 and R4 together form a bivalent residue and are bound to vicinal carbon atoms annulated morpholinyl substituents are formed. In the instance that R3 and R4 together form a bivalent residue and are spanning across the morpholine ring bridged morpholinyl substituents are formed. In the instance that R3 and R4 together form a bivalent residue and are bound to the same carbon atom of the morpholine, spiro morpholinyl substituents are formed.

In a preferred embodiment, $R^3$ and $R^4$ form together a bivalent residue —$R^5R^6$— selected from $C_1$-$C_3$alkylene optionally substituted with 1 to 4 F, —CH$_2$—O—CH$_2$—, —CH$_2$—NH—CH$_2$—, or any of the structures

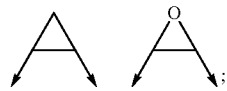

and forming a bridged morpholinyl substituent.

In another preferred embodiment, said $R^1$ and $R^2$ are independently of each other a morpholinyl of formula (II), wherein $R^3$ and $R^4$ form together a bivalent residue leading to a bridged morpholinyl, wherein $R^3$ and $R^4$ form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

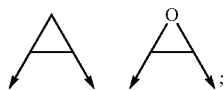

wherein the arrows denote the bonds in formula (II).

In a further preferred embodiment, said morpholinyl of formula (II)

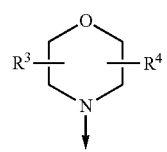

(II)

is independently of each other a morpholinyl of said formula (II), wherein $R^3$ and $R^4$ are independently of each other H, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxyC$_1$-$C_3$alkyl, CN, or $C(O)O$—$C_1$-$C_2$alkyl; or $R^3$ and $R^4$ form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

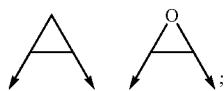

wherein the arrows denote the bonds in formula (II).

In a further preferred embodiment, said morpholinyl of formula (II) is independently of each other a morpholinyl of said formula (II), wherein $R^3$ and $R^4$ are independently of each other H or $CH_3$.

In a further preferred embodiment, said morpholinyl of formula (II) is independently of each other a morpholinyl of said formula (II), wherein $R^3$ and $R^4$ are independently of each other $C_2$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxyC$_1$-$C_3$alkyl, CN, or $C(O)O$—$C_1$-$C_2$alkyl; or $R^3$ and $R^4$ form together a bivalent residue —$R^5R^6$— selected from —$CH_2$— or $C_3$alkylene, preferably —$CH_2$—, —$CH_2CF_2$—, —CHFCHF—, —$CH_2CF_2CH_2$—, —$CH_2$—O—$CH_2$—, —$CH_2$—NH—$CH_2$—, or any of the structures

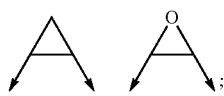

wherein the arrows denote the bonds in formula (II).

In a further preferred embodiment, said morpholinyl of formula (II) is independently of each other selected from

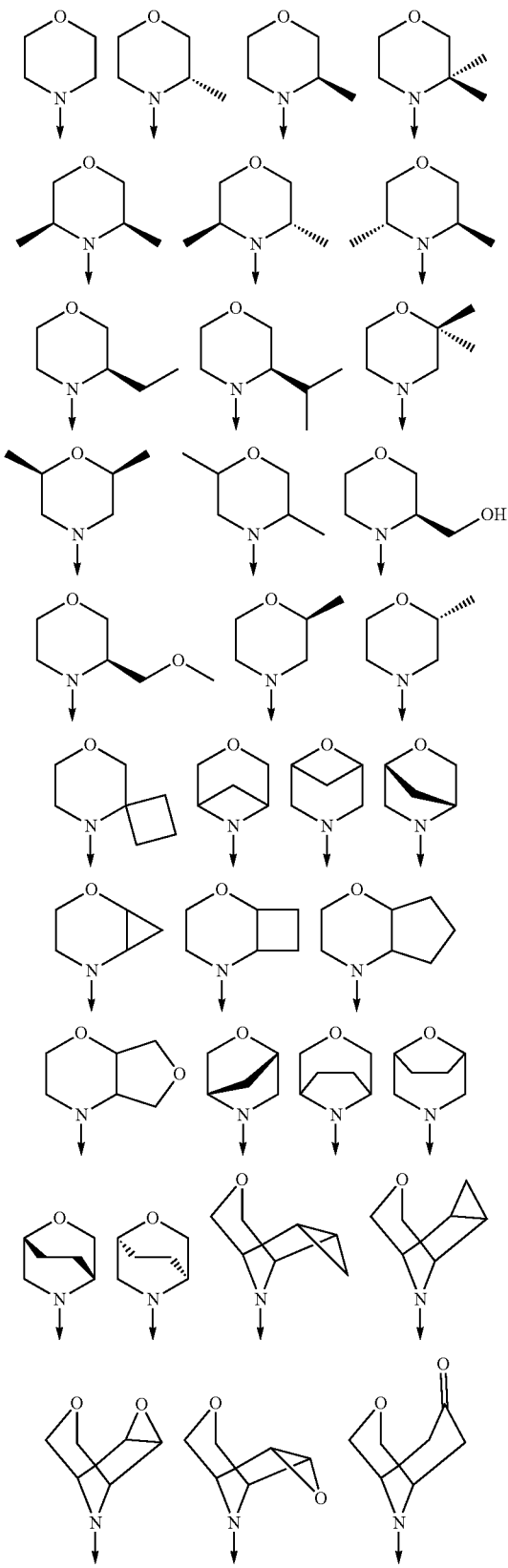

-continued

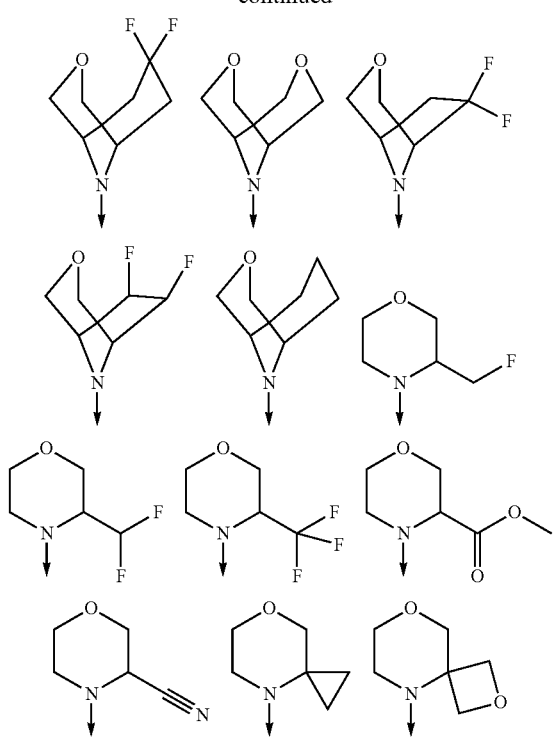

In a further preferred embodiment, said morpholinyl of formula (11) is independently of each other selected from

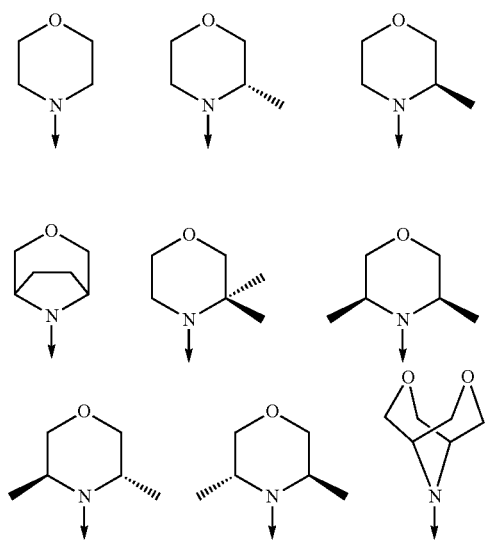

In a further preferred embodiment, said heterocyclic ring Z is a saturated 6-membered heterocyclic ring Z selected from thiomorpholinyl and piperazinyl, optionally substituted by 1 to 3 $R^7$; wherein $R^7$ is independently at each occurrence $C_1$-$C_3$alkyl, $CH_2OH$, $CH_2CH_2OH$, $CH_2F$, $CHF_2$, $CF_3$, $CH_2CF_3$, $C_1$-$C_2$alkoxy$C_1$-$C_3$alkyl, $C_3$-$C_6$cycloalkyl; or two $R^7$ substituents form together a bivalent residue —$R^8R^9$— selected from $C_1$-$C_3$alkylene optionally substituted with 1 to 4 F, —$CH_2$—O—$CH_2$— or —O—$CH_2CH_2$—O—;

In a further preferred embodiment, said heterocyclic ring Z is selected from

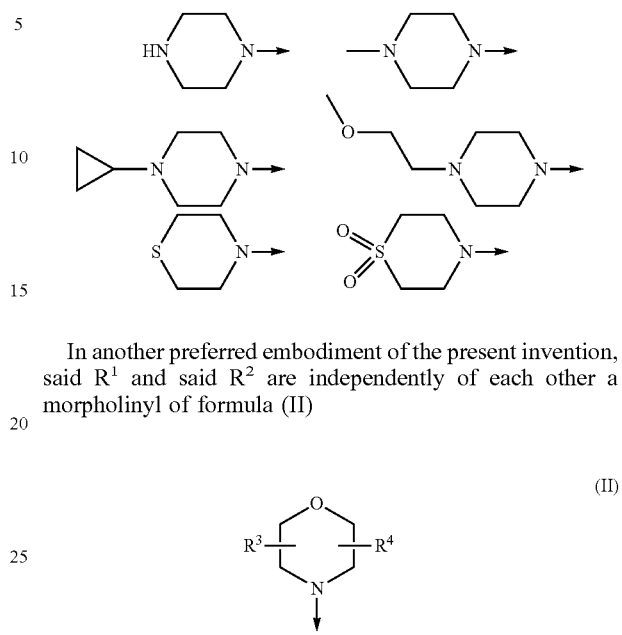

In another preferred embodiment of the present invention, said $R^1$ and said $R^2$ are independently of each other a morpholinyl of formula (II)

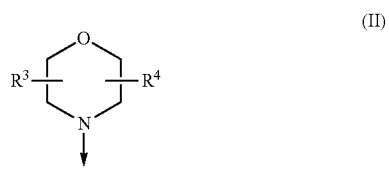
(II)

wherein the arrow denotes the bond in formula (I); and
wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxy$C_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —$CH_2$—O—$CH_2$—, —$CH_2$—NH—$CH_2$—, or any of the structures

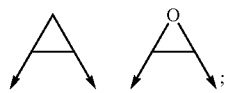;

wherein the arrows denote the bonds in formula (II).

In a further preferred embodiment, said $R^1$ is equal to said $R^2$, and said $R^1$ and said $R^2$ are independently of each other a morpholinyl of formula (11)

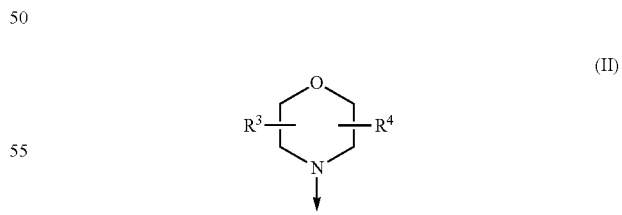
(II)

wherein the arrow denotes the bond in formula (I); and
wherein $R^3$ and R are independently of each other H, $C_1$-$C_3$alkyl optionally substituted with one or two OH, $C_1$-$C_2$fluoroalkyl, $C_1$-$C_2$alkoxy, $C_1$-$C_2$alkoxy$C_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —$CH_2$—O—$CH_2$—, —$CH_2$—NH—$CH_2$—, or any of the structures

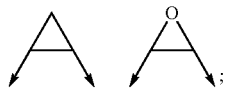

wherein the arrows denote the bonds in formula (II).

In a further preferred embodiment of the present invention, said $R^1$ and said $R^2$ are independently of each other a morpholinyl of formula (II)

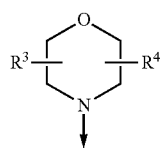

wherein the arrow denotes the bond in formula (I); and
wherein $R^3$ and $R^4$ are independently of each other H, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, CN, or $C(O)O$—$C_1$-$C_2$alkyl; or $R^3$ and R form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

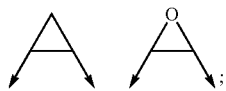

wherein the arrows denote the bonds in formula (II).

In a further preferred embodiment of the present invention, $R^1$ is equal to $R^2$, and said $R^1$ and said $R^2$ are a morpholinyl of formula (II)

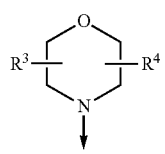

wherein the arrow denotes the bond in formula (I); and
wherein $R^3$ and $R^4$ are independently of each other H, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, CN, or $C(O)O$—$C_1$-$C_2$alkyl; or $R^3$ and $R^4$ form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

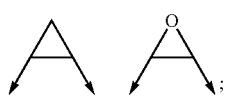

wherein the arrows denote the bonds in formula (II).

In another aspect and preferred embodiment, the present invention provides for a compound of (I)

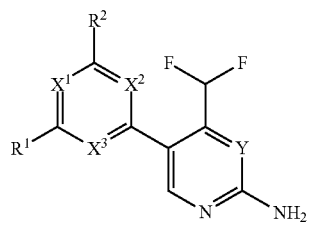

wherein $X^1$, $X^2$ and $X^3$ are, independently of each other, N or CH; with the proviso that at least two of $X^1$, $X^2$ and $X^3$ are N; Y is N or CH; and wherein $R^1$ and $R^2$ are independently of each other a morpholinyl of formula (II)

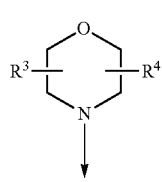

wherein the arrow denotes the bond in formula (I); and $R^1$ is not equal to $R^2$, and at least one of said $R^1$ and said $R^2$ are a morpholinyl of formula (II),

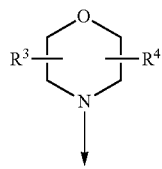

wherein $R^3$ and R are independently of each other $C_2$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, CN, or $C(O)O$—$C_1$-$C_2$alkyl; or $R^3$ and $R^4$ form together a bivalent residue —$R^5R^6$— selected from —$CH_2$— or $C_3$alkylene, preferably —$CH_2$—, —$CH_2CF_2$—, —CHFCHF—, —$CH_2CF_2CH_2$—, —$CH_2$—O—$CH_2$—, —$CH_2$—NH—$CH_2$—, or any of the structures

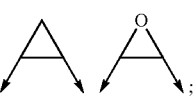

wherein the arrows denote the bonds in formula (II).

Preferably, said $R^3$ and R form together a bivalent residue —$R^5R^6$— selected from —$CH_2$— or $C_3$alkylene, preferably —$CH_2$—, —$CH_2CF_2$—, —CHFCHF—, —$CH_2CF_2CH_2$—, —$CH_2$—O—$CH_2$—, —$CH_2$—NH—$CH_2$—, or any of the structures

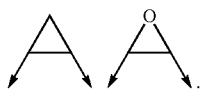

In another preferred embodiment, $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl.

In another preferred embodiment, $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl, and $X^1$, $X^2$ and $X^3$ are N; and tautomers, solvates and pharmaceutically acceptable salts thereof.

Preferably Y is N or CH; $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; and tautomers, solvates and pharmaceutically acceptable salts thereof.

In a further preferred embodiment, $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl, and $X^1$ and $X^3$ are N, and $X^2$ is CH; and tautomers, solvates and pharmaceutically acceptable salts thereof. Preferably Y is N or CH; $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; and tautomers, solvates and pharmaceutically acceptable salts thereof.

In a preferred embodiment, $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl, and $X^1$ and $X^2$ are N, and $X^3$ is CH; and tautomers, solvates and pharmaceutically acceptable salts thereof. Preferably Y is N or CH; $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; and tautomers, solvates and pharmaceutically acceptable salts thereof.

In a preferred embodiment, $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl, and $X^2$ and $X^3$ are N, and $X^1$ is CH; and tautomers, solvates and pharmaceutically acceptable salts thereof. Preferably, Y is N or CH; $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; and tautomers, solvates and pharmaceutically acceptable salts thereof.

In a further embodiment, there is provided a compound of formula (I) according to the invention for use in the prevention or treatment of a neurological disorder in a subject, wherein the neurological disorder is epilepsy or a neurodegenerative disease.

In a further embodiment, there is provided a compound of formula (I) according to the invention for use in the prevention or treatment of a neurodegenerative disease in a subject.

In a further embodiment, there is provided a compound of formula (I) according to the invention for use in the prevention or treatment of epilepsy in a subject.

In a further embodiment, there is provided a compound of formula (I) according to the invention for use in the prevention or treatment of epilepsy in a subject, wherein the compound of formula (I) is administered to said subject during primary epileptogenesis or during secondary epileptogenesis or in fully developed epilepsy.

In a further embodiment, there is provided a compound of formula (I) according to the invention for use in the prevention or treatment of epilepsy in a subject, wherein the epilepsy is symptomatic epilepsy or idiopathic epilepsy.

In a further embodiment, there is provided a compound of formula (I) according to the invention for use in the prevention or treatment of epilepsy in a subject, wherein the epilepsy is symptomatic epilepsy.

In a further embodiment, there is provided a compound of formula (I) according to the invention for use in the prevention or treatment of epilepsy in a subject, wherein the epilepsy is idiopathic epilepsy.

In a further embodiment, there is provided a compound of formula (I) according to the invention for use in the prevention or treatment of symptomatic epilepsy in a subject, wherein said symptomatic epilepsy is caused by brain injury, brain tumor, brain infection, adrenoleukodystrophy, Rasmussen's syndrome, Sturge-Weber syndrome, megalencephaly, polyhydramnios, tuberous sclerosis complex (TSC), symptomatic epilepsy syndrome, PMSE, PTEN mutations or focal cortical dysplasia (FCD).

In one embodiment, there is provided a compound of formula (I) according to the invention for use in the prevention or treatment of symptomatic epilepsy in a subject, wherein said symptomatic epilepsy is due to a disease characterized by upregulation of mTOR ("TORopathy").

In one embodiment, there is provided a compound of formula (I) for use in the prevention or treatment of symptomatic epilepsy in a subject, wherein said symptomatic epilepsy is due to a disease characterized by upregulation of mTOR ("TORopathy"), wherein said "TORopathy" is selected from the group consisting of TSC, polyhydramnios, megalencephaly, symptomatic epilepsy syndrome, PMSE, focal cortical dysplasia (FCD) and a "TORopathy" associated with PTEN mutations.

In a further embodiment, there is provided a compound of formula (I) according to the invention for use in the prevention or treatment of symptomatic epilepsy in a subject, wherein said symptomatic epilepsy is caused by brain injury, brain infection, adrenoleukodystrophy, Rasmussen's syndrome, Sturge-Weber syndrome, megalencephaly, polyhydramnios, tuberous sclerosis complex (TSC), symptomatic epilepsy syndrome, PMSE, PTEN mutations or focal cortical dysplasia (FCD).

In yet a further embodiment, there is provided a compound of formula (I) for use in the prevention or treatment of symptomatic epilepsy in a subject, wherein said symptomatic epilepsy is caused by brain injury, brain infection, adrenoleukodystrophy, Rasmussen's syndrome or Sturge-Weber syndrome.

In a preferred embodiment, there is provided a compound of formula (I) according to the invention for use in the prevention or treatment of symptomatic epilepsy in a subject, wherein said symptomatic epilepsy is caused by TSC.

In a further embodiment, there is provided a compound of formula (I) according to the invention for use in the prevention or treatment of idiopathic epilepsy in a subject, wherein said idiopathic epilepsy is selected from the group consisting of Doose syndrome (myoclonic astatic epilepsy of childhood), West syndrome, benign Rolandic epilepsy, Lennox-Gastaut syndrome, Landau-Kleffner syndrome, symptomatic epilepsy syndrome, PMSE and juvenile myoclonic epilepsy.

As indicated above, epilepsy can be partial or generalized. Thus, in one embodiment, there is provided a compound of formula (I) according to the invention for use in the prevention or treatment of epilepsy in a subject, wherein the epilepsy is partial epilepsy or generalized epilepsy.

In a further embodiment, there is provided a compound of formula (I) for use in the prevention or treatment of epilepsy in a subject, wherein the epilepsy is partial idiopathic epilepsy, partial symptomatic epilepsy, generalized idiopathic epilepsy or generalized symptomatic epilepsy.

In a preferred embodiment, there is provided a compound of formula (I) for use in the prevention or treatment of partial epilepsy in a subject, wherein said partial epilepsy is temporal lobe epilepsy.

In a further embodiment, there is provided a compound of formula (I) according to the invention for use in the prevention or treatment of a neurodegenerative disease in a subject, wherein said neurodegenerative disease is associated with or caused by protein misfolding and/or protein aggregation.

In a further embodiment, there is provided a compound of formula (I) according to the invention for use in the prevention or treatment of a neurodegenerative disease in a subject, wherein the neurodegenerative disease is selected from the group consisting of Huntington's disease, spinocerebellar ataxias, Parkinson's disease, morbus Alzheimer, amyotrophic lateral sclerosis (ALS), cystic fibrosis, familial amyloidotic polyneuropathy, spongiform encephalopathies, dementia with Lewy bodies, frontotemporal dementia with Parkinsonism, spinocerebellar ataxias, spinal and bulbar muscular atrophy, hereditary dentatorubral-pallidoluysian atrophy, familial British dementia, familial Danish dementia and prion disease.

In a preferred embodiment, there is provided a compound of formula (I) according to the invention for use in the prevention or treatment of a neurodegenerative disease in a subject, wherein the neurodegenerative disease is selected from the group consisting of Huntington's disease, morbus Alzheimer and prion disease.

In a particularly preferred embodiment, there is provided a compound of formula (I) according to the invention for use in the prevention or treatment of Huntington's disease in a subject.

In a preferred embodiment, there is provided a compound of formula (I) according to the invention, wherein said compound is selected from:
4-(difluoromethyl)-5-(4,6-dimorpholino-1,3,5-triazin-2-yl)pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
(S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof,
for use in the prevention or treatment of a neurological disorder in a subject, wherein the neurological disorder is epilepsy or Huntington's disease.

In a further preferred embodiment, there is provided a compound of formula (I) according to the invention, wherein said compound is selected from:
4-(difluoromethyl)-5-(4,6-dimorpholino-1,3,5-triazin-2-yl)pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
(S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof, for use in the prevention or treatment of epilepsy in a subject.

In a preferred embodiment, there is provided a compound of formula (I) according to the invention, wherein said compound is selected from:
4-(difluoromethyl)-5-(4,6-dimorpholino-1,3,5-triazin-2-yl)pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
(S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof,
for use in the prevention or treatment of Huntington's disease in a subject.

In a preferred embodiment, there is provided a compound of formula (I) according to the invention, wherein said compound is selected from 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; and (S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof, for use in the prevention or treatment of a neurological disorder in a subject, wherein the neurological disorder is epilepsy or Huntington's disease.

In a preferred embodiment, there is provided a compound of formula (I) according to the invention, wherein said compound is selected from 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; and (S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof, for use in the prevention or treatment of epilepsy in a subject.

In a preferred embodiment, there is provided a compound of formula (I) according to the invention, wherein said compound is selected from 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; and (S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof, for use in the prevention or treatment of Huntington's disease in a subject.

In a preferred embodiment, there is provided the compound 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; and tautomers, solvates and pharmaceutically acceptable salts thereof, for use in the prevention or treatment of a neurological disorder in a subject, wherein the neurological disorder is epilepsy or Huntington's disease.

In a particularly preferred embodiment, there is provided the compound 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; and tautomers, solvates and pharmaceutically acceptable salts thereof, for use in the prevention or treatment of epilepsy in a subject.

In a further particularly preferred embodiment, there is provided the compound 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; and tautomers, solvates and pharmaceutically acceptable salts thereof, for use in the prevention or treatment of Huntington's disease in a subject.

In a preferred embodiment, there is provided the compound (S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof, for use in the prevention or treatment of a neurological disorder in a subject, wherein the neurological disorder is epilepsy or Huntington's disease.

In a particularly preferred embodiment, there is provided the compound (S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof, for use in the prevention or treatment of epilepsy in a subject.

In a further particularly preferred embodiment, there is provided the compound (S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof, for use in the prevention or treatment of Huntington's disease in a subject.

In a preferred embodiment, there is provided a compound of formula (I) according to the invention, wherein R1 and R2 are independently of each other a morpholinyl of formula (II); and tautomers, solvates and pharmaceutically acceptable salts thereof, for use in the prevention or treatment of a neurological disorder in a subject, wherein the neurological disorder is epilepsy or Huntington's disease.

In a preferred embodiment, there is provided a compound of formula (I) according to the invention, wherein R1 and R2 are independently of each other a morpholinyl of formula (II); and tautomers, solvates and pharmaceutically acceptable salts thereof, for use in the prevention or treatment of epilepsy in a subject.

In a preferred embodiment, there is provided a compound of formula (I) according to the invention, wherein R1 and R2 are independently of each other a morpholinyl of formula (II); and tautomers, solvates and pharmaceutically acceptable salts thereof, for use in the prevention or treatment of Huntington's disease in a subject.

In a preferred embodiment, there is provided a compound of formula (I) according to the invention, wherein R1 is equal to R2; and tautomers, solvates and pharmaceutically acceptable salts thereof, for use in the prevention or treatment of a neurological disorder in a subject, wherein the neurological disorder is epilepsy or Huntington's disease.

In a preferred embodiment, there is provided a compound of formula (I) according to the invention, wherein R1 is equal to R2; and tautomers, solvates and pharmaceutically acceptable salts thereof, for use in the prevention or treatment of epilepsy in a subject.

In a preferred embodiment, there is provided a compound of formula (I) according to the invention, wherein R1 is equal to R2; and tautomers, solvates and pharmaceutically acceptable salts thereof, for use in the prevention or treatment of Huntington's disease in a subject.

In a preferred embodiment, there is provided a compound of formula (I) according to the invention, wherein R1 is not equal to R2; and tautomers, solvates and pharmaceutically acceptable salts thereof, for use in the prevention or treatment of a neurological disorder in a subject, wherein the neurological disorder is epilepsy or Huntington's disease.

In a preferred embodiment, there is provided a compound of formula (I) according to the invention, wherein R1 is not equal to R2; and tautomers, solvates and pharmaceutically acceptable salts thereof, for use in the prevention or treatment of epilepsy in a subject.

In a preferred embodiment, there is provided a compound of formula (I) according to the invention, wherein R1 is not equal to R2; and tautomers, solvates and pharmaceutically acceptable salts thereof, for use in the prevention or treatment of Huntington's disease in a subject.

In a further aspect of the invention, there is provided a method for treating or preventing a neurological disorder in a subject, comprising administering an effective amount of a compound of formula (I) according to the invention to said subject.

In one embodiment, there is provided a method for treating or preventing a neurological disorder in a subject, comprising administering an effective amount of a compound of formula (I) according to the invention to said subject, wherein the neurological disorder is epilepsy or Huntington's disease.

In a preferred embodiment, there is provided a method for treating or preventing epilepsy in a subject, comprising administering an effective amount of a compound of formula (I) according to the invention to said subject.

In a further preferred embodiment, there is provided a method for treating or preventing epilepsy in a subject, comprising administering an effective amount of a compound of formula (I) according to the invention to said subject, wherein said effective amount of a compound of formula (I) according to the invention is administered during primary epileptogenesis or during secondary epileptogenesis or in fully developed epilepsy.

In a further preferred embodiment, there is provided a method for treating or preventing Huntington's disease in a subject, comprising administering an effective amount of a compound of formula (I) according to the invention to said subject.

In a particularly preferred embodiment, there is provided a method for treating or preventing a neurological disorder in a subject, comprising administering an effective amount of a compound of formula (I) according to the invention to said subject, wherein said compound is selected from:
4-(difluoromethyl)-5-(4,6-dimorpholino-1,3,5-triazin-2-yl)pyrimidin-2-amine; 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; (S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof; and wherein the neurological disorder is epilepsy or Huntington's disease.

In a further aspect of the invention, there is provided the use of a compound of formula (I) according to the invention for treating or preventing a neurological disorder in a subject.

In one embodiment, there is provided the use of a compound of formula (I) according to the invention for treating or preventing a neurological disorder in a subject, wherein the neurological disorder is epilepsy or Huntington's disease.

In a particularly preferred embodiment, there is provided the use of a compound of formula (I) according to the invention for treating or preventing a neurological disorder in a subject, wherein said compound is selected from:
4-(difluoromethyl)-5-(4,6-dimorpholino-1,3,5-triazin-2-yl)pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
(S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof; and wherein the neurological disorder is epilepsy or Huntington's disease.

In a further aspect of the invention, there is provided the use of a compound of formula (I) according to the invention for the manufacture of a medicament for treating or preventing a neurological disorder in a subject.

In one embodiment, there is provided the use of a compound of formula (I) according to the invention for the manufacture of a medicament for treating or preventing a neurological disorder in a subject, wherein the neurological disorder is epilepsy or Huntington's disease.

In a particularly preferred embodiment, there is provided the use of a compound of formula (I) according to the invention for the manufacture of a medicament for treating or preventing a neurological disorder in a subject, wherein said compound is selected from:
4-(difluoromethyl)-5-(4,6-dimorpholino-1,3,5-triazin-2-yl)pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
(S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof; and wherein the neurological disorder is epilepsy or Huntington's disease.

Most preferred for the present invention are the following compounds shown by formula: (The names of the corresponding structures were produced using ChemDraw Ultra, version 13.0.1 as well as lower and upper software versions thereof, CambridgeSoft Corp., Cambridge MA).

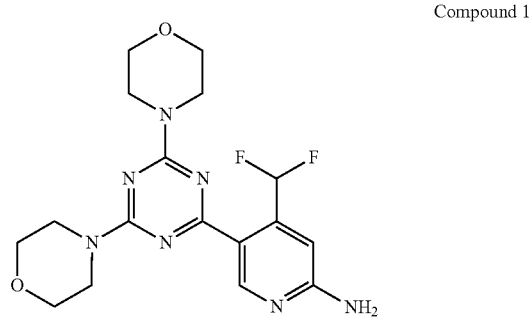 [SMILES: Nc1cc(C(F)F)c(-c2nc(N3CCOCC3)nc(N3CCOCC3)n2)cn1]

Compound 1

4-(difluoromethyl)-5-(4,6-dimorpholino-1,3,5-triazin-2-yl)pyridin-2-amine

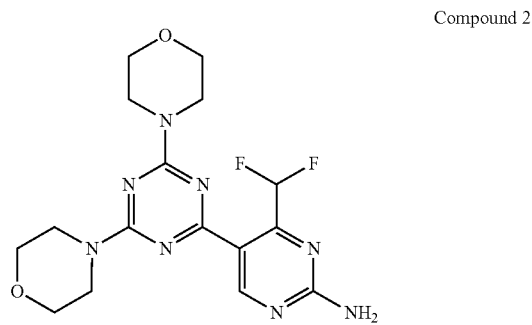 [SMILES: Nc1ncc(-c2nc(N3CCOCC3)nc(N3CCOCC3)n2)c(C(F)F)n1]

Compound 2

4-(difluoromethyl)-5-(4,6-dimorpholino-1,3,5-triazin-2-yl)pyrimidin-2-amine

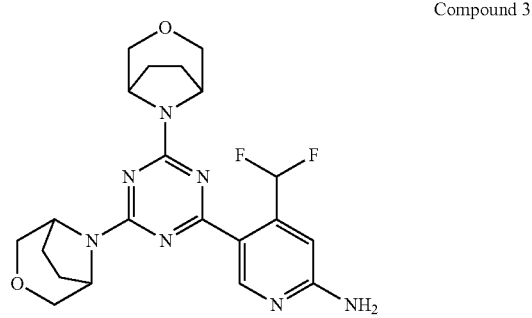 [SMILES: Nc1cc(C(F)F)c(-c2nc(N3C4CCC3COC4)nc(N3C4CCC3COC4)n2)cn1]

Compound 3

5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine 5-(4,6-bis((S)-3-methylmorpholino)-1,3,5-triazin-2-yl)-4-(difluoromethyl)pyridin-2-amine Compound 4

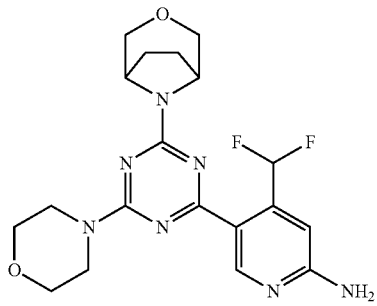

5-(4-(3-oxa-8-azabicyclo[3.2.1]octan-8-yl)-6-morpholino-1,3,5-triazin-2-yl)-4-(difluoromethyl)pyridin-2-amine Compound 7

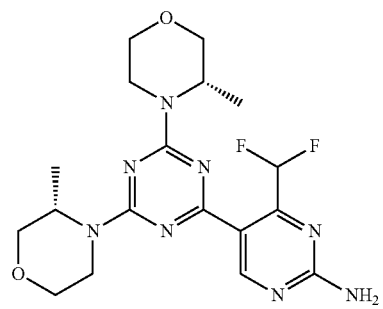

5-(4,6-bis((S)-3-methylmorpholino)-1,3,5-triazin-2-yl)-4-(difluoromethyl)pyrimidin-2-amine Compound 5

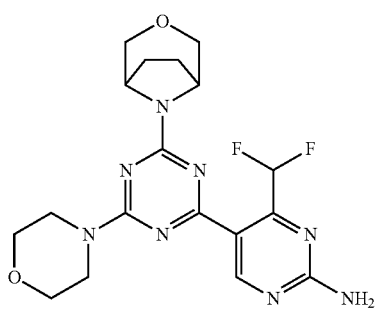

5-(4-(3-oxa-8-azabicyclo[3.2.1]octan-8-yl)-6-morpholino-1,3,5-triazin-2-yl)-4-(difluoromethyl)pyrimidin-2-amine Compound 8

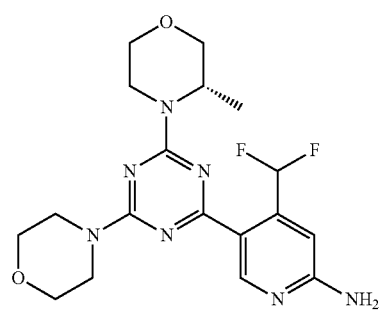

(S)-4-(difluoromethyl)-5-(4-(3-methylmorpholino)-6-morpholino-1,3,5-triazin-2-yl)pyridin-2-amine Compound 6

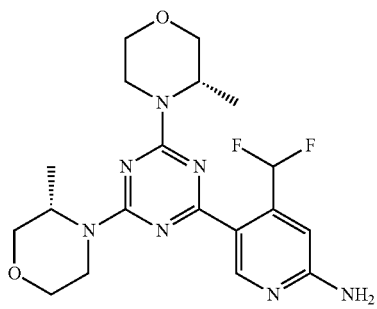

Compound 9

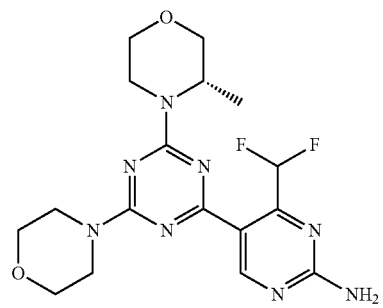

| 41 | 42 |
|---|---|
| (S)-4-(difluoromethyl)-5-(4-(3-methylmorpholino)-6-morpholino-1,3,5-triazin-2-yl)pyrimidin-2-amine | 4-(difluoromethyl)-5-(4-morpholino-6-(piperazin-1-yl)-1,3,5-triazin-2-yl)pyridin-2-amine |

Compound 10

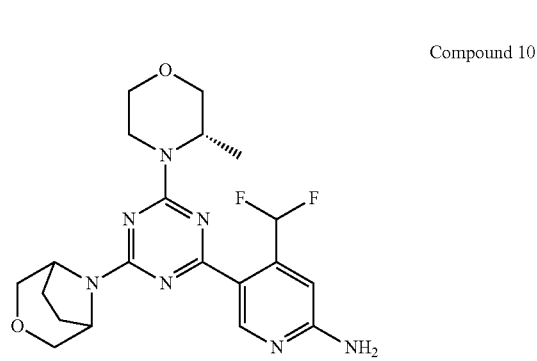 [SMILES: C[C@H]1COCCN1c1nc(-c2cnc(N)cc2C(F)F)nc(N2C3CCC2COC3)n1]

5-(4-(3-oxa-8-azabicyclo[3.2.1]octan-8-yl)-6-((S)-3-methylmorpholino)-1,3,5-triazin-2-yl)-4-(difluoromethyl)pyridin-2-amine Compound 13

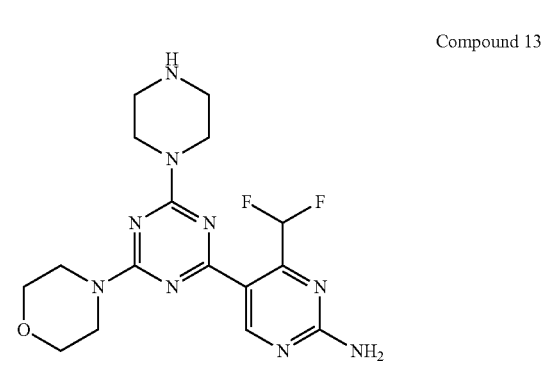

4-(difluoromethyl)-5-(4-morpholino-6-(piperazin-1-yl)-1,3,5-triazin-2-yl)pyrimidin-2-amine Compound 11

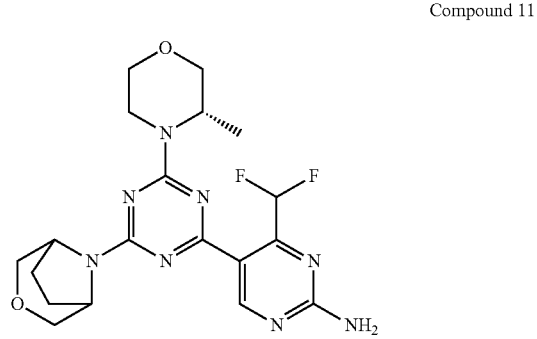 [SMILES: C[C@H]1COCCN1c1nc(-c2cnc(N)nc2C(F)F)nc(N2C3CCC2COC3)n1]

5-(4-(3-oxa-8-azabicyclo[3.2.1]octan-8-yl)-6-((S)-3-methylmorpholino)-1,3,5-triazin-2-yl)-4-(difluoromethyl)pyrimidin-2-amine Compound 14

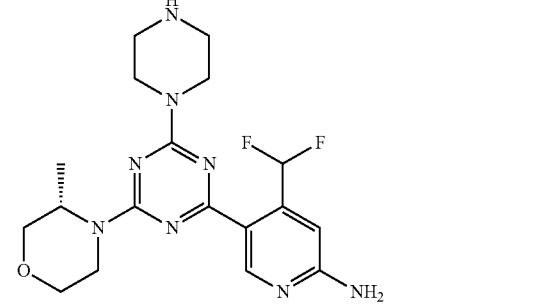

(S)-4-(difluoromethyl)-5-(4-(3-methylmorpholino)-6-(piperazin-1-yl)-1,3,5-triazin-2-yl)pyridin-2-amine Compound 12

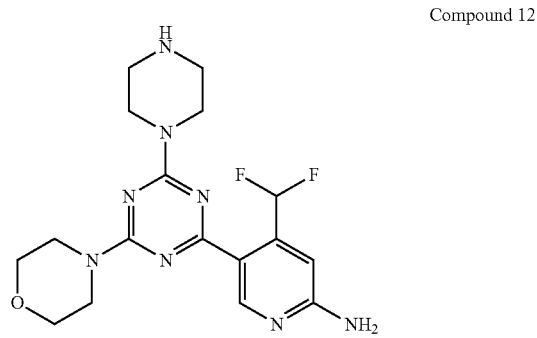 [SMILES: Nc1cc(C(F)F)c(-c2nc(N3CCNCC3)nc(N3CCOCC3)n2)cn1]

Compound 15

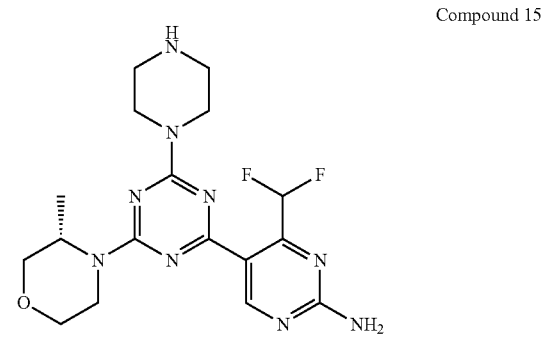 [SMILES: C[C@H]1COCCN1c1nc(-c2cnc(N)cc2C(F)F)nc(N2CCNCC2)n1]

43

(S)-4-(difluoromethyl)-5-(4-(3-methylmorpholino)-6-(piperazin-1-yl)-1,3,5-triazin-2-yl)pyrimidin-2-amine Compound 16

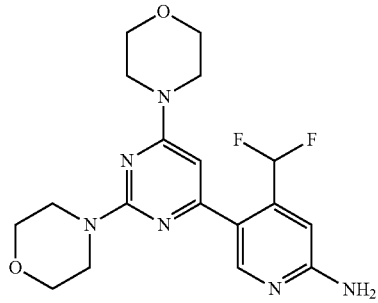

4-(difluoromethyl)-5-(2,6-dimorpholinopyrimidin-4-yl)pyridin-2-amine

Compound 17

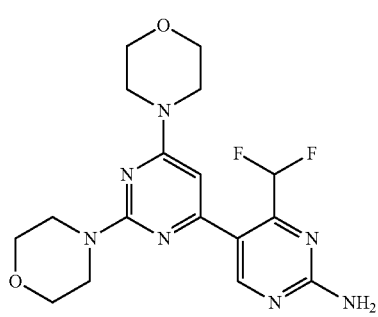

4'-(difluoromethyl)-2,6-dimorpholino-[4,5'-bipyrimidin]-2'-amine

Compound 18

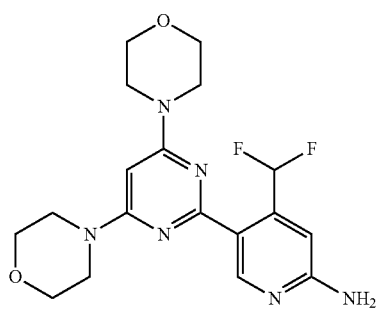

44

4-(difluoromethyl)-5-(4,6-dimorpholinopyrimidin-2-yl)pyridin-2-amine

Compound 19

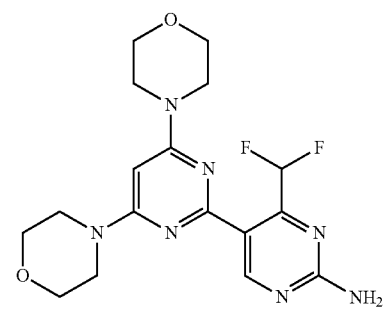

4-(difluoromethyl)-4,6-dimorpholino-[2,5'-bipyrimidin]-2'-amine

Compound 20

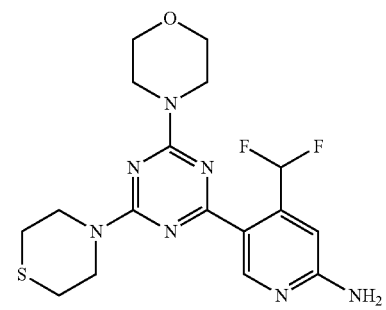

4-(difluoromethyl)-5-(4-morpholino-6-thiomorpholino-1,3,5-triazin-2-yl)pyridin-2-amine Compound 21

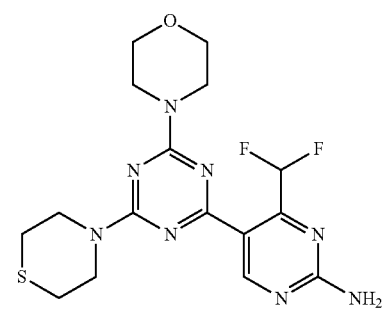

45

4-(difluoromethyl)-5-(4-morpholino-6-thiomorpholino-1,3,5-triazin-2-yl)pyrimidin-2-amine

46

2-(3-oxa-8-azabicyclo[3.2.1]octan-8-yl)-4'-(difluoromethyl)-6-morpholino-[4,5'-bipyrimidin]-2'-amine Further preferred are the following compounds

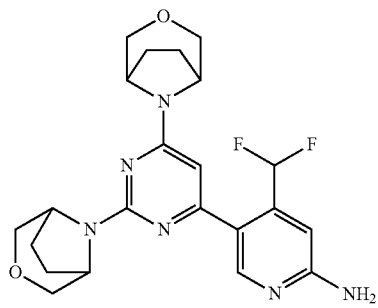

Compound 22

5-(6-(3-oxa-8-azabicyclo[3.2.1]octan-8-yl)-2-(3-oxa-8-azabicyclo[3.2.1]octan-8-yl)pyrimidin-4-yl)-4-(difluoromethyl)pyridin-2-amine

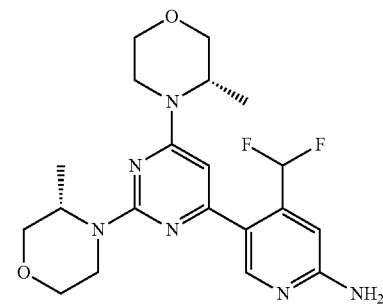

Compound 25

5-(2,6-bis((S)-3-methylmorpholino)pyrimidin-4-yl)-4-(difluoromethyl)pyridin-2-amine

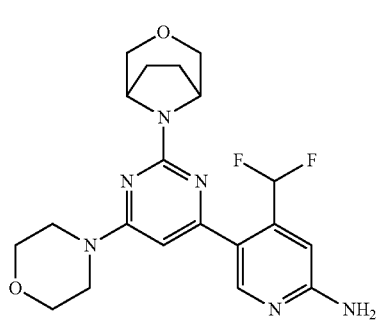

Compound 23

5-(2-(3-oxa-8-azabicyclo[3.2.1]octan-8-yl)-6-morpholinopyrimidin-4-yl)-4-(difluoromethyl)pyridin-2-amine

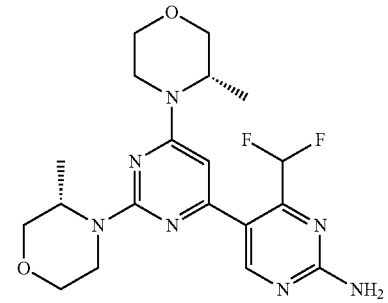

Compound 26

4'-(difluoromethyl)-2,6-bis((S)-3-methylmorpholino)-[4,5'-bipyrimidin]-2'-amine

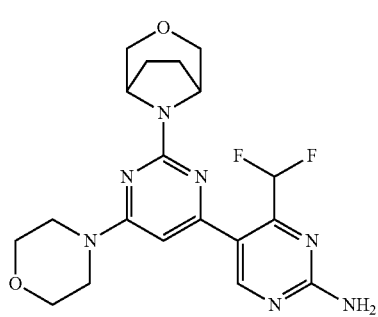

Compound 24

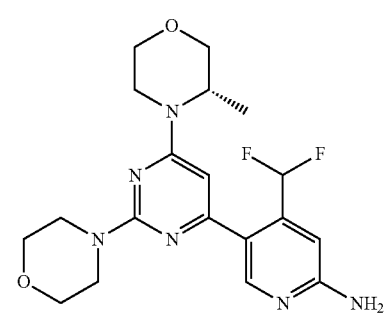

Compound 27

47

48

(S)-4-(difluoromethyl)-5-(6-(3-methylmorpholino)-
2-morpholinopyrimidin-4-yl)pyridin-2-amine 5-[4,6-bis(2,2-dimethylmorpholin-4-yl)-1,3,5-tri-
azin-2-yl]-4-(difluoromethyl)pyridin-2-amine Compound 28

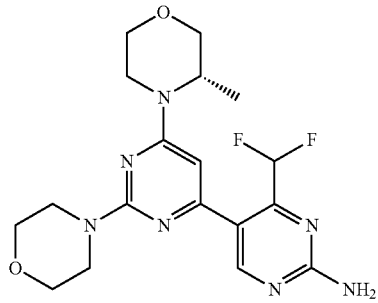

Compound 31

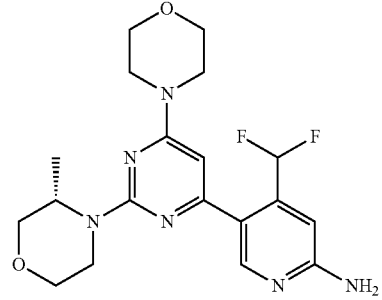

(S)-4'-(difluoromethyl)-6-(3-methylmorpholino)-2-
morpholino-[4,5'-bipyrimidin]-2'-amine (S)-4-(difluoromethyl)-5-(2-(3-methylmorpholino)-
6-morpholinopyrimidin-4-yl)pyridin-2-amine Compound 29

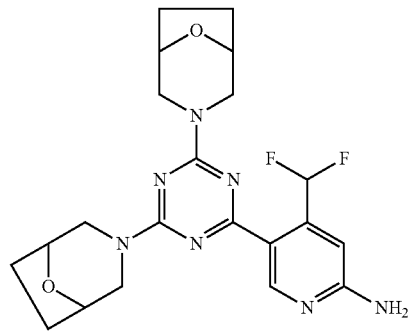

Compound 32

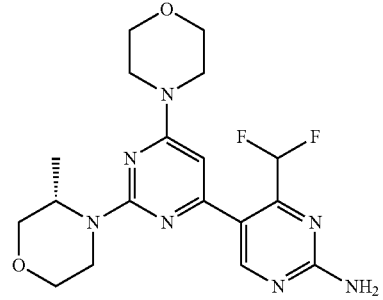

5-(4-(8-Oxa-3-azabicyclo[3.2.1]octan-3-yl)-6-(8-
oxa-3-azabicyclo[3.2.1]octan-3-yl)-1,3,5-triazin-2-
yl)-4-(difluoromethyl)pyridin-2-amine (S)-4'-(difluoromethyl)-2-(3-methylmorpholino)-6-
morpholino-[4,5'-bipyrimidin]-2'-amine Compound 30

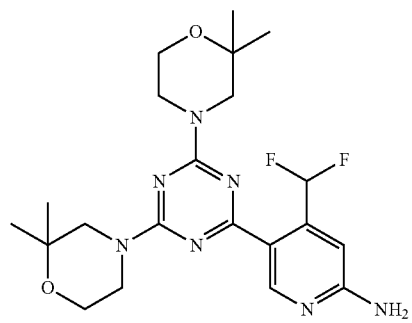

Compound 33

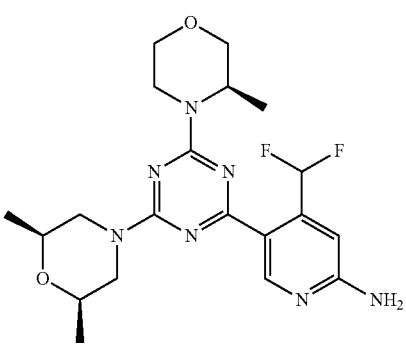

| 49 | 50 |
|---|---|
| 4-(difluoromethyl)-5-[4-[(2S,6R)-2,6-dimethylmorpholin-4-yl]-6-[(3R)-3-methylmorpholin-4-yl]-1,3,5-triazin-2-yl]pyridin-2-amine | 4-(difluoromethyl)-5-[4-(3,7-dioxa-9-azabicyclo[3.3.1]nonan-9-yl)-6-(3-oxa-8-azabicyclo[3.2.1]octan-8-yl)-1,3,5-triazin-2-yl]pyridin-2-amine |

Compound 34

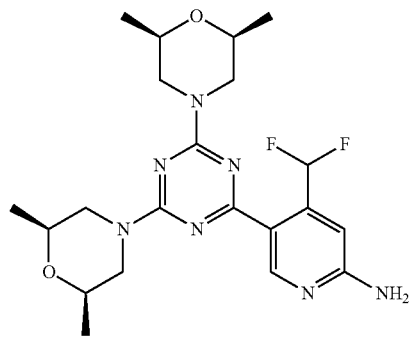

5-[4,6-bis[(2R,6S)-2,6-dimethylmorpholin-4-yl]-1,3,5-triazin-2-yl]-4-(difluoromethyl)pyridin-2-amine Compound 39

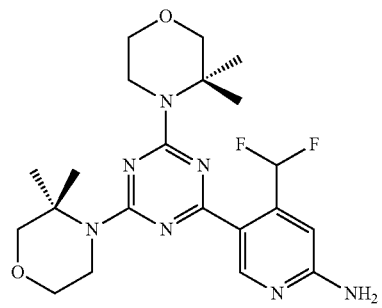

5-[4,6-bis(3,3-dimethylmorpholin-4-yl)-1,3,5-triazin-2-yl]-4-(difluoromethyl)pyridin-2-amine Compound 37

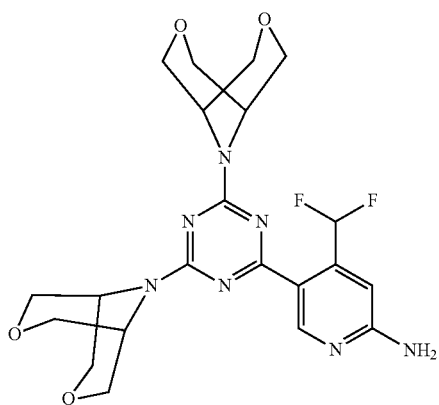

5-[4,6-bis(3,7-dioxa-9-azabicyclo[3.3.1]nonan-9-yl)-1,3,5-triazin-2-yl]-4-(difluoromethyl)pyridin-2-amine Compound 40

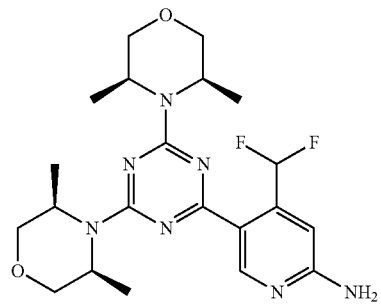

5-[4,6-bis[(3R,5S)-3,5-dimethylmorpholin-4-yl]-1,3,5-triazin-2-yl]-4-(difluoromethyl)pyridin-2-amine Compound 38

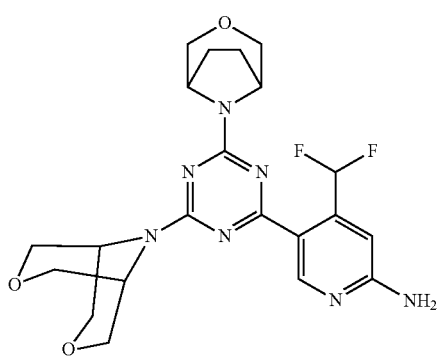

Compound 41

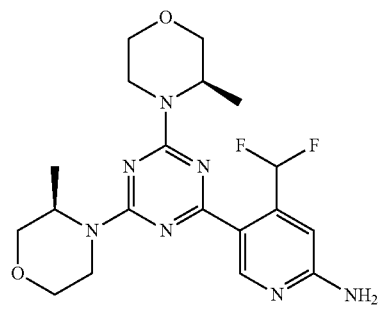

51

5-[4,6-bis[(3R)-3-methylmorpholin-4-yl]-1,3,5-triazin-2-yl]-4-(difluoromethyl)pyridin-2-amine

52

4-(difluoromethyl)-5-[4-(3,3-dimethylmorpholin-4-yl)-6-[(3R)-3-methylmorpholin-4-yl]-1,3,5-triazin-2-yl]pyridin-2-amine Compound 42

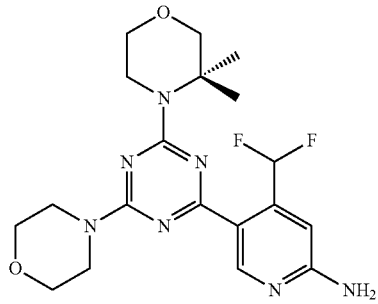

4-(difluoromethyl)-5-[4-(3,3-dimethylmorpholin-4-yl)-6-morpholino-1,3,5-triazin-2-yl]pyridin-2-amine Compound 46

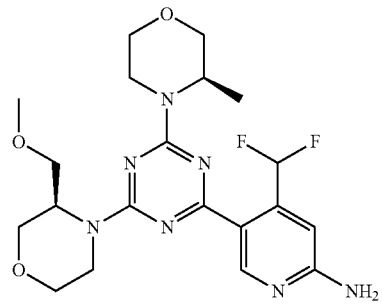

4-(difluoromethyl)-5-[4-[(3R)-3-(methoxymethyl)morpholin-4-yl]-6-[(3R)-3-methylmorpholin-4-yl]-1,3,5-triazin-2-yl]pyridin-2-amine Compound 44

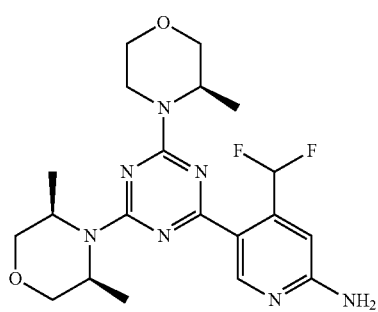

4-(difluoromethyl)-5-[4-[(3R,5S)-3,5-dimethylmorpholin-4-yl]-6-[(3R)-3-methylmorpholin-4-yl]-1,3,5-triazin-2-yl]pyridin-2-amine Compound 47

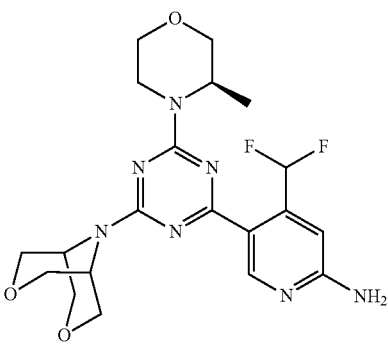

4-(difluoromethyl)-5-[4-(3,7-dioxa-9-azabicyclo[3.3.1]nonan-9-yl)-6-[(3R)-3-methylmorpholin-4-yl]-1,3,5-triazin-2-yl]pyridin-2-amine Compound 45

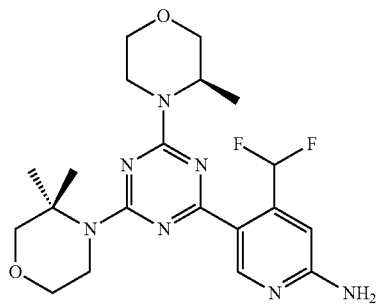

Compound 50

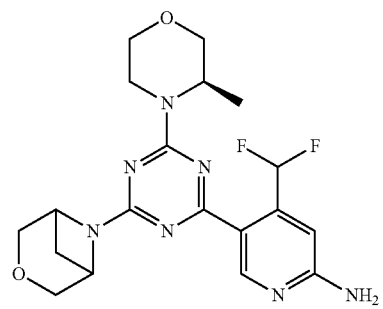

53

4-(difluoromethyl)-5-[4-[(3R)-3-methylmorpholin-4-yl]-6-(3-oxa-6-azabicyclo[3.1.1]heptan-6-yl)-1,3,5-triazin-2-yl]pyridin-2-amine Compound 51

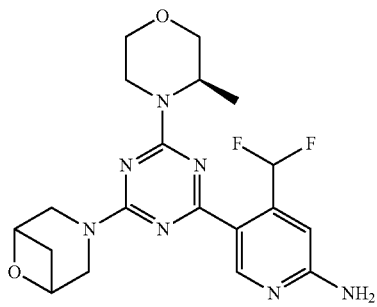

4-(difluoromethyl)-5-[4-[(3R)-3-methylmorpholin-4-yl]-6-(6-oxa-3-azabicyclo[3.1.1]heptan-3-yl)-1,3,5-triazin-2-yl]pyridin-2-amine Compound 52

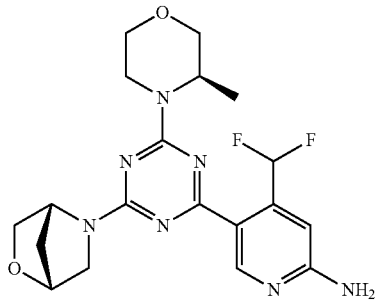

4-(difluoromethyl)-5-[4-[(3R)-3-methylmorpholin-4-yl]-6-[(R,4R)-2-oxa-5-azabicyclo[2.2.1]heptan-5-yl]-1,3,5-triazin-2-yl]pyridin-2-amine Compound 53

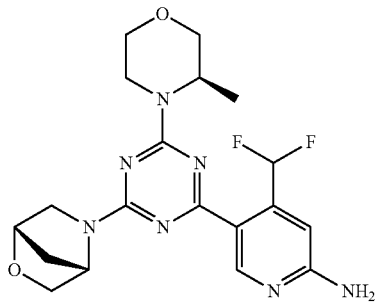

54

4-(difluoromethyl)-5-[4-[(3R)-3-methylmorpholin-4-yl]-6-[(1S,4S)-2-oxa-5-azabicyclo[2.2.1]heptan-5-yl]-1,3,5-triazin-2-yl]pyridin-2-amine Compound 54

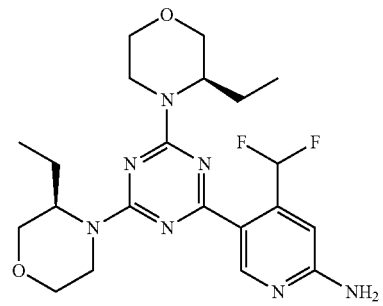

5-[4,6-bis[(3R)-3-ethylmorpholin-4-yl]-1,3,5-triazin-2-yl]-4-(difluoromethyl)pyridin-2-amine Compound 55

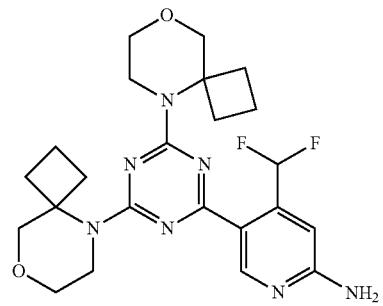

5-[4,6-bis(8-oxa-5-azaspiro[3.5]nonan-5-yl)-1,3,5-triazin-2-yl]-4-(difluoromethyl)pyridin-2-amine Compound 56

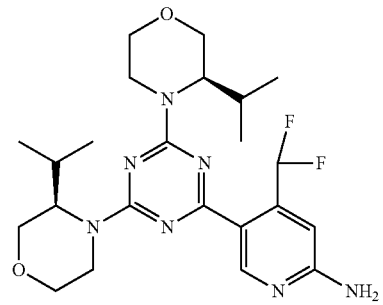

55

5-[4,6-bis[(3R)-3-isopropylmorpholin-4-yl]-1,3,5-triazin-2-yl]-4-(difluoromethyl)pyridin-2-amine

56

[(3R)-4-[4-[6-amino-4-(difluoromethyl)-3-pyridyl]-6-(3,3-dimethylmorpholin-4-yl)-1,3,5-triazin-2-yl]morpholin-3-yl]methanol Compound 66

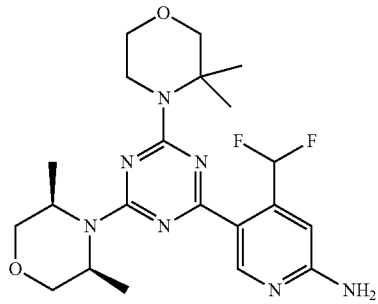

4-(difluoromethyl)-5-[4-(3,3-dimethylmorpholin-4-yl)-6-[(3R,5S)-3,5-dimethylmorpholin-4-yl]-1,3,5-triazin-2-yl]pyridin-2-amine Compound 69

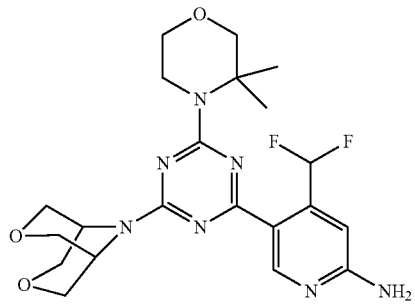

4-(difluoromethyl)-5-[4-(3,3-dimethylmorpholin-4-yl)-6-(3,7-dioxa-9-azabicyclo[3.3.1]nonan-9-yl)-1,3,5-triazin-2-yl]pyridin-2-amine Compound 67

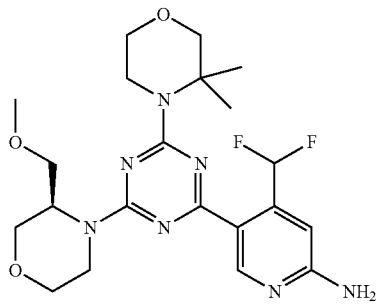

4-(difluoromethyl)-5-[4-(3,3-dimethylmorpholin-4-yl)-6-[(3R)-3-(methoxymethyl)morpholin-4-yl]-1,3,5-triazin-2-yl]pyridin-2-amine Compound 70

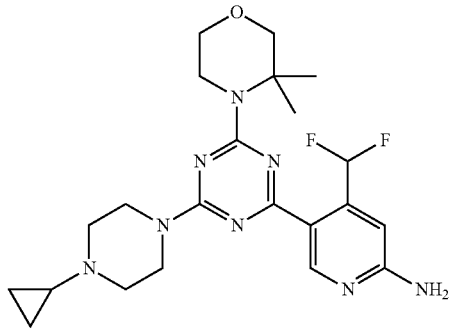

5-[4-(4-cyclopropylpiperazin-1-yl)-6-(3,3-dimethyl-morpholin-4-yl)-1,3,5-triazin-2-yl]-4-(difluoromethyl)pyridin-2-amine Compound 68

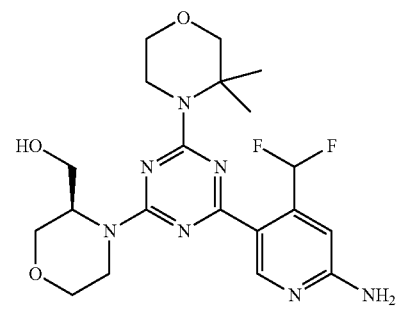

Compound 71

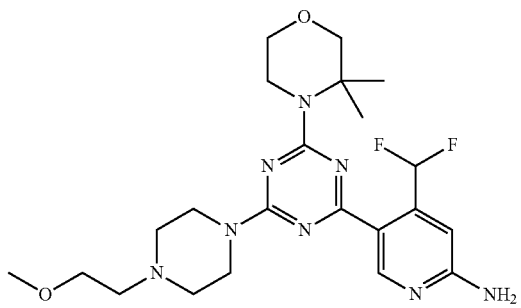

57
4-(difluoromethyl)-5-[4-(3,3-dimethylmorpholin-4-yl)-6-[4-(2-methoxyethyl)piperazin-1-yl]-1,3,5-triazin-2-yl]pyridin-2-amine 58
4-(difluoromethyl)-5-[4-[(3S,5S)-3,5-dimethylmorpholin-4-yl]-6-[(3R)-3-methylmorpholin-4-yl]-1,3,5-triazin-2-yl]pyridin-2-amine Compound 77

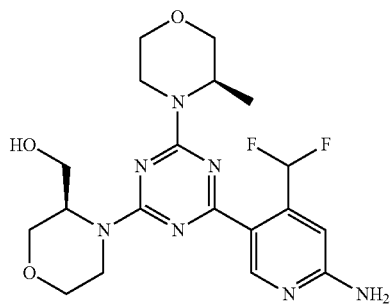

[(3R)-4-[4-[6-amino-4-(difluoromethyl)-3-pyridyl]-6-[(3R)-3-methylmorpholin-4-yl]-1,3,5-triazin-2-yl]morpholin-3-yl]methanol Further preferred compounds are Compound 78

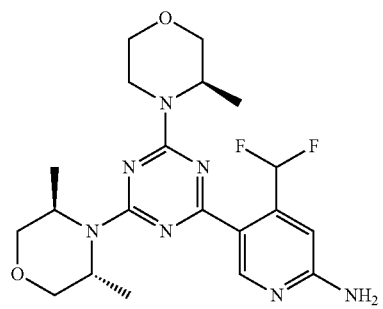

4-(difluoromethyl)-5-[4-[(3R,5R)-3,5-dimethylmorpholin-4-yl]-6-[(3R)-3-methylmorpholin-4-yl]-1,3,5-triazin-2-yl]pyridin-2-amine Compound 79

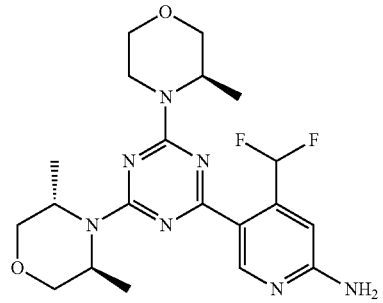

Compound 80

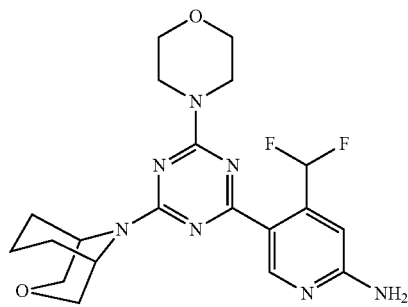

4-(difluoromethyl)-5-[4-morpholino-6-(3-oxa-9-azabicyclo[3.3.1]nonan-9-yl)-1,3,5-triazin-2-yl]pyridin-2-amine Compound 82

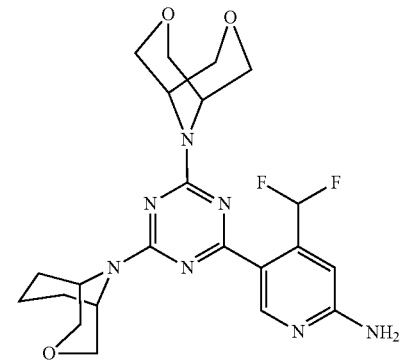

4-(difluoromethyl)-5-[4-(3,7-dioxa-9-azabicyclo[3.3.1]nonan-9-yl)-6-(3-oxa-9-azabicyclo[3.3.1]nonan-9-yl)-1,3,5-triazin-2-yl]pyridin-2-amine Compound 83

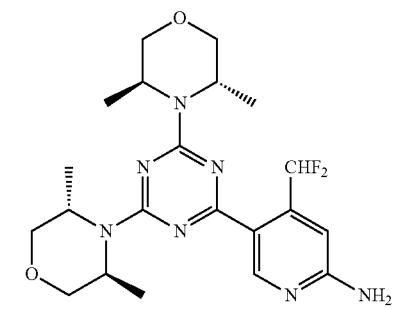

5-[4,6-bis[(3S,5S)-3,5-dimethylmorpholin-4-yl]-1,3,5-triazin-2-yl]-4-(difluoromethyl)pyridin-2-amine Compound 84

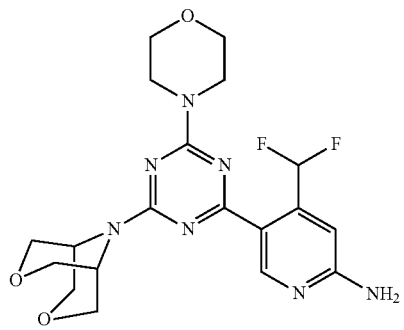

4-(difluoromethyl)-5-[4-(3,7-dioxa-9-azabicyclo[3.3.1]nonan-9-yl)-6-morpholino-1,3,5-triazin-2-yl]pyridin-2-amine Compound 85

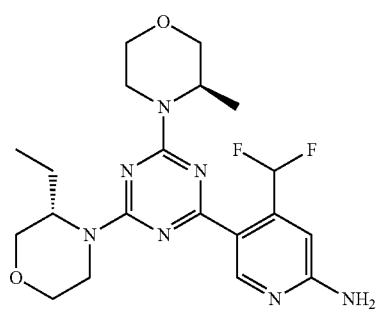

4-(difluoromethyl)-5-[4-[(3S)-3-ethylmorpholin-4-yl]-6-[(3R)-3-methylmorpholin-4-yl]-1,3,5-triazin-2-yl]pyridin-2-amine Compound 86

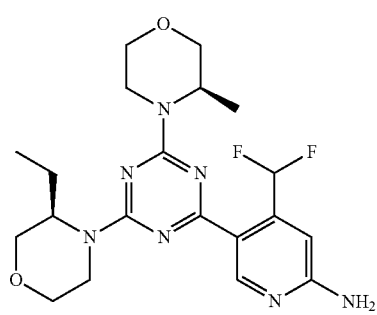

4-(difluoromethyl)-5-[4-[(3R)-3-ethylmorpholin-4-yl]-6-[(3R)-3-methylmorpholin-4-yl]-1,3,5-triazin-2-yl]pyridin-2-amine Compound 88

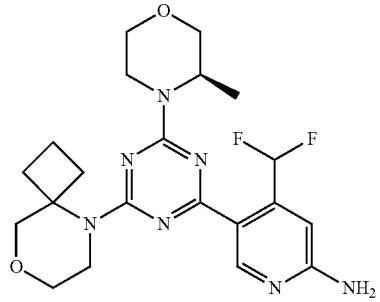

4-(difluoromethyl)-5-[4-[(3R)-3-methylmorpholin-4-yl]-6-(8-oxa-5-azaspiro[3.5]nonan-5-yl)-1,3,5-triazin-2-yl]pyridin-2-amine Preparation of Compounds of the Invention The compounds of the invention may be synthesized by synthetic routes that include processes analogous to those well known in the chemical arts, particularly in light of the description contained herein. The starting materials are generally available from commercial sources or are readily prepared using methods well known to those skilled in the art.

In preparing compounds of the invention, protection of remote functionality (e.g., primary or secondary amine) of intermediates may be necessary. The need for such protection will vary depending on the nature of the remote functionality and the conditions of the preparation methods. Suitable amino-protecting groups include tert-butyloxycarbonyl (BOC), bis-tert-butyloxycarbonyl or dimethylaminomethylenyl. The need for such protection is readily determined by one skilled in the art. For a general description of protecting groups and their use, see T. W. Greene, *Protective Groups in Organic Synthesis*, John Wiley & Sons, New York, 1991.

Methods of Separation

In the methods of preparing the compounds of this invention, it may be advantageous to separate reaction products from one another and/or from starting materials. The desired products of each step or series of steps are separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; high, medium and low pressure liquid chromatography methods and apparatus; small scale analytical; and preparative thin or thick layer chromatography, as well as techniques of small scale thin layer and flash chromatography.

Selection of appropriate methods of separation depends on the nature of the materials involved, for example, presence or absence of polar functional groups in chromatography, stability of materials in acidic and basic media in multiphase extraction, and the like. One skilled in the art will apply techniques most likely to achieve the desired separation.

EXAMPLES

The Examples are intended to illustrate the present invention without restricting it.

The chemical reactions described in the Examples may be readily adapted to prepare a number of other lipid kinase inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

As a rule, $^1$H NMR and mass spectra have been obtained for the compounds prepared. In the Examples described below, unless otherwise indicated, all temperatures are set forth in degrees Celsius (° C.). Reagents were purchased from commercial suppliers such as Sigma Aldrich, Fluorochem, Acros, Lancaster, TCI or Maybridge, and were used without further purification unless otherwise indicated. The reactions set forth below were done generally under a positive pressure of nitrogen or with a drying tube (unless otherwise stated) in anhydrous solvents, and the reaction flasks were typically fitted with rubber septa for the introduction of substrates and reagents via syringe. Glassware was oven dried. Column chromatography was performed using Merck silica gel. $^1$H NMR spectra were recorded on a Bruker instrument operating at 400 MHz. $^1$H NMR spectra were obtained for solutions in various deuterated solvents such as CDCl$_3$, (CD$_3$)$_2$SO, CD$_3$OD or (CD$_3$)$_2$CO. The chemical shift δ values were reported in ppm and corrected to the signal of the deuterated solvents (7.26 ppm for CDCl$_3$) or TMS (0 ppm). $^{19}$F NMR spectra were calibrated relative to CFCl$_3$ (δ=0 ppm) as external standard. $^{19}$F NMR spectra were recorded $^1$H-decoupled. When peak multiplicities are reported, the following abbreviations are used: s (singlet), d (doublet), t (triplet), m (multiplet), quint (quintet), br (broadened). Coupling constants, when given, are reported in Hertz (Hz). MALDI-ToF Mass spectra (MS) have been obtained on a Voyager-De™ Pro measured in m/z.

The following abbreviations are used hereinafter: BSA (bovine serum albumin), DMSO (dimethyl sulfoxide), ESI (electrospray ionization), HCl (hydrochloric acid), M (molar), MALDI (Matrix-assisted Laser Desorption/Ionization), MS (mass spectrometry), PBS (phosphate buffered saline), TLC (thin layer chromatography), nd (not determined).

Example 1

Preparation of Intermediate Compounds and of Compounds of the Invention

Preparation of Intermediate Compounds

The following methods were used to prepare the intermediates compounds used to produce compounds of formula (I).

Method 1: 8-(4-(3-oxa-8-azabicyclo[3.2.1]octan-8-yl)-6-chloro-1,3,5-triazin-2-yl)-3-oxa-8-azabicyclo[3.2.1]octane (i1)

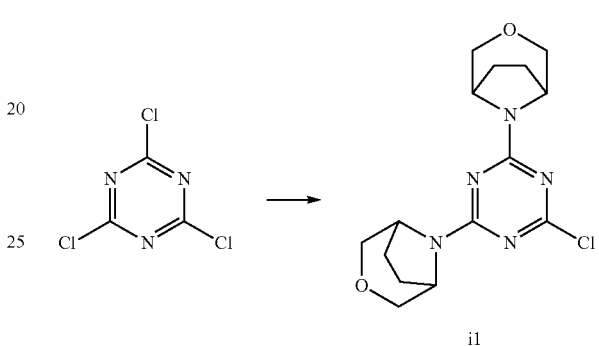

3-Oxa-8-azabicyclo[3.2.1]octane-HCl (Advanced ChemBlocks Inc, product number A-861, 2.00 g, 13.4 mmol, 2.0 eq.) and N,N-diisopropylethylamine (4.80 mL, 27.6 mmol, 4.1 eq.) are charged into a flask and dissolved in dichloromethane (20 mL). The flask is placed in an ice bath and the solution subsequently cooled down to 0° C. This solution is then added dropwise to a solution of cyanuric chloride in dichloromethane (20 mL) at 0° C. The resulting reaction mixture is stirred overnight, while it is allowed to warm up to room temperature. Additional dichloromethane (100 mL) is added and the organic layer is washed with a saturated aqueous solution of sodium bisulfate. The organic layer is then dried over anhydrous sodium sulfate, filtered and the solvent is evaporated under reduced pressure. Purification by flash chromatography (cyclohexane/ethyl acetate 4:1) gives the desired intermediate i1 as a colorless solid (79% yield). $^1$H NMR (400 MHz, CDCl$_3$): δ 4.70-4.54 (m, 4H), 3.80-3.58 (m, 8H), 2.14-1.89 (m, 8H); MS (MALDI): m/z=338.4 ([M+H]$^+$).

Method 1 is also used for the preparation of the following intermediate compounds i2 to i10, and intermediates i79 to i81 and i90.

| Reagent | | Structure | NMR | MS |
|---|---|---|---|---|
| i2 | morpholine | triazine with two morpholines and Cl | $^1$H NMR (400 MHz, CDCl$_3$): δ 3.78 (m, 8 H), 3.70 (m, 8 H). | MS (MALDI): m/z = 285.9 ([M + H]$^+$). |

| Reagent | Structure | NMR | MS |
|---|---|---|---|
| i3 | (S)-3-methylmorpholine | 2,6-bis((S)-3-methylmorpholino)-4-chloro-1,3,5-triazine | ¹H NMR (400 MHz, CDCl₃): δ 4.75-4.56 (m, 2 H), 4.34-4.30 (m, 2 H), 3.94 (dd, $^2J_{H,H}$ = 12.0 Hz, $^3J_{H,H}$ = 4.0 Hz, 2 H), 3.74 (d, $^2J_{H,H}$ = 12.0 Hz, 2 H), 3.63 (dd, $^2J_{H,H}$ = 12.0 Hz, $^3J_{H,H}$ = 4.0 Hz, 2 H), 3.49 (dt, $^2J_{H,H}$ = 12.0 Hz, $^3J_{H,H}$ = 4.0 Hz, 2 H), 3.25 (dt, $^2J_{H,H}$ = 12.0 Hz, $^3J_{H,H}$ = 4.0 Hz, 2 H), 1.31 (d, $^3J_{H,H}$ = 8.0 Hz, 6 H). | MS (MALDI): m/z = 314.4 ([M + H]⁺). |
| i4 | 3,3-dimethylmorpholine | 2,6-bis(3,3-dimethylmorpholino)-4-chloro-1,3,5-triazine | ¹H NMR (400 MHz, CDCl₃): δ 3.81-3.72 (m, 8 H), 3.43 (s, 4 H), 1.43 (br s, 12 H). | MS (MALDI): m/z = 342.5 ([M + H]⁺). |
| i5 | (R)-3-methylmorpholine | 2,6-bis((R)-3-methylmorpholino)-4-chloro-1,3,5-triazine | ¹H NMR (400 MHz, CDCl₃): δ 4.75-4.56 (m, 2 H), 4.34-4.30 (m, 2 H), 3.94 (dd, $^2J_{H,H}$ = 12.0 Hz, $^3J_{H,H}$ = 4.0 Hz, 2 H), 3.74 (d, $^2J_{H,H}$ = 12.0 Hz, 2 H), 3.63 (dd, $^2J_{H,H}$ = 12.0 Hz, $^3J_{H,H}$ = 4.0 Hz, 2 H), 3.49 (dt, $^2J_{H,H}$ = 12.0 Hz, $^3J_{H,H}$ = 4.0 Hz, 2 H), 3.25 (dt, $^2J_{H,H}$ = 12.0 Hz, $^3J_{H,H}$ = 4.0 Hz, 2 H), 1.31 (d, $^3J_{H,H}$ = 8.0 Hz, 6 H). | MS (MALDI): m/z = 314.3 ([M + H]⁺). |
| i6 | (3R,5S)-3,5-dimethylmorpholine | 2,6-bis((3R,5S)-3,5-dimethylmorpholino)-4-chloro-1,3,5-triazine | ¹H NMR (400 MHz, CDCl₃): δ 4.40-4.37 (m, 4 H), 3.74 (d, $^3J_{H,H}$ = 11.6 Hz, 4 H), 3.53 (dd, $^3J_{H,H}$ = 11.6 Hz, $^2J_{H,H}$ = 4.0 Hz, 4 H), 1.26 (d, $^3J_{H,H}$ = 6.9 Hz, 12 H). | MS (MALDI): m/z = 342.8 ([M + H]⁺). |
| i7 | 3,7-dioxa-9-azabicyclo[3.3.1]nonane | 2,6-bis(3,7-dioxa-9-azabicyclo[3.3.1]nonan-9-yl)-4-chloro-1,3,5-triazine | ¹H NMR (400 MHz, CDCl₃): δ 4.53 (br s, 2 H), 4.36 (br s, 2 H), 4.12-4.06 (m, 8 H), 3.92-3.83 (m, 8 H). | MS (MALDI): m/z = 370.3 ([M + H]⁺). |

| Reagent | Structure | NMR | MS |
|---|---|---|---|
| i8 | 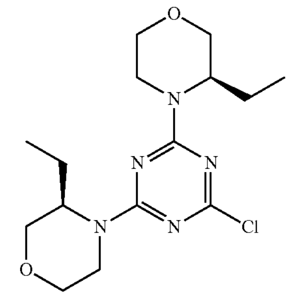 [SMILES: CC[C@@H]1COCCN1c1nc(Cl)nc(N2CCOC[C@H]2CC)n1] | $^1$H NMR (400 MHz, (CD$_3$)$_2$SO): δ 4.36-4.21 (m, 4 H), 3.85-3.75 (m, 4 H), 3.48-3.45 (m, 2 H), 3.40-3.34 (m, 2 H), 3.14-3.09 (m, 2 H), 1.72 (m, 4 H), 0.82 (m, 6 H). | MS (MALDI): m/z = 342.3 ([M]$^+$). |
| i9 | 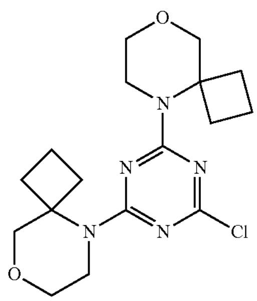 [SMILES: Clc1nc(N2CCOCC23CCC3)nc(N2CCOCC23CCC3)n1] | $^1$H NMR (400 MHz, (CD$_3$)$_2$SO): δ 3.64 (m, 8 H), 3.351-3.48 (m, 4 H), 2.46-2.38 (m, 4 H), 2.20-2.16 (m, 4 H), 1.73-1.66 (m, 4 H). | MS (MALDI): m/z = 366.7 ([M + H]$^+$). |
| i10 | 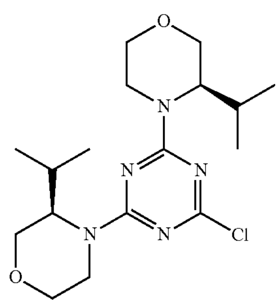 [SMILES: CC(C)[C@@H]1COCCN1c1nc(Cl)nc(N2CCOC[C@H]2C(C)C)n1] | $^1$H NMR (400 MHz, (CD$_3$)$_2$SO): δ 4.40-4.25 (m, 2 H), 4.20-4.05 (m, 2 H), 4.08 (m, 2 H), 3.95 (m, 2 H), 3.83 (m, 4 H), 3.08 (m, 2 H), 2.30 (m, 2 H), 0.98 (m, 6 H), 0.48 (m, 6 H). | MS (MALDI): m/z = 370.4 ([M + H]$^+$). |
| i79 | 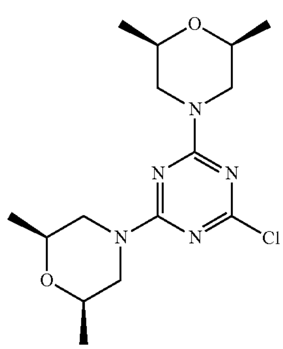 | $^1$H NMR (400 MHz, CDCl$_3$): δ 4.59-4.31 (m, 4 H), 3.66-3.46 (m, 4 H), 2.70 (m, 4 H), 1.14 (m, 12 H). | MS (MALDI): m/z = 342.4 ([M + H]$^+$). |
| i80 | 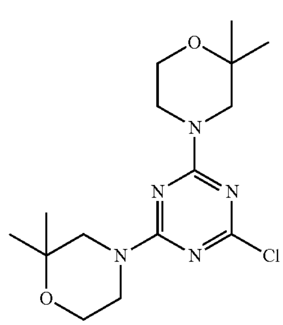 | $^1$H NMR (400 MHz, CDCl$_3$): δ 3.73-3.64 (m, 8 H), 3.57 (s, 2 H), 3.51 (s, 2 H), 1.14 (s, 12 H). | MS (MALDI): m/z = 342.3 ([M + H]$^+$). |

| Reagent | Structure | NMR | MS |
|---|---|---|---|
| i81 | 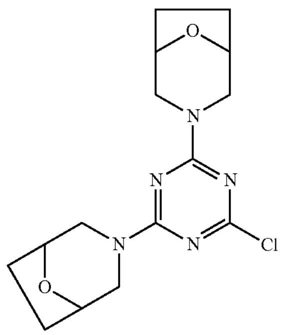 [SMILES: Clc1nc(N2CC3CCC(C2)O3)nc(N2CC3CCC(C2)O3)n1] | $^1$H NMR (400 MHz, CDCl$_3$): δ 4.41 (br s, 4 H), 4.32-4.16 (m, 4 H), 3.24-3.10 (m, 4 H), 1.99-1.84 (m, 4 H), 1.84-1.67 (m, 4 H). | MS (MALDI): m/z = 338.4 ([M + H]$^+$). |
| i90 | 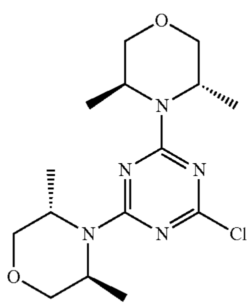 [SMILES: C[C@H]1COC[C@H](C)N1c1nc(Cl)nc(N2[C@@H](C)COC[C@@H]2C)n1] | $^1$H NMR (400 MHz, CDCl$_3$): δ 4.20 (m, 4 H), 4.10 (m, 4 H), 3.66 (m, 4 H), 1.35 (d, $^3J_{H,H}$ = 6.9 Hz, 12 H) | MS (MALDI): m/z = 342.8 ([M + H]$^+$). |

Method 2: 2,4-dichloro-6-morpholino-1,3,5-triazine (i11)

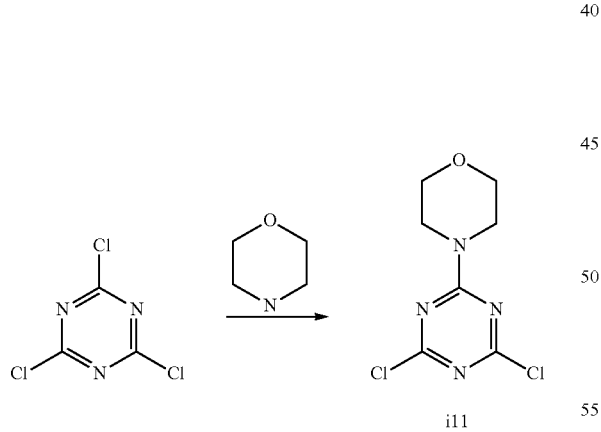

To a solution of cyanuric chloride (18.1 g, 0.100 mol, 1.0 eq.) in dichloromethane (200 mL) is dropwise added a solution of morpholine (17.4 g, 0.200 mol, 2.0 eq.) at −78° C. over 2 hours. The resulting mixture is allowed to warm to 0° C. with stirring and mixed with an ice cold saturated solution of sodium bisulfate in water. The phases are separated and the organic phase is washed with half concentrated brine dried over sodium sulfate and evaporated to yield the title compound i11 as a colorless solid. $^1$H NMR (400 MHz, CDCl$_3$): δ 3.90-3.86 (m, 4H), 3.77-3.72 (m, 4H).

Method 3: 8-(4-chloro-6-morpholino-1,3,5-triazin-2-yl)-3-oxa-8-azabicyclo-[3.2.1]octane (i12)

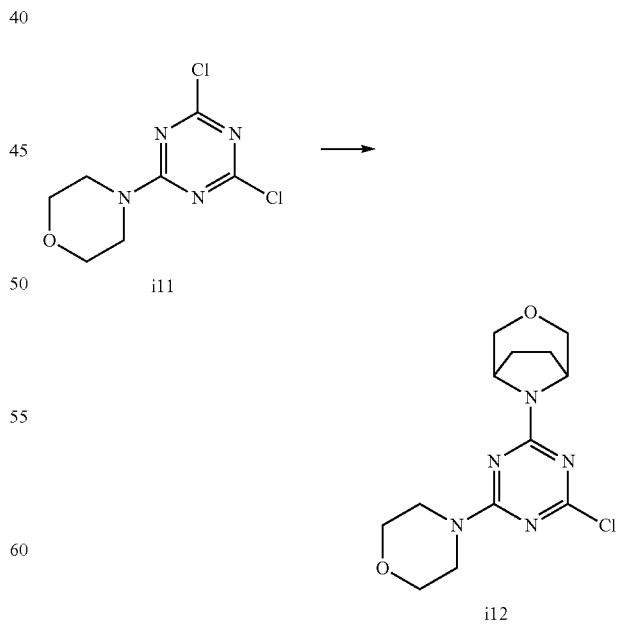

3-Oxa-8-azabicyclo[3.2.1]octane·HCl (Advanced ChemBlocks Inc, product number A-861, 200 mg, 1.34 mmol, 1.1 eq.) and N,N-diisopropylethylamine (470 μL, 2.69 mmol, 2.1 eq.) are charged in a flask and dissolved in ethanol (3 mL). The flask is placed in an ice bath. A solution of compound i11 (300 mg, 1.28 mmol, 1.0 eq.) in ethanol (2 mL) is added to the above solution at 0° C. The resulting mixture is stirred overnight, while allowing it to warm up to room temperature. Deionized water (20 mL) is added and the aqueous layer is extracted with ethyl acetate (3×30 mL). The combined organic layer is dried over anhydrous sodium sulfate, filtered and the solvent is evaporated under reduced pressure. Purification by flash chromatography (cyclohexane/ethyl acetate 9:1→8:2) gives the desired intermediate 112 as a colorless solid (78% yield). $^1$H NMR (400 MHz, CDCl$_3$): δ 4.69-4.56 (m, 2H), 3.86-3.59 (m, 12H), 2.12-1.91 (m, 4H); MS (MALDI): m/z=312.7 ([M+H]$^+$).

Method 3 is also used for the preparation of the following intermediate compounds 113 to i16, and intermediates i87 and i91.

| | Reagent | Structure | NMR |
|---|---|---|---|
| i13 | (S)-3-methylmorpholine | 4-(6-chloro-4-morpholino-1,3,5-triazin-2-yl)-(S)-3-methylmorpholine-morpholine adduct | $^1$H NMR (400 MHz, CDCl$_3$): δ 4.71-4.61 (m, 1 H), 4.34-4.31 (m, 1 H), 3.96-3.92 (m, 1 H), 3.79-3.70 (m, 9 H), 3.65-3.61 (m, 1 H), 3.51-3.45 (m, 1 H), 3.29-3.21 (m, 1 H), 1.36-1.30 (d, $^3J_{H,H}$ = 6.9 Hz, 3 H). |
| i14 | tert-butyl piperazine-1-carboxylate | tert-butyl 4-(6-chloro-4-morpholino-1,3,5-triazin-2-yl)piperazine-1-carboxylate | $^1$H NMR (400 MHz, CDCl$_3$): δ 3.79-3.71 (m, 12 H), 3.46 (m, 4 H), 1.48 (s, 9 H). |
| i15 | thiomorpholine | 4-(4-chloro-6-thiomorpholino-1,3,5-triazin-2-yl)morpholine | $^1$H NMR (400 MHz, CDCl$_3$): δ 4.12-3.98 (m, 4 H), 3.84-3.70 (m, 4 H), 3.70-3.62 (m, 4 H), 2.66-2.56 (m, 4 H). |
| i16 | (R)-3-methylmorpholine | 4-(4-chloro-6-((R)-3-methylmorpholino)-1,3,5-triazin-2-yl)morpholine | $^1$H NMR (400 MHz, CDCl$_3$): δ 3.77 (m, 4 H), 3.68-3.63 (m, 8 H), 3.44 (s, 2 H), 1.44 (s, 6 H). |

-continued

| Reagent | | Structure | NMR |
|---|---|---|---|
| i87 | 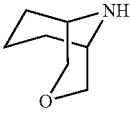 | 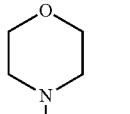 | ¹H NMR (400 MHz, CDCl₃): δ 4.52 (m, 1 H), 4.43 (m, 1 H), 3.93 (m, 2 H), 3.65 (m, 10 H), 2.48 (m, 1 H), 1.88-1.72 (m, 4 H), 1.57 (m, 1 H) |
| i91 | 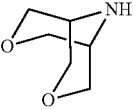 | 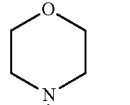 | ¹H NMR (400 MHz, CDCl₃): δ 4.44 (m, 1 H), 4.32 (m, 1 H), 4.00 (m, 4 H), 3.74-3.65 (m, 12 H); |

Method 4: (S)-4-(4,6-dichloro-1,3,5-triazin-2-yl)-3-methylmorpholine (i17)

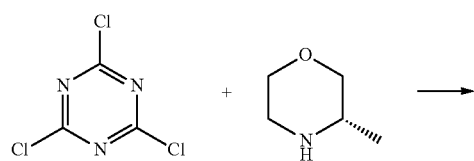

To a solution of cyanuric chloride (450 mg, 2.44 mol, 1.0 eq.) in dichloromethane (4 mL) is slowly added a solution of (S)-3-methylmorpholine (Activate Scientific, product number AS3424, 0.28 mL, 2.44 mol, 1.0 eq.) and triethylamine (0.35 mL, 2.51 mol, 1.02 eq.) in dichloromethane (2 mL) at −50° C. The resulting mixture is stirred for 2 hours at −50° C., then allowed to warm to 0° C. with stirring and mixed with an ice cold saturated solution of sodium bisulfate in water. The phases are separated and the organic phase is washed with brine dried over sodium sulfate and evaporated to yield the title compound 117 as a colorless solid (95% yield). ¹H NMR (400 MHz, CDCl₃): δ 4.78-4.69 (m, 1H), 4.43-4.39 (m, 1H), 3.98-3.96 (m, 1H), 3.78-3.76 (m, 1H), 3.67-3.65 (m, 1H), 3.51-3.47 (m, 1H), 3.40-3.37 (m, 1H), 1.36 (m, 3H).

Method 5: 8-(4-chloro-6-((S)-3-methylmorpholino)-1,3,5-triazin-2-yl)-3-oxa-8-azabicyclo[3.2.1]octane (i18)

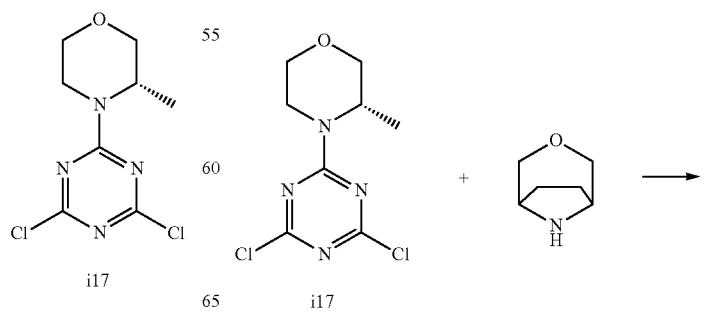

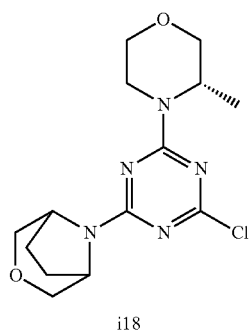

i18

3-Oxa-8-azabicyclo[3.2.1]octane·HCl (Advanced Chem-Blocks Inc, product number A-861, 383 mg, 2.55 mmol, 1.1 eq.) and N,N-diisopropylethylamine (1.0 mL, 5.60 mmol, 2.4 eq.) are charged in a flask and dissolved in ethanol (4 mL). The flask is placed in an ice bath. A solution of compound 117 (580 mg, 2.33 mmol, 1.0 eq.) in ethanol (2 mL) is added to the above solution at 0° C. The resulting mixture is stirred for 4 hours, while allowing it to warm up to room temperature. Deionized water (20 mL) is added and the aqueous layer is extracted with ethyl acetate (3×30 mL). The combined organic layer is dried over anhydrous sodium sulfate, filtered and the solvent is evaporated under reduced pressure. Purification by flash chromatography (cyclohexane/ethyl acetate 9:1→8:2) gives the desired intermediate i18 as a colorless solid (88% yield). $^1$H NMR (400 MHz, CDCl$_3$): δ 4.75-4.52 ((m, 3H), 4.37-4.24 (m, 1H), 3.95-3.92 (m, 1H), 3.73-3.70 (m, 3H), 3.64-3.61 (m, 3H), 3.52-3.42 (m, 1H), 3.29-3.17 (m, 1H), 2.11-1.89 (m, 4H), 1.31 (m, 3H).

Method 6: tert-butyl 4-(4,6-dichloro-1,3,5-triazin-2-yl)piperazine-1-carboxylate (i19)

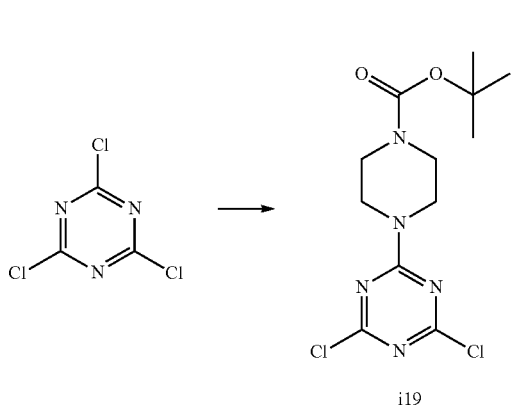 [SMILES: Clc1nc(Cl)nc(Cl)n1 ; CC(C)(C)OC(=O)N1CCN(c2nc(Cl)nc(Cl)n2)CC1]

i19

To a cooled (−50° C.) solution of cyanuric chloride (1.0 g, 5.42 mmol, 1.0 eq.) in dichloromethane (4 mL) is added dropwise a solution of tert-butyl piperazine-1-carboxylate (Sigma, product number 343536, 1.02 g, 5.48 mmol, 1.01 eq.) and triethylamine (0.767 mL, 5.53 mmol, 1.02 eq.) in dichloromethane (2 mL). The resulting reaction mixture is stirred at −50° C. for 4 hours. A saturated aqueous solution of sodium bisulfate (10 mL) and dichloromethane (20 mL) are added. The mixture is transferred to a separating funnel. The organic layer is separated, washed with a saturated aqueous solution of sodium bisulfate (20 mL), dried over anhydrous sodium sulfate, filtered and then the solvent is evaporated under reduced pressure to give pure intermediate 119 (80% yield). $^1$H NMR (400 MHz, CDCl$_3$): δ 3.88-3.85 (m, 4H), 3.53-3.51 (m, 4H), 1.49 (m, 9H).

Method 7: tert-butyl 4-(4-(3-oxa-8-azabicyclo[3.2.1]octan-8-yl)-6-chloro-1,3,5-triazin-2-yl)piperazine-1-carboxylate (i20)

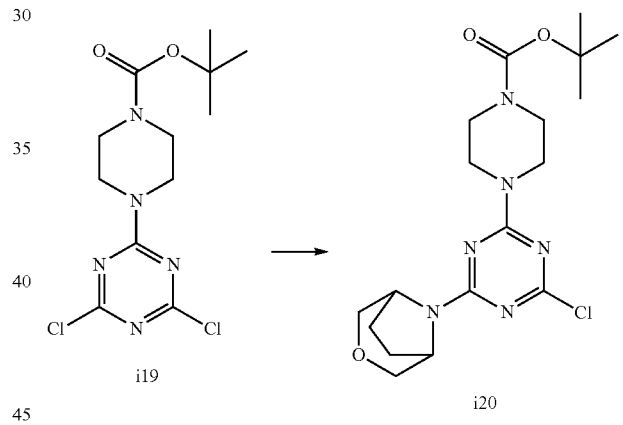

i19                                    i20

3-Oxa-8-azabicyclo[3.2.1]octane-HCl (Advanced Chem-Blocks Inc, product number A-861, 235 mg, 1.57 mmol, 1.0 eq.) and N,N-diisopropylethylamine (592 µL, 3.14 mmol, 2.1 eq.) are charged in a flask and dissolved in ethanol (6 mL). The flask is placed in an ice bath. A solution of compound 119 (500 mg, 1.5 mmol, 1.0 eq.) in ethanol (2 mL) is added to the above solution at 0° C. The resulting mixture is stirred overnight, while allowed to warm up to room temperature. Deionized water (10 mL) is added and the aqueous layer is extracted with ethyl acetate (3×30 mL). The combined organic layer is dried over anhydrous sodium sulfate, filtered and the solvent is evaporated under reduced pressure. Purification by flash chromatography (cyclohexane/ethyl acetate 8:2) gave the desired intermediate i20 as a colorless solid (77% yield). $^1$H NMR (400 MHz, CDCl$_3$): δ 4.68-4.60 (m, 2H), 3.76-3.70 (m, 6H), 3.64-3.62 (m, 2H), 3.47-3.45 (m, 4H), 2.08-1.95 (m, 4H), 1.48 (br s, 9H); MS (MALDI): m/z=411.8 ([M+H]$^+$).

Method 7 is also used for the preparation of the following intermediate compound i21.

| Reagent | Structure | NMR | MS |
|---|---|---|---|
| i21 | (structure of (S)-3-methylmorpholine and Boc-piperazine-triazine-chloro-(S)-3-methylmorpholine product) | $^1$H NMR (400 MHz, CDCl$_3$): δ 4.76-4.61 (m, 1 H), 4.35-4.30 (m, 1 H), 3.94 (dd, $^2J_{H,H}$ = 12 Hz, $^3J_{H,H}$ = 4.0 Hz, 1 H), 3.76-3.72 (m, 5 H), 3.65 (dd, $^2J_{H,H}$ = 12 Hz, $^3J_{H,H}$ = 4.0 Hz, 1 H), 3.51-3.44 (m, 5 H), 3.25 (dt, $^2J_{H,H}$ = 12 Hz, $^3J_{H,H}$ = 4.0 Hz, 1 H), 1.48 (s, 9 H), 1.30 (d, $^3J_{H,H}$ = 8.0 Hz, 3 H). | MS (MALDI): m/z = 399.1 ([M + H]$^+$). |

Method 8: 4,4'-(6-chloropyrimidine-2,4-diyl)dimorpholine (i22) and 4,4'-(2-chloropyrimidine-4,6-diyl)dimorpholine (i23)

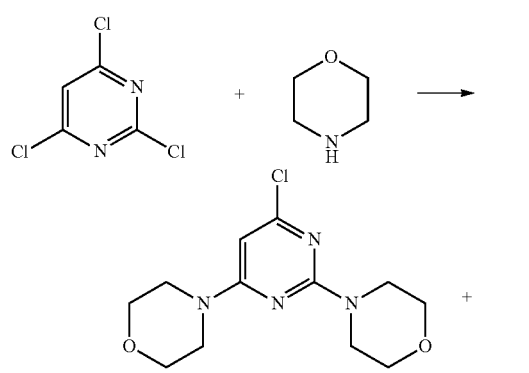

2,4,6-Trichloropyrimidine (Manchester Organics, product number Y17832, 11.2 g, 61 mmol, 1.0 eq.), N,N-diisopropylethylamine (23.3 mL, 134.2 mmol, 2.2 eq.) and morpholine (11.7 mL, 134.2 mmol, 2.2 eq.) are charged in a flask and dissolved in ethanol (120 mL). The flask is equipped with a refluxed condenser and placed in an oil bath preheated at 100° C. The reaction mixture is stirred at this temperature for 18 hours. After this time, the reaction mixture is cooled down to room temperature and volatiles are removed under reduced pressure. The resulting mixture is dissolved in dichloromethane (100 mL) and washed twice with an aqueous solution of sodium bisulfate (2×80 mL). The organic layer is dried over anhydrous sodium sulfate, filtered and concentrated under reduced pressure using a rotary evaporator. Products i22 and i23 are isolated by flash chromatography on silica gel (cyclohexane/ethyl acetate 3:1 to 1:1). The product fractions are pooled and evaporated to yield I22 as a colorless powder (13.8 g, 80%) and I23 as a colorless powder (2.2 g, 13% yield).

4,4'-(6-chloropyrimidine-2,4-diyl)dimorpholine (i22): $^1$H NMR (400 MHz, CDCl$_3$): δ 5.85 (s, 1H), 3.71-3.75 (m, 12H), 3.52-3.55 (m, 4H); MS (MALDI): m/z: 285.4 ([M+H]$^+$).

4,4'-(2-chloropyrimidine-4,6-diyl)dimorpholine (i23): $^1$H NMR (400 MHz, CDCl$_3$): δ 5.38 (s, 1H), 3.73-3.76 (m, 8H), 3.52-3.54 (m, 8H); MS (MALDI): m/z: 285.2 ([M+H]$^+$).

Method 9: 8-(4-(3-oxa-8-azabicyclo[3.2.1]octan-8-yl)-6-chloropyrimidin-2-yl)-3-oxa-8-azabicyclo[3.2.1]octane (i24)

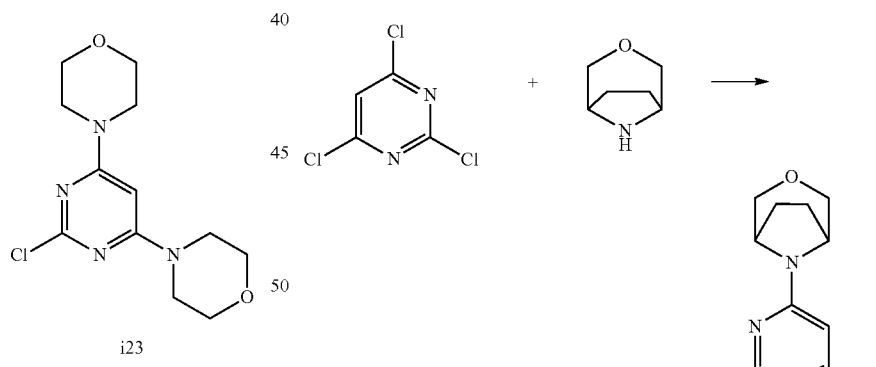

A solution of 2,4,6-trichloropyrimidine (0.676 mL, 5.88 mmol, 1.0 eq.), 3-oxa-8-azabicyclo[3.2.1]octane hydrochloride (1.76 g, 11.8 mmol, 2.0 eq.), and N,N-diisopropylethylamine (4.10 mL, 23.5 mmol, 4.0 eq.) in ethyl acetate (18 volumes) is heated for 16 hours (100° C.). Then, the solvent is removed under reduced pressure and the residue is dissolved in dichloromethane (60 volumes) and washed with a saturated aqueous sodium bisulfate (3×60 volumes). The organic layer is dried over anhydrous sodium sulfate, filtered and concentrated under reduced pressure. Purification by column chromatography on silica gel (cyclohexane/ethyl acetate 3:1 to 1:1) affords the desired intermediate i24 as a colorless solid (1.23 g, 62%). $^1$H NMR (400 MHz, CDCl$_3$): δ 5.80 (s, 1H), 4.59 (s, 2H), 4.35 (m, 2H), 3.76 (t, $^2J_{H,H}$=10.8 Hz, 4H), 3.59 (d, $^2J_{H,H}$=10.8 Hz, 4H), 2.03 (m, 8H); MS (MALDI): m/z=337.7 ([M+H]$^+$).

Method 9 is also used for the preparation of the following intermediate compound i25.

| Reagent | Structure | NMR | MS |
|---|---|---|---|
| i25 | 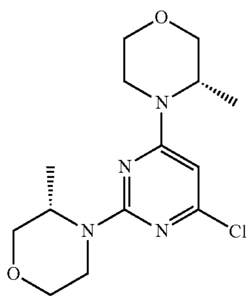 [SMILES: C[C@H]1COCCN1c1cc(Cl)nc(N2CCOC[C@@H]2C)n1] | $^1$H NMR (400 MHz, CDCl$_3$): δ 5.83 (s, 1 H), 4.64-4.57 (m, 1 H), 4.27 (dd, $^3J_{H,H}$ = 2.4 Hz, $^2J_{H,H}$ = 13.5 Hz, 1 H), 4.20-4.11 (m, 1 H), 3.97-3.87 (m, 3 H), 3.77-3.63 (m, 4 H), 3.56-3.46 (m, 2 H), 3.26-3.15 (m, 2 H), 1.28 (d, $^3J_{H,H}$ = 3.2 Hz, 3 H), 1.27 (d, $^3J_{H,H}$ = 3.2 Hz, 3 H). | MS (MALDI): m/z = 313.6 ([M + H]$^+$). |

Method 10: 4-(4,6-dichloropyrimidin-2-yl)morpholine (i26) and 4-(2,6-dichloropyrimidin-4-yl)morpholine (i27)

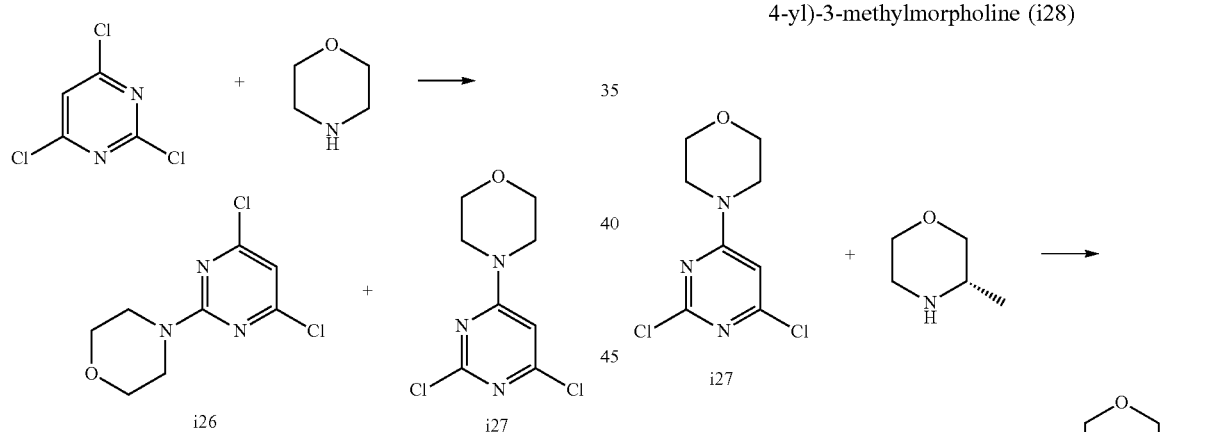

To a solution of 2,4,6-trichloropyrimidine (14.0 mL, 122 mmol, 1.0 eq.) in EtOH (150 mL) is added a solution of morpholine (11.2 mL, 256 mmol, 2.1 eq.) and N,N-diisopropylethylamine (44.6 mL, 256 mmol, 2.1 eq.) in EtOH (150 mL) dropwise at 0° C. The reaction mixture is stirred overnight at room temperature and the solvent is removed under reduced pressure. The crude product is extracted with dichloromethane (3×100 mL) and the organic phase is successively washed with saturated aqueous sodium bisulfate (3×400 mL). The combined organic layers are dried over anhydrous sodium sulfate, filtered and evaporated under reduced pressure. The crude mixture is purified by flash column chromatography (SiO$_2$, cyclohexane/ethyl acetate 9:1 to 3:1) to yield i26 (5.02 g, 18%) and 127 (16.7 g, 59%), both as colorless solids.

4-(4,6-dichloropyrimidin-2-yl)morpholine (i26): $^1$H NMR (400 MHz, CDCl$_3$): δ 6.56 (s, 1H), 3.78 (m, 4H) 3.74 (m, 4H).

4-(2,6-dichloropyrimidin-4-yl)morpholine (i27): $^1$H NMR (400 MHz, CDCl$_3$): δ 6.41 (s, 1H), 3.78 (m, 4H), 3.65 (m, 4H).

Method 11: (S)-4-(2-chloro-6-morpholinopyrimidin-4-yl)-3-methylmorpholine (i28)

A solution of 127 (694 mg, 2.97 mmol, 1.0 eq.), (S)-3-methylmorpholine (0.500 mL, 4.46 mmol, 1.5 eq.) and N,N-diisopropylethylamine (1.29 mL, 7.43 mmol, 2.5 eq.) in EtOH (5.0 mL) is heated to reflux for 3 days. Then, the solvent is removed under reduced pressure. The residue is dissolved in dichloromethane (60 volumes) and washed with saturated aqueous sodium bisulfate (3×60 volumes). The organic layer is dried over anhydrous sodium sulfate, filtered and concentrated under reduced pressure. The crude mixture is purified by flash chromatography (SiO$_2$, cyclohexane/ethyl acetate 3:1 to 1:1) to afford the title compound (S)-4-(2-chloro-6-morpholinopyrimidin-4-yl)-3-methylmorpholine (i28) as a colorless solid (425 mg, 48%). $^1$H NMR (400 MHz, CDCl$_3$): δ 5.85 (s, 1H), 4.62 (dd, $^2J_{H,H}$=13.6 Hz, $^3J_{H,H}$=2.9 Hz, 1H), 4.25 (dd, $^2J_{H,H}$=13.6 Hz, $^3J_{H,H}$=2.9 Hz, 1H), 3.93 (dd, $^2J_{H,H}$=11.4 Hz, $^3J_{H,H}$=3.8 Hz, 1H), 3.75, (t, $^3J_{H,H}$=5.0 Hz, 4H), 3.71 (s, 1H), 3.66 (dd, $^2J_{H,H}$=11.3 Hz, $^3J_{H,H}$=3.2 Hz, 1H), 3.53 (m, 5H), 3.23 (m, 1H), 1.26 (d, $^2J_{H,H}$=11.3 Hz, 3H); MS (MALDI): m/z=299.4 ([M+H]$^+$).

Method 11 is also used for the preparation of the following intermediate compound i29.

| Reagent | Structure | NMR | MS |
|---|---|---|---|
| i29 | 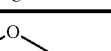 | $^1$H NMR (400 MHz, CDCl$_3$): δ 5.86 (s, 1 H), 4.60 (br s, 2 H), 3.80-3.72 (m, 6 H), 3.62-3.56 (m, 2 H), 3.56-3.50 (m, 4 H), 2.08-1.90 (m, 4 H). | MS (MALDI): m/z = 309.6 ([M + H]$^+$). |

Method 12: (S)-4-(6-chloro-2-morpholinopyrimidin-4-yl)-3-methylmorpholine (i30)

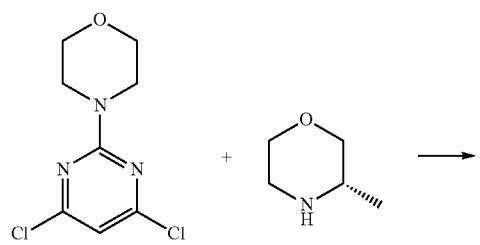

i26

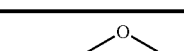

i30

A solution of (S)-3-methylmorpholine (194 mg, 1.32 mmol, 1.5 eq.), i26 (300 mg, 1.28 mmol, 1.0 eq.) and N,N-diisopropylethylamine (3.0 eq.) in DMF (17 volumes) is heated for 16 hours (130° C.). Then, the solvent is removed under reduced pressure. The residue is dissolved in dichloromethane (100 volumes) and washed with saturated aqueous sodium bisulfate (3×100 volumes). The organic layer is dried over anhydrous sodium sulfate, filtered and concentrated under reduced pressure. The crude mixture is purified by flash chromatography (SiO$_2$, cyclohexane/ethyl acetate 5:1) to afford the title compound i30 as a colorless solid (257 mg, 67%). $^1$H NMR (400 MHz, CDCl$_2$): δ 5.84 (s, 1H), 4.18 (m, 1H), 3.94 (m, 2H), 3.71 (m, 10H), 3.53, (dt, $^2J_{H,H}$=12.0 Hz, $^3J_{H,H}$=3.1 Hz, 1H), 3.20 (dt, $^2J_{H,H}$=12.8 Hz, $^3J_{H,H}$=3.8 Hz, 1H), 1.27 (d, $^3J_{H,H}$=6.8 Hz, 3H); MS (MALDI): m/z=298.4 ([M]$^+$).

Method 14: 8-(4,6-dichloro-1,3,5-triazin-2-yl)-3-oxa-8-azabicyclo[3.2.1]octane (i32)

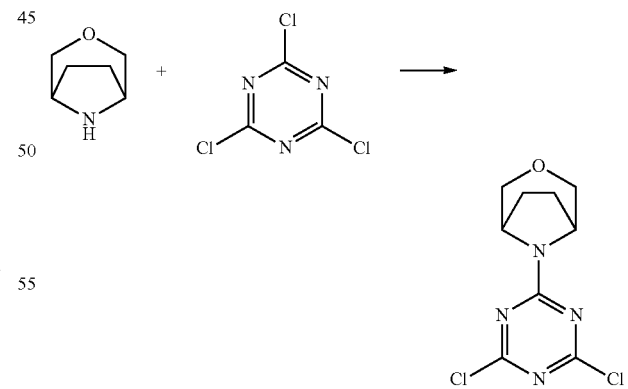

i32

A solution of cyanuric chloride (1.97 g, 10.7 mmol, 1.0 eq.) in dichloromethane (10 mL) is cooled to −50° C. A solution of 3-oxa-8-azabicyclo[3.2.1]octane hydrochloride (1.60 g, 10.7 mmol, 1.0 eq.) and N,N-diisopropylethylamine (3.73 mL, 21.4 mmol, 2.0 eq.) in dichloromethane (40 mL)

is slowly added over a period of 5 hours. The mixture is stirred for another 5 hours at this temperature. Then, dichloromethane (20 mL) and saturated aqueous sodium bisulfate (50 mL) are added and the mixture is allowed to warm to room temperature. The layers are separated and the organic layer is washed with saturated aqueous sodium bisulfate (2×50 mL). The organic layer is dried over anhydrous sodium sulfate and the solvent is removed under reduced pressure. The crude mixture is recrystallized from n-heptane/dichloromethane (20 mL/13 mL) to afford the title compound 8-(4,6-dichloro-1,3,5-triazin-2-yl)-3-oxa-8-azabicyclo[3.2.1]octane (i32) as a colorless solid (2.47 g, 47%). $^1$H NMR (400 MHz, CDCl$_3$): δ 4.74 (m, 2H), 3.72 (d, $^3J_{H,H}$=1.5 Hz, 4H), 2.08 (m, 4H).

Method 14 is also used for the preparation of the following intermediate compounds i33 and i34.

| Reagent | Structure | NMR |
|---|---|---|
| i33 | ![] | $^1$H NMR (400 MHz, CDCl$_3$): δ 4.54-4.60 (m, 1 H), 4.20 (dd, $^3J_{H,H}$ = 2.9 Hz, $^2J_{H,H}$ = 14 Hz, 1 H), 3.92 (dd, $^3J_{H,H}$ = 3.4 Hz, $^2J_{H,H}$ = 12 Hz, 1 H), 3.71 (d, $^2J_{H,H}$ = 12 Hz, 1 H), 3.57 (dd, $^3J_{H,H}$ = 3.2 Hz, $^2J_{H,H}$ = 12 Hz, 1 H), 3.42 (m, 1 H), 3.32 (m, 1 H), 1.27 (d, $^3J_{H,H}$ = 6.9 Hz, 3 H). |
|  | ![] | |
| i34 | ![] ![] | $^1$H NMR (400 MHz, (CD$_3$)$_2$SO): δ 3.88-3.81 (m, 4 H), 3.51 (s, 2 H), 1.46 (s, 6 H). |

Method 15: 9-(4-(3-oxa-8-azabicyclo[3.2.1]octan-8-yl)-6-chloro-1,3,5-triazin-2-yl)-3,7-dioxa-9-azabicyclo[3.3.1]nonane (i35)

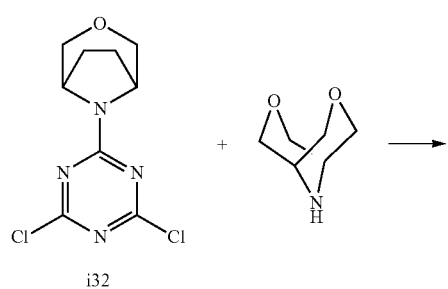

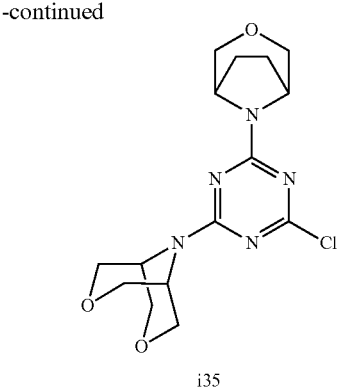

i35

To a solution of 3,7-dioxa-9-azabicyclo[3.3.1]nonane (i84 mg, 0.700 mmol, 1.0 eq.) and N,N-diisopropylethylamine (0.170 mL, 0.970 mmol, 1.4 eq.) in 1,4-dioxane (1.0 mL) a solution of i32 (100 mg, 0.770 mmol, 1.1 eq.) in 1,4-dioxane (2.0 mL) is added. The resulting mixture is heated for 1 hour at 70° C. Then, dichloromethane (50 mL) and water (50 mL) are added.

The aqueous layer is extracted with dichloromethane (3×50 mL), the combined organic layers are dried over anhydrous sodium sulfate and the solvent is evaporated. The crude mixture is purified by automated flash chromatography on silica gel (cyclohexane/ethyl acetate 2:1 to 0:1) to afford the title compound 9-(4-(3-oxa-8-azabicyclo[3.2.1]octan-8-yl)-6-chloro-1,3,5-triazin-2-yl)-3,7-dioxa-9-azabicyclo[3.3.1]nonane (i5) as a colorless solid (192 mg, 77%). $^1$H NMR (400 MHz, (CD$_3$)$_2$SO): δ 4.70 (m, 1H), 4.55 (m, 2H), 4.44 (m, 1H), 4.12 (m, 4H), 3.90 (m, 4H), 3.72 (m, 2H), 3.64 (m, 2H), 2.08 (m, 2H), 1.97 (m, 2H); MS (MALDI): m/z=354.3 ([M]$^+$).

Method 16: 9-(4-chloro-6-((R)-3-methylmorpholino)-1,3,5-triazin-2-yl)-3,7-dioxa-9-azabicyclo[3.3.1]nonane (i36)

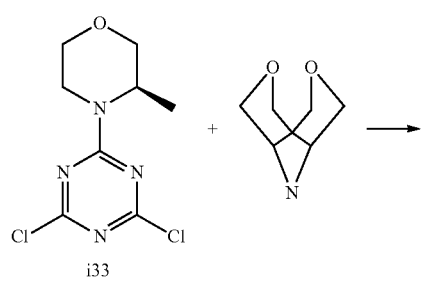

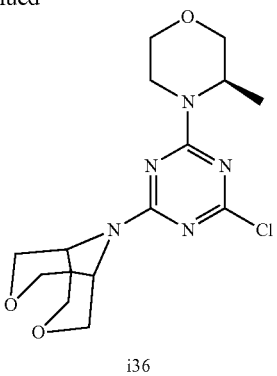

i36

To a solution of 3,7-dioxa-9-azabicyclo[3.3.1]nonane (173 mg, 1.27 mmol, 1.05 eq.) and N,N-diisopropylethylamine (0.50 mL, 2.52 mmol, 2.1 eq.) in tetrahydrofuran (5 mL) a solution of i33 (300 mg, 2.52 mmol, 2.1 eq.) in 1,4-dioxane (2.0 mL) is added. The resulting mixture is heated for 2 hours (70° C.). Then, ethyl acetate (20 mL) and saturated aqueous sodium bisulfate (20 mL) are added. The phases are separated and the organic layer is washed with saturated aqueous sodium bisulfate (2×20 mL). The organic layer is dried over anhydrous sodium sulfate and the solvent is removed under reduced pressure. The crude mixture is purified by automated flash chromatography (SiO$_2$, cyclohexane/ethyl acetate 2:1 to 0:1) to afford the title compound i36 as a colorless solid (316 mg, 76%). $^1$H NMR (400 MHz, (CD$_3$)$_2$SO): δ 4.55-4.53 (m, 1H), 4.42 (m, 1H), 4.32 (m, 1H), 4.25-4.16 (m, 1H), 4.01-3.97 (m, 4H), 3.87 (dd, $^3J_{H,H}$=3.8 Hz, $^2J_{H,H}$=11.2 Hz, 1H), 3.73-3.65 (m, 5H), 3.53 (dd, $^3J_{H,H}$=3.0 Hz, $^2J_{H,H}$=11.6 Hz, 1H), 3.38 (m, 1H), 3.15 (m, 1H), 1.20 (d, $^3J_{H,H}$=6.9 Hz, 3H).

Method 16 is also used for the preparation of the following intermediate compounds i37 to i53, intermediate i82 and intermediates i85, i86, i92, i93, i94.

| | Reagent | Structure | NMR | MS |
|---|---|---|---|---|
| i37 | ![reagent structure] | ![product structure] | $^1$H NMR (400 MHz, (CD$_3$)$_2$SO): δ 4.58-4.50 (m, 1 H), 4.44-4.35 (m, 2 H), 4.25-4.12 (m, 1 H), 3.90-3.86 (m, 1 H), 3.75-3.65 (m, 3 H), 3.56-3.49 (m, 3 H), 3.38 (m, 1 H), 3.16 (m, 1 H), 1.25 (d, $^3J_{H,H}$ = 6.9 Hz, 6 H), 1.19 (d, $^3J_{H,H}$ = 6.9 Hz, 3 H). | MS (MALDI): m/z = 328.2 ([M + H]$^+$). |
| i38 | ![reagent structure] | ![product structure] | $^1$H NMR (400 MHz, (CD$_3$)$_2$SO): δ 4.54-4.46 (m, 1 H), 4.18-4.13 (m, 1 H), 3.88 (m, 1 H), 3.80-3.65 (m, 5 H), 3.54 (m, 1 H), 3.44-3.36 (m, 3 H), 3.18 (m, 1 H), 1.44 (s, 6 H), 1.21 (d, $^3J_{H,H}$ = 6.9 Hz, 3 H). | |

| Reagent | Structure | NMR | MS |
|---|---|---|---|
| i39 | 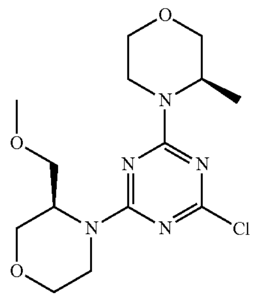 [SMILES: COC[C@@H]1COCCN1c1nc(Cl)nc(N2CCOC[C@H]2C)n1] | $^1$H NMR (400 MHz, (CD$_3$)$_2$SO): δ 4.65-4.51 (m, 2 H), 4.31-4.20 (m, 2 H), 3.66 (m, 3 H), 3.69-3.56 (m, 2 H), 3.54-3.48 (m, 3 H), 3.42-3.35 (m, 2 H), 3.31 (s, 3 H), 3.21-3.13 (m, 2 H), 1.21 (d, $^3J_{H,H}$ = 6.9 Hz, 3 H). | MS (MALDI): m/z = 344.2 ([M + H]$^+$). |
| i40 | 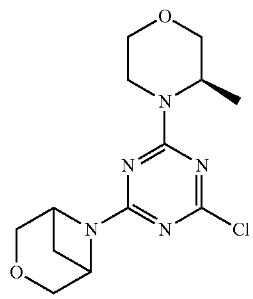 [SMILES: C[C@@H]1COCCN1c1nc(Cl)nc(N2C3COCC2C3)n1] | $^1$H NMR (400 MHz, (CD$_3$)$_2$SO): δ 4.55-4.51 (m, 1 H), 4.42-4.35 (m, 2 H), 4.12-4.25 (m, 2 H), 4.04-4.07 (m, 1 H), 3.86-3.88 (m, 1 H), 3.78-3.75 (m, 2 H), 3.69-3.65 (m, 1 H), 3.55-3.51 (m, 1 H), 3.38 (m, 1 H), 3.20-3.13 (m, 1 H), 2.68 (m, 1 H), 1.81 (m, 1 H), 1.20 (d, $^3J_{H,H}$ = 6.9 Hz, 3 H). | |
| i41 | 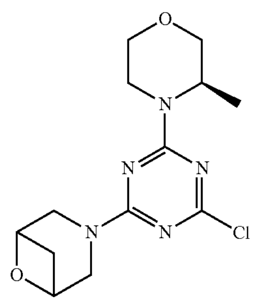 [SMILES: C[C@@H]1COCCN1c1nc(Cl)nc(N2CC3CC(C2)O3)n1] | $^1$H NMR (400 MHz, (CD$_3$)$_2$SO): δ 4.69-4.53 (m, 3 H), 4.31-4.15 (m, 1 H), 3.93-3.78 (m, 3 H), 3.71-3.53 (m, 4 H), 3.42-3.35 (m, 1 H), 3.22-3.16 (m, 1 H), 3.12-3.08 (m, 1 H), 1.81 (m, 1 H), 1.21 (d, $^3J_{H,H}$ = 6.9 Hz, 3 H). | |
| i42 | 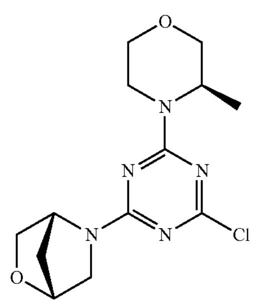 [SMILES: C[C@@H]1COCCN1c1nc(Cl)nc(N2C[C@H]3C[C@@H]2CO3)n1] | $^1$H NMR (400 MHz, (CD$_3$)$_2$SO): δ 4.95-4.88 (m, 1 H), 4.64 (m, 1 H), 4.54 (m, 1 H), 4.31-4.09 (m, 1 H), 3.89-3.85 (m, 1 H), 3.75-3.73 (m, 1 H), 3.66-3.63 (m, 2 H), 3.52 (m, 1 H), 3.45-3.32 (m, 3 H), 3.18-3.12 (m, 1 H), 1.90-1.83 (m, 2 H), 1.21 (d, $^3J_{H,H}$ = 6.9 Hz, 3 H). | MS (MALDI): m/z = 312.2 ([M + H]$^+$). |
| i43 | 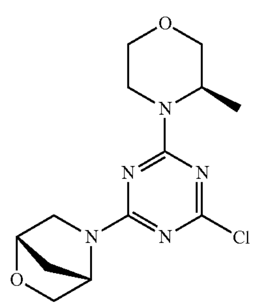 [SMILES: C[C@@H]1COCCN1c1nc(Cl)nc(N2C[C@@H]3C[C@H]2CO3)n1] | $^1$H NMR (400 MHz, (CD$_3$)$_2$SO): δ 4.94-4.88 (m, 1 H), 4.64 (m, 1 H), 4.54 (m, 1 H), 4.29-4.12 (m, 1 H), 3.89-3.85 (m, 1 H), 3.75-3.73 (m, 2 H), 3.66-3.63 (m, 2 H), 3.52 (m, 1 H), 3.45-3.32 (m, 2 H), 3.18-3.12 (m, 1 H), 1.90-1.83 (m, 2 H), 1.21 (d, $^3J_{H,H}$ = 6.9 Hz, 3 H). | MS (MALDI): m/z = 312.2 ([M + H]$^+$). |

-continued

| Reagent | Structure | NMR | MS |
|---|---|---|---|
| i53 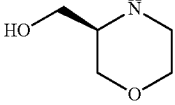 | 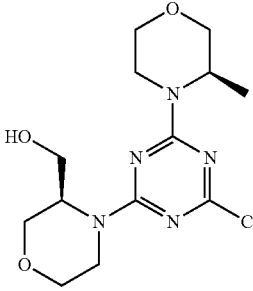 | $^1$H NMR (400 MHz, (CD$_3$)$_2$SO): δ 4.65 (m, 1 H), 4.55 (m, 1 H), 4.32 (m, 1 H), 4.22 (m, 2 H), 3.98 (m, 1 H), 3.86 (m, 2 H), 3.63 (m, 2 H), 3.55 (m, 1 H), 3.49-3.34 (m, 4 H), 3.17 (m, 1 H), 3.12 (m, 1 H), 1.21 (d, $^3J_{H,H}$ = 6.9 Hz, 3 H). | MS (MALDI): m/z = 330.1 ([M + H]$^+$). |
| i82 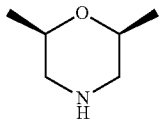 | 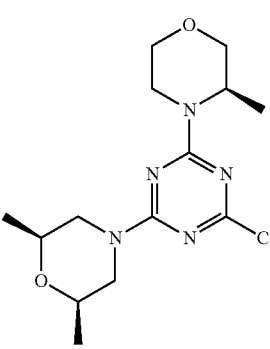 | $^1$H NMR (400 MHz, (CD$_3$)$_2$SO): δ 4.67-4.53 (m, 1 H), 4.45-4.34 (m, 2 H), 4.31-4.09 (m, 1 H), 3.88 (m, 1 H), 3.68 (m, 1 H), 3.55 (m, 3 H), 3.38 (m, 1 H), 3.13 (m, 1 H), 2.55 (m, 2 H), 1.20 (d, $^3J_{H,H}$ = 6.9 Hz, 3 H), 1.19 (d, $^3J_{H,H}$ = 6.9 Hz, 6 H). | MS (MALDI): m/z = 328.3 ([M + H]$^+$). |
| i85 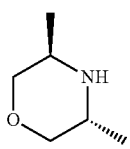 | 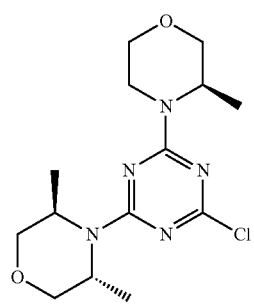 [SMILES: C[C@@H]1COCCN1c1nc(Cl)nc(N2[C@H](C)COC[C@H]2C)n1] | $^1$H NMR (400 MHz, (CD$_3$)$_2$SO): δ 4.53 (m, 1 H), 4.22 (m, 3 H), 4.11-4.08 (m, 2 H), 3.88 (m, 1 H), 3.66 (m, 3 H), 3.54 (m, 1 H), 3.36 (m, 1 H), 3.18 (m, 1 H), 1.33 (m, 6 H), 1.22 (d, $^3J_{H,H}$ = 6.9 Hz, 3 H) | MS (MALDI): m/z = 328.2 ([M + H]$^+$) |
| i86 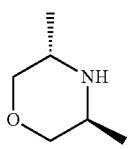 | 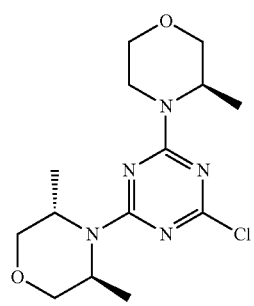 [SMILES: C[C@@H]1COCCN1c1nc(Cl)nc(N2[C@@H](C)COC[C@@H]2C)n1] | $^1$H NMR (400 MHz, (CD$_3$)$_2$SO): δ 4.55 (m, 1 H), 4.22-4.07 (m, 5 H), 3.88 (m, 1 H), 3.70-3.63 (m, 3 H), 3.54 (m, 1 H), 3.38 (m, 1 H), 3.19 (m, 1 H), 1.33 (m, 6 H), 1.21 (d, $^3J_{H,H}$ = 6.9 Hz, 3 H) | MS (MALDI): m/z = 328.5 ([M + H]$^+$). |

| Reagent | Structure | NMR | MS |
|---|---|---|---|
| i92 | 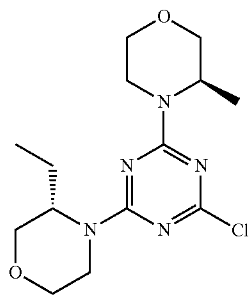 [SMILES: CC[C@H]1COCCN1c1nc(Cl)nc(N2CCOC[C@H]2C)n1] | ¹H NMR (400 MHz, (CD₃)₂SO): δ 4.54-4.15 (m, 4 H), 3.86 (m, 2 H), 3.77 (m, 1 H), 3.66 (m, 2 H), 3.55-3.46 (m, 2 H), 3.38 (m, 1 H), 3.14 (m, 2 H), 1.70 (m, 2 H), 1.22 (d, ³J$_{H,H}$ = 6.9 Hz, 3 H), 0.86 (m, 3 H) | MS (MALDI): m/z = 328.6 ([M + H]⁺). |
| i93 | 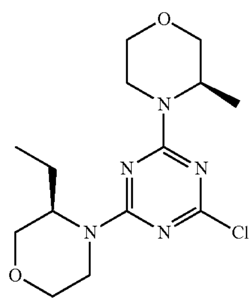 [SMILES: CC[C@@H]1COCCN1c1nc(Cl)nc(N2CCOC[C@H]2C)n1] | ¹H NMR (400 MHz, (CD₃)₂SO): δ 4.54-4.15 (m, 4 H), 3.86 (m, 2 H), 3.77 (m, 1 H), 3.66 (m, 2 H), 3.55-3.46 (m, 2 H), 3.38 (m, 1 H), 3.14 (m, 2 H), 1.70 (m, 2 H), 1.22 (d, ³J$_{H,H}$ = 6.9 Hz, 3 H), 0.86 (m, 3 H) | MS (MALDI): m/z = 328.1 ([M + H]⁺). |
| i94 | 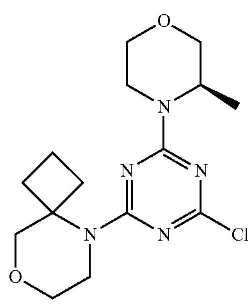 [SMILES: C[C@@H]1COCCN1c1nc(Cl)nc(N2CCOCC23CCC3)n1] | ¹H NMR (400 MHz, (CD₃)₂SO): δ 4.45 (m, 1 H), 4.11 (m, 1 H), 3.87 (m, 1 H), 3.66 (m, 5 H), 3.50 (m, 3 H), 3.38 (m, 1 H), 3.15 (m, 1 H), 2.44 (m, 2 H), 2.21 (m, 2 H), 1.70 (m, 2 H), 1.19 (d, ³J$_{H,H}$ = 6.9 Hz, 3 H) | MS (MALDI): m/z = 340.6 ([M + H]⁺). |

Method 17: 9-(4-chloro-6-(3,3-dimethylmorpholino)-1,3,5-triazin-2-yl)-3,7-dioxa-9-azabicyclo[3.3.1]nonane (i54)

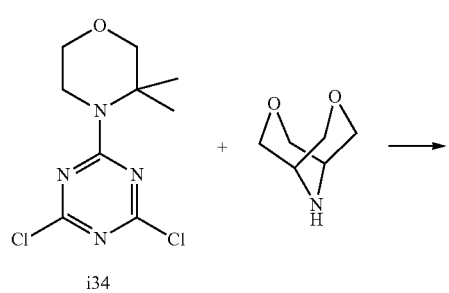

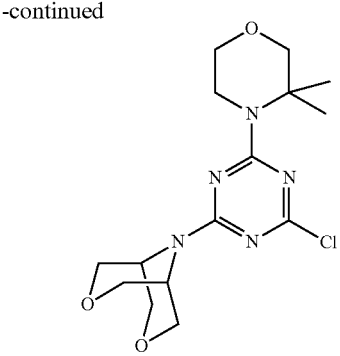

i54

To a solution of 3,7-dioxa-9-azabicyclo[3.3.1]nonane (i55 mg, 1.20 mmol, 1.05 eq.) and N,N-diisopropylethylamine (0.42 mL, 2.40 mmol, 2.1 eq.) in 1,4-dioxane (5 mL) a solution of i34 (300 mg, 1.14 mmol, 1 eq.) in 1,4-dioxane (1 mL) is added. The resulting mixture is heated for 2 hours (70° C.). Then, ethyl acetate (20 mL) and saturated aqueous sodium bisulfate (20 mL) are added. The phases are separated and the organic layer is washed with saturated aqueous sodium bisulfate (2×20 mL). The organic layer is dried over anhydrous sodium sulfate and the solvent is removed under reduced pressure. The crude mixture is purified by automated flash chromatography (SiO$_2$, cyclohexane/ethyl acetate 2:1 to 0:1) to afford the title compound 154 as a colorless solid (178 mg, 44%). $^1$H NMR (400 MHz, (CD$_3$)$_2$SO): δ 4.32 (m, 2H), 4.05-3.98 (m, 4H), 3.77 (m, 4H), 3.71 (m, 4H), 3.44 (m, 2H), 1.41 (s, 6H). MS (MALDI): m/z=356.3 ([M+H]$^+$).

Method 17 is also used for the preparation of the following intermediate compounds i55 to i64.

| | Reagent | Structure | NMR | MS |
|---|---|---|---|---|
| i55 | | 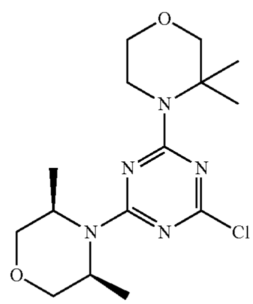 [SMILES: C[C@@H]1COC[C@H](C)N1c1nc(Cl)nc(N2CCOCC2(C)C)n1] | $^1$H NMR (400 MHz, (CD$_3$)$_2$SO): δ 4.36 (m, 2 H), 3.77-3.74 (m, 6 H), 3.55 (m, 2 H), 3.44 (m, 2 H), 1.44 (s, 6 H), 1.26 (d, $^3J_{H,H}$ = 6.9 Hz, 6 H). | MS (MALDI): m/z = 342.9 ([M + H]$^+$). |
| i56 | | 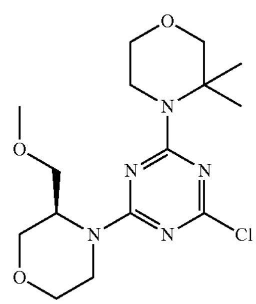 [SMILES: COC[C@@H]1COCCN1c1nc(Cl)nc(N2CCOCC2(C)C)n1] | $^1$H NMR (400 MHz, (CD$_3$)$_2$SO): δ 4.52 (m, 1 H), 4.20 (m, 1 H), 3.90 (m, 2 H), 3.77 (m, 4 H), 3.65 (m, 1 H), 3.51-3.41 (m, 5 H), 3.28 (s, 3H), 3.12 (m, 1 H), 1.44 (s, 3 H), 1.43 (s, 3 H). | |
| i57 | | 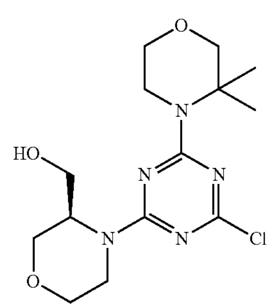 [SMILES: CC1(C)COCCN1c1nc(Cl)nc(N2CCOC[C@H]2CO)n1] | $^1$H NMR (400 MHz, (CD$_3$)$_2$SO): δ 4.98 (m, 1 H), 4.35 (m, 1 H), 4.18 (m, 1 H), 4.00 (m, 1 H), 3.87 (m, 1 H), 3.81-3.65 (m, 5 H), 3.51-3.35 (m, 5 H), 3.21-3.04 (m, 1 H), 1.44 (s, 3 H), 1.45 (s, 3 H). | MS (MALDI): m/z = 344.2 ([M + H]$^+$). |
| i58 | | 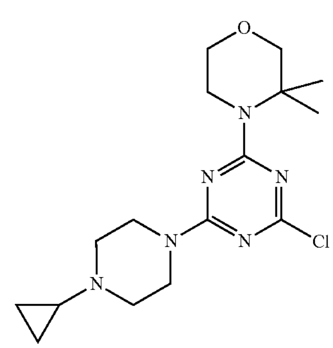 [SMILES: CC1(C)COCCN1c1nc(Cl)nc(N2CCN(C3CC3)CC2)n1] | $^1$H NMR (400 MHz, (CD$_3$)$_2$SO): δ 3.77 (m, 4 H), 3.65 (m, 4 H), 3.44 (m, 2 H), 2.56 (m, 4 H), 1.64 (m, 1 H), 1.44 (s, 6 H), 0.44 (m, 2 H), 0.35 (m, 2 H). | MS (MALDI): m/z = 353.0 ([M + H]$^+$). |

| Reagent | Structure | NMR | MS |
|---|---|---|---|
| i59 | 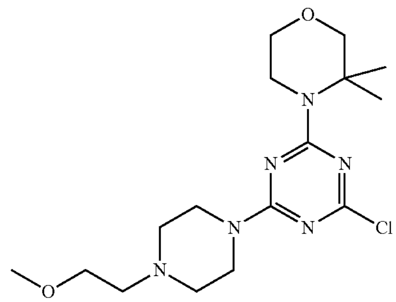 | $^1$H NMR (400 MHz, (CD$_3$)$_2$SO): δ 3.76 (m, 4 H), 3.68 (m, 4 H), 3.47-3.44 (m, 4 H), 3.24 (m, 3 H), 2.52-2.45 (m, 6 H), 1.44 (s, 6 H). | MS (MALDI): m/z = 371.1 ([M + H]$^+$). |

Method 18: 4-(difluoromethyl)pyridin-2-amine (i65)

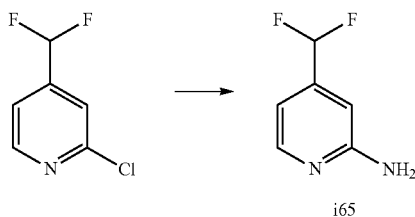 [SMILES: FC(F)c1ccnc(Cl)c1 ; Nc1cc(C(F)F)ccn1]

Palladium acetate (275 mg, 1.22 mmol, 0.05 eq.) and 2-dicyclohexylphosphino-2',4',6'-triisopropylbiphenyl (Sigma-Aldrich, product number 638064, 1.17 g, 2.45 mmol, 0.10 eq.) are dissolved in 1,4-dioxane (10 mL) under nitrogen atmosphere, and the resulting mixture is allowed to stir at room temperature for 45 minutes. This solution is then added to a mixture of tert-butylcarbamate (Sigma, product number 167398, 4.30 g, 36.7 mmol, 1.5 eq.), Cs$_2$CO$_3$ (15.9 g, 48.8 mmol, 2.0 eq.) and 2-chloro-4-difluoromethyl-pyridine (Manchester Organics, product number U15343, 4.00 g, 24.5 mmol, 1.0 eq.) in 1,4-dioxane (80 mL) under nitrogen atmosphere. The resulting reaction mixture is then heated at 90° C. for 3 hours, during which it turned brownish. After this time, the mixture is allowed to cool to room temperature. It is then diluted with ethyl acetate, washed with an aqueous saturated solution of ammonium chloride (2×30 mL) and deionized water. The organic layer is dried over anhydrous sodium sulfate, filtered and the solvent is evaporated under reduced pressure. The brownish residue is mixed with 4 M HCl in dioxane (50 mL, excess) and methanol (20 mL), and then heated at 80° C. for 45 minutes. Deionized water is added and the aqueous layer is washed with ethyl acetate (3×). The aqueous layer is then basified to pH=9, with solid sodium hydroxide. The aqueous layer is extracted with ethyl acetate (3×). The combined organic layer is dried over anhydrous sodium sulfate, filtered and concentrated to dryness under reduced pressure. The desired product i65 is obtained as a colorless solid, which is used in the next step without further purification (98% yield). $^1$H NMR (400 MHz, CDCl$_3$): δ 8.16 (d, $^2J_{H,H}$=5.2 Hz, 1H), 6.74 (d, $^2J_{H,H}$=4.8 Hz, 1H), 6.59 (s, 1H), 6.51 (t, $^2J_{H,H}$=56 Hz, 1H), 4.61 (br s, 2H); $^{19}$F NMR (376 MHz, CDCl$_3$): δ−116.0 (s, 2F).

Method 19: 5-bromo-4-(difluoromethyl)pyridin-2-amine (i66)

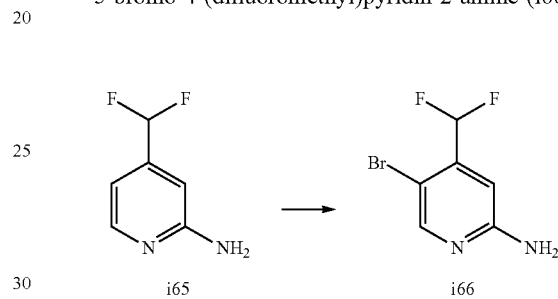

To a solution of compound i65 (3.00 g, 20.8 mmol, 1.0 eq.) in tetrahydrofuran (60 mL) is added N-bromosuccinimide (3.89 g, 21.9 mmol, 1.05 eq.) at 0° C. in an ice bath. The resulting mixture is stirred overnight, while it is allowed to warm up to room temperature. Ethyl acetate is added and the organic layer is washed with aqueous sodium carbonate (8%). The organic layer is then separated and acidified with an aqueous 3 M HCl-solution. The aqueous layer is washed with ethyl acetate (3×50 mL) and then basified to pH=10, with solid sodium hydroxide. The aqueous layer is extracted with ethyl acetate (3×50 mL). The combined organic layer is dried over anhydrous sodium sulfate, filtered and concentrated to dryness under reduced pressure. The desired product i66 is obtained as a brownish solid, which is used in the next step without further purification (79% yield). $^1$H NMR (400 MHz, CDCl$_3$): δ 8.20 (s, 1H), 6.75 (s, 1H), 6.71 (t, $^2J_{H,F}$=54 Hz, 1H); 4.62 (br s, 2H); $^{19}$F NMR (376 MHz, CDCl$_3$): δ−118.9 (s, 2F).

Method 20: N'-(5-bromo-4-(difluoromethyl)pyridin-2-yl)-N,N-dimethylformimidamide (i67)

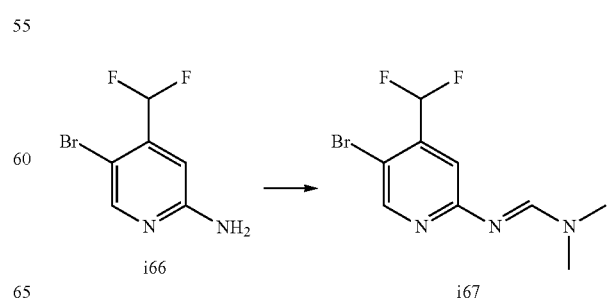

To a solution of compound i66 (3.68 g, 16.5 mmol, 1.0 eq.) in tetrahydrofuran (50 mL) is added N,N-dimethylformamide dimethyl acetal (Manchester Organics, product number 005030, 3.30 mL, 24.8 mmol, 1.5 eq.) and the resulting mixture is stirred at 60° C. for 3 hours. The mixture is allowed to cool to room temperature and the solvent is evaporated under reduced pressure. The crude product is purified by column chromatography on silica gel (cyclohexane/ethyl acetate 1:1) to afford the desired product i67 as a yellowish solid (82% yield). $^1$H NMR (400 MHz, CDCl$_3$): δ8.43 (s, 1H), 8.34 (br s, 1H), 7.17 (s, 1H), 6.73 (t, $^2J_{H,F}$=54 Hz, 1H), 3.12 (s, 3H), 3.10 (s, 3H); $^{19}$F NMR (376 MHz, CDCl$_3$): δ−118.6 (s, 2F); MS (MALDI): m/z=278.5 ([M+H]$^+$).

Method 21: N'-(4-(difluoromethyl)-5-(4,4,5,5-tetramethyl-1,3,2-dioxaborolan-2-yl)pyridin-2-yl)-N,N-dimethylformimidamide (i68)

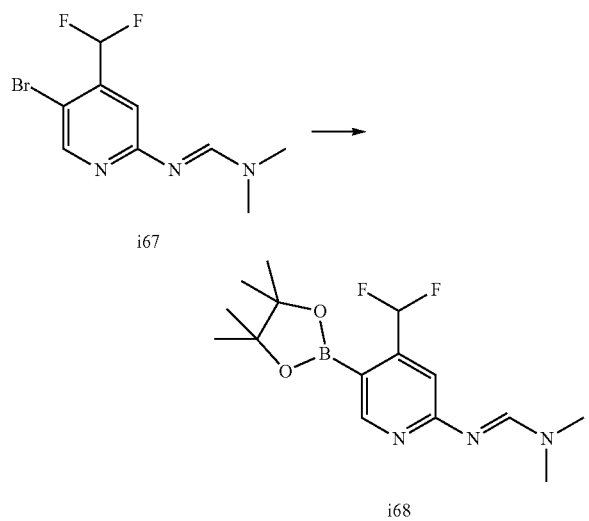

To a 2 M solution of isopropylmagnesium chloride (Sigma, product number 230111, 3.10 mL, 6.20 mmol, 1.15 eq.) in tetrahydrofuran (6 mL) is slowly added a solution of compound i67 (1.50 g, 5.39 mmol, 1.0 eq.) in tetrahydrofuran (5 mL) at 0° C. The resulting brownish mixture is stirred at 0° C. for 45 minutes and then at room temperature for 15 minutes. After this time, TLC monitoring (cyclohexane/ethyl acetate 1:1) showed complete consumption of starting material. 2-Isopropoxy-4,4,5,5-tetramethyl-1,3,2-dioxaborolane (Manchester Organics, product number W23343, 1.43 mL, 7.00 mmol, 1.3 eq.) is added and the mixture is heated at 60° C. for 3 hours. The mixture is then placed in an Erlenmeyer flask, cooled to 0° C. with an ice bath and quenched with a 15% aqueous solution of ammonium chloride. The layers are separated and the aqueous layer is extracted with ethyl acetate (3×40 mL). The combined organic layers are dried over anhydrous sodium sulfate, filtered and the solvent is evaporated under reduced pressure. Heptane is added and the organic layer is washed with a saturated aqueous solution of sodium bicarbonate, dried over anhydrous sodium sulfate, filtered and then concentrated to dryness under reduced pressure. The desired product i68 is obtained as a brownish oil, which is used in the next step without further purification (94% yield). $^1$H NMR (400 MHz, CDCl$_3$): δ 8.66 (s, 1H), 8.51 (s, 1H), 7.34-7.04 (m, 2H), 3.12 (s, 3H), 3.12 (s, 3H), 1.34 (s, 12H); $^{19}$F NMR (376 MHz, CDCl$_3$): δ−115.6 (s, 2F); MS (MALDI): m/z=326.0 ([M+H]$^+$).

Method 22: 4-(difluoromethyl)pyrimidin-2-amine (i69)

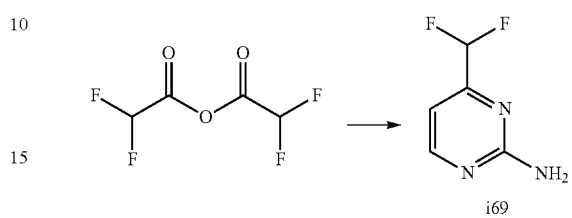

To a solution of ethyl vinyl ether (4.00 mL, 41.8 mmol, 1.0 eq.) in a mixture of pyridine (4.10 mL, 50.7 mmol, 1.2 eq.) and dichloromethane (40 mL), is added dropwise a solution of 2,2-difluoroacetic anhydride (Manchester Organics, (product number L24754, 5.90 mL, 50.1 mmol, 1.2 eq.) in dichloromethane (5 mL) at −70° C. in a dry ice/isopropanol bath. The resulting solution is allowed to warm up to room temperature overnight. The mixture is then washed with deionized water, dried over anhydrous sodium sulfate, filtered and the solvent is evaporated under reduced pressure to afford an orange oil.

At the same time, a suspension of guanidine·HCl (Sigma, product number 50940, 4.80 g, 50.2 mmol, 1.2 eq.) in ethanol (20 mL) is stirred at room temperature for 1 hour. To this solution are added sodium hydroxide pellets (2.00 g, 50.0 mmol, 1.2 eq.) in one portion. The resulting suspension is stirred at room temperature overnight.

The orange oil is diluted with dichloromethane (20 mL) and added dropwise over 1 hour to the ethanol suspension. The resulting suspension is stirred at room temperature for 2 hours. Dichloromethane is evaporated under reduced pressure. Deionized water (25 mL) is added to the residue. The resulting mixture is stirred vigorously for 2 hours and is then allowed to stand at room temperature overnight. The formed solid is filtered off, washed with deionized water (2×) and heptane (1×) and then dried in vacuo. The desired product i69 is obtained as a colorless solid (65% yield). $^1$H NMR (400 MHz, CDCl$_3$): δ 8.43 (d, $^2J_{H,H}$=4.8 Hz, 1H), 7.02 (brs, 2H), 6.76 (d, $^2J_{H,H}$=5.2 Hz, 1H), 6.67 (t, $^2J_{H,F}$=55 Hz, 1H); $^{19}$F NMR (376 MHz, CDCl$_3$): δ−120.5 (s, 2F).

Method 23: 5-bromo-4-(difluoromethyl)pyrimidin-2-amine (i70)

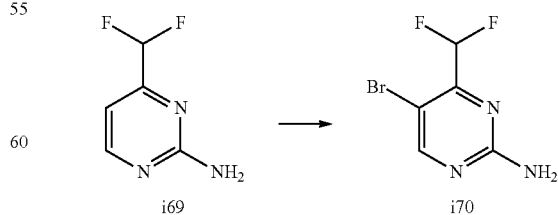

To a solution of compound i69 (3.00 g, 20.7 mmol, 1.0 eq.) in tetrahydrofuran (90 mL) is added N-bromosuccinimide (3.86 g, 21.7 mmol, 1.0 eq.) portionwise at 0° C. The reaction mixture is allowed to warm up to room temperature overnight. After this time, the solvent is evaporated under reduced pressure. The residue is taken up in ethyl acetate (200 mL), washed with an aqueous saturated solution of sodium carbonate (4×), dried over anhydrous sodium sulfate, filtered and then concentrated to dryness under reduced pressure. The desired product i70 is obtained as a yellowish solid, which is used in the next step without further purification (98% yield). $^1$H NMR (400 MHz, (CD$_3$)$_2$SO): δ 8.50 (s, 1H), 7.30 (br s, 2H), 6.87 (t, $^2J_{H,F}$=53 Hz, 1H); $^{19}$F NMR (376 MHz, (CD$_3$)$_2$SO): δ−121.4 (s, 2F).

Method 24: N-tert-butyl carboxylate-N-(5-bromo-4-(difluoromethyl)pyrimidin-2-yl)-carbamate (i71)

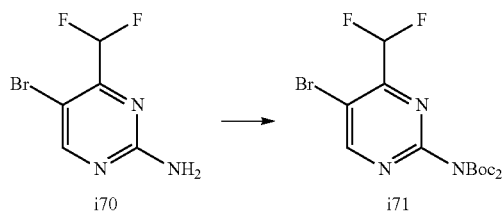

Compound i70 (4.35 g, 19.4 mmol, 1.0 eq.) and 4-(dimethylamino)pyridine (480 mg, 3.92 mmol, 0.20 eq.) are dissolved in tetrahydrofuran (50 mL). N,N-Diisopropylethylamine (7.50 mL, 42.1 mmol, 2.2 eq.) and di-tert-butyl dicarbonate (9.33 g, 42.7 mmol, 2.2 eq.) are then added at 0° C. and the resulting solution is allowed to warm up to room temperature overnight. The solvent is evaporated under reduced pressure. The crude product is purified by column chromatography on silica gel (cyclohexane/ethyl acetate 9:1→4:1) to afford the desired product i71 as a colorless solid (85% yield).

$^1$H NMR (400 MHz, CDCl$_3$): δ 8.92 (s, 1H), 6.73 (t, $^2J_{H,F}$=53 Hz, 1H), 1.47 (s, 18H); $^{19}$F NMR (376 MHz, CDCl$_3$): δ−120.4 (s, 2F).

General Procedure 1:

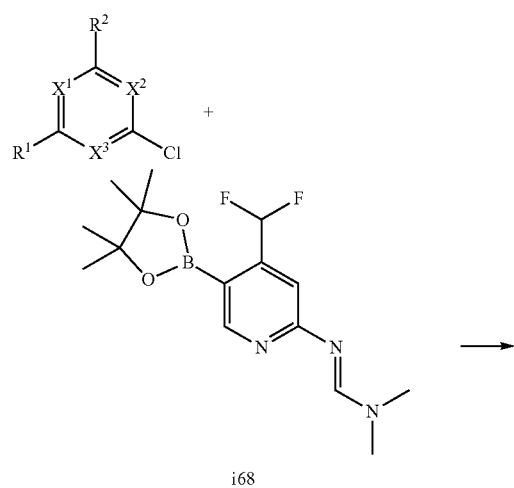

-continued

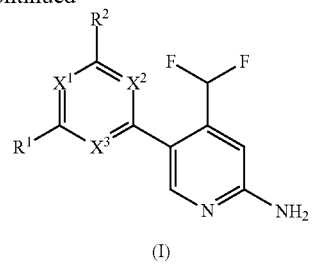

Substituted monochloro-triazine or substituted monochloro-pyrimidine (1.0 eq.), compound i68 (1.1 eq.), potassium phosphate tribasic (2.0 eq.) and chloro(2-dicyclohexylphosphino-2',4',6'-triisopropyl-1,1'-biphenyl) [2-(2'-amino-1,1'-biphenyl)]-palladium(II) (Sigma-Aldrich, product number 741825, 0.05 eq.) are charged in a flask. Under nitrogen atmosphere, 1,4-dioxane (30 volumes) and deionized water (1.5 volume) are added and the resulting mixture is then directly placed into an oil bath pre-heated at 95° C. The reaction mixture is stirred at this temperature for 2 hours. A 5 M aqueous HCl-solution (20 eq.) is added. The resulting mixture is heated to 60° C. overnight. The pH of the resulting mixture is adjusted to 8-9 by addition of a 2 M aqueous solution of sodium hydroxide, the mixture is then extracted with ethyl acetate (3×20 volumes). The combined organic layers are dried over anhydrous sodium sulfate, filtered and the solvent is evaporated under reduced pressure. Purification by flash chromatography affords the desired products of structure (1).

General Procedure 2:

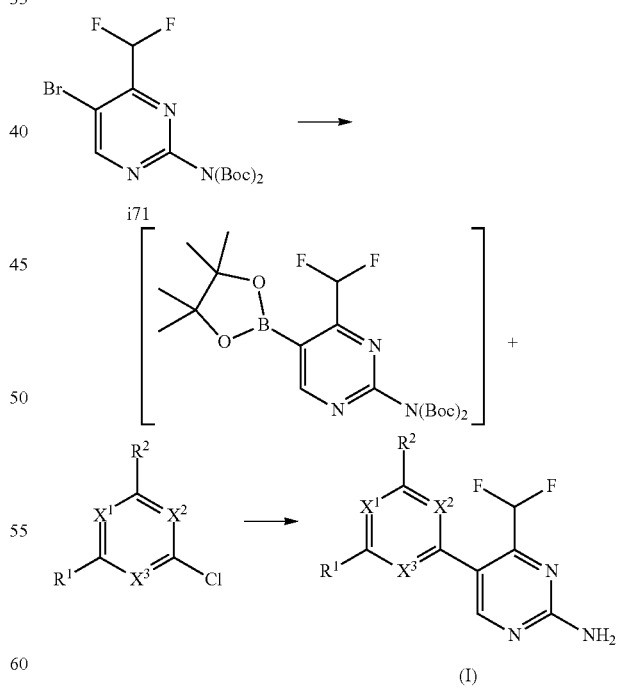

Compound i71 (1.0 eq.), 4,4,4',4',5,5,5',5'-octamethyl-2,2'-bi(1,3,2-dioxaborolane) (Manchester Organics, product number M23170, 1.5 eq.), potassium acetate (3.0 eq.) and [1,1'-bis(diphenylphosphino)-ferrocene]-dichloropalladium (II) (Sigma-Aldrich, product number 697230, 0.099 eq.) are dissolved in 1,4-dioxane (12.5 volumes) under nitrogen atmosphere. The resulting mixture is heated at 100° C. for 15 minutes (solution turned black). TLC monitoring (cyclohexane/ethyl acetate 3:1) is used to show complete consumption of starting material.

To the resulting mixture, substituted chloro-triazine or substituted chloropyrimidine (1.1 eq.), an aqueous solution of potassium carbonate (2 M, 3.0 eq.) and a previously mixed solution of triphenylphosphine (0.12 eq.) and palladium acetate (0.04 eq.) in tetrahydrofuran (100 volumes) are added. The resulting mixture is heated at 60° C. for 2 hours and subsequently allowed to cool to room temperature.

A 5 M aqueous HCl-solution (20 eq.) is added. The resulting mixture is heated to 60° C. overnight. The pH of the resulting mixture is adjusted to 8-9 by addition of a 2 M aqueous solution of sodium hydroxide, the mixture is then extracted with ethyl acetate (3×20 volumes). The combined organic layers are dried over anhydrous sodium sulfate, filtered and the solvent is evaporated under reduced pressure. Purification by flash chromatography affords the desired products.

Method 27: tert-butyl N-tert-butoxycarbonyl-N-(5-(4-chloro-6-morpholino-1,3,5-triazin-2-yl)-4-(difluoromethyl)pyrimidin-2-yl)carbamate (i74)

Intermediate i71 (2.00 g, 4.71 mmol, 1.0 eq.), bis(pinacolato)diboron (1.80 g, 7.09 mmol, 1.5 eq.), KOAc (1.60 g, 16.3 mmol, 3.4 eq.) and [1,1'-bis(diphenylphosphino)ferrocene]-dichloropalladium(II) (350 mg, 478 μmol, 0.10 eq.) are mixed in 1,4-dioxane under nitrogen atmosphere and heated at 95° C. for 45 minutes. A pre-catalyst solution of palladium(II) acetate (43.0 mg, 192 μmol, 0.04 eq.) and triphenylphosphine 148 mg, 564 μmol, 0.12 eq.) in tetrahydrofuran (2 mL) is also prepared and stirred at room temperature for 1 hour. This solution is then added to the cooled above solution at room temperature, followed by the addition of 4-(4,6-dichloro-1,3,5-triazin-2-yl)morpholine i11 (1.65 g, 7.05 mmol, 1.5 eq.) and aqueous $K_2CO_3$-solution (2.4 M, 5.90 mL, 14.2 mmol, 3.0 eq.). The resulting mixture is heated at 55° C. overnight. After this time, the mixture is poured onto an aqueous $NH_4Cl$-solution (15%) and extracted with ethyl acetate (3×). The combined organic layer is dried over anhydrous sodium sulfate, filtered and concentrated under reduced pressure. Purification by column chromatography on silica gel (cyclohexane/ethyl acetate 1:0 to 4:1) gives product i74 as a colorless solid (36% yield).

$^1$H NMR (400 MHz, $CDCl_3$): δ 9.57 (s, 1H), 7.55 (t, $^2J_{H,F}$=54 Hz, 1H), 3.99-3.91 (m, 4H), 3.84-3.76 (m, 4H), 1.49 (s, 18H); $^{19}$F NMR (376 MHz, $CDCl_3$): δ−121.0 (s, 2F).

Method 32: (E)-4-ethoxy-1,1-difluoro-but-3-en-2-one (i83)

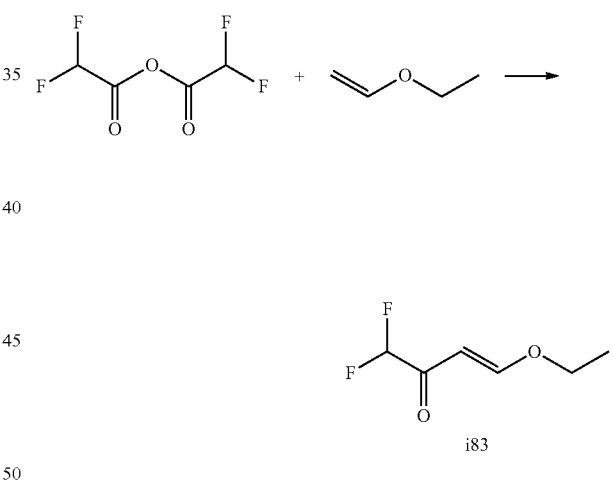

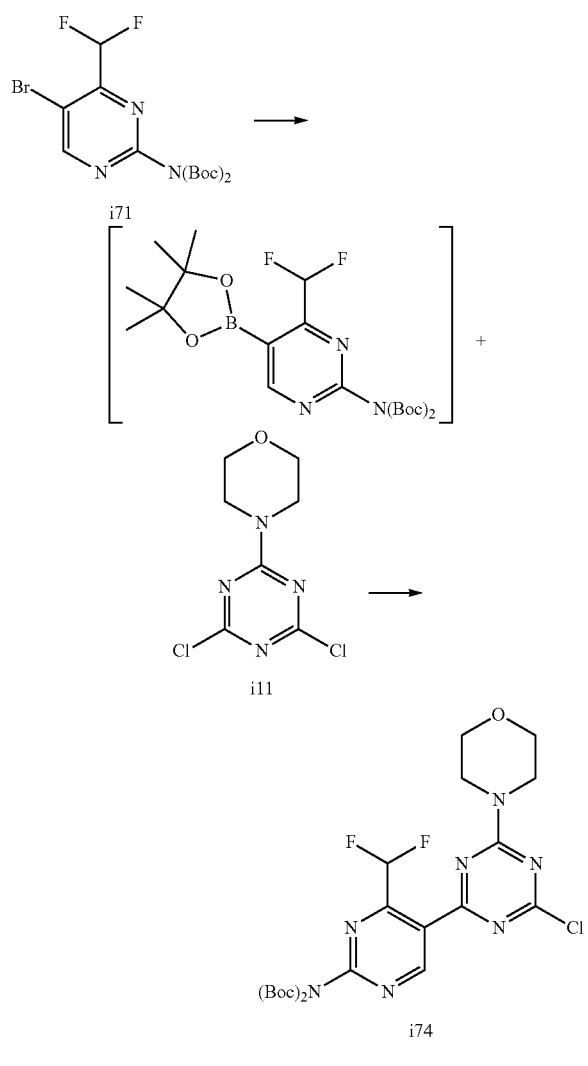

To a cooled (−70° C.) solution of pyridine (61.5 mL, 760.5 mmol, 1.2 eq) in dichloromethane (500 mL) is added ethyl vinyl ether (60 mL, 626.5 mmol, 1 eq), followed by a solution of difluoroacetic anhydride (88.5 mL, 760.5 mmol, 1.2 eq) in dichloromethane (75 mL). Then the mixture is slowly warmed to room temperature overnight. The mixture is transferred into a separating funnel and the organic layer is washed with water (6×800 mL) until the pH of the aqueous layer becomes neutral. The organic layer is dried over sodium sulfate and solvent is removed under reduced pressure to afford the desired product 183 as an orange oil (76.7 g, 81%). $^1$H NMR (400 MHz, $(CD_3)_2SO$): δ 7.92 (d, $^3J_{H,H}$=12.5 Hz, 1H), 6.34 (t, $^2J_{H,F}$=53.6 Hz, 1H), 5.87 (d, $^3J_{H,H}$=12.5 Hz, 1H), 4.14 (q, $^3J_{H,H}$=7.1 Hz, 2H), 1.28 (t, $^3J_{H,H}$=7.1 Hz, 3H); $^{19}$F NMR (400 MHz, $(CD_3)_2SO$): δ−127.39 (s, 2F).

Method 33: (E)-3-(difluoromethyl)-5-ethoxy-3-hydroxy-pent-4-enenitrile (i84)

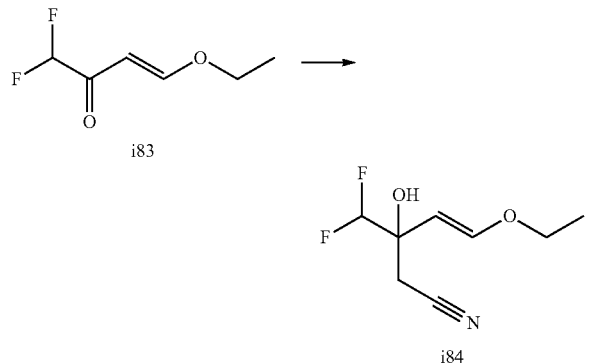

To a cooled (−70° C.) solution of n-butyl lithium 2.5M (102.9 mL, 256.7 mmol, 1 eq) in tetrahydrofuran (435 mL) is added acetonitrile (13.4 mL, 256.7 mmol, 1 eq). A white suspension is formed and is stirred at −70° C. for 1.5 hours. A solution of (E)-4-ethoxy-1,1-difluoro-but-3-en-2-one (183) (38.5 g, 256.7 mmol, 1 eq) in tetrahydrofuran (65 mL) is added to the white suspension (mixture becomes an orange solution). The mixture is stirred at −70° C. for 1 hour and slowly warmed to room temperature. Water (400 mL) is added. Then ethyl acetate (600 mL) is added. Layers are separated and aqueous layer is extracted with ethyl acetate (3×600 mL). Combined organic layers are dried over sodium sulfate and solvent is evaporated under reduced pressure. Filtration on a short pad of silica gel, using a mixture of cyclohexane/ethyl acetate (3:1) as eluent, gives the desired product 184 as a dark orange oil (43.4 g, 88%). $^1$H NMR (400 MHz, (CD$_3$)$_2$SO): δ 6.66 (d, $^3J_{H,H}$=12.8 Hz, 1H), 6.20 (s, 1H), 5.79 (t, $^2J_{H,F}$=55.8 Hz, 1H), 4.75 (d, $^3J_{H,H}$=12.8 Hz, 1H), 3.74 (q, $^3J_{H,H}$=7.0 Hz, 2H), 2.88 (d, $^3J_{H,H}$=16.8 Hz, 1H), 2.81 (d, $^3J_{H,H}$=16.8 Hz, 1H), 1.21 (t, $^3J_{H,H}$=7.0 Hz, 3H); $^{19}$F NMR (400 MHz, (CD$_3$)$_2$SO): δ−129.32 (d, $^2J_{F,F}$=311.2 Hz, 1F), −130.05 (d, $^2J_{F,F}$=311.2 Hz, 1F).

Method 34: 4-(difluoromethyl)pyridin-2-amine (i65)

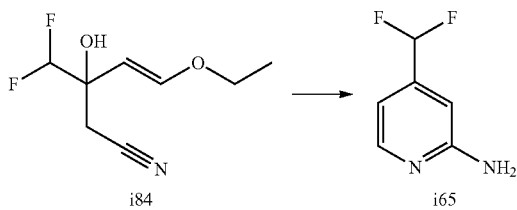

To a solution of (E)-3-(difluoromethyl)-5-ethoxy-3-hydroxy-pent-4-enenitrile (i84) (8.1 g, 42.4 mmol, 1 eq) in acetic acid (80 mL) is added O-methylhydroxylamine hydrochloride (Fluorochem, product number 078603) (10.6 g, 127.2 mmol, 3 eq). Mixture is stirred at 50° C. for 7 hours. Then reaction mixture is cooled down to room temperature and hydrobromic acid in acetic acid (33%) (14.2 mL, 84.8 mmol, 2 eq) is added. Reaction mixture is stirred at 90° C. overnight. Reaction mixture is degassed and placed under nitrogen. Reaction mixture is maintained at room temperature with a water bath with ice while zinc powder (8.12 g, 127.2 mmol, 3 eq) is added portionwise. Reaction mixture is stirred 3 h at room temperature. Mixture is filtered over a short pad of celite and the cake is washed with ethyl acetate. Then the major part of the solvent is removed under reduced pressure. 60 mL of aqueous ammonium hydroxide (28%) is added. Aqueous layer is extracted with dichloromethane (3×150 mL). Combined organic layers are dried over sodium sulfate. Compound i65 is recrystallized from dichloromethane and heptane as anti-solvent (solvent switch at the rotavap). Compound i65 is collected, as a light yellow solid, by filtration (5.12 g, 84%).

Method 35: 9-[4-chloro-6-(3-oxa-9-azabicyclo[3.3.1]nonan-9-yl)-1,3,5-triazin-2-yl]-3,7-dioxa-9-azabicyclo[3.3.1]nonane (i89)

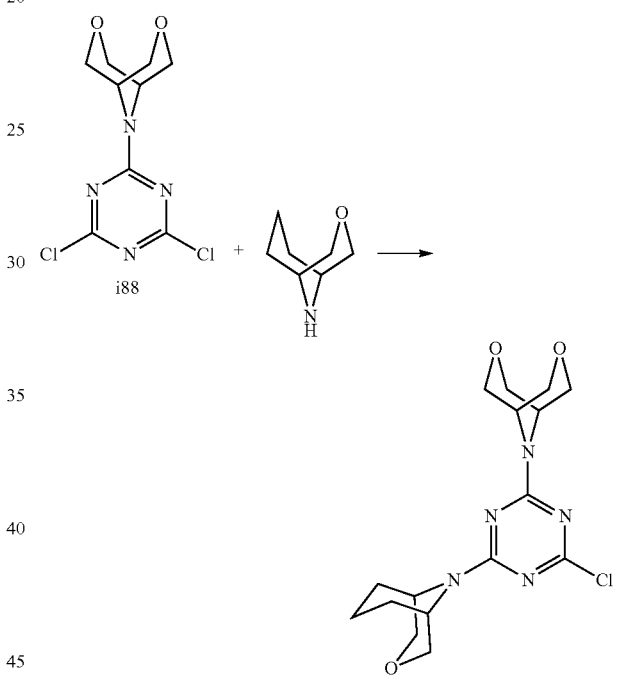

To a solution of 3-oxa-9-azabicyclo[3.3.1]nonane hydrochloride (176 mg, 1.20 mmol, 1.05 eq.) and N,N-diisopropylethylamine (0.42 mL, 2.40 mmol, 2.1 eq.) in 1,4-dioxane (5 mL) a solution of 188 (300 mg, 1.14 mmol, 1 eq.) in 1,4-dioxane (1 mL) is added. The resulting mixture is heated for 3 hours (75° C.). Then, ethyl acetate (20 mL) and saturated aqueous sodium bisulfate (20 mL) are added. The phases are separated and the organic layer is washed with saturated aqueous sodium bisulfate (2×20 mL). The organic layer is dried over anhydrous sodium sulfate and the solvent is removed under reduced pressure. The crude mixture is purified by automated flash chromatography (SiO$_2$, cyclohexane/ethyl acetate 2:1 to 0:1) to afford the title compound i89 as a colorless solid (297 mg, 75%). $^1$H NMR (400 MHz, (CD$_3$)$_2$SO): δ 4.58 (m, 1H), 4.44 (m, 1H), 4.40 (m, 1H), 4.32 (m, 1H), 4.00-3.97 (m, 4H), 3.94-3.90 (m, 2H), 3.72-3.64 (m, 6H), 2.46 (m, 1H), 1.90-1.70 (m, 4H), 1.53 (m, 1H). MS (MALDI): m/z=368.0 ([M+H]$^+$).

Preparation of Compounds of the Invention

Compound 1: 4-(difluoromethyl)-5-(4,6-dimorpholino-1,3,5-triazin-2-yl)pyridin-2-amine (1)

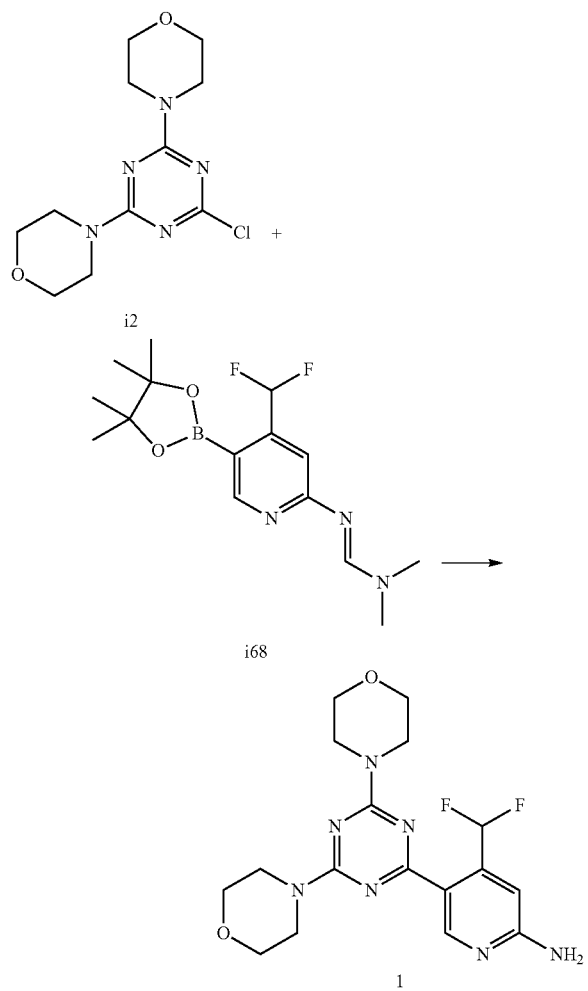

According to general procedure 1, compound 1 is obtained from starting materials i2 and i68 in 73% yield as a colorless solid. $^1$H NMR (400 MHz, CDCl$_3$): δ 9.02 (s, 1H), 7.65 (t, $^2J_{H,F}$=55 Hz, 1H), 6.83 (s, 1H), 4.85 (br s, 2H), 3.89-3.79 (m, 8H), 3.77-3.72 (m, 8H); $^{19}$F NMR (376 MHz, CDCl$_3$): δ−115.9 (s, 2F); MS (MALDI): m/z=393.9 ([M+H]$^+$).

Compound 2: 4-(difluoromethyl)-5-(4,6-dimorpholino-1,3,5-triazin-2-yl)pyrimidin-2-amine (2)

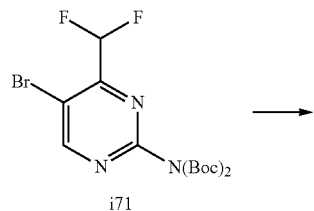

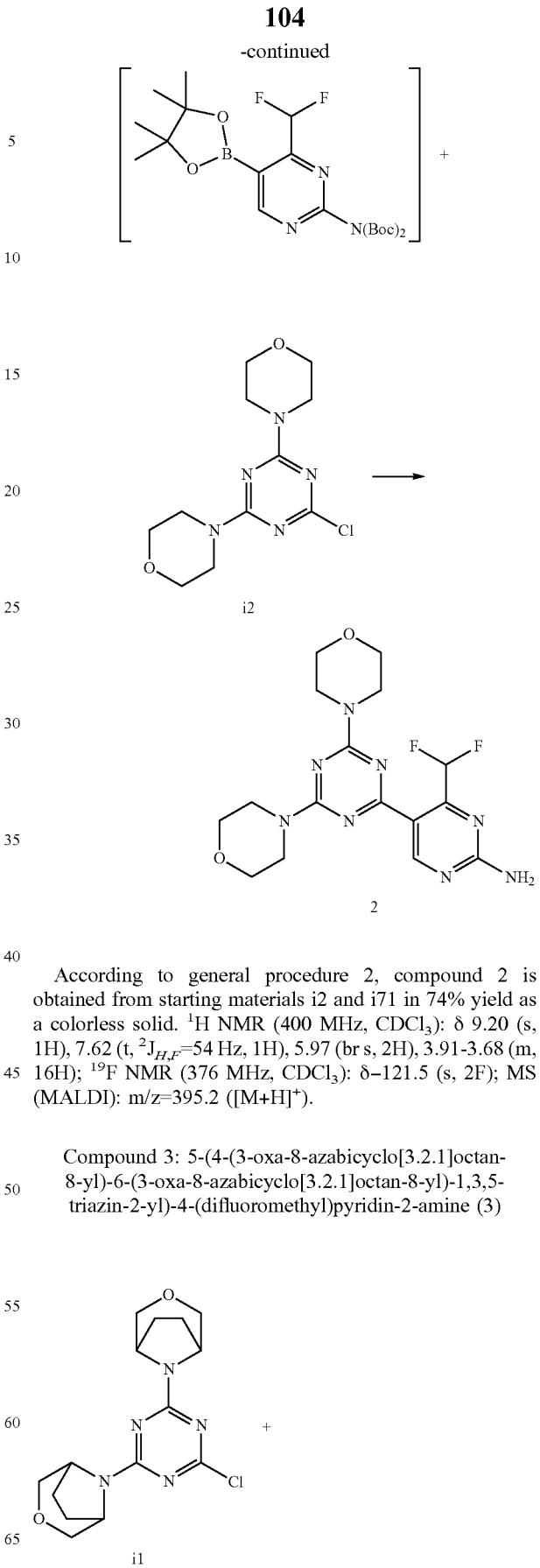

According to general procedure 2, compound 2 is obtained from starting materials i2 and i71 in 74% yield as a colorless solid. $^1$H NMR (400 MHz, CDCl$_3$): δ 9.20 (s, 1H), 7.62 (t, $^2J_{H,F}$=54 Hz, 1H), 5.97 (br s, 2H), 3.91-3.68 (m, 16H); $^{19}$F NMR (376 MHz, CDCl$_3$): δ−121.5 (s, 2F); MS (MALDI): m/z=395.2 ([M+H]$^+$).

Compound 3: 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine (3)

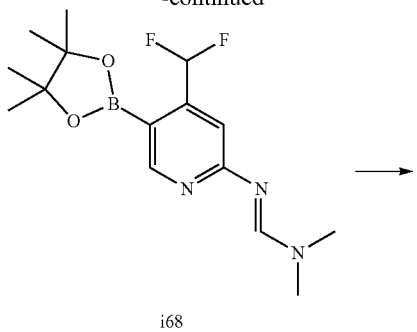

i68

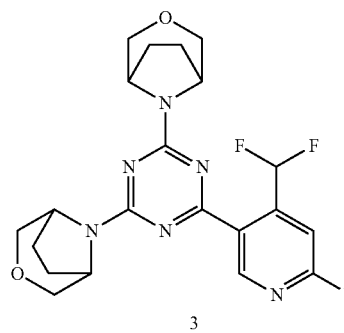

3

According to general procedure 1, compound 3 is obtained from starting materials i1 and i68 in 75% yield as a colorless solid. ¹H NMR (400 MHz, CDCl₃): δ 9.04 (s, 1H), 7.71 (t, $^2J_{H,F}$=55 Hz, 1H), 6.83 (s, 1H), 4.89 (br s, 2H), 4.71-4.64 (m, 4H), 3.79-3.76 (m, 4H), 3.67-3.62 (m, 4H), 2.09-1.98 (m, 8H); ¹⁹F NMR (376 MHz, CDCl₃): δ–115.4-(–117.3) (m, 2F); MS (MALDI): m/z=446.3 ([M+H]⁺).

Compound 4: 5-(4-(3-oxa-8-azabicyclo[3.2.1]octan-8-yl)-6-morpholino-1,3,5-triazin-2-yl)-4-(difluoromethyl)pyridin-2-amine (4)

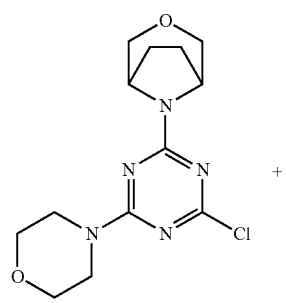

i12

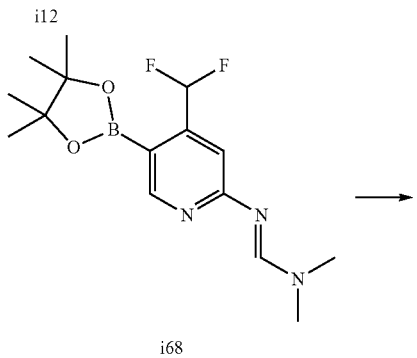

i68

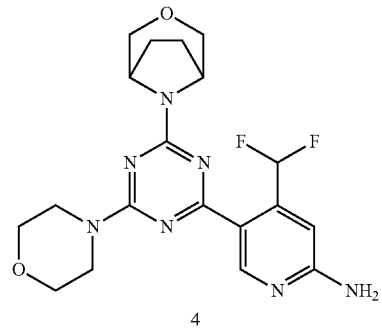

4

According to general procedure 1, compound 4 is obtained from starting materials i12 and i68 in 57% yield as a colorless solid. ¹H NMR (400 MHz, CDCl₃): δ 9.03 (s, 1H), 7.68 (m, 1H), 6.83 (s, 1H), 4.94 (br s, 2H), 4.70-4.65 (m, 2H), 3.93-3.57 (m, 12H), 2.14-1.92 (m, 4H); ¹⁹F NMR (376 MHz, CDCl₃): δ–116.0-(–116.2) (m, 2F); MS (MALDI): m/z=420.6 ([M+H]⁺).

Compound 5: 5-(4-(3-oxa-8-azabicyclo[3.2.1]octan-8-yl)-6-morpholino-1,3,5-triazin-2-yl)-4-(difluoromethyl)pyrimidin-2-amine (5)

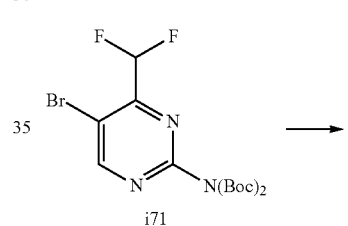

i71

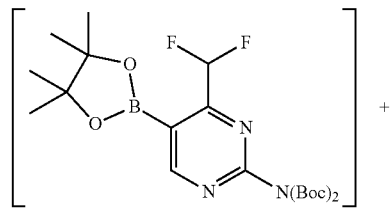

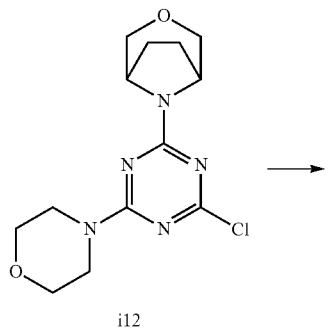

i12

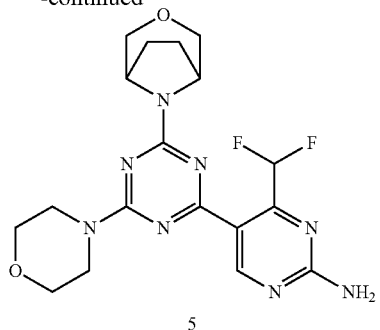

5

According to general procedure 2, compound 5 is obtained from starting materials i71 and i12 in 50% yield as a colorless solid. $^1$H NMR (400 MHz, CDCl$_3$): δ 9.23 (s, 1H), 7.65 (t, $^2J_{H,F}$=54 Hz, 1H), 5.66 (br s, 2H), 4.68 (m, 2H), 3.90-3.61 (m, 12H), 2.13-1.92 (4H); $^{19}$F NMR (376 MHz, CDCl$_3$): δ−120.4-(−121.5) (m, 2F); MS (MALDI): m/z=420.9 ([M+H]$^+$).

Compound 6: 5-(4,6-bis((S)-3-methylmorpholino)-1,3,5-triazin-2-yl)-4-(difluoromethyl)pyridin-2-amine (6)

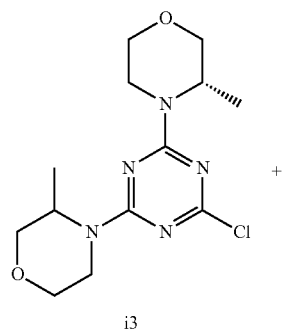

i3

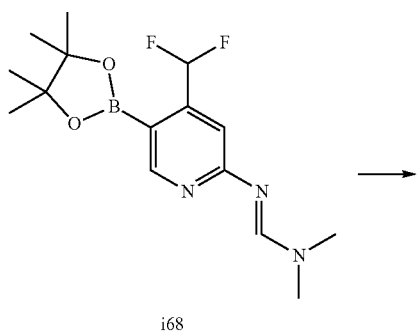

i68

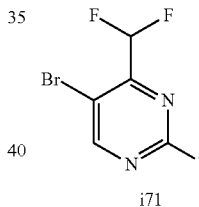

6

According to general procedure 1, compound 6 is obtained from starting materials i3 and i68 in 79% yield as a colorless solid. $^1$H NMR (400 MHz, CDCl$_3$): δ 8.87 (s, 1H), 7.70 (t, $^2J_{H,F}$=55 Hz, 1H), 6.86 (s, 1H), 5.48 (br s, 2H), 4.73-4.72 (m, 2H), 4.41-4.38 (m, 2H), 3.98 (dd, $J_{H,H}$=11.6, 3.8 Hz, 2H), 3.78 (d, $J_{H,H}$=12 Hz, 2H), 3.67 (dd, $J_{H,H}$=12, 3.2 Hz, 2H), 3.52 (td, $J_{H,H}$=12, 3.0 Hz, 2H), 3.27 (td, $J_{H,H}$=13, 3.8 Hz, 2H), 1.33 (d, $^3J_{H,H}$=6.8 Hz, 6H); $^{19}$F NMR (376 MHz, CDCl$_3$): δ−115.4-(−116.2) (m, 2F); MS (MALDI): m/z=421.9 ([M+H]$^+$).

Compound 7: 5-(4,6-bis((S)-3-methylmorpholino)-1,3,5-triazin-2-yl)-4-(difluoromethyl)pyrimidin-2-amine (7)

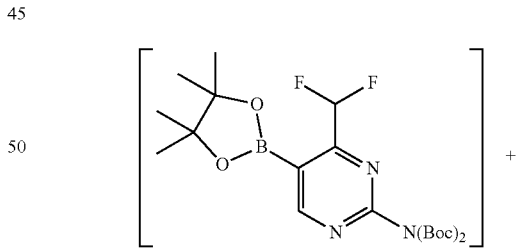

i71

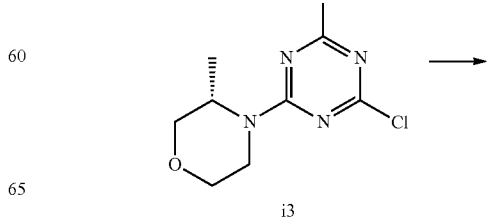

i3

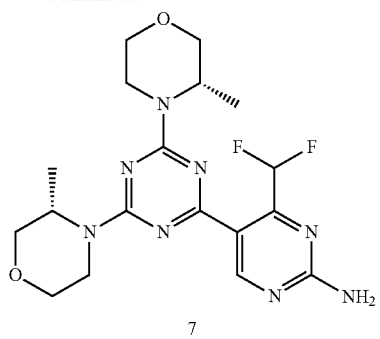

7

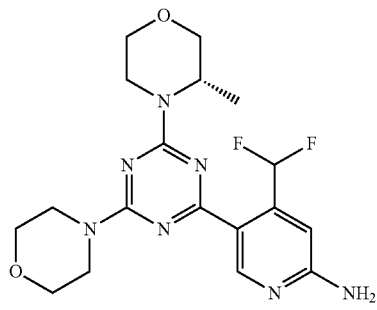

8

According to general procedure 2, compound 7 is obtained from starting materials i71 and i3 in 52% yield as a colorless solid. $^1$H NMR (400 MHz, CDCl$_3$): δ 9.24 (s, 1H), 7.66 (t, $^2J_{H,F}$=54 Hz, 1H), 5.77 (br s, 2H), 4.73 (br s, 2H), 4.45-4.32 (m, 2H), 3.98 (dd, $J_{H,H}$=12, 3.6 Hz, 2H), 3.78 (d, $J_{H,H}$=12 Hz, 2H), 3.67 (dd, $J_{H,H}$=11, 2.8 Hz, 2H), 3.52 (td, $J_{H,H}$=12, 2.8 Hz, 2H), 3.27 (td, $J_{H,H}$=13, 3.2 Hz, 2H), 1.33 (d, $^3J_{H,H}$=6.8 Hz, 6H); $^{19}$F NMR (376 MHz, CDCl$_3$): δ−120.5-(−122.7) (m, 2F); MS (MALDI): m/z=423.3 ([M+H]$^+$).

According to general procedure 1, compound 8 is obtained from starting materials i13 and i68 in 47% yield as a colorless solid. $^1$H NMR (400 MHz, CDCl$_3$): δ 9.03 (s, 1H), 7.70 (t, $^2J_{H,F}$=55 Hz, 1H), 6.84 (s, 1H), 4.78 (br s, 2H), 4.75 (m, 1H), 4.42-4.38 (m, 1H), 4.00-3.96 (m, 1H), 3.84-3.66 (m, 10H), 3.55-3.50 (m, 1H), 3.30-3.25 (m, 1H), 1.33 (d, $J_{H,H}$=6.8 Hz, 3H); $^{19}$F NMR (376 MHz, CDCl$_3$): δ−116.1-(−115.9) (m, 2F); MS (MALDI): m/z=408.9 ([M+H]$^+$).

Compound 8: (S)-4-(difluoromethyl)-5-(4-(3-methylmorpholino)-6-morpholino-1,3,5-triazin-2-yl)pyridin-2-amine (8)

Compound 9: (S)-4-(difluoromethyl)-5-(4-(3-methylmorpholino)-6-morpholino-1,3,5-triazin-2-yl)pyrimidin-2-amine (9)

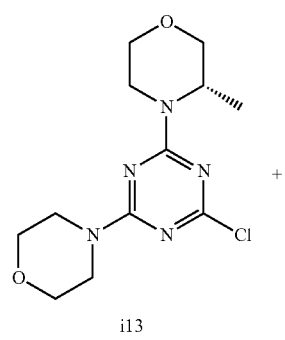

i13

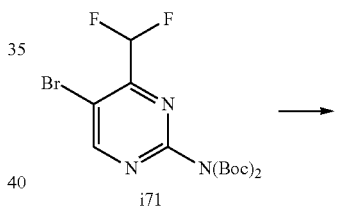

i71

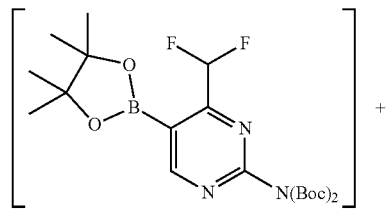

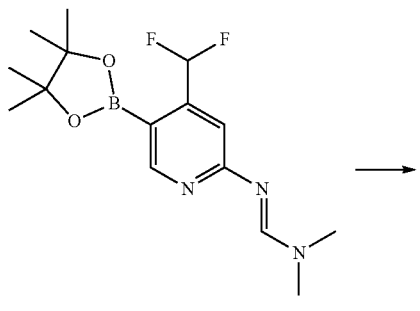

i68

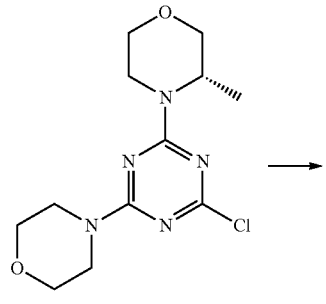

i13

111

-continued

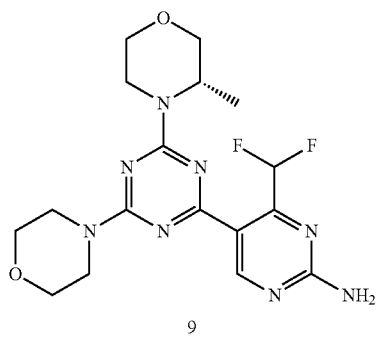

9

According to general procedure 2, compound 9 is obtained from starting materials i71 and i13 in 60% yield as a colorless solid. $^1$H NMR (400 MHz, CDCl$_3$): δ 9.24 (s, 1H), 7.66 (t, $^2J_{H,F}$=54 Hz, 1H), 5.67 (br s, 2H), 4.74 (m, 1H), 4.41-4.38 (m, 1H), 4.00-3.97 (m, 1H), 3.90-3.72 (m, 9H), 3.68-3.36 (m, 1H), 3.56-3.49 (m, 1H), 3.32-3.25 (m, 1H), 1.33 (d, $^3J_{H,H}$=6.9 Hz, 3H); $^{19}$F NMR (376 MHz, CDCl$_3$): δ−121.3-(−121.6) (m, 2F); MS (MALDI): m/z=409.4 ([M+H]$^+$).

Compound 10: 5-(4-(3-oxa-8-azabicyclo[3.2.1]octan-8-yl)-6-((S)-3-methylmorpholino)-1,3,5-triazin-2-yl)-4-(difluoromethyl)pyridin-2-amine (10)

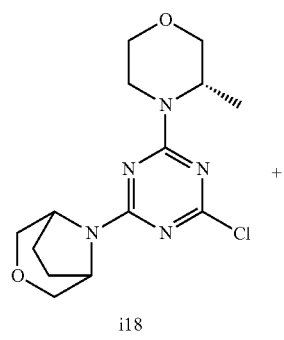

i18

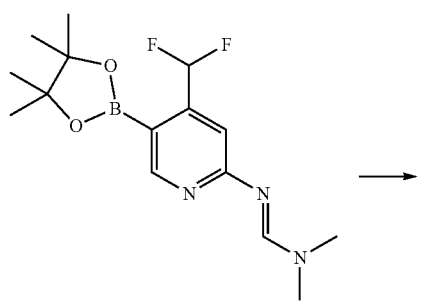

i68

112

-continued

10

According to general procedure 1, compound 10 is obtained from starting materials i18 and i68 in 42% yield as a colorless solid. $^1$H NMR (400 MHz, CDCl$_3$): δ 9.04 (s, 1H), 7.69 (t, $^2J_{H,F}$=55 Hz, 1H), 6.84 (s, 1H), 4.85 (br s, 2H), 4.71-4.65 (m, 3H), 4.42-4.39 (m, 1H), 3.98-3.95 (m, 1H), 3.79-3.76 (m, 3H), 3.70-3.65 (m, 3H), 3.56-3.53 (m, 1H), 3.30-3.27 (m, 1H), 2.10-1.99 (m, 4H), 1.33 (m, 3H); $^{19}$F NMR (376 MHz, CDCl$_3$): δ−115.9-(−116.2) (m, 2F); MS (MALDI): m/z=434.2 ([M+H]$^+$).

Compound 11: 5-(4-(3-oxa-8-azabicyclo[3.2.1]octan-8-yl)-6-((S)-3-methylmorpholino)-1,3,5-triazin-2-yl)-4-(difluoromethyl)pyrimidin-2-amine (11)

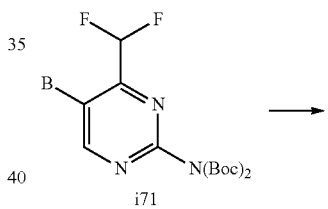

i71

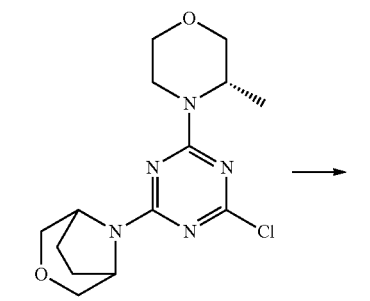

i18

-continued

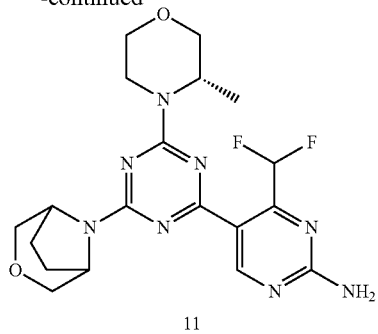

11

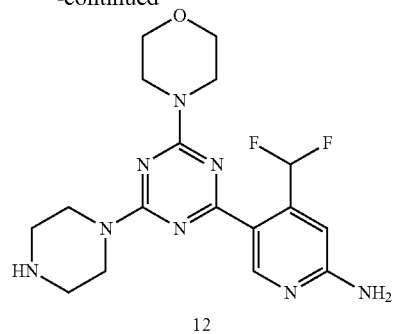

12

According to general procedure 2, compound 11 is obtained from starting materials i71 and i18 in 46% yield as a colorless solid. $^1$H NMR (400 MHz, CDCl$_3$): δ 9.25 (s, 1H), 7.68 (t, $^2J_{H,F}$=55 Hz, 1H), 5.81 (br s, 2H), 4.71-4.65 (m, 3H), 4.42-4.38 (m, 1H), 4.00-3.96 (m, 1H), 3.81-3.60 (m, 6H), 3.55-3.50 (m, 1H), 3.31-3.24 (m, 1H), 2.11-2.00 (m, 4H), 1.37-1.28 (m, 3H); $^{19}$F NMR (376 MHz, CDCl$_3$): δ−121.5-(−121.7) (m, 2F); MS (MALDI): m/z=434.6 ([M+H]$^+$).

Compound 12: 4-(difluoromethyl)-5-(4-morpholino-6-(piperazin-1-yl)-1,3,5-triazin-2-yl)pyridin-2-amine (12)

According to general procedure 1, compound i2 is obtained from starting materials i68 and i14 in 86% yield as a colorless solid. $^1$H NMR (400 MHz, (CD$_3$)$_2$SO): δ 8.85 (s, 1H), 7.74 (t, $^2J_{H,F}$=55 Hz, 1H), 6.84 (s, 2H), 6.75 (s, 1H), 3.82-3.70 (m, 8H), 3.69-3.60 (m, 4H), 2.88-2.80 (m, 4H); $^{19}$F NMR (376 MHz, (CD$_3$)$_2$SO): δ−115.4 (s, 2F); MS (MALDI): m/z=393.8 ([M+H]$^+$).

Compound 13: 4-(difluoromethyl)-5-(4-morpholino-6-(piperazin-1-yl)-1,3,5-triazin-2-yl)pyrimidin-2-amine (13)

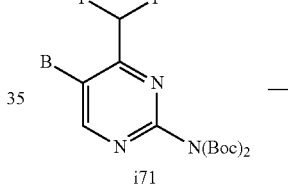

i71

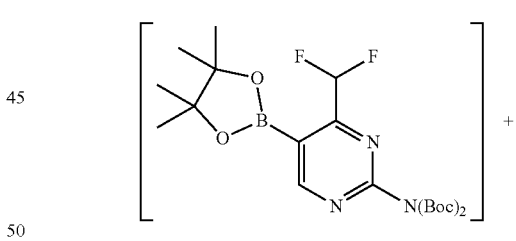

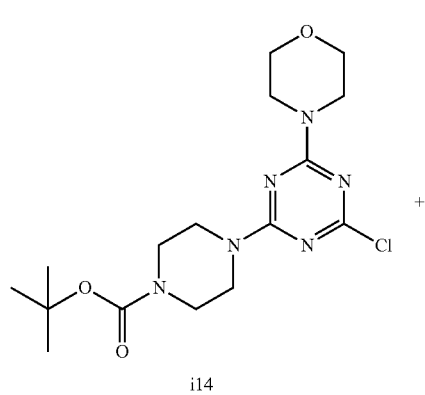

i14

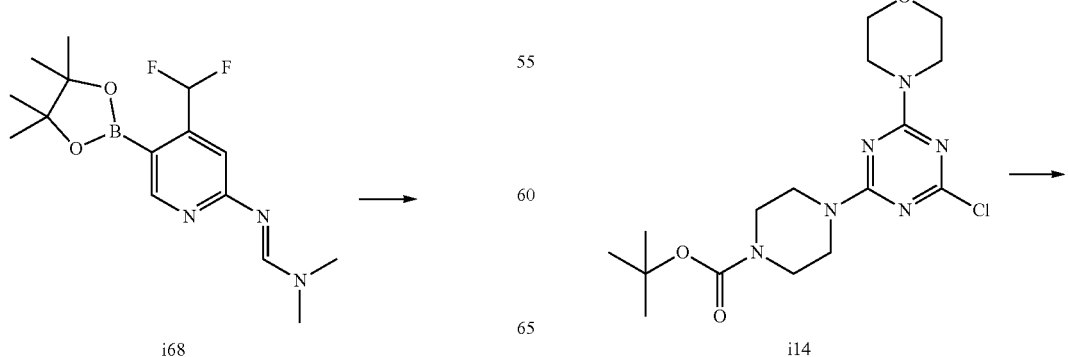

i68 i14

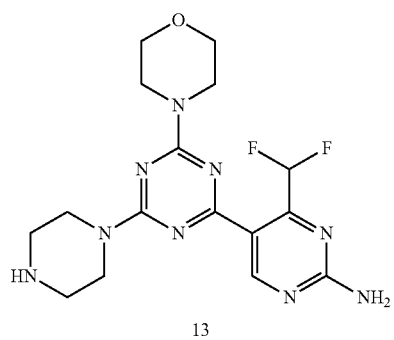

13

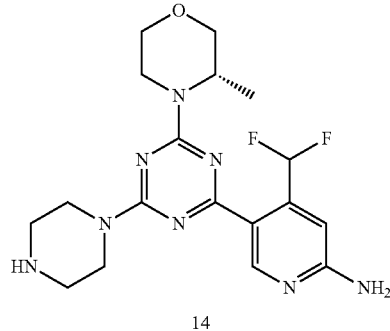

14

According to general procedure 2, compound 13 is obtained from starting materials i71 and i14 in 55% yield as a colorless solid. $^1$H NMR (400 MHz, CDCl$_3$): δ 9.23 (s, 1H), 7.64 (t, $^2J_{H,F}$=55 Hz, 1H), 5.60 (br s, 2H), 3.83-3.75 (m, 12H), 2.94-2.88 (m, 4H); $^{19}$F NMR (376 MHz, CDCl$_3$): δ−111.4 (s, 2F); MS (MALDI): m/z=394.1 ([M+H]$^+$).

Compound 14: (S)-4-(difluoromethyl)-5-(4-(3-methylmorpholino)-6-(piperazin-1-yl)-1,3,5-triazin-2-yl)pyridin-2-amine (14)

According to general procedure 1, compound 14 is obtained from starting materials i21 and i68 in 47% yield as a colorless solid. $^1$H NMR (400 MHz, CDCl$_3$): δ 9.02 (s, 1H), 7.67 (t, $^2J_{H,F}$=56 Hz, 1H), 6.84 (s, 1H), 4.90 (br s, 2H), 4.74 (s, 1H), 4.40 (d, $J_{H,H}$=16 Hz, 1H), 3.98 (dd, $J_{H,H}$=4.0 Hz, 12 Hz, 1H), 3.91 (m, 4H), 3.78 (d, $J_{H,H}$=12 Hz, 1H), 3.68 (dd, $J_{H,H}$=4.0, 12 Hz, 1H), 3.56 (t, $J_{H,H}$=4.0 Hz, 1H), 3.26 (dt, $J_{H,H}$=4.0, 12 Hz, 1H), 2.99 (t, $J_{H,H}$=4.0 Hz, 4H), 1.32 (d, $J_{H,H}$=8.0 Hz, 3H); $^{19}$F NMR (376 MHz, CDCl$_3$): δ−115.9 (s, 2F); MS (MALDI): m/z=407.2 ([M+H]$^+$).

Compound 15: (S)-4-(difluoromethyl)-5-(4-(3-methylmorpholino)-6-(piperazin-1-yl)-1,3,5-triazin-2-yl)pyrimidin-2-amine (15)

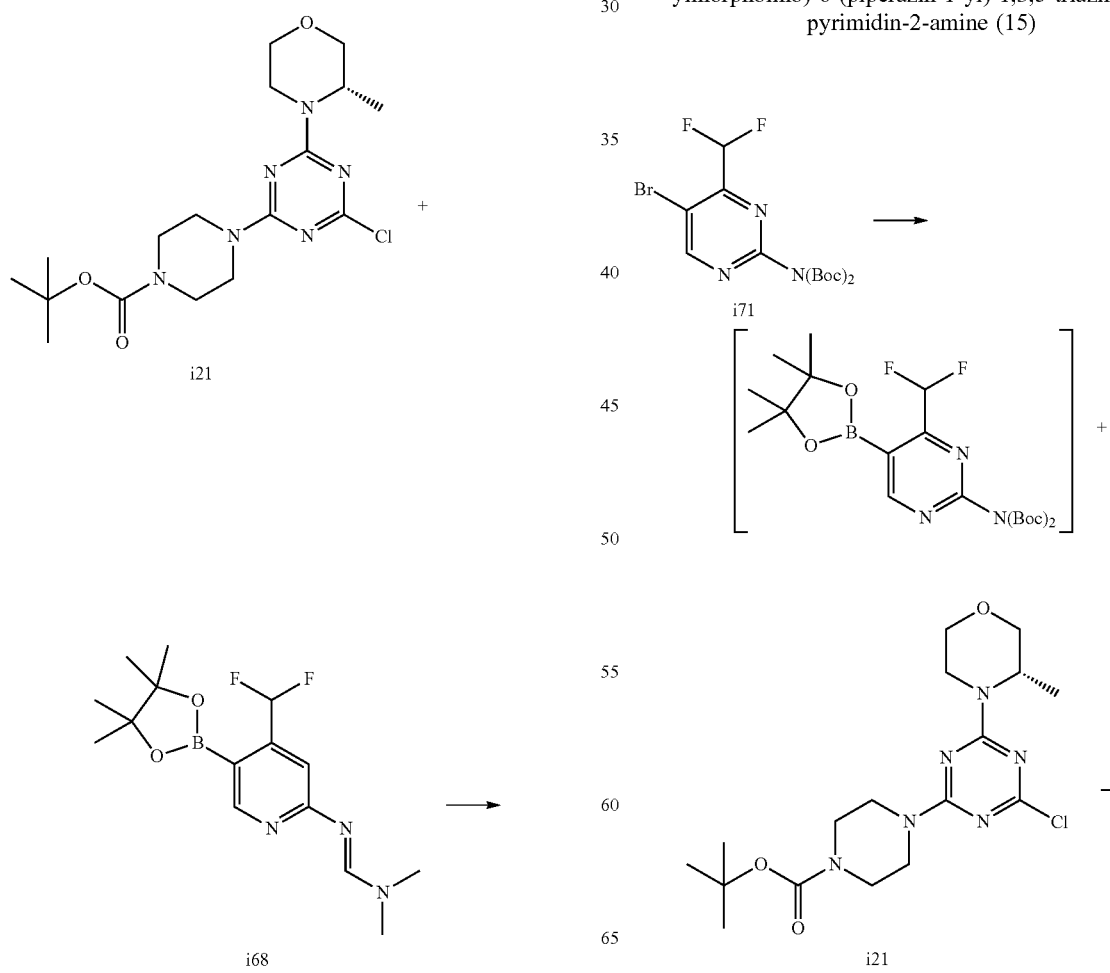

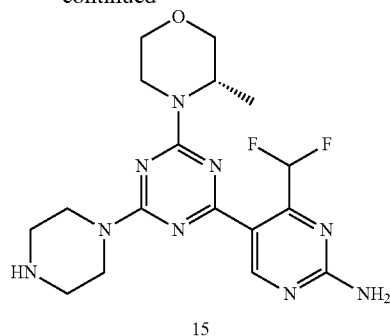

15

According to general procedure 2, compound 15 is obtained from starting materials i71 and i21 in 30% yield as a colorless solid. $^1$H NMR (400 MHz, CDCl$_3$): δ 9.24 (s, 1H), 7.66 (t, $^2J_{H,F}$=56 Hz, 1H), 5.69 (br s, 2H), 4.74 (s, 1H), 4.40 (d, $J_{H,H}$=16 Hz, 1H), 4.38 (dd, $J_{H,H}$=4.0, 12 Hz, 1H), 3.83 (m, 4H), 3.78 (d, $J_{H,H}$=12 Hz, 1H), 3.68 (dd, $J_{H,H}$=4.0, 12 Hz, 1H), 3.54 (dt, $J_{H,H}$=4.0, 12 Hz, 1H), 3.28 (dt, $J_{H,H}$=4.0, 12 Hz, 1H), 2.92 (t, $J_{H,H}$=8.0 Hz, 4H), 1.33 (t, $J_{H,H}$=8.0 Hz, 3H); $^{19}$F NMR (376 MHz, CDCl$_3$): δ−121.4 (s, 2F); MS (MALDI): m/z=408.7 ([M+H]$^+$).

Compound 16: 4-(difluoromethyl)-5-(2,6-dimorpholinopyrimidin-4-yl)pyridin-2-amine (16)

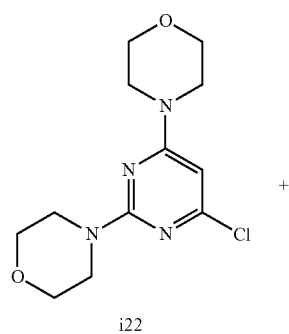

i22

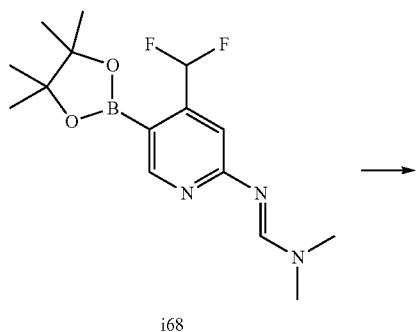

i68

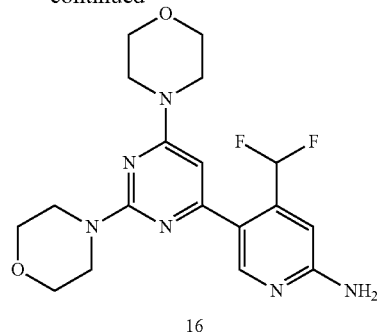

16

According to general procedure 1, compound 16 is obtained from starting materials i22 and i68 in 73% yield as a colorless solid. $^1$H NMR (400 MHz, CDCl$_3$): δ 8.31 (s, 1H), 7.30 (t, $^2J_{H,F}$=55 Hz, 1H), 6.85 (s, 1H), 6.04 (s, 1H), 4.73 (br s, 2H), 3.81-3.72 (m, 12H), 3.65-3.59 (m, 4H); $^{19}$F NMR (376 MHz, CDCl$_3$): δ−115.1 (s, 2F); MS (MALDI): m/z=393.3 ([M+H]$^+$).

Compound 17: 4'-(difluoromethyl)-2,6-dimorpholino-[4,5'-bipyrimidin]-2'-amine (17)

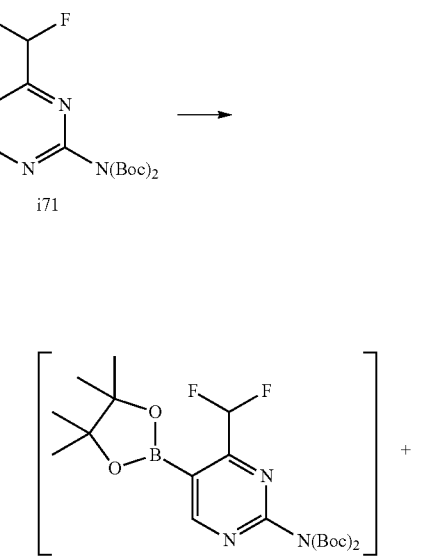

i71

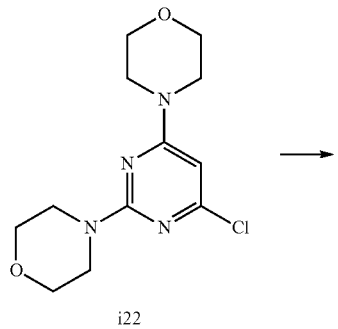

i22

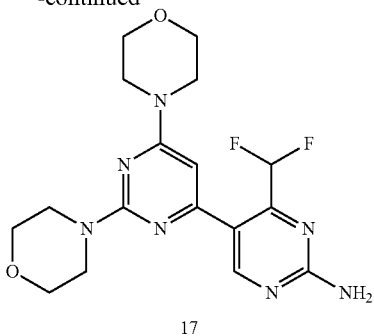

17

According to general procedure 2, compound 17 is obtained from starting materials i71 and i22 in 7% yield as a colorless solid. $^1$H NMR (400 MHz, CDCl$_3$): δ 8.60 (s, 1H), 7.11 (t, $^2J_{H,F}$=55 Hz, 1H), 6.02 (s, 1H), 5.46 (br s, 2H), 3.80-3.74 (m, 12H), 3.64-3.60 (m, 4H); $^{19}$F NMR (376 MHz, CDCl$_3$): δ−119.5 (s, 2F); MS (MALDI): m/z=394.3 ([M+H]$^+$).

Compound 18: 4-(difluoromethyl)-5-(4,6-dimorpholinopyrimidin-2-yl)pyridin-2-amine (18)

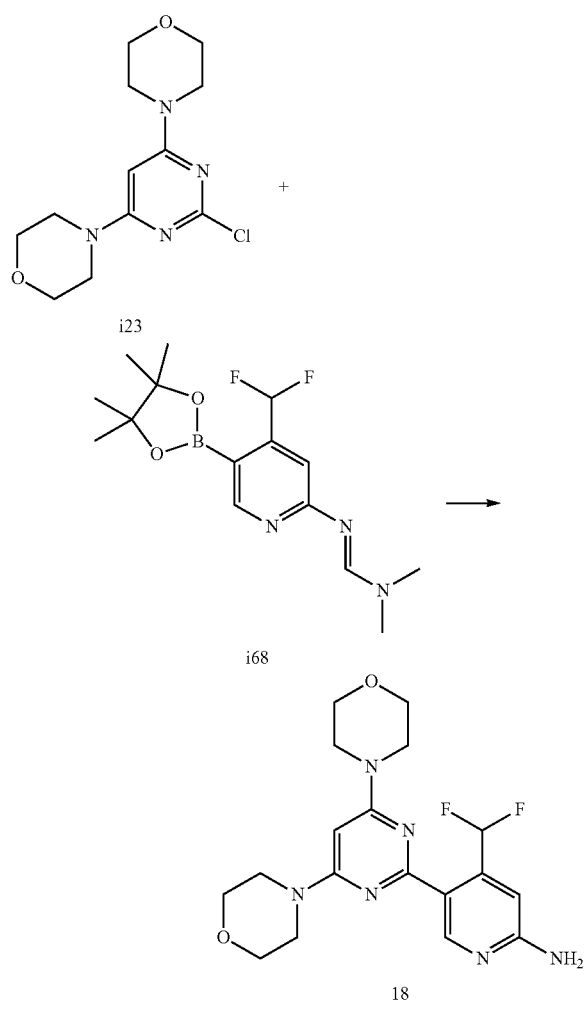

According to general procedure 1, compound i8 is obtained from starting materials i23 and i68 in 89% yield as a colorless solid. $^1$H NMR (400 MHz, CDCl$_3$): δ 8.94 (s, 1H), 7.61 (t, $^2J_{H,F}$=55 Hz, 1H), 6.83 (s, 1H), 5.50 (s, 1H), 4.74 (br s, 2H), 3.82-3.78 (m, 8H), 3.61-3.57 (m, 8H); $^{19}$F NMR (376 MHz, CDCl$_3$): δ−115.4 (s, 2F); MS (MALDI): m/z=393.3 ([M+H]$^+$).

Compound 19: 4'-(difluoromethyl)-4,6-dimorpholino-[2,5'-bipyrimidin]-2'-amine (19)

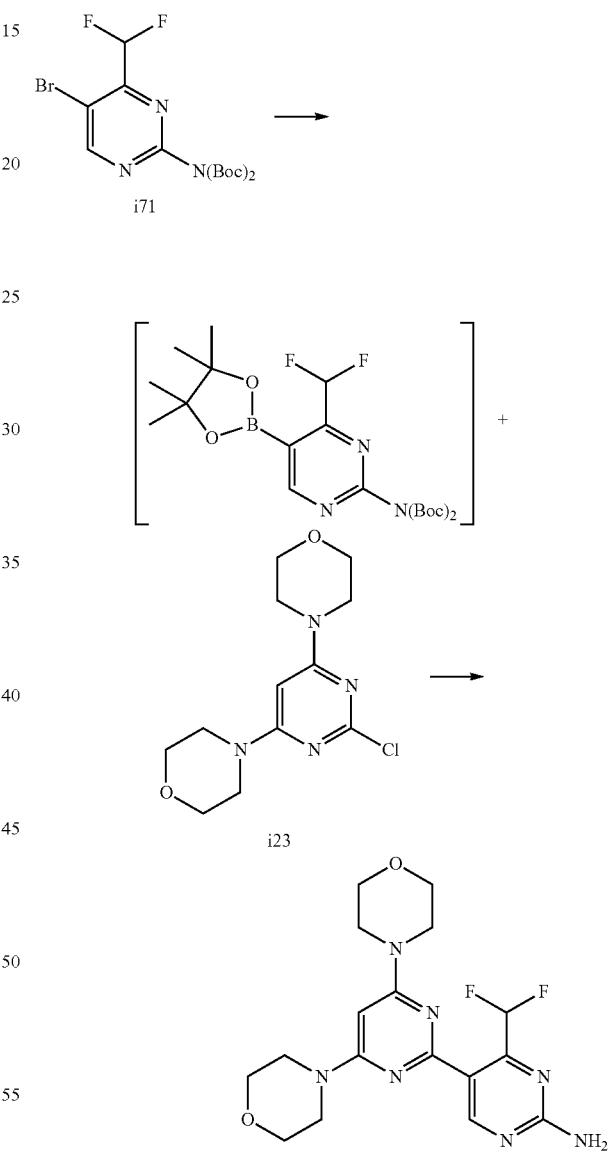

According to general procedure 2, compound 19 is obtained from starting materials i71 and i23 in 7% yield as a colorless solid. $^1$H NMR (400 MHz, CDCl$_3$): δ 9.16 (s, 1H), 7.58 (t, $^2J_{H,F}$=55 Hz, 1H), 5.75 (br s, 2H), 5.50 (s, 1H), 3.82-3.79 (m, 8H), 3.61-3.58 (m, 8H); $^{19}$F NMR (376 MHz, CDCl$_3$): δ−121.1 (s, 2F); MS (MALDI): m/z=395.3 ([M+H]$^+$).

121

Compound 20: 4-(difluoromethyl)-5-(4-morpholino-6-thiomorpholino-1,3,5-triazin-2-Yl)pyridin-2-amine (20)

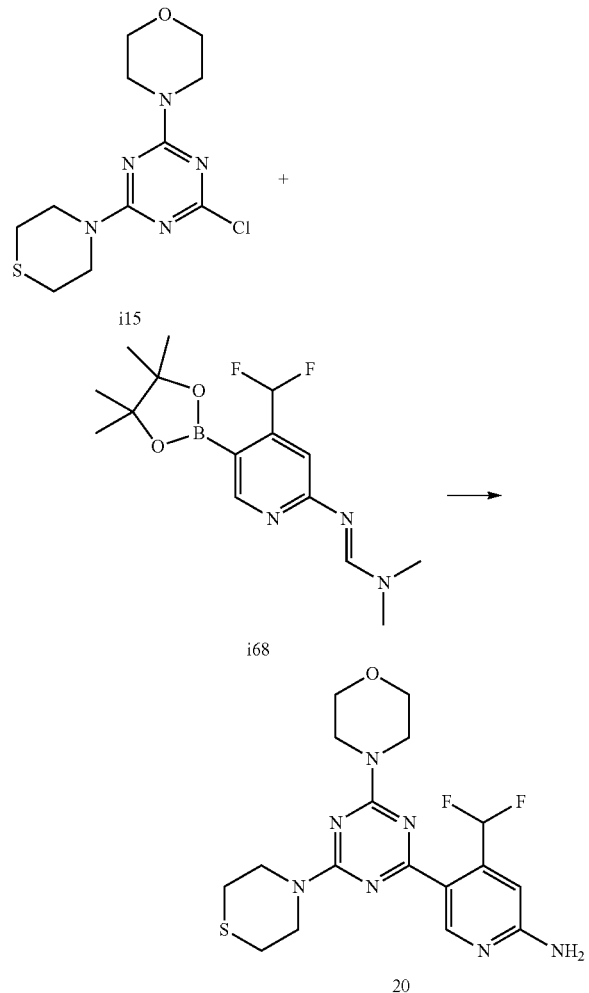

According to general procedure 1, compound 20 is obtained from starting materials i15 and i68 in 77% yield as a colorless solid. $^1$H NMR (400 MHz, CDCl$_3$): δ 9.02 (s, 1H), 7.65 (t, $^2J_{H,F}$=55 Hz, 1H), 6.84 (s, 1H), 4.83 (br s, 2H), 4.23-4.07 ((m, 4H), 3.90-3.79 ((m, 4H), 3.79-3.71 (m, 4H), 2.71-2.62 (m, 4H); $^{19}$F NMR (376 MHz, CDCl$_3$): δ−116.0 (s, 2F); MS (MALDI): m/z=410.3 ([M+H]$^+$).

Compound 21: 4-(difluoromethyl)-5-(4-morpholino-6-thiomorpholino-1,3,5-triazin-2-yl)pyrimidin-2-amine (21)

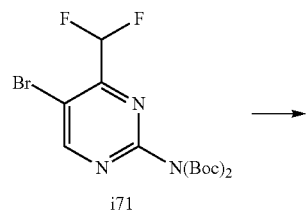

122

-continued

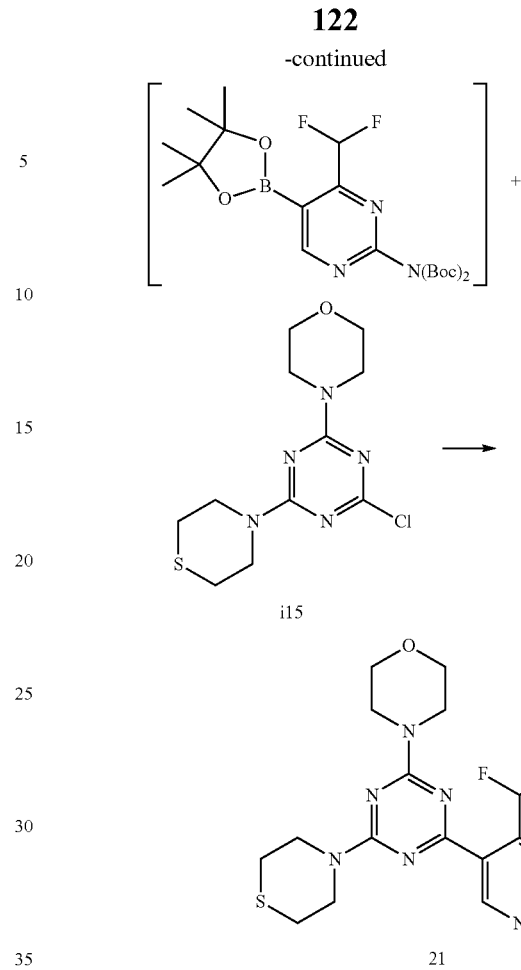

According to general procedure 2, compound 21 is obtained from starting materials i71 and i15 in 70% yield as a colorless solid. $^1$H NMR (400 MHz, CDCl$_3$): δ 9.21 (s, 1H), 7.60 (t, $^2J_{H,F}$=54 Hz, 1H), 5.90 (br s, 2H), 4.22-4.06 (m, 4H), 3.91-3.78 (m, 4H), 3.78-3.71 (m, 4H), 2.71-2.62 (m, 4H); $^{19}$F NMR (376 MHz, CDCl$_3$): δ−120.5-(−121.5) (m, 2F); MS (MALDI): m/z=411.2 ([M+H]$^+$).

Compound 22: 5-(6-(3-oxa-8-azabicyclo[3.2.1]octan-8-yl)-2-(3-oxa-8-azabicyclo[3.2.1]octan-8-yl)pyrimidin-4-yl)-4-(difluoromethyl)pyridin-2-amine (22)

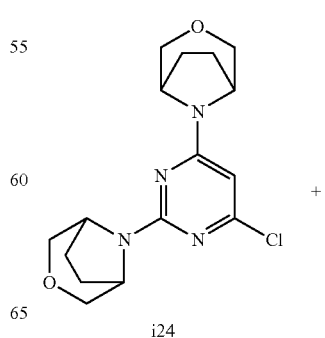

123

-continued

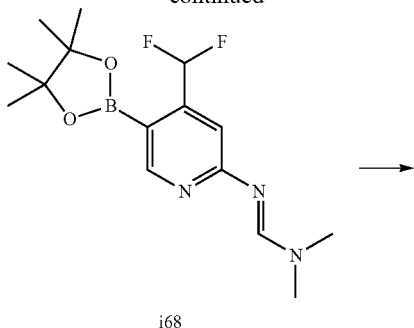

i68

→

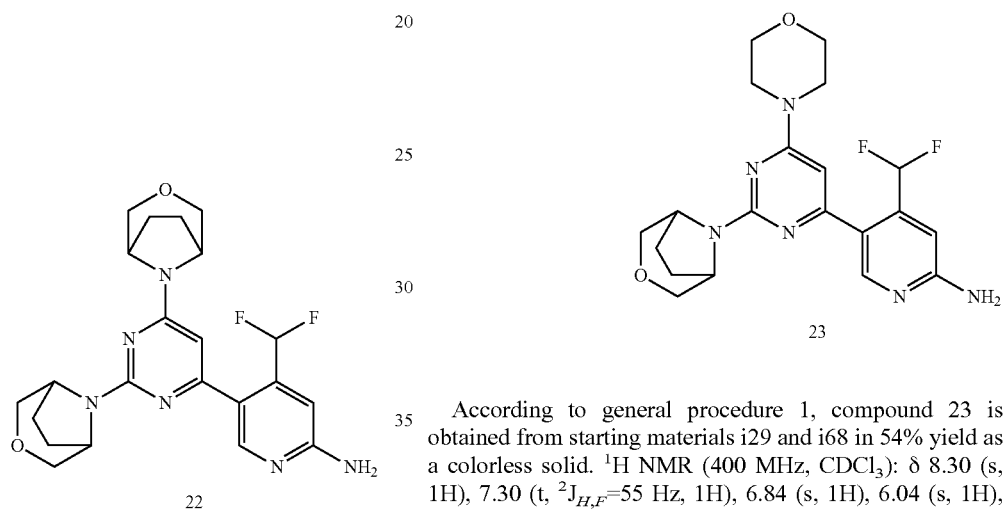

According to general procedure 1, compound 22 is obtained from starting materials i24 and i68 in 61% yield as a colorless solid. $^1$H NMR (400 MHz, (CD$_3$)$_2$SO): δ 8.34 (s, 1H), 7.55 (t, $^2J_{H,F}$=55 Hz, 1H), 6.76 (s, 1H), 6.60 (br s, 2H), 6.36 (s, 1H), 4.64-4.47 (m, 4H), 3.67-3.49 (m, 4H), 3.56-3.49 (m, 4H), 1.98-1.79 (m, 8H); $^{19}$F NMR (376 MHz, (CD$_3$)$_2$SO): δ−114.9-(−115.2) (m, 2F); MS (MALDI): m/z=445.3 ([M+H]$^+$).

Compound 23: 5-(2-(3-oxa-8-azabicyclo[3.2.1]oc-tan-8-yl)-6-morpholinopyrimidin-4-yl)-4-(difluo-romethyl)pyridin-2-amine (23)

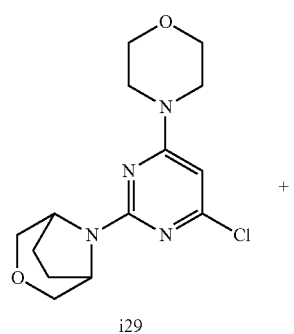

i29

124

-continued

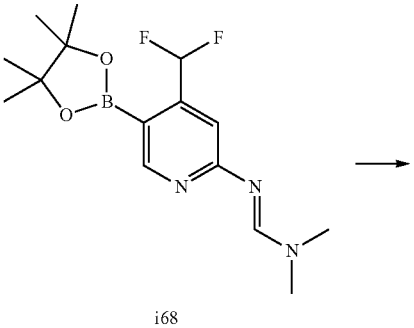

i68

→

23

According to general procedure 1, compound 23 is obtained from starting materials i29 and i68 in 54% yield as a colorless solid. $^1$H NMR (400 MHz, CDCl$_3$): δ 8.30 (s, 1H), 7.30 (t, $^2J_{H,F}$=55 Hz, 1H), 6.84 (s, 1H), 6.04 (s, 1H), 4.85 (br s, 2H), 4.62 (br s, 2H), 3.82-3.74 (m, 6H), 3.65-3.56 (m, 6H), 2.09-2.00 (m, 2H), 2.00-1.91 (m, 2H); $^{19}$F NMR (376 MHz, CDCl$_3$): δ−115.2-(−116.2) (m, 2F); MS (MALDI): m/z=419.0 ([M+H]$^+$).

Compound 24: 2-(3-oxa-8-azabicyclo[3.2.1]octan-8-yl)-4'-(difluoromethyl)-6-morpholino-[4,5'-bipyrimi-din]-2'-amine (24)

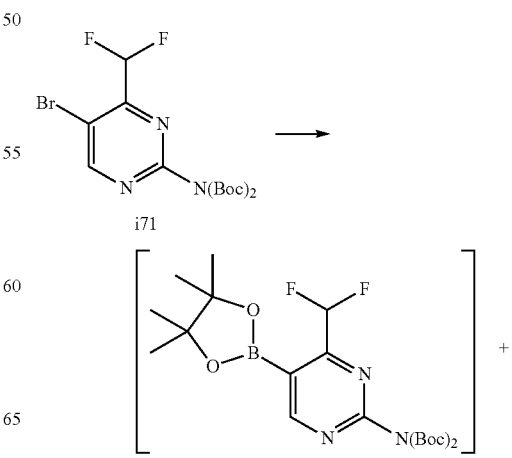

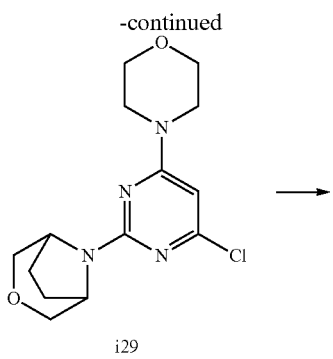

i29

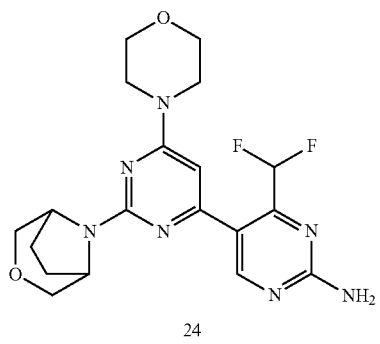

24

According to general procedure 2, compound 24 is obtained from starting materials i29 and i71 in 72% yield as a colorless solid. $^1$H NMR (400 MHz, (CD$_3$)$_2$SO): δ 8.71 (s, 1H), 7.35 (s, 2H), 7.32 (t, $^2J_{H,F}$=54 Hz, 1H), 6.45 (s, 1H), 4.54 (br s, 2H), 3.71-3.50 (m, 12H), 1.95-1.78 (m, 4H); $^{19}$F NMR (376 MHz, (CD$_3$)$_2$SO): δ–119.2 (s, 2F); MS (MALDI): m/z=420.6 ([M+H]$^+$).

Compound 25: 5-(2,6-bis((S)-3-methylmorpholino)pyrimidin-4-yl)-4-(difluoromethyl)pyridin-2-amine (25)

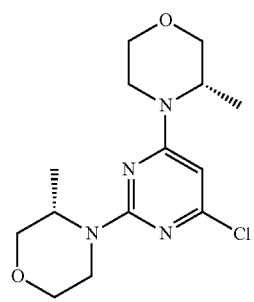

i25

+

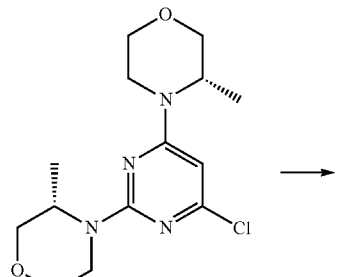

i68

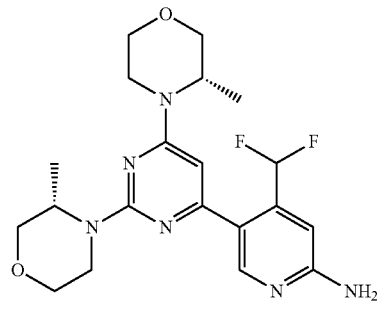

25

According to general procedure 1, compound 25 is obtained from starting materials i25 and i68 in 57% yield as a colorless solid. $^1$H NMR (400 MHz, (CD$_3$)$_2$SO): δ 8.31 (s, 1H), 7.52 (t, $^2J_{H,F}$=55 Hz, 1H), 6.76 (s, 1H), 6.59 (br s, 2H), 6.30 (s, 1H), 4.60-4.50 (m, 1H), 4.44-4.33 (m, 1H), 4.24-4.15 (m, 1H), 4.12-4.04 (m, 1H), 3.94-3.83 (m, 2H), 3.74-3.64 (m, 2H), 3.59-3.51 (m, 2H), 3.45-3.35 (m, 2H), 3.14-3.02 (m, 2H), 1.18 (t, $^3J_{H,H}$=7.2 Hz, 6H); $^{19}$F NMR (376 MHz, (CD$_3$)$_2$SO): δ–113.7-(–115.9) (m, 2F); MS (MALDI): m/z=421.1 ([M+H]$^+$).

Compound 26: 4'-(difluoromethyl)-2,6-bis((S)-3-methylmorpholino)-[4,5'-bipyrimidin]-2'-amine (26)

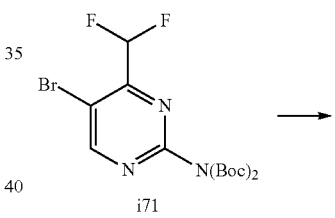

i71

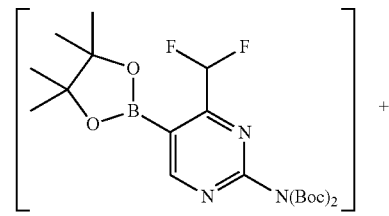

+

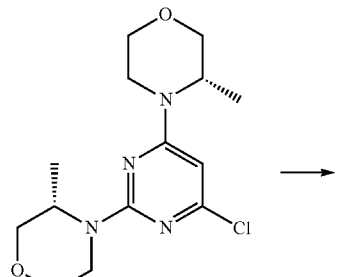

i25

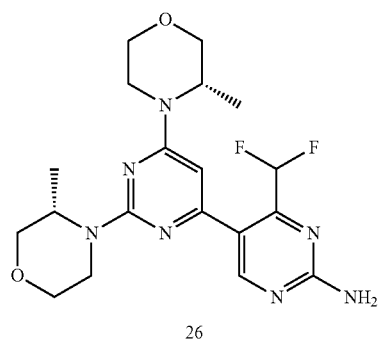

26

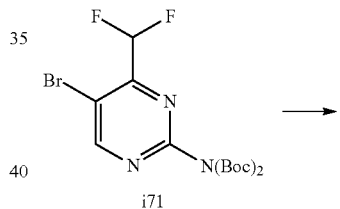

27

According to general procedure 2, compound 26 is obtained from starting materials i25 and i71 in 56% yield as a colorless solid. $^1$H NMR (400 MHz, CDCl$_3$): δ 8.60 (s, 1H), 7.14 (t, $^2J_{H,F}$=54 Hz, 1H), 5.98 (s, 1H), 5.48 (br s, 2H), 4.71-4.62 (m, 1H), 4.34-4.23 (m, 2H), 4.08-3.92 (m, 3H), 3.83-3.65 (m, 4H), 3.61-3.49 (m, 2H), 3.25 (dt, $^2J_{H,H}$=13 Hz, $^3J_{H,H}$=3.6 Hz, 2H), 1.33-1.27 (m, 6H); $^{19}$F NMR (376 MHz, CDCl$_3$): δ−119.5 (s, 1F), 119.7 (m, 1F); MS (MALDI): m/z=422.2 ([M+H]$^+$).

According to general procedure 1, compound 27 is obtained from starting materials i30 and i68 in 74% yield as a colorless solid. $^1$H NMR (400 MHz, CDCl$_3$): δ 8.31 (s, 1H), 7.30 (t, $^2J_{H,F}$=55 Hz, 1H), 6.85 (s, 1H), 6.02 (s, 1H), 4.75 (br s, 2H), 4.35-4.25 (m, 1H), 4.06-3.96 (m, 2H), 3.83-3.69 (m, 10H), 3.58 (dt, $^2J_{H,H}$=12 Hz, $^3J_{H,H}$=3.2 Hz, 1H), 3.25 (dt, $^2J_{H,H}$=13 Hz, $^3J_{H,H}$=3.8 Hz, 1H), 1.31 (d, $^3J_{H,H}$=6.8 Hz, 3H); $^{19}$F NMR (376 MHz, CDCl$_3$): δ−114.9-(−115.0) (m, 2F); MS (MALDI): m/z=407.1 ([M+H]$^+$).

Compound 27: (S)-4-(difluoromethyl)-5-(6-(3-methylmorpholino)-2-morpholinopyrimidin-4-yl)pyridin-2-amine (27)

Compound 28: (S)-4'-(difluoromethyl)-6-(3-methylmorpholino)-2-morpholino-[4,5'-bipyrimidin]-2'-amine (28)

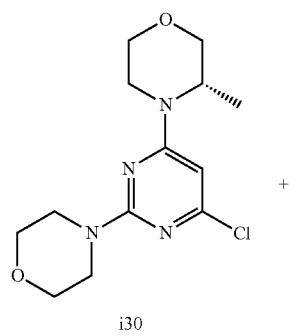

i30

+

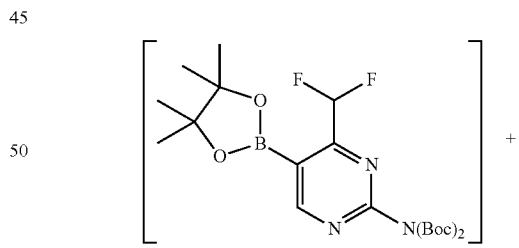

i71

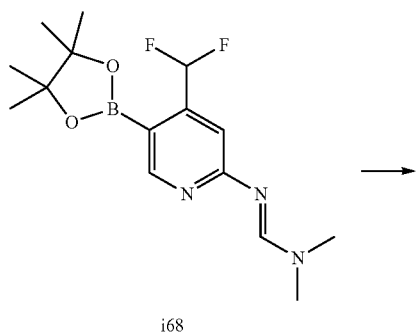

i68

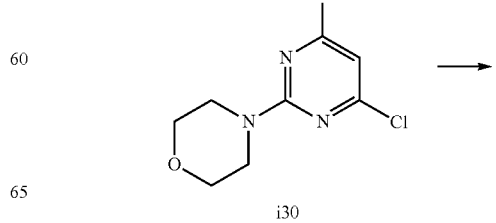

i30

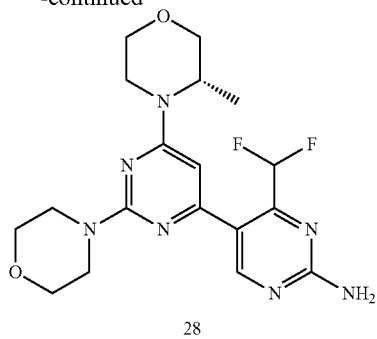

28

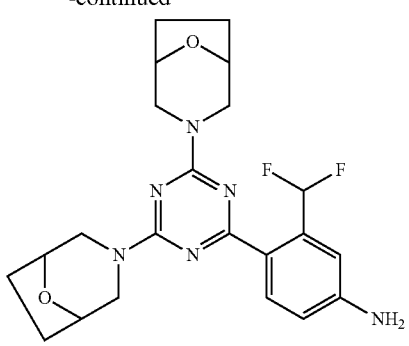

29

According to general procedure 2, compound 28 is obtained from starting materials i30 and i71 in 53% yield as a colorless solid. $^1$H NMR (400 MHz, CDCl$_3$): δ 8.60 (s, 1H), 7.13 (t, $^2J_{H,F}$=54 Hz, 1H), 6.01 (s, 1H), 5.47 (br s, 2H), 4.71-4.63 (m, 1H), 4.31 (dd, $^2J_{H,H}$=14 Hz, $^3J_{H,H}$=2.4 Hz, 1H), 3.97 (dd, $^2J_{H,H}$=11 Hz, $^3J_{H,H}$=3.4 Hz, 1H), 3.79 (t, $^3J_{H,H}$=4.6 Hz, 4H), 3.72-3.66 (m, 2H), 3.65-3.58 (m, 3H), 3.58-3.50 (m, 2H), 3.30-3.21 (m, 1H), 1.30 (d, $^3J_{H,H}$=6.8 Hz, 3H); $^{19}$F NMR (376 MHz, CDCl$_3$): δ−119.7 (br s, 2F); MS (MALDI): m/z=408.9 ([M+H]$^+$).

Compound 29: 5-(4-(8-Oxa-3-azabicyclo[3.2.1]octan-3-yl)-6-(8-oxa-3-azabicyclo[3.2.1]octan-3-yl)-1,3,5-triazin-2-yl)-4-(difluoromethyl)pyridine-2-amine (29)

According to general procedure 1, compound 29 is obtained from starting materials i68 and i81 in 89% yield as a colorless solid. $^1$H NMR (400 MHz, CDCl$_3$): δ 9.03 (s, 1H), 7.69 (t, $^2J_{H,F}$=55 Hz, 1H), 6.83 (s, 1H), 4.85 (br s, 2H), 4.50-4.24 (m, 8H), 3.28-3.12 (m, 4H), 1.94 (br s, 4H), 1.86-1.71 (m, 4H); $^{19}$F NMR (376 MHz, CDCl$_3$): δ−115.1-(−117.2)((m, 2F); MS (MALDI): m/z=446.3 ([M+H]$^+$).

Compound 30: 5-[4,6-bis(2,2-dimethylmorpholin-4-yl)-1,3,5-triazin-2-yl]-4-(difluoromethyl)pyridin-2-amine (30)

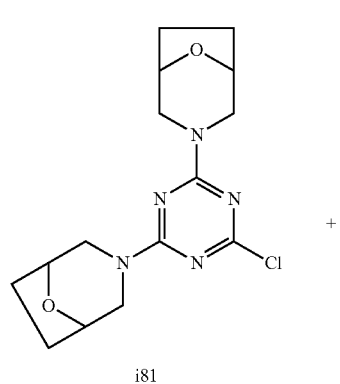

i81

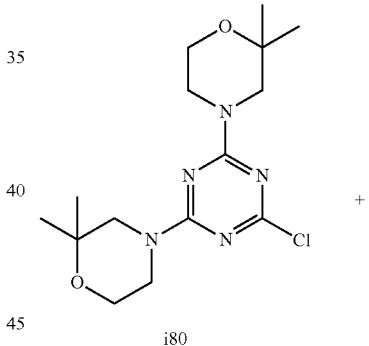

i80

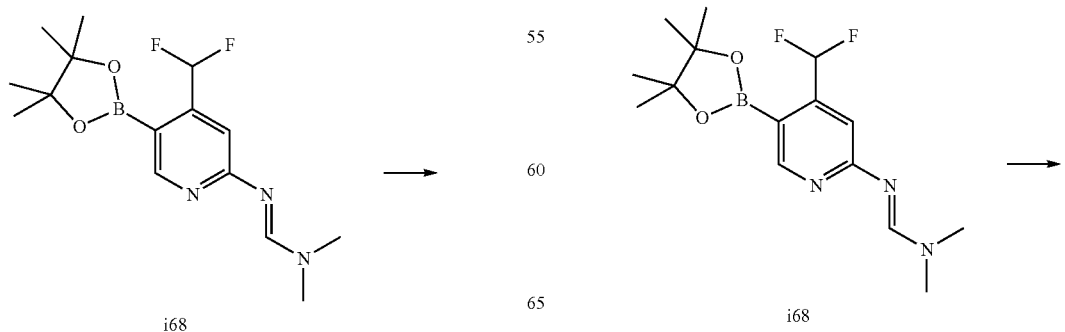

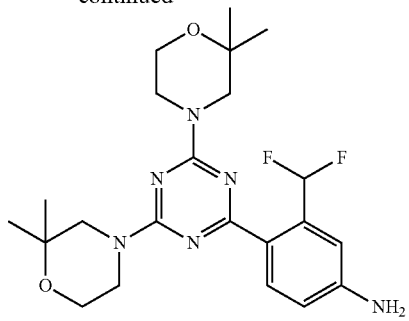

30

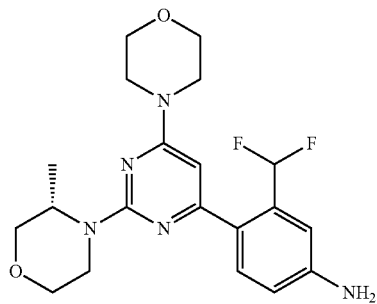

31

According to general procedure 1, compound 30 is obtained from starting materials i68 and i80 in 63% yield as a colorless solid. $^1$H NMR (400 MHz, (CD$_3$)$_2$SO): δ 8.86 (s, 1H), 7.71 (t, $^2$J$_{H,F}$=55 Hz, 1H), 6.84 (br s, 2H), 6.76 (s, 1H), 3.81-3.56 (m, 12H), 1.14 (s, 12H); MS (MALDI): m/z=450.0 ([M+H]$^+$).

Compound 31: (S)-4-(difluoromethyl)-5-(2-(3-methylmorpholino)-6-morpholinopyrimidin-4-yl)pyridin-2-amine (31)

According to general procedure 1, compound 31 is obtained from starting materials i28 and i68 in 58% yield as a colorless solid. $^1$H NMR (400 MHz, (CD$_3$)$_2$SO): δ 8.31 (s, 1H), 7.52 (t, $^2$J$_{H,F}$=55 Hz, 1H), 6.74 (s, 1H), 6.59 (br s, 2H), 6.35 (s, 1H), 4.59-4.51 (m, 1H), 4.22-4.14 (m, 1H), 3.91-3.84 (m, 1H), 3.72-3.50 (m, 10H), 3.44-3.35 (m, 1H), 3.14-3.03 (m, 1H), 1.16 (d, $^3$J$_{H,H}$=6.7 Hz, 3H); $^{19}$F NMR (376 MHz, (CD$_3$)$_2$SO): δ–113.7-(–115.3) (m, 2F); MS (MALDI): m/z=407.1 ([M+H]$^+$).

Compound 32: (S)-4'-(difluoromethyl)-2-(3-methylmorpholino)-6-morpholino-[4,5'-bipyrimidin]-2'-amine (32)

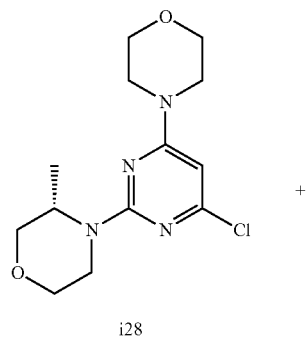

i28

+

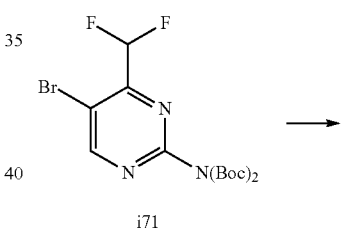

i71

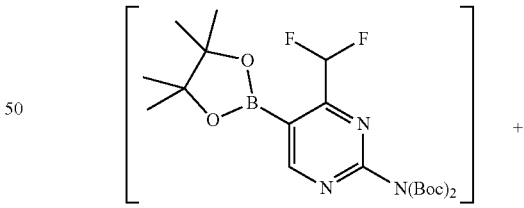

+

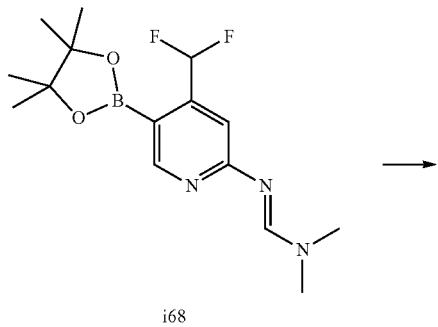

i68

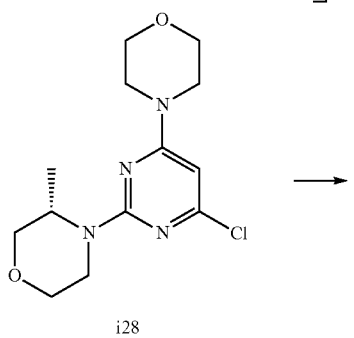

i28

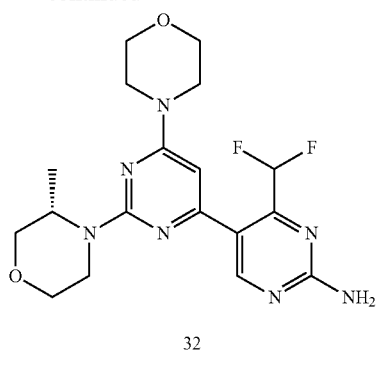

32

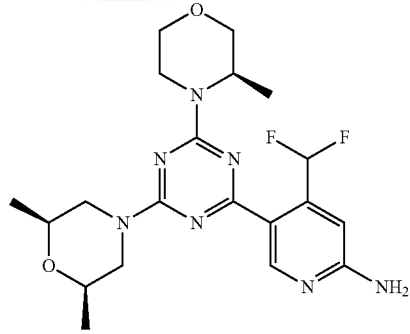

33

According to general procedure 2, compound 32 is obtained from starting materials i28 and i71 in 63% yield as a colorless solid. $^1$H NMR (400 MHz, CDCl$_3$): δ 8.60 (s, 1H), 7.13 (t, $^2J_{H,F}$=54 Hz, 1H), 5.99 (s, 1H), 5.46 (br s, 2H), 4.34-4.25 (m, 1H), 4.06-3.97 (m, 2H), 3.82-3.68 (m, 10H), 3.58 (dt, $^2J_{H,H}$=12 Hz, $^3J_{H,H}$=3.2 Hz, 1H), 3.26 (dt, $^2J_{H,H}$=13 Hz, 3J$_{H,H}$=3.7 Hz, 1H), 1.31 (d, $^3J_{H,H}$=6.8 Hz, 3H); $^{19}$F NMR (376 MHz, (CD$_3$)$_2$SO): δ−119.5 (s, 2F); MS (MALDI): m/z=408.7 ([M+H]$^+$).

According to general procedure 1, compound 33 is obtained from starting materials i68 and i82 in 71% yield as a colorless solid. $^1$H NMR (400 MHz, (CD$_3$)$_2$SO): δ 8.87 (s, 1H), 7.74 (t, $^2J_{H,F}$=55 Hz, 1H), 6.83 (br s, 2H), 6.76 (s, 1H), 4.71-4.62 (m, 1H), 4.45-4.34 (m, 2H), 4.31-4.09 (m, 1H), 3.90 (m, 1H), 3.71 (m, 1H), 3.55 (m, 3H), 3.38 (m, 1H), 3.13 (m, 1H), 2.55 (m, 2H), 1.20 (d, $^3J_{H,H}$=6.9 Hz, 3H), 1.19 (d, $^3J_{H,H}$=6.9 Hz, 6H); MS (MALDI): m/z=436.1 ([M+H]$^+$).

Compound 33: 4-(difluoromethyl)-5-[4-[(2S,6R)-2,6-dimethylmorpholin-4-yl]-6-[(3R)-3-methylmorpholin-4-yl]-1,3,5-triazin-2-yl]pyridin-2-amine (33)

Compound 34: 5-[4,6-bis[(2R,6S)-2,6-dimethylmorpholin-4-yl]-1,3,5-triazin-2-yl]-4-(difluoromethyl)pyridin-2-amine (34)

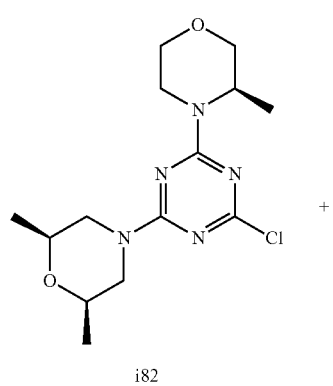

i82

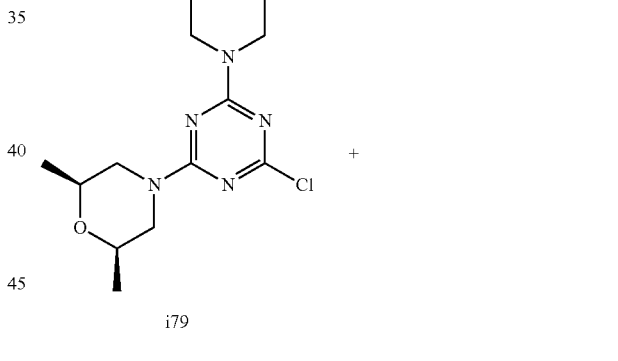

i79

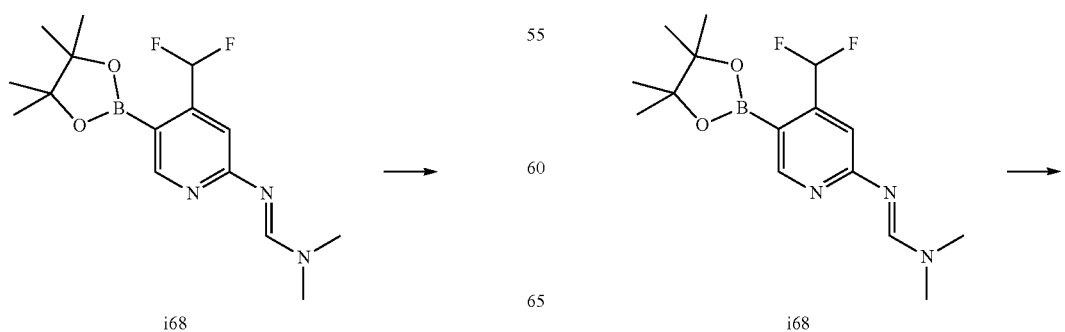

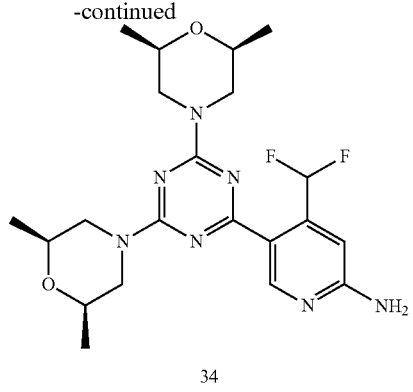

34

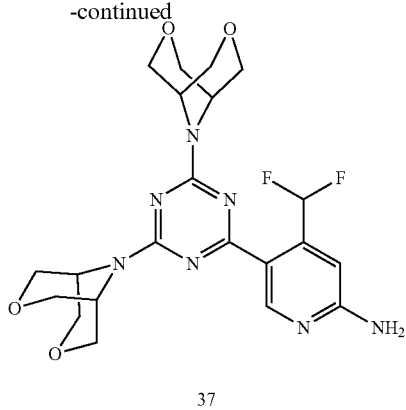

37

According to general procedure 1, compound 34 is obtained from starting materials i68 and i79 in 75% yield as a colorless solid. $^1$H NMR (400 MHz, (CD$_3$)$_2$SO): δ 8.86 (s, 1H), 7.71 (t, $^2J_{H,F}$=55 Hz, 1H), 6.83 (br s, 2H), 6.76 (s, 1H), 4.64-4.46 (m, 4H), 3.60-3.48 (m, 4H), 2.63 (m, 4H), 1.14 (m, 12H); MS (MALDI): m/z=450.0 ([M+H]$^+$).

According to general procedure 1, compound 37 is obtained from starting materials i7 and i68 in 39% yield as a colorless solid. $^1$H NMR (400 MHz, (CD$_3$)$_2$SO): δ 8.85 (s, 1H), 7.68 (t, $J_{H,F}$=55 Hz, 1H), 6.87 (br s, 2H), 6.74 (s, 1H), 4.51 (br s, 2H), 4.45 (br s, 2H), 4.07-3.93 (m, 8H), 3.79-3.67 (m, 8H); $^{19}$F NMR (376 MHz, (CD$_3$)$_2$SO): δ−115.8 (s, 2F); MS (MALDI): m/z=478.1 ([M+H]$^+$).

Compound 37: 5-[4,6-bis(3,7-dioxa-9-azabicyclo[3.3.1]nonan-9-yl)-1,3,5-triazin-2-yl]-4-(difluoromethyl)pyridin-2-amine (37)

Compound 38: 4-(difluoromethyl)-5-[4-(3,7-dioxa-9-azabicyclo[3.3.1]nonan-9-yl)-6-(3-oxa-8-azabicyclo[3.2.1]octan-8-yl)-1,3,5-triazin-2-yl]pyridin-2-amine (38)

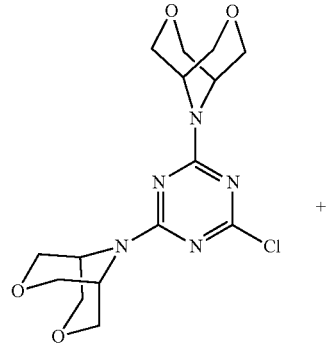

i7

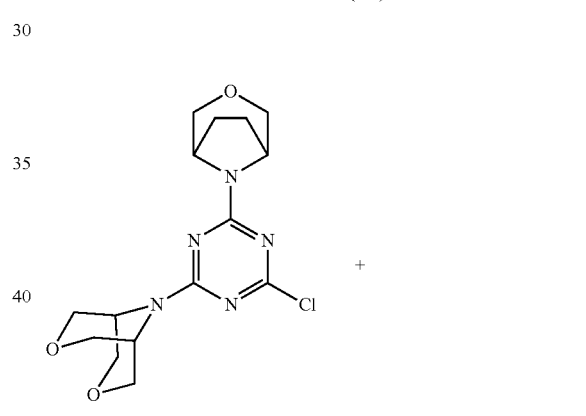

i35

+

+

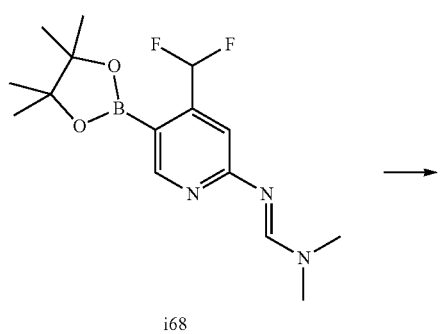

i68

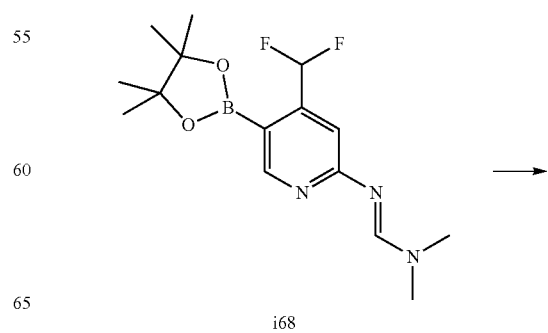

i68

→

→

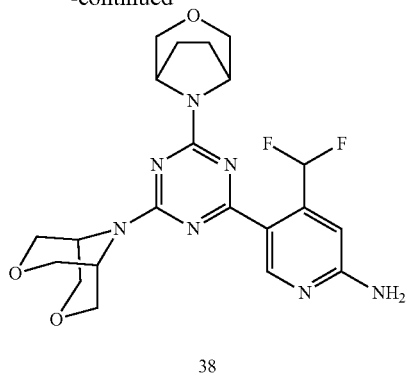

38

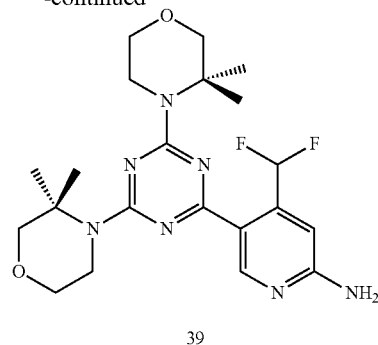

39

According to general procedure 1, compound 38 is obtained from starting materials i35 and i68 in 67% yield as a colorless solid. $^1$H NMR (400 MHz, (CD$_3$)$_2$SO): δ 8.87 (s, 1H), 7.73 (t, J$_{H,F}$=55 Hz, 1H), 6.87 (br s, 2H), 6.75 (s, 1H), 4.70-4.54 (m, 2H), 4.53-4.43 (m, 2H), 4.05-3.97 (m, 4H), 3.79-3.67 (m, 4H), 3.63-3.55 (m, 4H) 2.00-1.83 (m, 4H); $^{19}$F NMR (376 MHz, (CD$_3$)$_2$SO): δ–115.8 (s, 1F), –115.9 (s, 1F); MS (MALDI): m/z=462.1 ([M+H]$^+$).

Compound 39: 5-[4,6-bis(3,3-dimethylmorpholin-4-yl)-1,3,5-triazin-2-yl]-4-(difluoromethyl)pyridin-2-amine (39)

According to general procedure 1, compound 39 is obtained from starting materials i4 and i68 in 28% yield as a colorless solid. $^1$H NMR (400 MHz, (CD$_3$)$_2$SO): δ 8.78 (s, 1H), 7.70 (t, $^2$J$_{H,F}$=55 Hz, 1H), 6.82 (br s, 2H), 6.77 (s, 1H), 3.87-3.75 (m, 8H), 3.45 (br s, 4H), 1.49 (s, 12H); $^{19}$F NMR (376 MHz, (CD$_3$)$_2$SO): δ–114.9-(–115.1) (m, 2F); MS (MALDI): m/z=450.1 ([M+H]$^+$).

Compound 40: 5-[4,6-bis[(3R,5S)-3,5-dimethylmorpholin-4-yl]-1,3,5-triazin-2-yl]-4-(difluoromethyl)pyridin-2-amine (40)

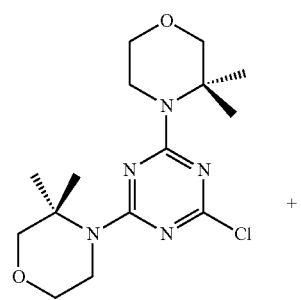

i4

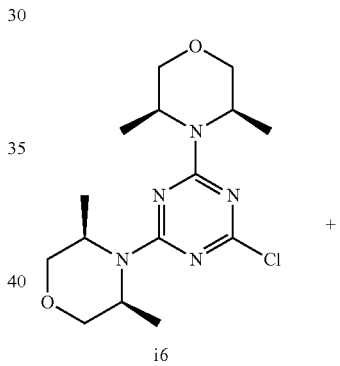

i6

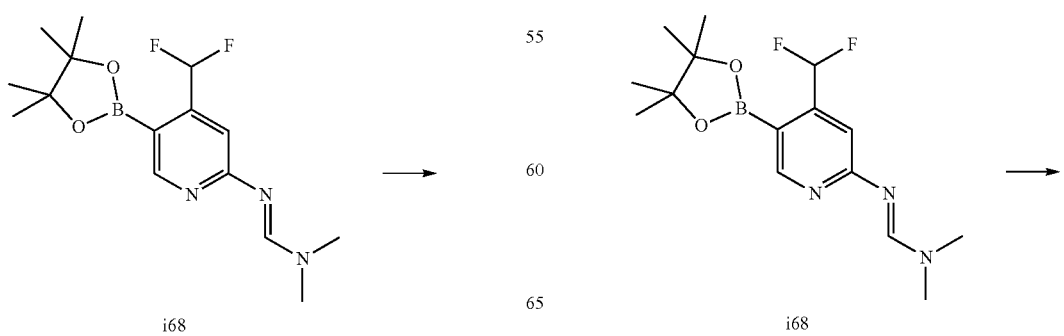

i68

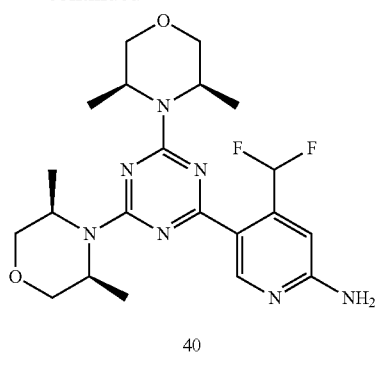

40

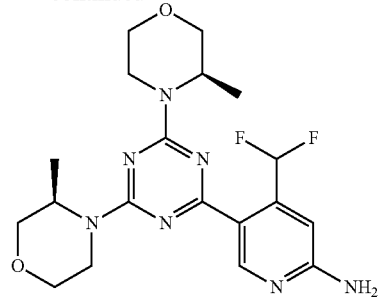

41

According to general procedure 1, compound 40 is obtained from starting materials i6 and i68 in 42% yield as a colorless solid. $^1$H NMR (400 MHz, (CD$_3$)$_2$SO): δ 8.90 (s, 1H), 7.82 (t, $^2J_{H,F}$=55 Hz, 1H), 6.84 (br s, 2H), 6.77 (s, 1H), 4.59-4.43 (m, 4H), 3.82-3.73 (m, 4H), 3.60-3.51 (m, 4H), 1.29 (d, 2J$_{H,H}$=6.9 Hz, 12H); $^{19}$F NMR (376 MHz, (CD$_3$)$_2$SO): δ−114.9-(−115.0) (m, 2F); MS (MALDI): m/z=450.2 ([M+H]$^+$).

Compound 41: 5-[4,6-bis[(3R)-3-methylmorpholin-4-yl]-1,3,5-triazin-2-yl]-4-(difluoromethyl)pyridin-2-amine (41)

According to general procedure 1, compound 41 is obtained from starting materials 15 and i68 in 98% yield as a colorless solid. $^1$H NMR (400 MHz, CDCl$_3$): δ 9.04 (s, 1H), 7.70 (t, $^2J_{H,F}$=52.0 Hz, 1H), 6.84 (s, 1H), 4.88 (br s, 2H), 4.77-4.72 (m, 2H), 4.41 (d, 2J$_{H,H}$=12.0 Hz, 2H), 3.98 (dd, $^2J_{H,H}$=12.0 Hz, $^3J_{H,H}$=4.0 Hz, 2H), 3.78 (d, $^2J_{H,H}$=12.0 Hz, 2H), 3.68 (dd, $^2J_{H,H}$=12.0 Hz, $^3J_{H,H}$=4.0 Hz, 2H), 3.53 (dt, $^2J_{H,H}$=12.0 Hz, $^3J_{H,H}$=4.0 Hz, 2H), 3.28 (dt, $^2J_{H,H}$=12.0 Hz, $^3J_{H,H}$=4.0 Hz, 2H), 1.33 (d, $^2J_{H,H}$=8.0 Hz, 6H); $^{19}$F NMR (376 MHz, CDCl$_3$): δ−115.9 (s, 1F), −116.0 (s, 1F); MS (MALDI): m/z=421.7 ([M+H]$^+$).

Compound 42: 4-(difluoromethyl)-5-[4-(3,3-dimethylmorpholin-4-yl)-6-morpholino-1,3,5-triazin-2-yl]pyridin-2-amine (42)

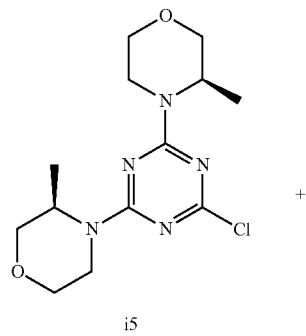

i5

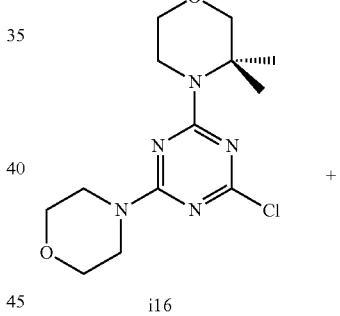

i16

+

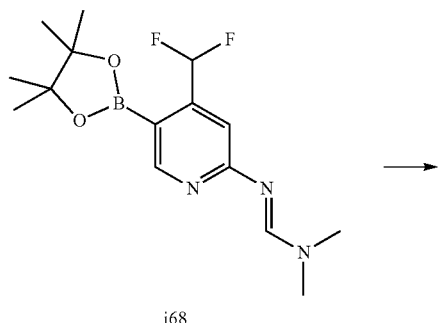

i68

⟶

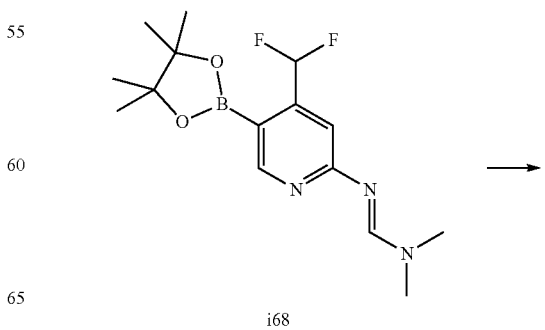

i68

⟶

-continued

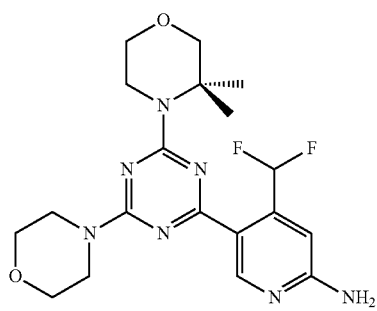

42

According to general procedure 1, compound 42 is obtained from starting materials i6 and i68 in 35% yield as a colorless solid. $^1$H NMR (400 MHz, (CD$_3$)$_2$SO): δ 8.83 (s, 1H), 7.73 (t, $^2J_{H,F}$=55 Hz, 1H), 6.84 (br s, 2H), 6.76 (s, 1H), 3.85-3.76 (m, 4H), 3.76-3.63 (m, 8H), 3.45 (br s, 2H), 1.49 (s, 6H); $^{19}$F NMR (376 MHz, (CD$_3$)$_2$SO): δ−116 (s, 2F); MS (MALDI): m/z=422.1 ([M+H]$^+$).

Compound 44: 4-(difluoromethyl)-5-[4-[(3R,5S)-3,5-dimethylmorpholin-4-yl]-6-[(3R)-3-methylmorpholin-4-yl]-1,3,5-triazin-2-yl]pyridin-2-amine (44)

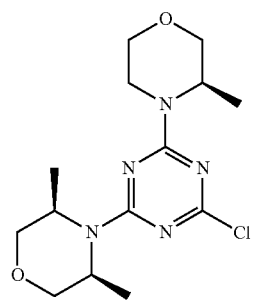

i37

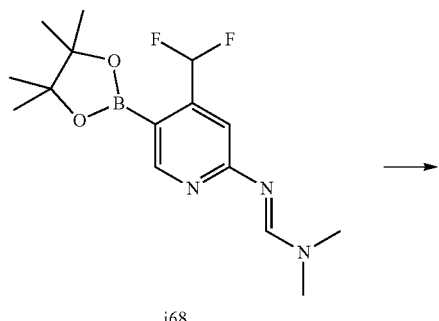

i68

-continued

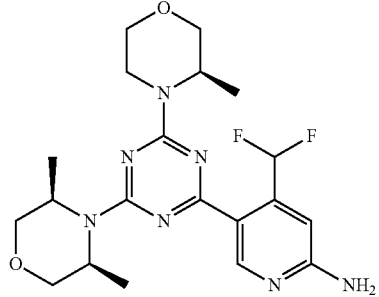

44

According to general procedure 1, compound 44 is obtained from starting materials i37 and i68 in 75% yield as a colorless solid. $^1$H NMR (400 MHz, (CD$_3$)$_2$SO): δ 8.89 (s, 1H), 7.79 (t, $^2J_{H,F}$=55 Hz, 1H), 6.83 (br s, 2H), 6.76 (s, 1H), 4.65 (br s, 1H), 4.50 (br s, 2H), 4.37-4.25 (m, 1H), 3.93 (dd, $^3J_{H,H}$=11 Hz, $^3J_{H,H}$=3.2 Hz, 1H), 3.79-3.67 (m, 3H), 3.59-3.51 (m, 3H), 3.45-3.36 (m, 1H), 3.22-3.11 (m, 1H), 1.30 (d, $^3J_{H,H}$=6.7 Hz, 6H), 1.24 (d, $^3J_{H,H}$=6.7 Hz, 3H); $^{19}$F NMR (376 MHz, (CD$_3$)$_2$SO): δ−115.0 (br s, 2F); MS (MALDI): m/z=436.1 ([M+H]$^+$).

Compound 45: 4-(difluoromethyl)-5-[4-(3,3-dimethylmorpholin-4-yl)-6-[(3R)-3-methylmorpholin-4-yl]-1,3,5-triazin-2-yl]pyridin-2-amine (45)

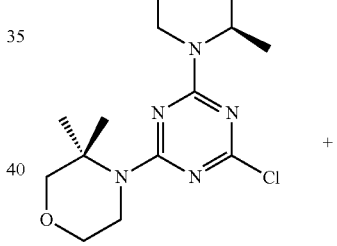

i38

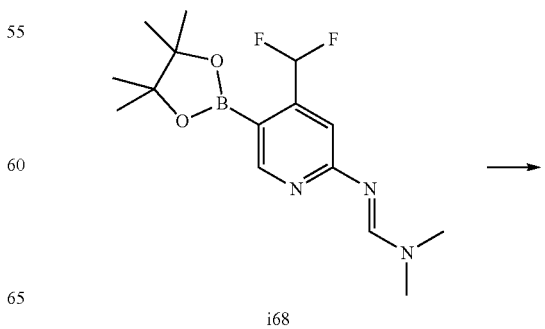

i68

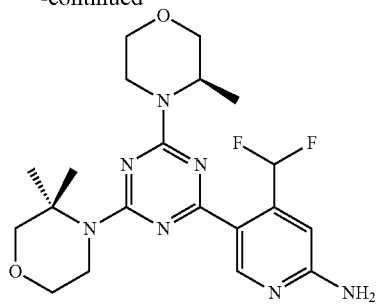

45

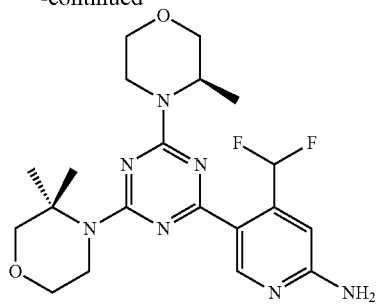

46

According to general procedure 1, compound 45 is obtained from starting materials i38 and i68 in 71% yield as a colorless solid. $^1$H NMR (400 MHz, (CD$_3$)$_2$SO): δ 8.84 (s, 1H), 7.74 (t, $^2J_{H,F}$=55 Hz, 1H), 6.83 (br s, 2H), 6.76 (s, 1H), 4.58 (br s, 1H), 4.31-4.19 (m, 1H), 3.93 (dd, $^2J_{H,H}$=12 Hz, $^3J_{H,H}$=3.9 Hz, 1H), 3.84-3.81 (m, 4H), 3.76-3.69 (m, 1H), 3.58 (dd, $^2J_{H,H}$=11 Hz, $^3J_{H,H}$=3.2 Hz, 1H), 3.46-3.38 (m, 3H), 3.23-3.13 (m, 1H), 1.50 (br s, 6H), 1.23 (d, $^3J_{H,H}$=6.7 Hz, 3H); $^{19}$F NMR (376 MHz, (CD$_3$)$_2$SO): δ–114.8-(–115.5) (m, 2F); MS (MALDI): m/z=436.0 ([M+H]$^+$).

Compound 46: 4-(difluoromethyl)-5-[4-[(3R)-3-(methoxymethyl)morpholin-4-yl]-6-[(3R)-3-methyl-morpholin-4-yl]-1,3,5-triazin-2-yl]pyridin-2-amine (46)

According to general procedure 1, compound 46 is obtained from starting materials i39 and i68 in 67% yield as a colorless solid. $^1$H NMR (400 MHz, (CD$_3$)$_2$SO): δ 8.87 (s, 1H), 7.77 (t, $^2J_{H,F}$=55 Hz, 1H), 6.84 (br s, 2H), 6.76 (s, 1H), 4.67 (br s, 2H), 4.44-4.24 (m, 2H), 3.96-3.83 (m, 3H), 3.75-3.63 (m, 2H), 3.60-3.36 (m, 5H), 3.31 (s, 3H), 3.21-3.04 (m, 2H), 1.23 (d, $^3J_{H,H}$=6.7 Hz, 3H); $^{19}$F NMR (376 MHz, (CD$_3$)$_2$SO): δ–115.0 (br s, 2F); MS (MALDI): m/z=452.3 ([M+H]$^+$).

Compound 47: 4-(difluoromethyl)-5-[4-(3,7-dioxa-9-azabicyclo[3.3.1]nonan-9-yl)-6-[(3R)-3-methyl-morpholin-4-yl]-1,3,5-triazin-2-yl]pyridin-2-amine (47)

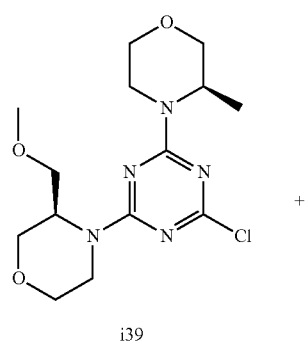

i39

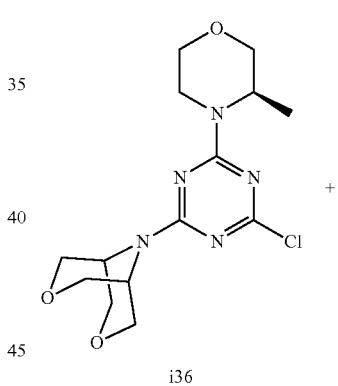

i36

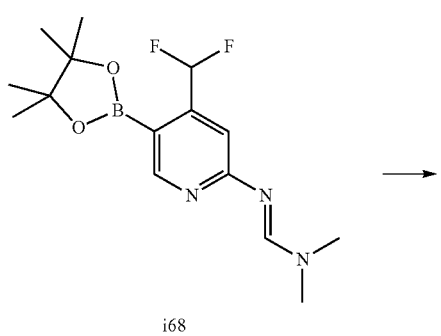

i68

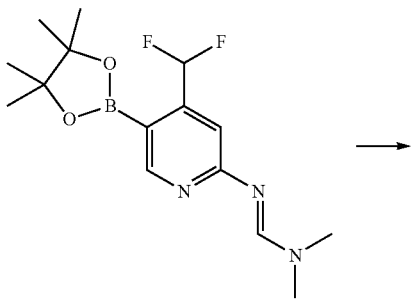

i68

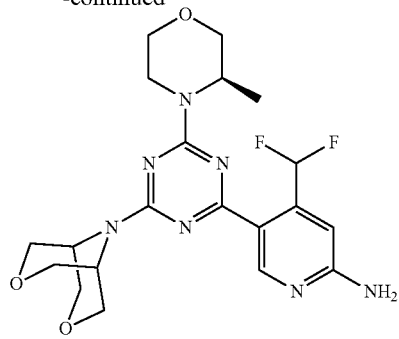

47

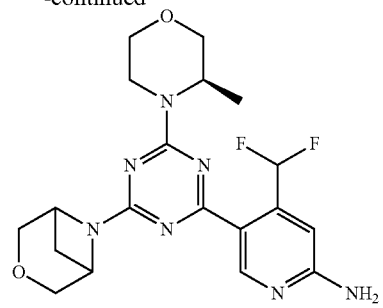

50

According to general procedure 1, compound 47 is obtained from starting materials i36 and i68 in 85% yield as a colorless solid. $^1$H NMR (400 MHz, (CD$_3$)$_2$SO): δ 8.86 (s, 1H), 7.72 (t, $^2J_{H,F}$=55 Hz, 1H), 6.84 (br s, 2H), 6.75 (s, 1H), 4.64 (br s, 1H), 4.53-4.42 (m, 2H), 4.37-4.25 (m, 1H), 4.05-3.96 (m, 4H), 3.92-3.84 (m, 1H), 3.77-3.66 (m, 5H), 3.60-3.52 (m, 1H), 3.44-3.35 (m, 1H), 3.22-3.10 (m, 1H), 1.23 (d, $^3J_{H,H}$=6.7 Hz, 3H); $^{19}$F NMR (376 MHz, (CD$_3$)$_2$SO): δ −114.9-(−117.1) (m, 2F); MS (MALDI): m/z=450.0 ([M+H]$^+$).

According to general procedure 1, compound 50 is obtained from starting materials i40 and i68 in 52% yield as a colorless solid. $^1$H NMR (400 MHz, (CD$_3$)$_2$SO): δ 8.90 (s, 1H), 7.82 (t, $^2J_{H,F}$=55 Hz, 1H), 6.87 (br s, 2H), 6.76 (s, 1H), 4.55-4.51 (m, 1H), 4.34-4.14 (m, 3H), 4.12-4.25 (m, 2H), 3.92-3.80 (m, 1H), 3.76-3.68 (m, 3H), 3.55-3.51 (m, 1H), 3.38 (m, 1H), 3.20-3.13 (m, 1H), 2.68 (m, 1H), 1.78 (m, 1H), 1.20 (d, $^3J_{H,H}$=6.9 Hz, 3H); $^{19}$F NMR (376 MHz, (CD$_3$)$_2$SO): δ −115.0 (br s, 2F); MS (MALDI): m/z=420.6 ([M+H]$^+$).

Compound 50: 4-(difluoromethyl)-5-[4-[(3R)-3-methylmorpholin-4-yl]-6-(3-oxa-6-azabicyclo[3.1.1]heptan-6-yl)-1,3,5-triazin-2-yl]pyridin-2-amine (50)

Compound 51: 4-(difluoromethyl)-5-[4-[(3R)-3-methylmorpholin-4-yl]-6-(6-oxa-3-azabicyclo[3.1.1]heptan-3-yl)-1,3,5-triazin-2-yl]pyridin-2-amine (51)

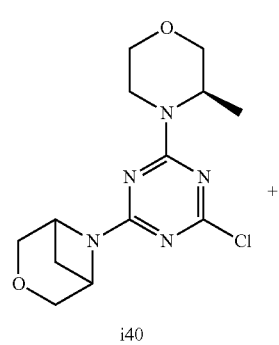

i40

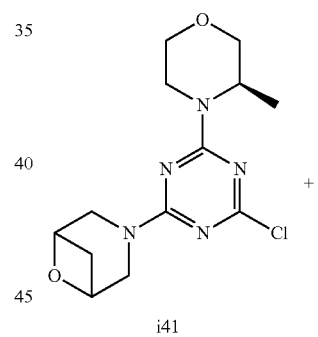

i41

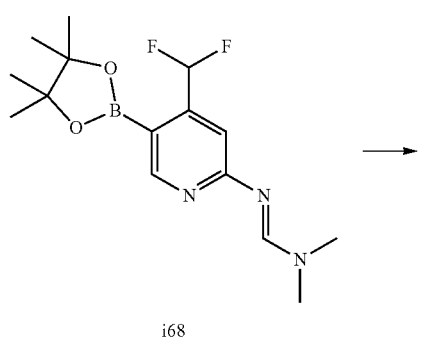

i68

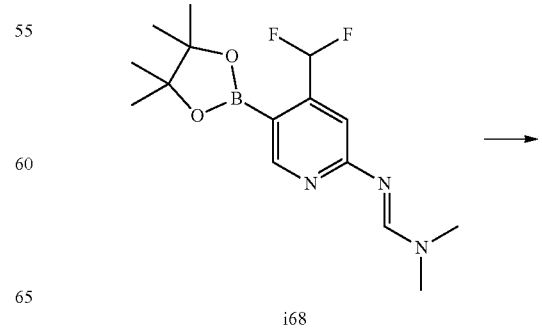

i68

-continued

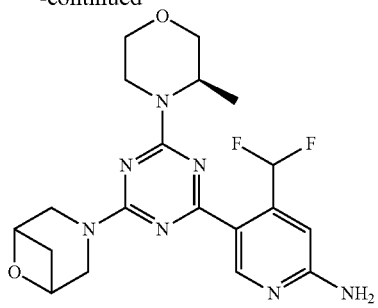

51

52

According to general procedure 1, compound 51 is obtained from starting materials i41 and i68 in 36% yield as a colorless solid. $^1$H NMR (400 MHz, (CD$_3$)$_2$SO): δ 8.99 (s, 1H), 7.89 (t, $^2$J$_{H,F}$=55 Hz, 1H), 6.84 (br s, 2H), 6.77 (s, 1H), 4.69 (m, 3H), 4.37 (m, 1H), 3.91-3.85 (m, 3H), 3.75-3.53 (m, 4H), 3.42-3.35 (m, 1H), 3.22-3.15 (m, 1H), 3.12-3.08 (m, 1H), 1.85 (m, 1H), 1.24 (d, $^3$J$_{H,H}$=6.9 Hz, 3H); $^{19}$F NMR (376 MHz, (CD$_3$)$_2$SO): δ−116.0 (br s, 2F); MS (MALDI): m/z=420.6 ([M+H]$^+$).

According to general procedure 1, compound 52 is obtained from starting materials i142 and i68 in 44% yield as a colorless solid (1:1 mixture of rotamers). $^1$H NMR (400 MHz, (CD$_3$)$_2$SO): δ 8.89 (m, 1H), 7.77 (m, 1H), 6.84 (br s, 2H), 6.76 (s, 1H), 5.02-4.97 (m, 1H), 4.68-4.66 (m, 2H), 4.31 (m, 1H), 3.89-3.85 (m, 1H), 3.79-3.57 (m, 3H), 3.57-3.44 (m, 4H), 3.22 (m, 1H), 1.90-1.83 (m, 2H), 1.21 (d, 3J$_{H,H}$=6.9 Hz, 3H); $^{19}$F NMR (376 MHz, (CD$_3$)$_2$SO): δ−115.5 (br s, 2F); MS (MALDI): m/z=420.2 ([M+H]$^+$).

Compound 52: 4-(difluoromethyl)-5-[4-[(3R)-3-methylmorpholin-4-yl]-6-[(1R,4R)-2-oxa-5-azabicyclo[2.2.1]heptan-5-yl]-1,3,5-triazin-2-yl]pyridin-2-amine (52)

Compound 53: 4-(difluoromethyl)-5-[4-[(3R)-3-methylmorpholin-4-yl]-6-[(1S,4S)-2-oxa-5-azabicyclo[2.2.1]heptan-5-yl]-1,3,5-triazin-2-yl]pyridin-2-amine (53)

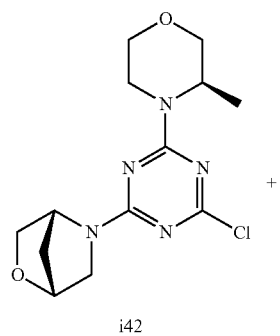

i42

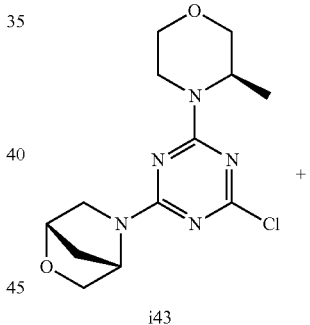

i43

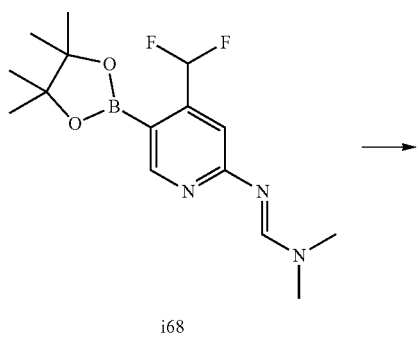

i68

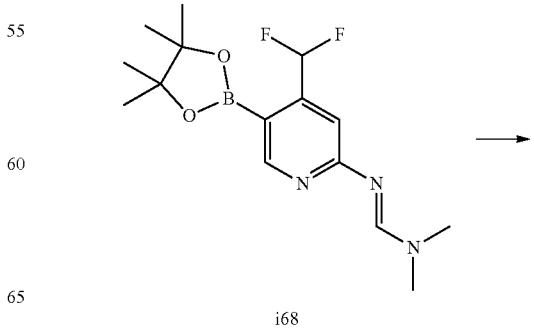

i68

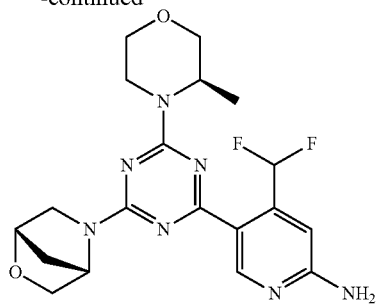

53

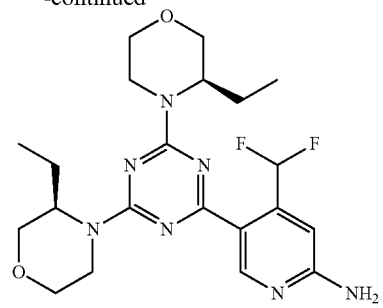

54

According to general procedure 1, compound 53 is obtained from starting materials i43 and i68 in 53% yield as a colorless solid (1:1 mixture of rotamers). $^1$H NMR (400 MHz, (CD$_3$)$_2$SO): δ 8.90 (m, 1H), 7.77 (m, 1H), 6.84 (br s, 2H), 6.76 (s, 1H), 5.02-4.96 (m, 1H), 4.68-4.62 (m, 2H), 3.90 (m, 1H), 3.80 (m, 1H), 3.70 (m, 2H), 3.57 (m, 2H), 3.45 (m, 3H), 3.20 (m, 1H), 1.90-1.83 (m, 2H), 1.21 (d, $^3J_{H,H}$=6.9 Hz, 3H); $^{19}$F NMR (376 MHz, (CD$_3$)$_2$SO): δ−115.0 (br s, 2F); MS (MALDI): m/z=420.2 ([M+H]$^+$).

Compound 54: 5-[4,6-bis[(3R)-3-ethylmorpholin-4-yl]-1,3,5-triazin-2-yl]-4-(difluoromethyl)pyridin-2-amine (54)

According to general procedure 1, compound 54 is obtained from starting materials i8 and i68 in 61% yield as a colorless solid. $^1$H NMR (400 MHz, (CD$_3$)$_2$SO): δ 8.87 (s, 1H), 7.77 (t, $^2J_{H,F}$=55 Hz, 1H), 6.83 (br s, 2H), 6.76 (s, 1H), 4.47 (m, 4H), 3.89-3.81 (m, 4H), 3.51-3.34 (m, 4H), 3.12 (m, 2H), 1.71 (m, 4H), 0.86 (m, 6H). $^{19}$F NMR (376 MHz, (CD$_3$)$_2$SO): δ −115.0 (br s, 2F); MS (MALDI): m/z=450.3 ([M+H]$^+$).

Compound 55: 5-[4,6-bis(8-oxa-5-azaspiro[3.5]nonan-5-yl)-1,3,5-triazin-2-yl]-4-(difluoromethyl)pyridin-2-amine (55)

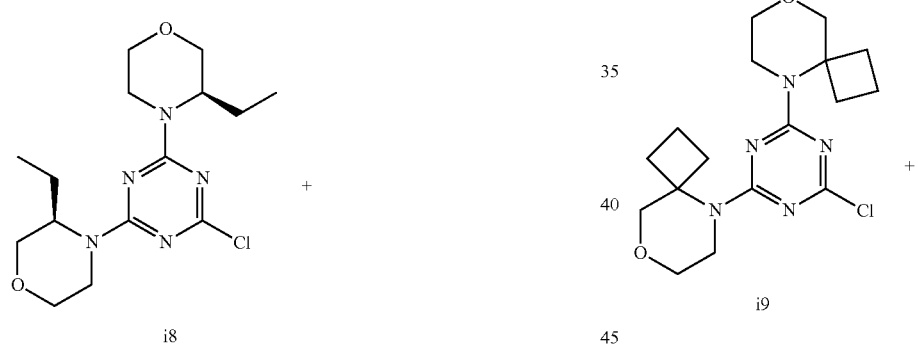

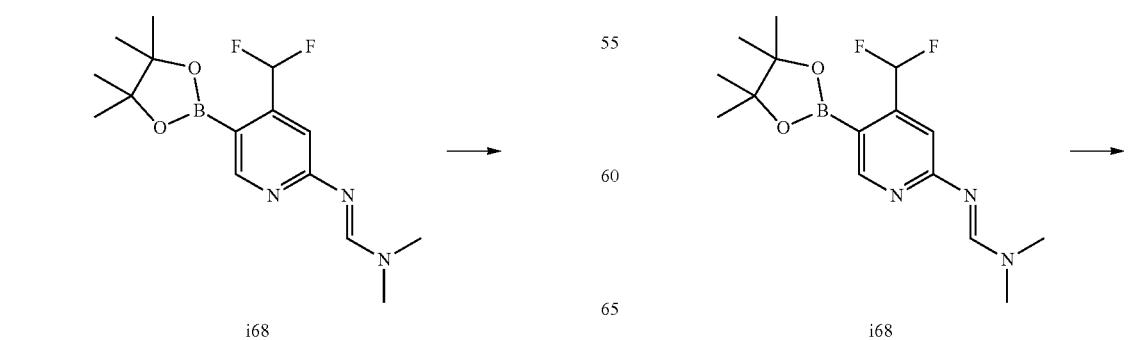

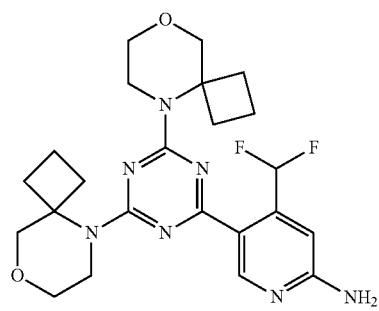

55

According to general procedure 1, compound 55 is obtained from starting materials i9 and i68 in 59% yield as a colorless solid. $^1$H NMR (400 MHz, (CD$_3$)$_2$SO): δ 8.74 (s, 1H), 7.65 (t, $^2J_{H,F}$=55 Hz, 1H), 6.81 (br s, 2H), 6.75 (s, 1H), 3.68 (m, 8H), 3.49 (m, 4H), 2.46-2.38 (m, 4H), 2.25-2.16 (m, 4H), 1.72-1.66 (m, 4H); $^{19}$F NMR (376 MHz, (CD$_3$)$_2$SO): δ−115.5 (br s, 2F); MS (MALDI): m/z=474.3 ([M+H]$^+$).

Compound 56: 5-[4,6-bis[(3R)-3-isopropylmorpholin-4-yl]-1,3,5-triazin-2-yl]-4-(difluoromethyl)pyridin-2-amine (56)

56

According to general procedure 1, compound 56 is obtained from starting materials i10 and i68 in 59% yield as a colorless solid. $^1$H NMR (400 MHz, (CD$_3$)$_2$SO): δ 8.87 (s, 1H), 7.76 (t, $^2J_{H,F}$=55 Hz, 1H), 6.82 (br s, 2H), 6.76 (s, 1H), 4.50 (m, 2H), 4.29 (m, 2H), 4.02-3.84 (m, 4H), 3.40 (m, 4H), 3.08 (m, 2H), 2.34 (m, 2H), 1.02 (m, 6H), 0.77 (m, 6H); $^{19}$F NMR (376 MHz, (CD$_3$)$_2$SO): δ−115.0 (br s, 2F); MS (MALDI): m/z=478.4 ([M+H]$^+$).

Compound 66: 4-(difluoromethyl)-5-[4-(3,3-dimethylmorpholin-4-yl)-6-[(3R,5S)-3,5-dimethylmorpholin-4-yl]-1,3,5-triazin-2-yl]pyridin-2-amine (66)

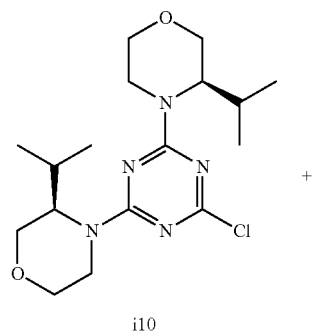

i10

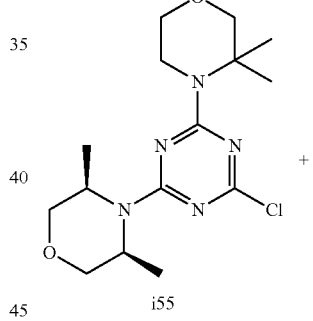

i55

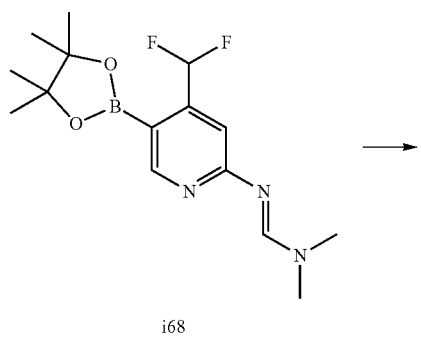

i68

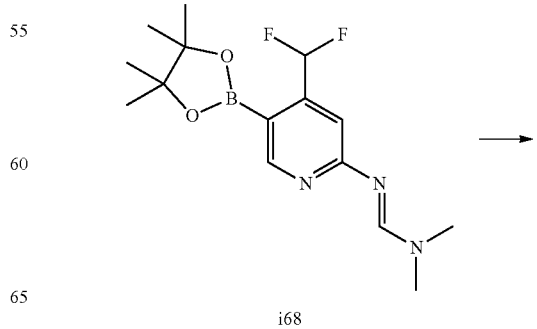

i68

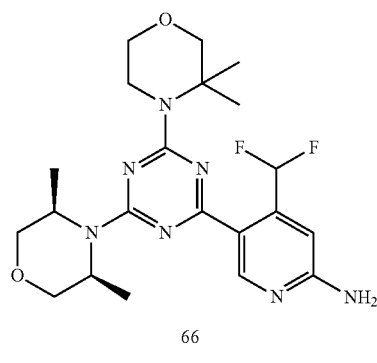

66

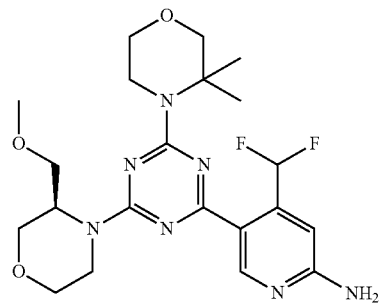

67

According to general procedure 1, compound 66 is obtained from starting materials i55 and i68 in 61% yield as a colorless solid. $^1$H NMR (400 MHz, (CD$_3$)$_2$SO): δ 8.87 (s, 1H), 7.77 (t, $^2J_{H,F}$=55 Hz, 1H), 6.83 (br s, 2H), 6.76 (s, 1H), 4.46 (m, 2H), 3.81-3.77 (m, 6H), 3.55 (m, 2H), 3.44 (m, 2H), 1.49 (s, 6H), 1.28 (d, $^3J_{H,H}$=6.9 Hz, 6H); $^{19}$F NMR (376 MHz, (CD$_3$)$_2$SO): δ−115.0 (br s, 2F); MS (MALDI): m/z=450.4 ([M+H]$^+$).

According to general procedure 1, compound 67 is obtained from starting materials i56 and i68 in 37% yield as a colorless solid. $^1$H NMR (400 MHz, (CD$_3$)$_2$SO): δ 8.84 (s, 1H), 7.89 (t, $^2J_{H,F}$=55 Hz, 1H), 6.85 (br s, 2H), 6.76 (s, 1H), 4.60 (m, 1H), 4.31 (m, 1H), 3.92 (m, 2H), 3.83 (m, 4H), 3.65 (m, 1H), 3.51-3.41 (m, 5H), 3.28 (s, 3H), 3.12 (m, 1H), 1.49 (s, 3H), 1.48 (s, 3H); $^{19}$F NMR (376 MHz, (CD$_3$)$_2$SO): δ−115.5 (br s, 2F); MS (MALDI): m/z=466.4 ([M+H]$^+$).

Compound 67: 4-(difluoromethyl)-5-[4-(3,3-dimethylmorpholin-4-yl)-6-[(3R)-3-(methoxymethyl)morpholin-4-yl]-1,3,5-triazin-2-yl]pyridin-2-amine (67)

Compound 68: [(3R)-4-[4-[6-amino-4-(difluoromethyl)-3-pyridyl]-6-(3,3-dimethylmorpholin-4-yl)-1,3,5-triazin-2-yl]morpholin-3-yl]methanol (68)

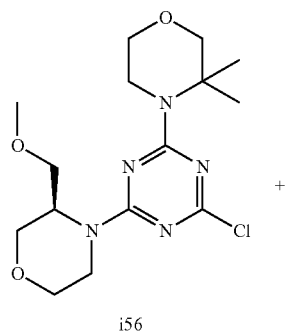

i56

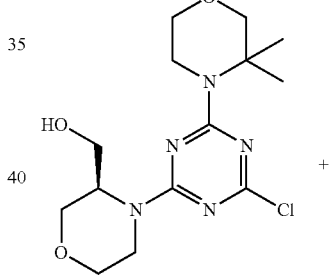

i57

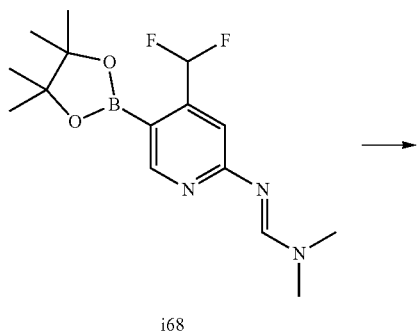

i68

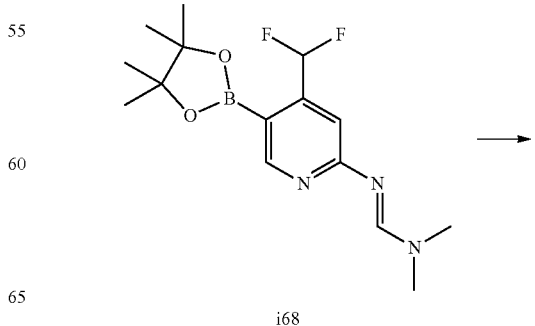

i68

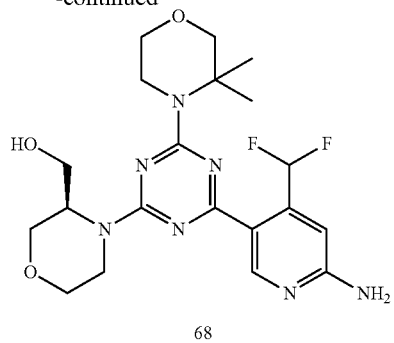

68

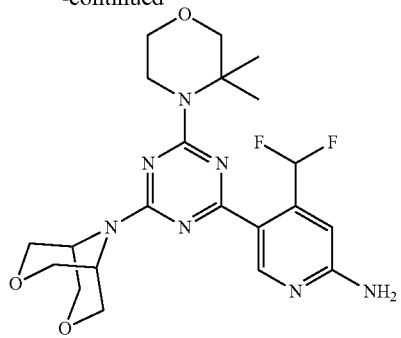

69

According to general procedure 1, compound 68 is obtained from starting materials i57 and i68 in 58% yield as a colorless solid. $^1$H NMR (400 MHz, (CD$_3$)$_2$SO): δ 8.83 (s, 1H), 7.77 (m, 1H), 6.84 (br s, 2H), 6.76 (s, 1H), 4.91 (m, 1H), 4.35 (m, 2H), 4.05 (m, 1H), 3.97-3.70 (m, 6H), 3.54-3.38 (m, 5H), 3.12 (m, 1H), 1.49 (s, 3H), 1.48 (s, 3H); $^{19}$F NMR (376 MHz, (CD$_3$)$_2$SO): δ−115.5 (br s, 2F); MS (MALDI): m/z=452.2 ([M+H]$^+$).

According to general procedure 1, compound 69 is obtained from starting materials i54 and i68 in 57% yield as a colorless solid. $^1$H NMR (400 MHz, (CD$_3$)$_2$SO): δ 8.83 (s, 1H), 7.69 (t, $^2$J$_{H,F}$=55 Hz, 1H), 6.85 (br s, 2H), 6.76 (s, 1H), 4.47-4.37 (m, 2H), 4.01 (m, 4H), 3.80-3.71 (m, 8H), 3.45 (m, 2H), 1.48 (s, 6H); $^{19}$F NMR (376 MHz, (CD$_3$)$_2$SO): δ−115.7 (br s, 2F); MS (MALDI): m/z=464.3 ([M+H]$^+$).

Compound 69: 4-(difluoromethyl)-5-[4-(3,3-dimethylmorpholin-4-yl)-6-(3,7-dioxa-9-azabicyclo[3.3.1]nonan-9-yl)-1,3,5-triazin-2-yl]pyridin-2-amine (69)

Compound 70: 5-[4-(4-cyclopropylpiperazin-1-yl)-6-(3,3-dimethylmorpholin-4-yl)-1,3,5-triazin-2-yl]-4-(difluoromethyl)pyridin-2-amine (70)

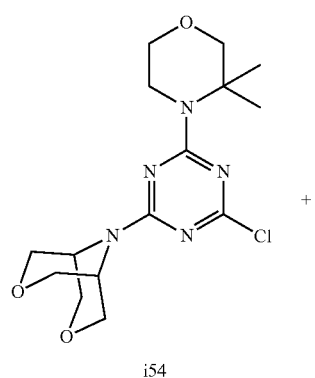

i54

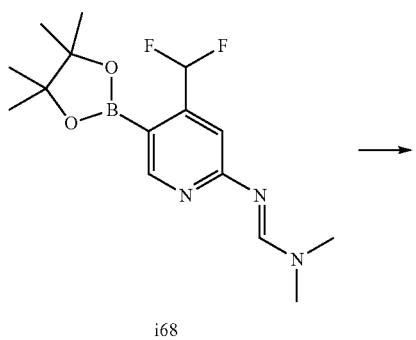

i68

+

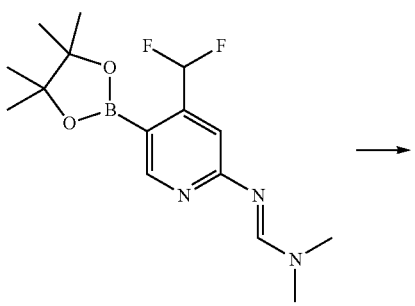

i58 i68

+

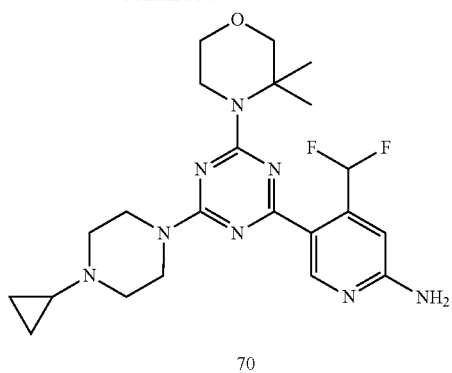

70

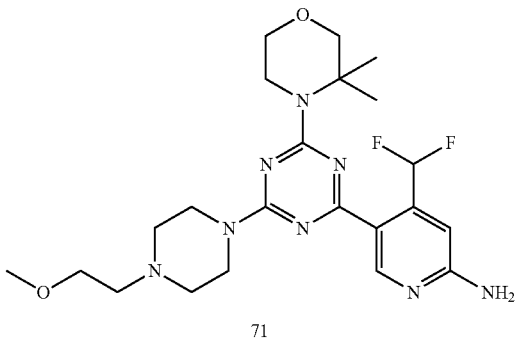

71

According to general procedure 1, compound 70 is obtained from starting materials i58 and i68 in 12% yield as a colorless solid. $^1$H NMR (400 MHz, (CD$_3$)$_2$SO): δ 8.82 (s, 1H), 7.72 (t, $^2$J$_{H,F}$=55 Hz, 1H), 6.83 (br s, 2H), 6.76 (s, 1H), 3.82 (m, 4H), 3.71 (m, 4H), 3.44 (m, 2H), 2.58 (m, 4H), 1.64 (m, 1H), 1.44 (s, 6H), 0.45 (m, 2H), 0.36 (m, 2H); $^{19}$F NMR (376 MHz, (CD$_3$)$_2$SO): δ−115.4 (br s, 2F); MS (MALDI): m/z=460.4 ([M]$^+$).

Compound 71: 4-(difluoromethyl)-5-[4-(3,3-dimethylmorpholin-4-yl)-6-[4-(2-methoxyethyl)piperazin-1-yl]-1,3,5-triazin-2-yl]pyridin-2-amine (71)

According to general procedure 1, compound 71 is obtained from starting materials i59 and i68 in 42% yield as a colorless solid. $^1$H NMR (400 MHz, (CD$_3$)$_2$SO): δ 8.82 (s, 1H), 7.73 (t, $^2$J$_{H,F}$=55 Hz, 1H), 6.83 (br s, 2H), 6.76 (s, 1H), 3.88-3.69 (m, 10H), 3.47-3.44 (m, 4H), 3.24 (m, 3H), 2.52-2.45 (m, 4H), 1.44 (s, 6H); $^{19}$F NMR (376 MHz, (CD$_3$)$_2$SO): δ−115.4 (br s, 2F); MS (MALDI): m/z=478.4 ([M]$^+$).

Compound 77: [(3R)-4-[4-[6-amino-4-(difluoromethyl)-3-pyridyl]-6-[(3R)-3-methylmorpholin-4-yl]-1,3,5-triazin-2-yl]morpholin-3-yl]methanol (77)

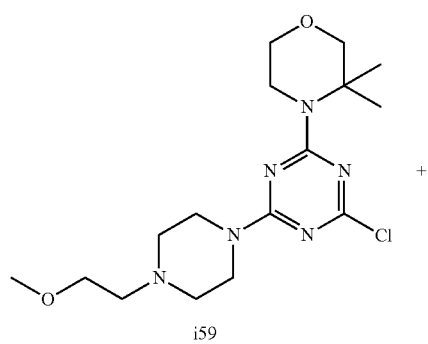

i59

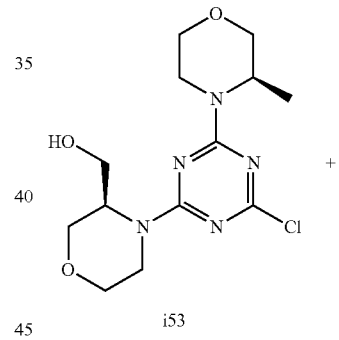

i53

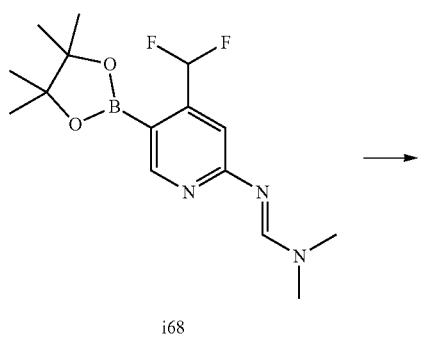

i68

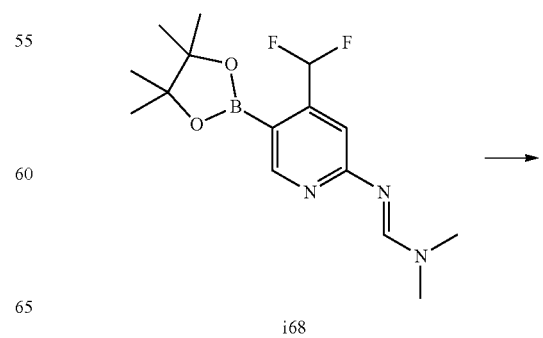

i68

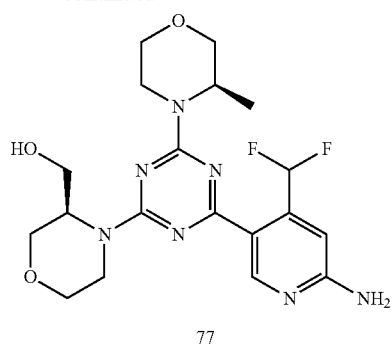

77

According to general procedure 1, compound 77 is obtained from starting materials i53 and i68 in 31% yield as a colorless solid. $^1$H NMR (400 MHz, (CD$_3$)$_2$SO): δ 8.88 (s, 1H), 7.78 (t, $^2J_{H,F}$=55 Hz, 1H), 6.84 (br s, 2H), 6.76 (s, 1H), 4.96 (m, 1H), 4.73 (m, 1H), 4.58-4.24 (m, 3H), 4.05 (m, 1H), 3.90 (m, 2H), 3.72 (m, 2H), 3.59 (m, 1H), 3.51-3.36 (m, 4H), 3.23-3.02 (m, 2H), 1.23 (d, $^3J_{H,H}$=6.9 Hz, 3H); MS (MALDI): m/z=438.3 ([M+H]$^+$).

Compound 78: 4-(difluoromethyl)-5-[4-[(3R,5R)-3,5-dimethylmorpholin-4-yl]-6-[(3R)-3-methylmorpholin-4-yl]-1,3,5-triazin-2-yl]pyridin-2-amine (78)

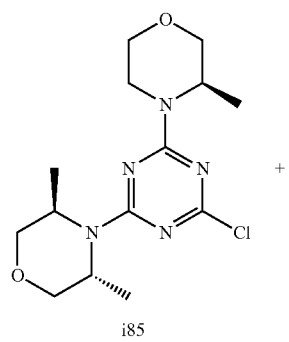

i85

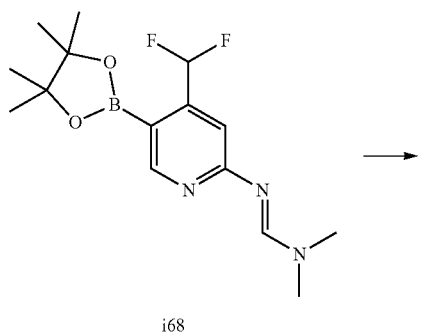

i68

According to general procedure 1, compound 78 is obtained from starting materials i85 and i68 in 71% yield as a colorless solid. $^1$H NMR (400 MHz, (CD$_3$)$_2$SO): δ 8.90 (s, 1H), 7.82 (t, $^2J_{H,F}$=55 Hz, 1H), 6.84 (br s, 2H), 6.76 (s, 1H), 4.66 (m, 1H), 4.32 (m, 3H), 4.15-4.11 (m, 2H), 3.92 (m, 1H), 3.70 (m, 3H), 3.57 (m, 1H), 3.40 (m, 1H), 3.18 (m, 1H), 1.37 (m, 6H), 1.24 (d, $^3J_{H,H}$=6.9 Hz, 3H); $^{19}$F NMR (376 MHz, (CD$_3$)$_2$SO): δ−114.9 (br s, 2F); MS (MALDI): m/z=435.4 ([M]$^+$).

Compound 79: 4-(difluoromethyl)-5-[4-[(3S,5S)-3,5-dimethylmorpholin-4-yl]-6-[(3R)-3-methylmorpholin-4-yl]-1,3,5-triazin-2-yl]pyridin-2-amine (79)

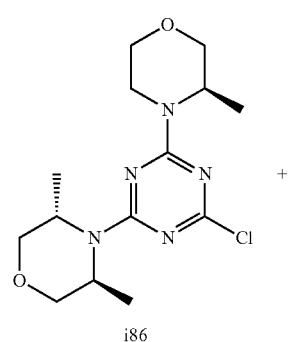

i86

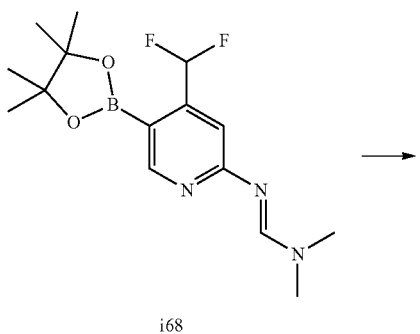

i68

161

-continued

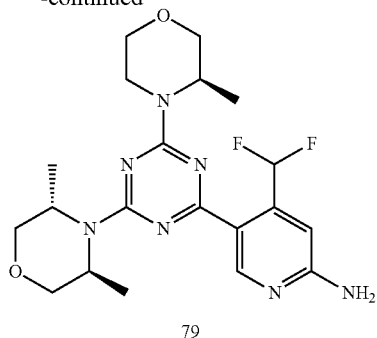

79

According to general procedure 1, compound 79 is obtained from starting materials i86 and i68 in 65% yield as a colorless solid. $^1$H NMR (400 MHz, (CD$_3$)$_2$SO): δ 8.91 (s, 1H), 7.82 (t, $^2J_{H,F}$=55 Hz, 1H), 6.85 (br s, 2H), 6.76 (s, 1H), 4.66 (m, 1H), 4.32 (m, 3H), 4.15-4.11 (m, 2H), 3.92 (m, 1H), 3.70 (m, 3H), 3.57 (m, 1H), 3.40 (m, 1H), 3.19 (m, 1H), 1.37 (m, 6H), 1.24 (d, $^3J_{H,H}$=6.9 Hz, 3H); $^{19}$F NMR (376 MHz, (CD$_3$)$_2$SO): δ–114.9 (br s, 2F); MS (MALDI): m/z=434.3 ([M]+).

Compound 80: 4-(difluoromethyl)-5-[4-morpholino-6(3-oxa-9-azabicyclo[3.3.1]nonan-9-yl)-1,3,5-triazin-2-yl]pyridin-2-amine (80)

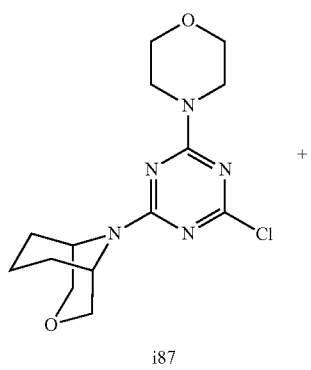

i87

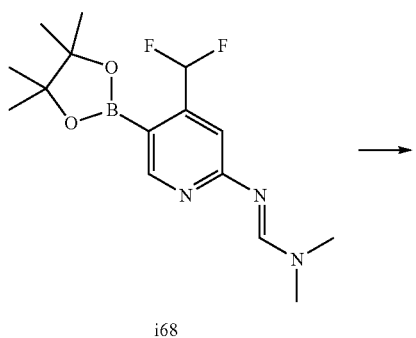

i68

162

-continued

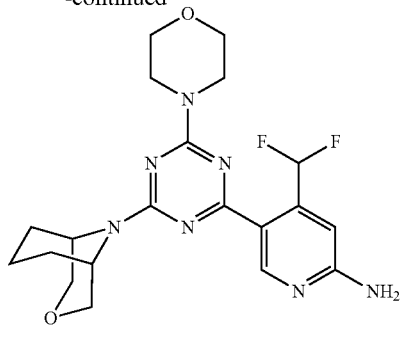

80

According to general procedure 1, compound 80 is obtained from starting materials i87 and i68 in 57% yield as a colorless solid. $^1$H NMR (400 MHz, (CD$_3$)$_2$SO): δ 8.85 (s, 1H), 7.73 (t, $^2J_{H,F}$=55 Hz, 1H), 6.84 (br s, 2H), 6.75 (s, 1H), 4.61-4.57 (m, 2H), 3.95 (m, 2H), 3.75-3.65 (m, 10H), 2.48 (m, 1H), 1.88-1.72 (m, 4H), 1.57 (m, 1H); $^{19}$F NMR (376 MHz, (CD$_3$)$_2$SO): δ–115.4 (m, 2F); MS (MALDI): m/z=434.3 ([M+H]$^+$).

Compound 82: 4-(difluoromethyl)-5-[4-(3,7-dioxa-9-azabicyclo[3.3.1]nonan-9-yl)-6-(3-oxa-9-azabicyclo[3.3.1]nonan-9-yl)-1,3,5-triazin-2-yl]pyridin-2-amine (82)

i89

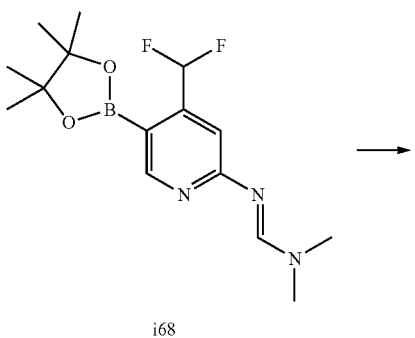

i68

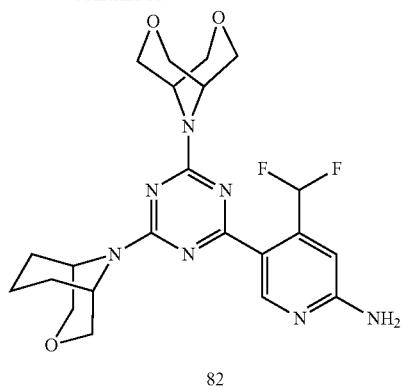

82

According to general procedure 1, compound 82 is obtained from starting materials i89 and i68 in 51% yield as a colorless solid. $^1$H NMR (400 MHz, (CD$_3$)$_2$SO): δ 8.84 (s, 1H), 7.70 (t, $^2J_{H,F}$=55 Hz, 1H), 6.85 (br s, 2H), 6.75 (s, 1H), 4.62 (m, 1H), 4.54 (m, 1H), 4.52 (m, 1H), 4.44 (m, 1H), 4.04-3.92 (m, 6H), 3.75-3.62 (m, 6H), 2.45 (m, 1H), 1.89-1.75 (m, 4H), 1.57 (m, 1H); $^{19}$F NMR (376 MHz, (CD$_3$)$_2$SO): δ−115.7 (m, 2F); MS (MALDI): m/z=476.2 ([M+H]$^+$).

Compound 83: 5-[4,6-bis[(3S,5S)-3,5-dimethylmorpholin-4-yl]-1,3,5-triazin-2-yl]-4-(difluoromethyl)pyridin-2-amine (83)

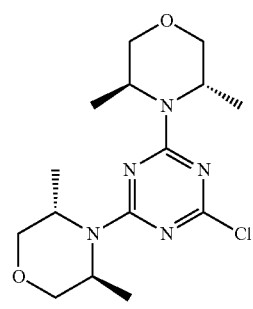

i90

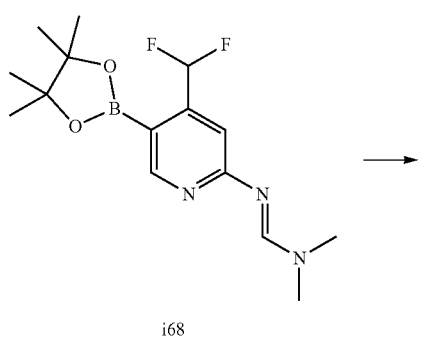

i68

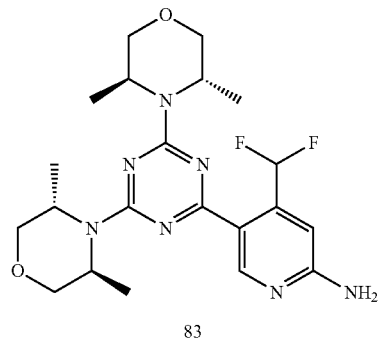

83

According to general procedure 1, compound 83 is obtained from starting materials i90 and i68 in 56% yield as a colorless solid. $^1$H NMR (400 MHz, (CD$_3$)$_2$SO): δ 8.92 (s, 1H), 7.87 (t, $^2J_{H,F}$=55 Hz, 1H), 6.84 (br s, 2H), 6.77 (s, 1H), 4.32 (m, 4H), 4.14 (m, 4H), 3.70 (m, 4H), 1.39 (d, $^3J_{H,H}$=6.9 Hz, 12H); $^{19}$F NMR (376 MHz, (CD$_3$)$_2$SO): δ−115.5 (br s, 2F); MS (MALDI): m/z=448.3 ([M]$^+$).

Compound 84: 4-(difluoromethyl)-5-[4-(3,7-dioxa-9-azabicyclo[3.3.1]nonan-9-yl)-6-morpholino-1,3,5-triazin-2-yl]pyridin-2-amine (84)

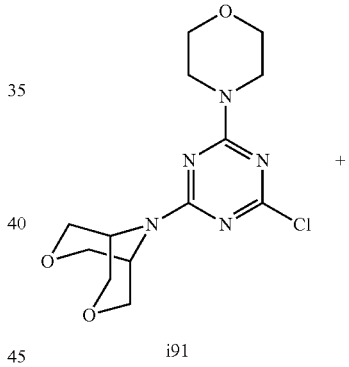

i91

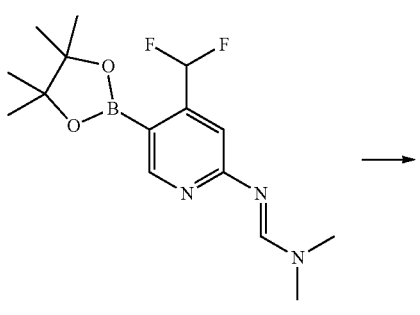

i68

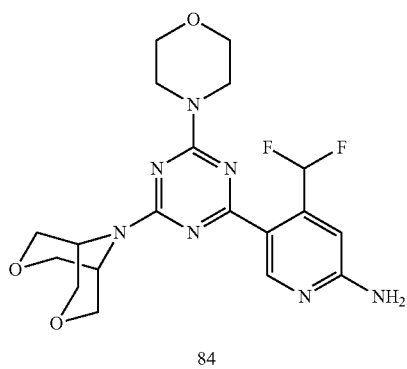

84

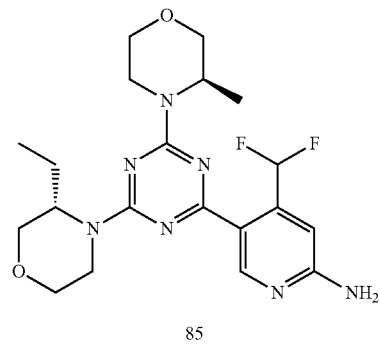

85

According to general procedure 1, compound 84 is obtained from starting materials i91 and i68 in 63% yield as a colorless solid. $^1$H NMR (400 MHz, (CD$_3$)$_2$SO): δ 8.86 (s, 1H), 7.71 (t, $^2J_{H,F}$=55 Hz, 1H), 6.87 (br s, 2H), 6.75 (s, 1H), 4.49 (m, 2H), 4.02 (m, 4H), 3.74-3.65 (m, 12H); $^{19}$F NMR (376 MHz, (CD$_3$)$_2$SO): δ−115.6 (br s, 2F); MS (MALDI): m/z=436.4 ([M+H]$^+$).

Compound 85: 4-(difluoromethyl)-5-[4-[(3S)-3-ethylmorpholin-4-yl]-6-[(3R)-3-methylmorpholin-4-yl]-1,3,5-triazin-2-yl]pyridin-2-amine (85)

According to general procedure 1, compound 85 is obtained from starting materials i92 and i68 in 52% yield as a colorless solid. $^1$H NMR (400 MHz, (CD$_3$)$_2$SO): δ 8.88 (s, 1H), 7.77 (t, $^2J_{H,F}$=55 Hz, 1H), 6.85 (br s, 2H), 6.76 (s, 1H), 4.70-4.25 (m, 4H), 3.90 (m, 3H), 3.72 (m, 1H), 3.60-3.45 (m, 4H), 3.16 (m, 2H), 1.73 (m, 2H), 1.22 (d, $^3J_{H,H}$=6.9 Hz, 3H), 0.86 (m, 3H); $^{19}$F NMR (376 MHz, (CD$_3$)$_2$SO): δ−114.9 (br s, 2F); MS (MALDI): m/z=436.9 ([M+H]$^+$).

Compound 86: 4-(difluoromethyl)-5-[4-[(3R)-3-ethylmorpholin-4-yl]-6-[(3R)-3-methylmorpholin-4-yl]-1,3,5-triazin-2-yl]pyridin-2-amine (86)

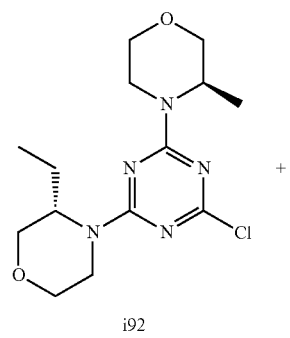

i92

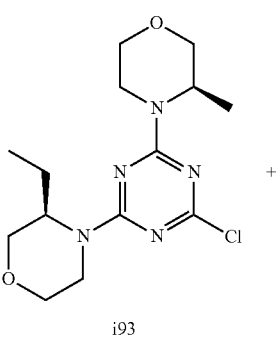

i93

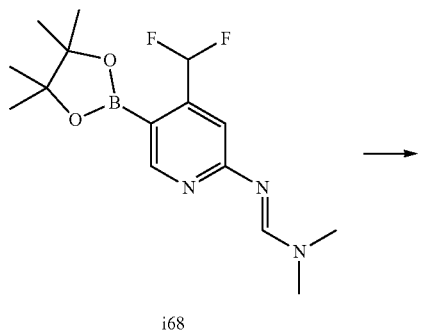

i68

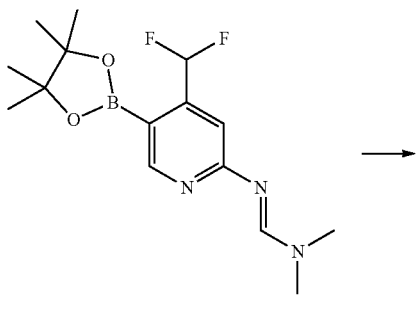

i68

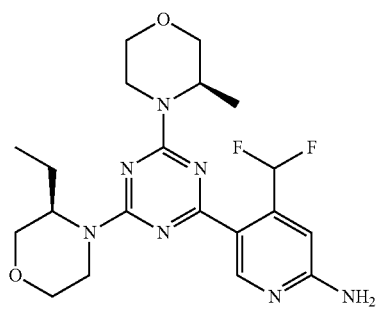

86

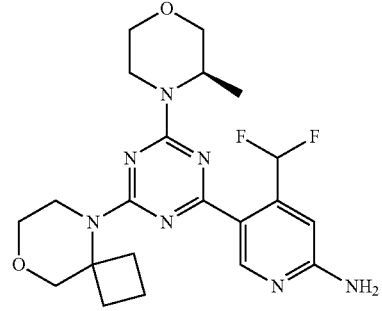

88

According to general procedure 1, compound 86 is obtained from starting materials i93 and i68 in 47% yield as a colorless solid. $^1$H NMR (400 MHz, (CD$_3$)$_2$SO): δ 8.88 (s, 1H), 7.77 (t, $^2J_{H,F}$=55 Hz, 1H), 6.85 (br s, 2H), 6.76 (s, 1H), 4.65 (m, 1H), 4.49-4.30 (m, 3H), 3.93-3.82 (m, 3H), 3.72 (m, 1H), 3.57 (m, 1H), 3.50 (m, 1H), 3.43-3.37 (m, 2H), 3.19-3.14 (m, 2H), 1.73 (m, 2H), 1.22 (d, $^3J_{H,H}$=6.9 Hz, 3H), 0.86 (m, 3H); $^{19}$F NMR (376 MHz, (CD$_3$)$_2$SO): δ −115.3 (br s, 2F); MS (MALDI): m/z=436.9 ([M+H]$^+$).

Compound 88: 4-(difluoromethyl)-5-[4-[(3R)-3-methylmorpholin-4-yl]-6-(8-oxa-5-azaspiro[3.5]nonan-5-yl)-1,3,5-triazin-2-yl]pyridin-2-amine (88)

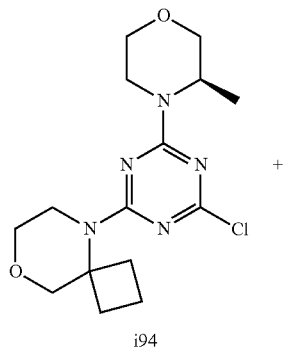

i94

+

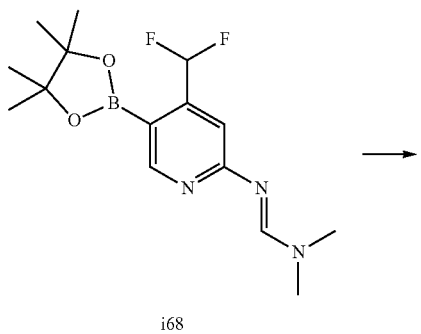

i68

⟶

According to general procedure 1, compound 88 is obtained from starting materials i94 and i68 in 50% yield as a colorless solid. $^1$H NMR (400 MHz, (CD$_3$)$_2$SO): δ 8.82 (s, 1H), 7.71 (t, $^2J_{H,F}$=55 Hz, 1H), 6.84 (br s, 2H), 6.75 (s, 1H), 4.55 (m, 1H), 4.23 (m, 1H), 3.91 (m, 1H), 3.78 (m, 2H), 3.69 (m, 3H), 3.56 (m, 1H), 3.50 (m, 2H), 3.41 (m, 1H), 3.16 (m, 1H), 2.50 (m, 2H), 2.26 (m, 2H), 1.73 (m, 2H), 1.21 (d, $^3J_{H,H}$=6.9 Hz, 3H); $^{19}$F NMR (376 MHz, (CD$_3$)$_2$SO): δ −114.9 (br s, 2F); MS (MALDI): m/z=446.8 ([M+H]$^+$).

Example 2

In Vitro mTOR Binding Assay and In-Cell Western Blot

In Vitro mTOR Binding Assay

N-terminally GST-tagged mTOR (Cat. No. PR8683B; 0.45 mg/ml; truncated version: amino acids 1360-2549), Alexa Fluor® 647 labeled kinase Tracer 314 (Cat. No. PV6087), LanthaScreen Eu-anti-GST Tag antibody (Cat. No. PV5594) were purchased from Life Technologies. The 1×mTOR Kinase Buffer consists of 50 mM HEPES pH 7.5, 5 mM MgCl$_2$, 1 mM EGTA, and 0.01% Pluronic F-127 (Sigma Cat. No. P2443-250G).

A 10-point 4-fold serial dilution (highest concentration at 10 μmol/L and lowest concentration at 40 pmol/L) of each compound was tested for mTOR binding in duplicate in a 384-well plate. To perform the LanthaScreen kinase binding assay 5 μl of the test compounds concentrated 3× the final concentration, 5 μl of 9 nM GST-mTOR/6 nM Eu-anti-GST antibody mixture and 5 μl of 30 nM Tracer 314 solution were mixed together resulting to a final concentration of 3 nM GST-mTOR, 2 nM Eu-anti-GST antibody and 10 nM Tracer 314 per well. After 30 min incubation at RT, time-resolved FRET was measured with a Synergy 4 multi-mode microplate reader (Biotek Instruments) using the following settings: 100 microsecs delay before data collection, 200 microsecs time for data collection, 10 measurements per data point. Emission filter: 665 nm/8 nm with sensitivity set to 190 and 620 nm/10 nm with sensitivity set to 130; Excitation filter: 340 nm/30 nm; Dichroic mirror 400 nm.

For data analysis, the mean background (wells with only mTOR kinase buffer) was subtracted and the emission ratio calculated by dividing the signal emitted at 665 nm from the acceptor (Alexa Fluor®647 labeled Tracer 314) by the signal emitted at 620 nm from the donor (Eu-labeled antibody). IC$_{50}$ values of each compound were determined by plotting the emission ratio versus the compound concentrations (in logarithmic scale) and then by fitting a sigmoidal dose-response curve with variable slope to the data using GraphPad™ Prism.

In-Cell Western Blot

A2058 cells are plated at 20,000 cells/well in a 96-well plate (Perkin Elmer, Cat. No. 6005558) and 24 hours later treated with different compounds for 1 hour. For each compound 7 different concentrations are applied on cells (5 µM, 1.25 µM, 0.625 µM, 0.3125 µM, 0.155 µM, 0.08 µM and 0.04 µM). Cells are fixed with 4% paraformaldehyde for 30 minutes at room temperature, washed 2 times with 1% BSA in PBS, permeabilized with 0.1% Triton X-100 in PBS/1% BSA for 30 minutes at room temperature and blocked with 5% goat serum in PBS/1% BSA/0.1% Triton X-100 for 30 minutes at room temperature. Cells are stained with primary antibody either with rabbit anti-pPKB S473 (1:500; Cell Signaling Technology, Cat. No. 4058) combined with mouse anti-α-tubulin (1:2000; used for normalization; Sigma, Cat. No. T9026) or with rabbit anti-pS6 S235/S236 (1:500; Cell Signaling Technology, Cat. No. 4856) combined with mouse anti-α-tubulin (1:2000; used for normalization) over night at 4° C. After 3 times 5 minutes wash with PBS/1% BSA/0.1% triton cells are treated with the secondary antibodies goat-anti-mouse IRDye680 (LICOR, Cat. No. 926-68070) and goat-anti-rabbit IRDye800 (LICOR, 926-32211)(each diluted 1:500 in PBS/1% BSA/0.1% triton) for 1 hour while shaking in the dark. Cells are washed 3 times 5 minutes with PBS/1% BSA/0.1% triton and plate scanned with the Odyssey Infrared Scanning system using both 700 and 800 nm channels. As control for 0% inhibition vehicle (0.2% DMSO) is added to cells. To correct for background staining in the data analysis wells are treated only with secondary antibodies.

For data analysis the mean background signal from channel 700 nm and 800 nm are subtracted from each signal in channel 700 nm and 800 nm, respectively. The signals in each channel are normalized to the 0% inhibition and then signal ratio 800 nm over 700 nm is performed to obtain the values for either pPKB S473 or pS6 S235/S236 normalized to α-Tubulin.

$IC_{50}$ values of each compound are determined by plotting the normalized pPBK S473 and pS6 S235/S236 signals, respectively, versus the compound concentrations (in logarithmic scale) and then by fitting a sigmoidal dose-response curve with variable slope to the data using GraphPad™ Prism.

TABLE 1

Comparative biological activities

| | This invention Compound 1 | WO2010/052569 | This invention Compound 2 | WO2010/052569 |
|---|---|---|---|---|
| | 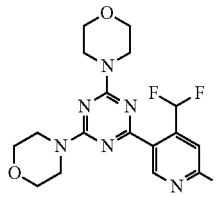 | 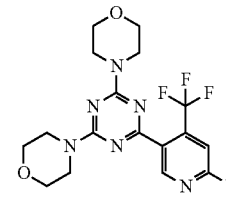 | 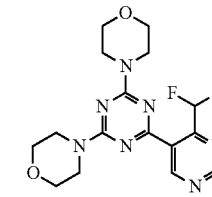 | 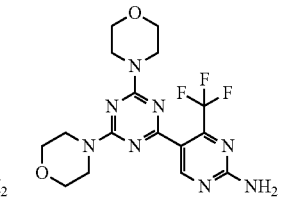 |
| pPKB S473 $IC_{50}$ [nM] | 108 | 149 | 34 | 64 |
| pS6 S235/236 $IC_{50}$ [nM] | 196 | 340 | 80 | 650 |
| mTOR $IC_{50}$ [nM] | 8 | 190 | 59 | 199 |

TABLE 2

Comparative biological activities

| | This invention Compound 6 | WO2010/052569 | This invention Compound 7 | WO2010/052569 |
|---|---|---|---|---|
| | 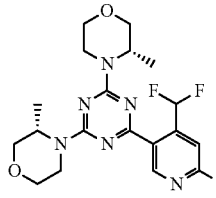 | 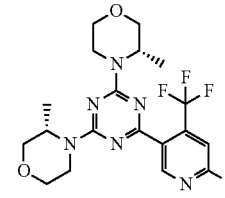 | 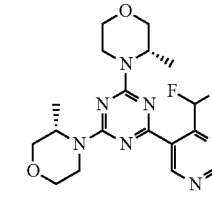 | 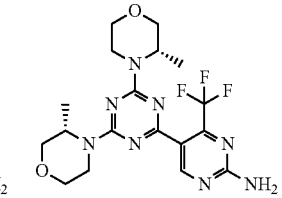 |
| pPKB S473 $IC_{50}$ [nM] | 155 | 255 | 59 | 118 |
| pS6 S235/236 $IC_{50}$ [nM] | 215 | 433 | 97 | 224 |

TABLE 2-continued

Comparative biological activities

| | This invention Compound 6 | WO2010/052569 | This invention Compound 7 | WO2010/052569 |
|---|---|---|---|---|
| | 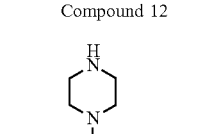 | | | |
| mTOR IC$_{50}$ [nM] | 23 | nd | 71 | nd |

TABLE 3

Comparative biological activities

| | This invention Compound 8 | WO2010/052569 | This invention Compound 9 | WO2010/052569 |
|---|---|---|---|---|
| | 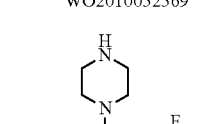 | | | |
| pPKB S473 IC$_{50}$ [nM] | 74 | 196 | 35 | 91 |
| pS6 S235/236 IC$_{50}$ [nM] | 68 | 90 | 72 | 164 |
| mTOR IC$_{50}$ [nM] | 10 | nd | 24 | nd |

TABLE 4

Comparative biological activities

| | This invention Compound 12 | WO2010052569 | This invention Compound 13 | WO2010052569 |
|---|---|---|---|---|
| | 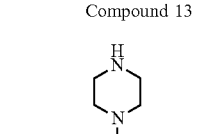 | | | |
| pPKB S473 IC$_{50}$ [nM] | 208 | 302 | 43 | 116 |
| pS6 S235/236 IC$_{50}$ [nM] | 515 | 743 | 150 | 416 |
| mTOR IC$_{50}$ [nM] | 543 | 796 | 1015 | 2834 |

TABLE 5
Comparative biological activities
| | This invention Compound 16 | WO2007/084786 | This invention Compound 17 | WO2007/084786 |
|---|---|---|---|---|
| | 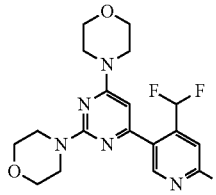 | 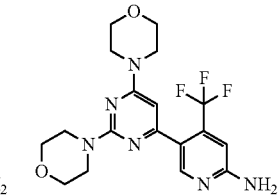 | 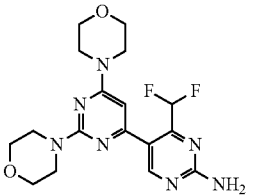 [SMILES: Nc1ncc(-c2cc(N3CCOCC3)nc(N3CCOCC3)n2)c(C(F)F)n1] | 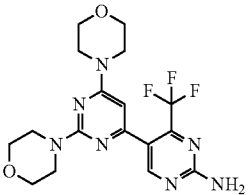 [SMILES: Nc1ncc(-c2cc(N3CCOCC3)nc(N3CCOCC3)n2)c(C(F)(F)F)n1] |
| pPKB S473 $IC_{50}$ [nM] | 207 | 263 | 90 | 194 |
| pS6 S235/236 $IC_{50}$ [nM] | 184 | 277 | 149 | 384 |
| mTOR $IC_{50}$ [nM] | 30 | 179 | 155 | 644 |
TABLE 6
Comparative biological activities
| | This invention Compound 18 | WO2008/098058 | This invention Compound 19 | WO2008/098058 |
|---|---|---|---|---|
| | 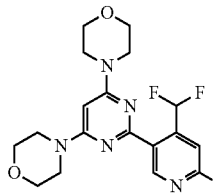 | 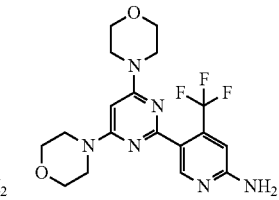 | 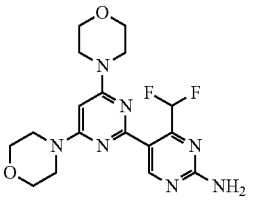 [SMILES: Nc1ncc(-c2nc(N3CCOCC3)cc(N3CCOCC3)n2)c(C(F)F)n1] | 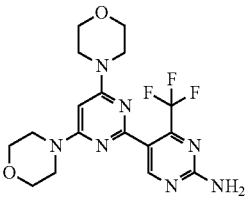 [SMILES: Nc1ncc(-c2nc(N3CCOCC3)cc(N3CCOCC3)n2)c(C(F)(F)F)n1] |
| pPKB S473 $IC_{50}$ [nM] | 243 | 555 | 78 | 175 |
| pS6 S235/236 $IC_{50}$ [nM] | 256 | 665 | 147 | 370 |
| mTOR $IC_{50}$ [nM] | 31 | 366 | 158 | 1925 |

TABLE 7
Comparative biological activities
| | This invention Compound 20 | WO2010052569 | This invention Compound 21 | WO2010052569 |
|---|---|---|---|---|
| | 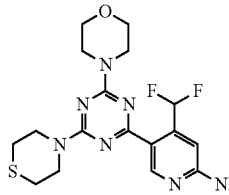 | 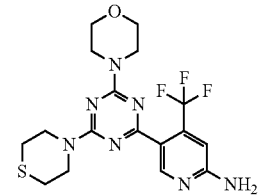 | 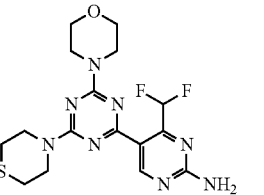 | 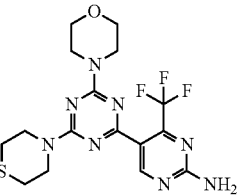 |
| pPKB S473 $IC_{50}$ [nM] | 146 | 311 | 57 | 343 |
| pS6 S235/236 $IC_{50}$ [nM] | 250 | 559 | 216 | 996 |
| mTOR $IC_{50}$ [nM] | 13 | 118 | 54 | 394 |
TABLE 8
Comparative biological activities
| | This invention Compound 25 | WO2007/084786 | This invention Compound 26 | WO2007/084786 |
|---|---|---|---|---|
| | 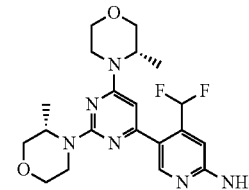 | 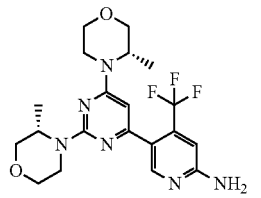 [SMILES: C[C@H]1COCCN1c1cc(-c2cnc(N)cc2C(F)(F)F)nc(N2CCOC[C@@H]2C)n1] | 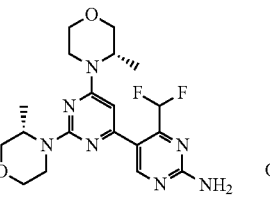 | 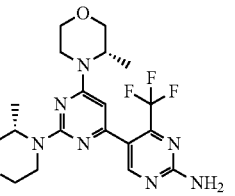 |
| pPKB S473 $IC_{50}$ [nM] | 303 | 452 | 87 | 193 |
| pS6 S235/236 $IC_{50}$ [nM] | 294 | 553 | 191 | 617 |
| mTOR $IC_{50}$ [nM] | 32 | 152 | 47 | 287 |

TABLE 9
Comparative biological activities
| | This invention Compound 27 | WO2007/084786 | This invention Compound 28 | WO2007/084786 |
|---|---|---|---|---|
| | 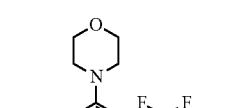 | 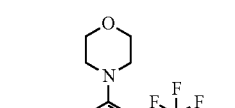 | 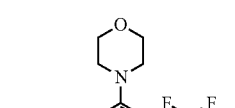 | 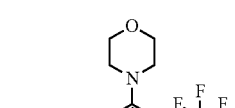 |
| pPKB S473 IC$_{50}$ [nM] | 614 | 883 | 77 | 290 |
| pS6 S235/236 IC$_{50}$ [nM] | 766 | 1100 | 146 | 1027 |
| mTOR IC$_{50}$ [nM] | 65 | 376 | 23 | 1253 |
TABLE 10
Comparative biological activities
| | This invention Compound 23 | WO2007/084786 | This invention Compound 24 | WO2007/084786 |
|---|---|---|---|---|
| | 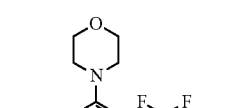 | 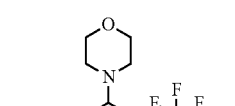 | 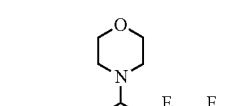 | 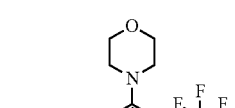 |
| pPKB S473 IC$_{50}$ [nM] | 285 | 564 | 84 | 340 |
| pS6 S235/236 IC$_{50}$ [nM] | 230 | 562 | 167 | 740 |
| mTOR IC$_{50}$ [nM] | 40 | 88 | 35 | 121 |

TABLE 11

Comparative biological activities

| | This invention Compound 31 | WO2007/084786 | This invention Compound 32 | WO2007/084786 |
|---|---|---|---|---|
| pPKB S473 IC$_{50}$ [nM] | 146 | 248 | 100 | 191 |
| pS6 S235/236 IC$_{50}$ [nM] | 124 | 228 | 387 | 535 |
| mTOR IC$_{50}$ [nM] | 15 | 28 | 293 | 186 |

TABLE 12

Results of in-cell Western Blot and mTOR binding

| Compound | In-cell Western blot pPKB S473 IC$_{50}$ [nM] | In-cell Western blot pS6 S235/S236 IC$_{50}$ [nM] | binding mTOR IC$_{50}$ [nM] |
|---|---|---|---|
| 1 | 108 | 196 | 8 |
| 2 | 34 | 80 | 59 |
| 3 | 231 | 105 | 8 |
| 4 | 178 | 135 | nd |
| 5 | 85 | 135 | nd |
| 6 | 155 | 215 | 23 |
| 7 | 59 | 97 | 71 |
| 8 | 74 | 68 | 10 |
| 9 | 35 | 72 | 24 |
| 10 | 138 | 93 | nd |
| 11 | 61 | 96 | nd |
| 12 | 219 | 407 | 543 |
| 13 | 37 | 120 | 1015 |
| 14 | 349.5 | 883 | nd |
| 15 | 49 | 286 | nd |
| 16 | 207 | 184 | 30 |
| 17 | 90 | 149 | 155 |
| 18 | 243 | 256 | 31 |
| 19 | 78 | 147 | 158 |
| 20 | 146 | 250 | 13 |
| 21 | 57 | 216 | 54 |
| 22 | 57 | 216 | 18 |
| 23 | 285 | 230 | 40 |
| 24 | 84 | 167 | 35 |
| 25 | 303 | 294 | 32 |
| 26 | 87 | 191 | 47 |
| 27 | 614 | 766 | 65 |
| 28 | 77 | 146 | 23 |
| 31 | 146 | 124 | 15 |
| 32 | 100 | 387 | 293 |
| 37 | 533 | 268 | 49 |
| 38 | 219 | 79 | nd |
| 39 | 106 | 47 | 1 |
| 40 | 252 | 160 | 5 |
| 41 | 436 | 261 | 22 |
| 42 | 54 | 45 | 3 |
| 44 | 197 | 87 | 5 |
| 45 | 234 | 93 | 7 |
| 46 | 956 | 426 | 36 |
| 47 | 469 | 176 | 29 |
| 50 | 1561 | 407 | nd |
| 51 | 875 | 352 | nd |
| 52 | 1050 | 332 | nd |
| 53 | 1318 | 612 | nd |
| 54 | 354 | 209 | nd |
| 55 | 942 | 526 | nd |
| 56 | >10000 | >10000 | nd |
| 66 | 244 | 139 | 4 |
| 67 | 787 | 395 | nd |
| 68 | 682 | 415 | nd |
| 69 | 244 | 140 | 21 |
| 70 | 914 | 906 | nd |
| 71 | 2337 | 3141 | nd |
| 77 | 476 | | nd |
| 78 | 506 | 392 | 38 |
| 79 | 200 | 136 | 10 |
| 80 | 94 | 117 | nd |
| 82 | 329 | 169 | 40 |
| 83 | 379 | 294 | 32 |
| 84 | 116 | 146 | nd |
| 85 | 249 | 241 | nd |
| 86 | 231 | 236 | nd |
| 88 | 271 | 192 | 18 |

Example 3

Tolerability of Compound 3 and Compound 8 in Mice

Maximal Tolerated Dose (MTD) of Cpd. 3 and Cpd. 8 in BALB/c Nude Mice

In order to find a dose that could be used for further experiments and in order to show tolerability of compounds of the present invention, female BALB/c nude mice were treated with Cpd. 3 and Cpd. 8 by per oral (p.o.) gavage twice for five days with a two day dose holiday in between. Compounds were administered in the following vehicle: 20% Hydroxypropyl-β-cyclodextrin (HPBCD), 10% DMSO and 70% water. The major endpoint was to evaluate the body weight loss and animal survival. The body weights were recorded daily for the dosing days and at least twice weekly thereafter. The animal death was checked daily for survival. Animals were to be evaluated for 7 days post the final dose. The tolerated dose was defined as the dose that results in less than 20% mean body-weight loss, and no treatment related death during the study. The randomized block design was used to assign experimental animals to groups. First, the experimental animals were divided into homogeneous blocks according to their initial body weight. Secondly, within each block, randomization of experimental animals to treatments was conducted.

Animal supplier: Shanghai Lingchang Bio-Technology Co. Ltd (LC, Shanghai, China). Animal Certificate No.: 2013001803305. The mice were kept in individual ventilated cage (IVC) systems at constant temperature and humidity with 5 animals in each cage.

Diet: Mouse diet, C060 irradiation sterilized dry granule food. Animals had free access during the entire study period. Water: RO water, autoclaved before using. Animals had free access to sterile drinking water.

OVCAR-3 and SUDHL/6 tumor bearing BALB/c nude mice were treated with Cpd. 3, p.o. at 100 mg/kg for 21 or 15 consecutive days, respectively under the same conditions. Body weight of the mice was stable.

The following MTDs were determined in BALB/c mice: Cpd. 3: 100 mg/kg, Cpd. 8: 25 mg/kg. In conclusion, both Cpd. 3 and Cpd. 8 are well tolerated at therapeutically effective doses (see Example 4).

Example 4

Pharmacokinetics (PK) of Cpd. 3 and Cpd. 8

In order to determine distribution of compounds in the body, PK of compounds was determined in rats and mice. For the treatment of neurological disorders it is essential to employ compounds that cross the blood brain barrier and reach efficacious concentrations in the brain.

A. PK in Sprague Dawley (SD) Rats

A single oral administration of cpd. 3, 10 mg/kg was given to female SD rats in a vehicle consisting of DMSO/HPBCD 20% (10/90). Animals were housed in controlled environment and enclosures provided sterile and adequate space with bedding material, food and water, environmental and social enrichment (group housing). Rats were randomized according to their individual body weight, treated and blood, brain and liver were collected and snap frozen at the following time points: 0.5, 2, 4 and 8 hours. Blood (approximately 500-700 μL, collected via cardiac puncture under anesthesia) was immediately transferred into tubes containing lithium-heparin as anticoagulant (Ref: T MLH, Venoject®, Terumo). Tubes were centrifuged at 1,300 g for 10 minutes at +4° C. The resulting plasma was collected and snap frozen in liquid nitrogen and stored at −80° C. until analysis.

Compound concentrations were detected by HPLC-MS/MS. The calibration curves were drawn using standards of known concentrations.

Results are depicted in FIG. 1A. Cpd. 3 shows good oral bioavailability and excellent penetration into the brain. A Cmax of 1.4 ng/ml in plasma and 1.3 ng/ml in brain indicate exposures that are high enough for target engagement (table 1).

B. PK in B57BL/6J Mice

A single, oral administration of Cpd. 3 and Cpd. 8, 50 mg/kg was administered to B57BL/6J mice by gavage. Animals were housed in temperature controlled rooms with free access to food and water. Test items were weighed in a glass vial and dissolved first in DMSO. Tween 80 was added subsequently and finally, the formulation was completed with HPβCD 20%. The formulations were administered via gavage at t=0 h, and at each of 8 time points, three mice of each treatment group were anesthetized with isoflurane for blood sampling via puncture of the retrobulbar venous plexus. Blood was collected in tubes containing K3-EDTA and stored on ice until centrifugation at 3000×g (10 min. 4° C.). The plasma supernatant was separated and kept at −20° C. until being assayed. Thigh muscle and brain of mice were snap frozen. The brain and muscle samples were homogenized in PBS using the Precellys 24/Dual homogeniser.

Samples were analyzed by LC-MS. Calibration standards were prepared by spiking 20 μl of drug free blank plasma with calibration solution. A volume of 40 μl acetonitrile containing the internal standard (150 ng/ml Diazepam for 2015PQR002 samples and 300 ng/ml Griseofulvin for 2015PQR004 samples) was then added to 20 μl of brain or muscle homogenate, brain/muscle calibration standard and brain/muscle QC sample. Samples were vigorously shaken and centrifuged for 10 minutes at 6000 g and 20° C. The particle free supernatant was diluted with 1 volume of water. An aliquot was transferred to 200 μl sampler vials and subsequently subjected to LC-MS with an injection volume of 1.5 μl.

Figure 1B:
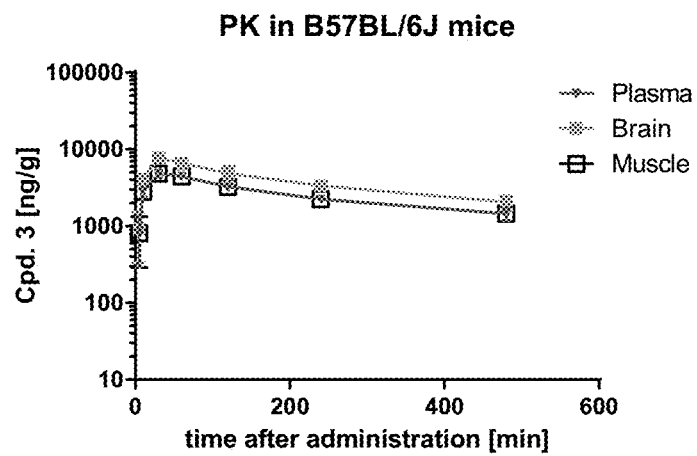
FIG. 1B: Pharmacokinetic analysis of Cpd. 3 and Compound 8 (Cpd. 8) levels in balb 6 mice. After a single oral administration of Cpd. 3 or Cpd. 8 (50 mg/kg), tissue samples were analyzed for compound levels at different time points by LC-MS. n=3
Figure 1B:
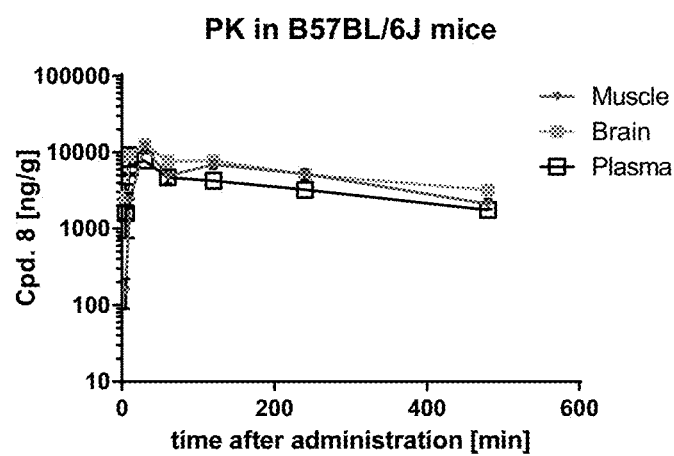
Figure 2A:
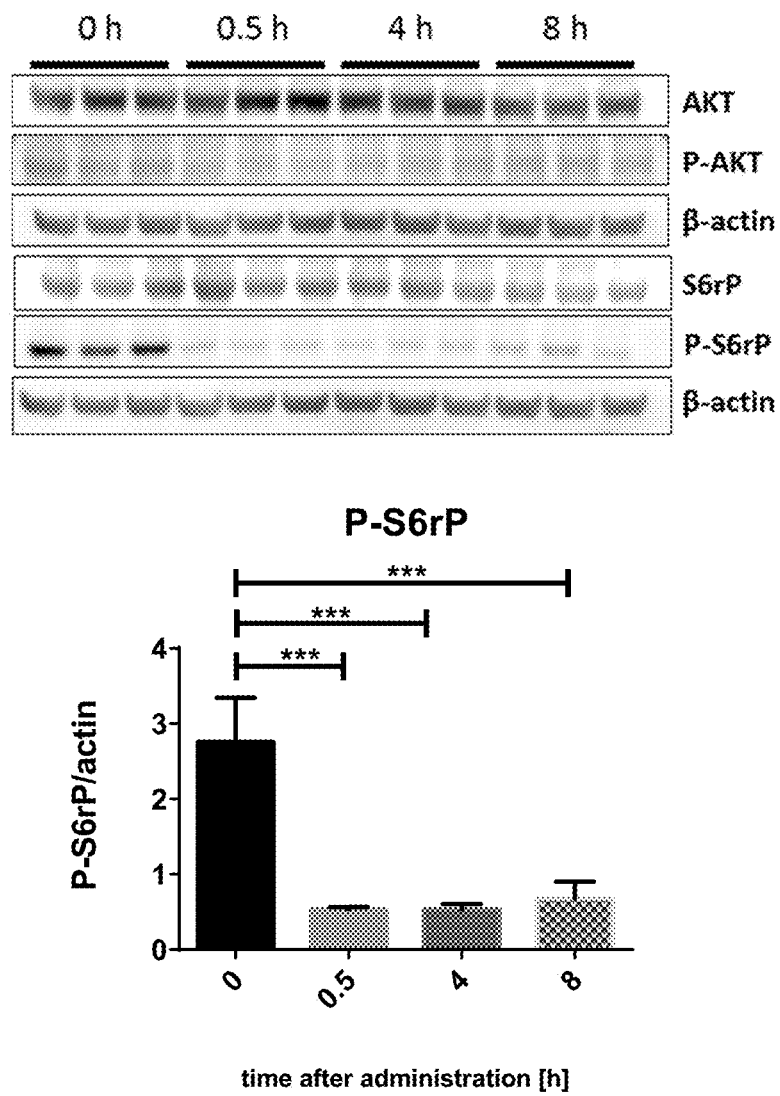
FIG. 2A: Pharmacodynamic analysis of Cpd. 3 administered to balb 6 mice in a single oral application of 50 mg/kg. Brain lysates were analyzed by western blot. mTOR signaling is inhibited by Cpd.3 as indicated by reduction of S6 phosphorylation at time points between 30 minutes and 8 hours. Quantification of western blot bands shows significance of reduction of mTOR signaling pathway. n=3, analysis of variance (ANOVA), * p<0.0005,  p<0.005, * p<0.05
Figure 2B:
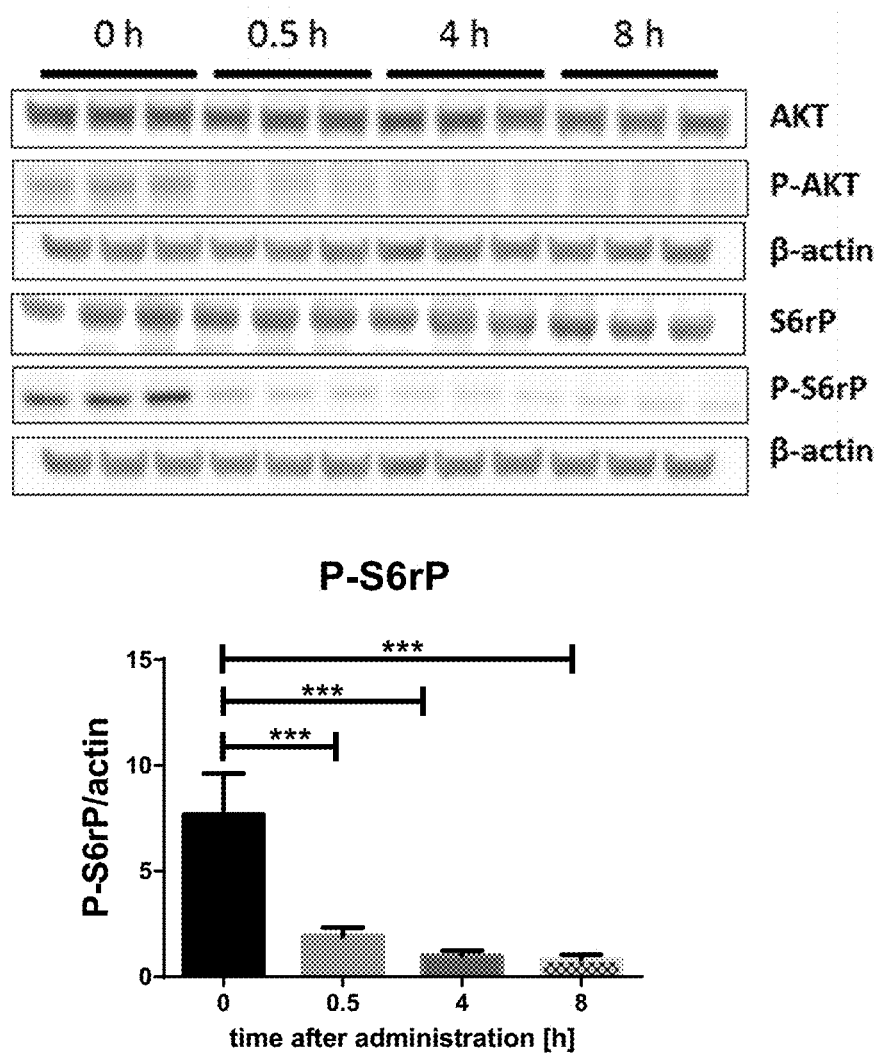
FIG. 2B: Pharmacodynamic analysis of Cpd. 8 administered to balb 6 mice in a single oral application of 50 mg/kg. Brain lysates were analyzed by western blot. mTOR signaling is inhibited by Cpd. 8 as indicated by reduction of S6 phosphorylation at time points between 30 minutes and 8 hours. Quantification of western blot bands shows significance of reduction of mTOR signaling pathway. n=3, ANOVA, * p<0.0005,  p<0.005, * p<0.05
Figure 2C:
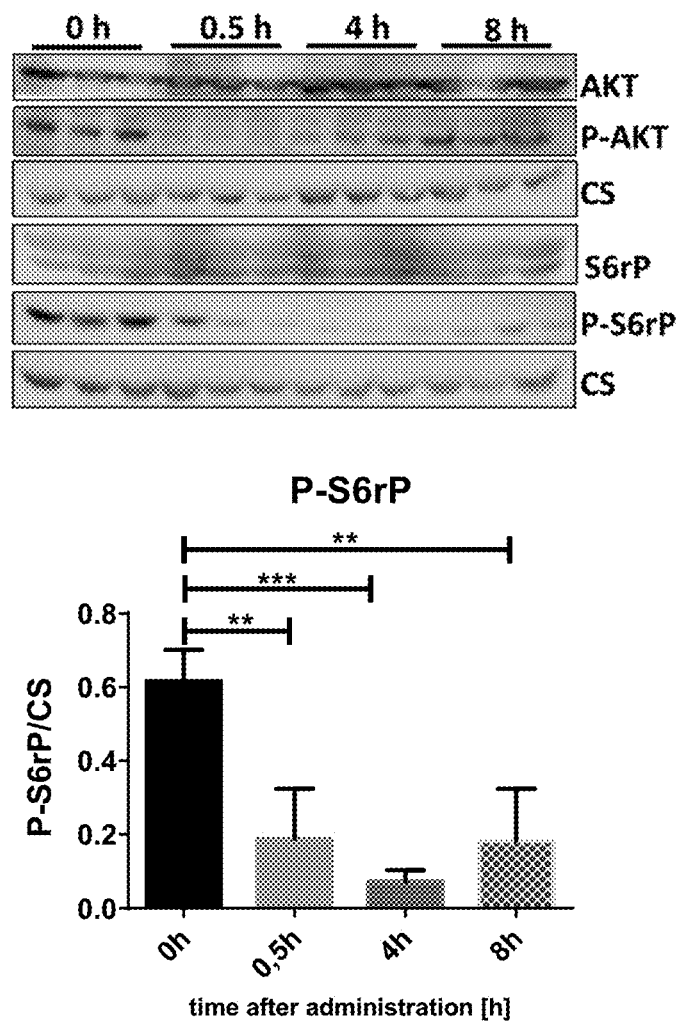
FIG. 2C: Pharmacodynamic analysis of Cpd. 3 administered to balb 6 mice in a single oral application of 50 mg/kg. Thigh muscle lysates were analyzed by western blot. mTOR signaling is inhibited by Cpd. 3 as indicated by reduction of S6 phosphorylation at time points between 30 minutes and 8 hours. Quantification of western blot bands shows significance of reduction of mTOR signaling pathway. n=3, ANOVA, * p<0.0005,  p<0.005, * p<0.05
Figure 2D:
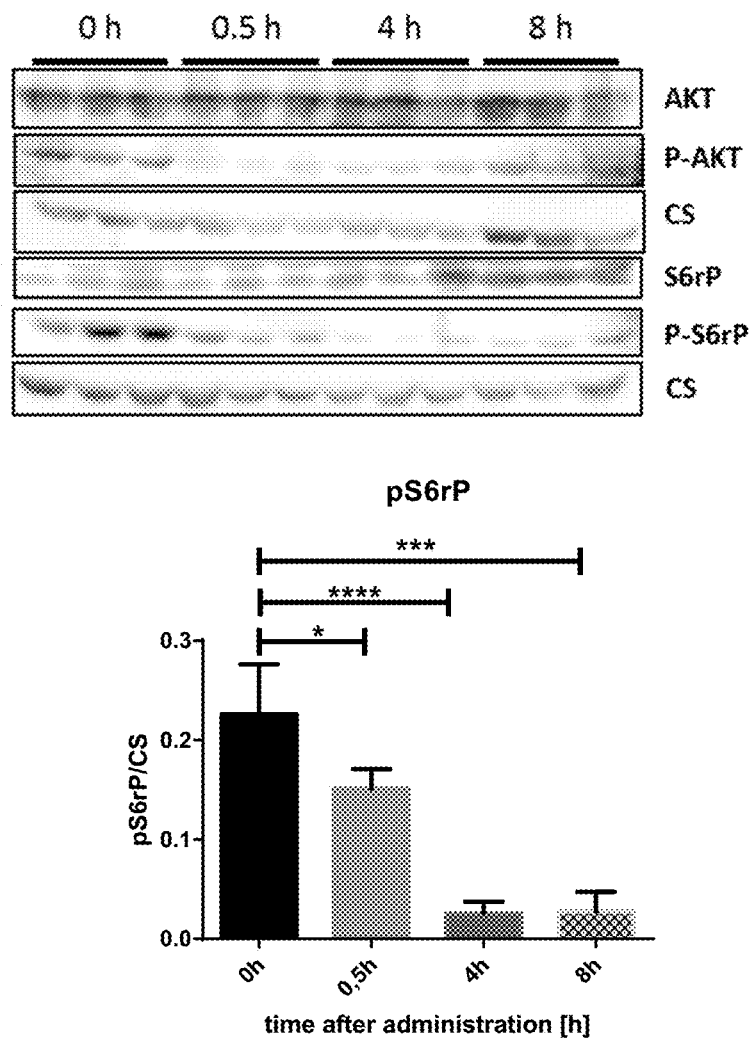
FIG. 2D: Pharmacodynamic analysis of Cpd. 8 administered to balb 6 mice in a single oral application of 50 mg/kg. Thigh muscle lysates were analyzed by western blot. mTOR signaling is inhibited by Cpd. 8 as indicated by reduction of S6 phosphorylation at time points between 30 minutes and 8 hours. Quantification of western blot bands shows significance of reduction of mTOR signaling pathway. n=3, ANOVA, * p<0.0005,  p<0.005, * p<0.05

Both, Cpd. 3 and Cpd. 8 have good oral bioavailability in mice (FIG. 1B). Distribution between plasma and brain indicates penetration over the blood brain barrier. The half-life of the compounds in mice has been estimated to be about 4.7-4.8 hours. Pharmacological parameters are shown in table 1.

TABLE 1

PK parameters of Cpd. 3 and Cpd. 8 after a single, oral application to rats or mice.

| Species | rat | mouse |
| --- | --- | --- |
| Route of administration | po | po |
| Dose (mg/kg) | 10 | 50 |
| Plasma Cmax (μg/ml) | 1.4 | 4.8 |
| Brain Cmax (μg/g) | 1.3 | 7.7 |
| Plasma Tmax (hr) | 0.5 | 0.5 |
| Brain Tmax (hr) | 0.5 | 0.5 |
| Plasma t1/2 (hr) | | 5.3 |
| Brain t1/2 (hr) | | 5.0 |
| Plasma AUC (h*μg/ml) | 0.4 | 20.5 |
| Brain AUC (h*μg/ml) | 2.5 | 30.6 |

Example 5

Target Engagement of Cpd. 3 and Cpd. 8 in Brain and Muscle

Brain and thigh muscle was sampled from B57BL/6J mice used for PK analysis (EXAMPLE 4). Tissue was snap frozen in liquid nitrogen and stored at −80° C. Tissue was thawed and lysed in RIPA buffer 1 ml/half brain. Complete protease inhibitor and PhosStop phosphatase inhibitor (Roche) was added to the buffer before lysis. Tissue was homogenized manually and centrifuged twice at 16000 rpm, 4° C. for 20 minutes. Supernatant was frozen with 10% glycerol at −80° C. Protein concentration was performed using Bradford reagent. For western blot analysis of AKT and S6rP phosphorylation, 30 μg of protein was denatured with β-mercaptoethanol at 95° C. and separated on SDS page gels at 100 V. Then proteins were transferred to a nitrocellulose membrane (Bio-Rad, USA) at 80 V. Nonspecific binding was blocked with 5% bovine serum albumin (BSA) (Sigma-Aldrich, USA). Membranes were incubated over night with primary antibody dissolved in TBST, 5% BSA at 4° C. and with secondary antibody coupled to horseradish peroxidase (GE Healthcare, UK) for 1 hour at RT and washed. Imaging of protein bands was performed using Luminol (Biozym, Hamburg, Germany. On a Li-Cor Odyssey FC reader. Quantification of S6-phosphorylation was determined with the same imaging system.

The following antibodies were used:
AKT, P-AKT (S473), S6rP, P-S6rP(S235/236): Cell Signaling (UK)
β-actin: Sigma Aldrich, USA Target engagement of Cpd. 3 and Cpd. 8 could be shown in brain and thigh muscle after a single oral administration to mice (FIG. 2). Compounds cross the blood brain barrier and inhibit mTOR signaling cascade as shown by significantly reduced phosphorylation of S6rP and AKT. Signaling was altered at 30 min after administration and lasted for at least 8 hours.

Example 6 mTOR Pathway Activation in Epileptic Mice

To evaluate whether mTOR signaling was activated in the epileptic model used for this study, chronic epilepsy was induced by administration of pilocarpine, an agonist at muscarinic acetylcholine receptors. Systemic injections of pilocarpine in rats or mice result in a generalized convulsive status epilepticus (SE) with subsequent development of spontaneous epileptic seizures within the following couple of weeks. Six weeks after SE induction with pilocarpine almost 100% of the mice have developed chronic epilepsy.

A ramping-up dosing protocol was used which has the advantage that pilocarpine can be individually applied according to the susceptibility of each mouse. Pilocarpine (Sigma-Aldrich, Germany) was administered to female NMRI mice intraperitoneally at a dose of 100 mg/kg (Pilo-SE group). If mice did not display SE, further injections of 100 mg/kg pilocarpine were performed every 20 min until SE developed. As soon as a mouse showed generalized seizure activity, pilocarpine injections were stopped. To reduce peripheral side effects of pilocarpine, methylscopolamine (Sigma-Aldrich, Germany) was administered 30 minutes prior to the first injection of pilocarpine. Animals were continuously monitored and duration of convulsive SE was registered [referred to Racine's scale. SE onset was defined as continuous ongoing seizure activity following occurrence of one or two generalized tonic-clonic seizures [stage 4 or 5 on the Racine scale]. SE was characterized by head nodding in an upright (sitting) body position, Straub tail, and slight to moderate convulsions of forelimbs, sometimes interrupted by further generalized tonic-clonic seizures. In order to reduce mortality, SE was terminated by diazepam (10 mg/kg i.p.; diazepam-ratiopharm 10, injection solution) 90 min after SE onset. The following 2-5 days mice were injected with 0.9% sodium chloride solution twice daily and fed with baby pap because most of the mice do not eat or drink by themselves during the first days after SE. In the sham-SE group mice were treated with the same treatment scheme as the pilo-SE group but pilocarpine was replaced by 0.9% sodium chloride solution. The mortality in the pilo-SE model in mice is relatively high (overall about 50%) and can vary markedly between experimental groups/days. Therefore we had to start with a large number of mice for SE induction in order to reliably obtain a group size of 20-22 animals for the MEST.

A. mTOR Signaling in Brain Samples

Brain samples from pilocarpine treated mice and untreated mice were snap frozen and tissue was lysed in buffer containing 25 mM Tris-HCl, pH 8, 50 mM NaCl, 0.5% (w/v) sodium deoxycholate (DOC), and 0.5% (w/v) Triton X-100 and supplemented with complete protease inhibitor (Roche, Mannheim, Germany) and Phosphostop (NEB, USA). Disruption of cell lysates was performed by drawing up the cell suspension twenty times into a syringe with a small gauge needle (21 G) on ice. Protein concentrations in the lysates were determined by using the Pierce BCA Protein Assay kit (Thermo Scientific, Bonn, Germany) according to the manufacturer's instructions. Equal amounts of total protein were separated on 4-20% SDS-PAGE gels and transferred to PVDF membranes which were blocked overnight in 5% milk in phosphate buffered saline supplemented with Tween-20 (PBST: 137 mM NaCl, 2.7 mM KCl, 4.3 mM Na2HPO4, 1.4 mM KH2PO4, pH 7.3, 0.05% (w/v) Tween-20) at 4° C. Membranes were incubated with primary antibodies anti S6 1:1000, anti S6 Phospho Serin (240/244) 1:1000, anti S6 Phospho Serin (235/236) 1:2000 (NEB) and anti-Actin 1:100 (Sigma-Aldrich) for 1 h in 2% milk in PBST at room temperature (RT) and washed three times for 10 min in PBS-T. Secondary antibodies anti-rabbit-HRP 1:1000 (Dako, Hamburg, Germany) were incubated for 1 h in 2% milk in PBST at RT and washed three times for 10 min in PBST. Proteins were detected by enhanced chemiluminescence using SuperSignal West Femto Chemiluminescent Substrate (Thermo Scientific) and the ChemiDoc system (Bio-Rad, Munich, Germany) with QuantityOne software (Bio-Rad) according to the manufacturer's protocol. Relative protein expressions were quantified densitometrically with QuantityOne (Bio-Rad) software and calculated by normalization to the reference signals of actin with Graph-Pad Prism software (GraphPad, San Diego, CA, USA).

Figure 3A:
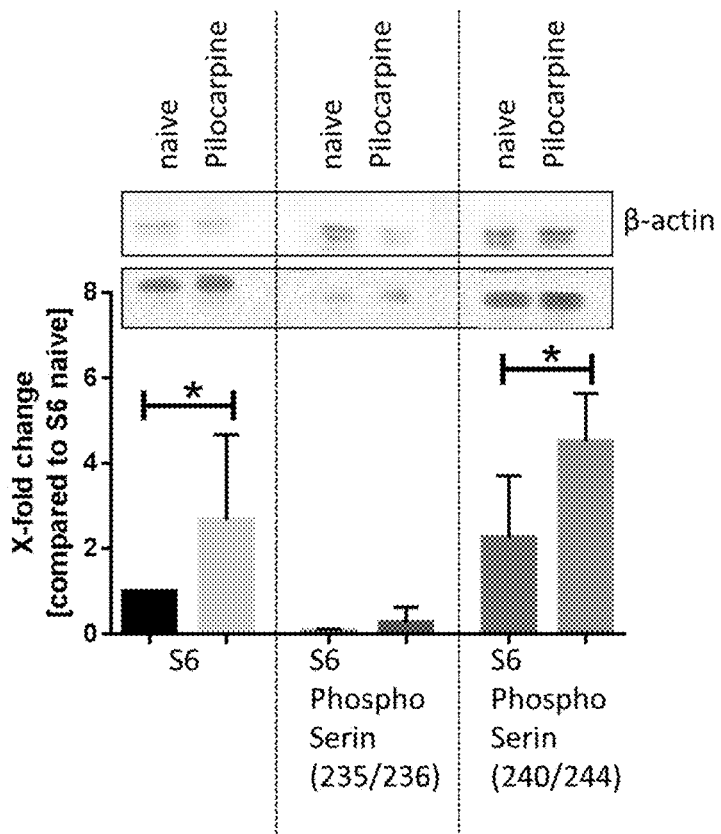
FIG. 3A: Western blot analysis of lysed mouse brains from pilocarpine-pretreated, epileptic mice and their untreated counterparts. mTOR signaling is elevated in the pilocarpine status epilepticus (SE) model. n=9 (naïve mice), n=8 (epileptic mice), ANOVA * p<0.05

Epilepsy-induced mice showed significantly elevated levels of total S6-protein as well as P-S6rP (Ser 240/244) (FIG. 3) in brain samples. As S6rP phosphorylation is a downstream event of mTOR activation, mTOR signaling was hyperactivated in mice that had been pre-treated with pilocarpine to induce epileptic seizures. In conclusion, the data indicate that mTOR overactivation is involved in epileptogenesis of the pilocarpine model.

B. mTOR Signaling in Brain Samples after Administration of Cpd. 3 Cpd. 8 and Everolimus Pilocarpine pre-treated and naïve mice were treated with a single oral dose of Cpd. 3 (40 mg/kg), Cpd. 8 (25 mg/kg), everolimus (5 mg/kg) or vehicle. 5 mice per group were utilized and sacrificed after 3 hours. Brain lysates were generated and analyzed by western blot as described under EXAMPLE 6 A. S6 phosphorylation (S235/236) was quantified with QuantityOne software (Bio-Rad) according to the manufacturer's protocol.

Figure 3B:
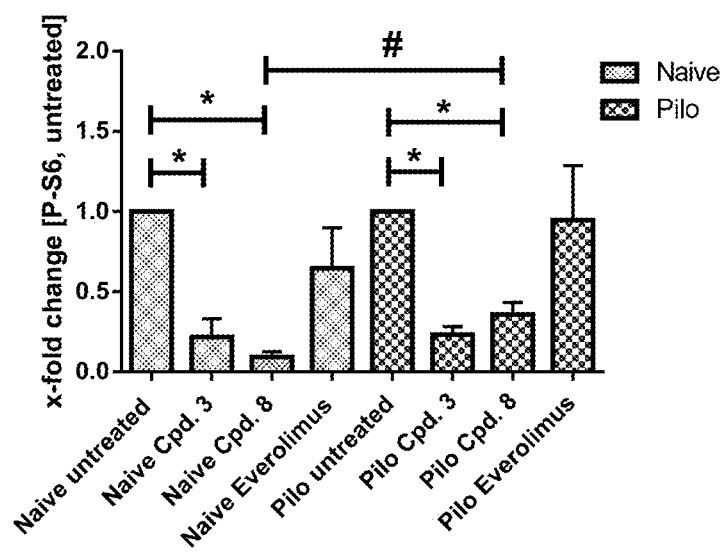
FIG. 3B: Western Blot analysis of lysed mouse brain from epileptic/pilocarpine pre-treated and naïve mice that were treated with a single oral dose of Compound 3 and 8 significantly inhibited S6 phosphorylation in brain. Stronger effects were observed in naïve mice. Everolimus did not show significant mTOR signaling inhibition in brain. MEAN±SEM, ANOVA, * p<0.05, #p<0.05, n=5
Figure 4A:
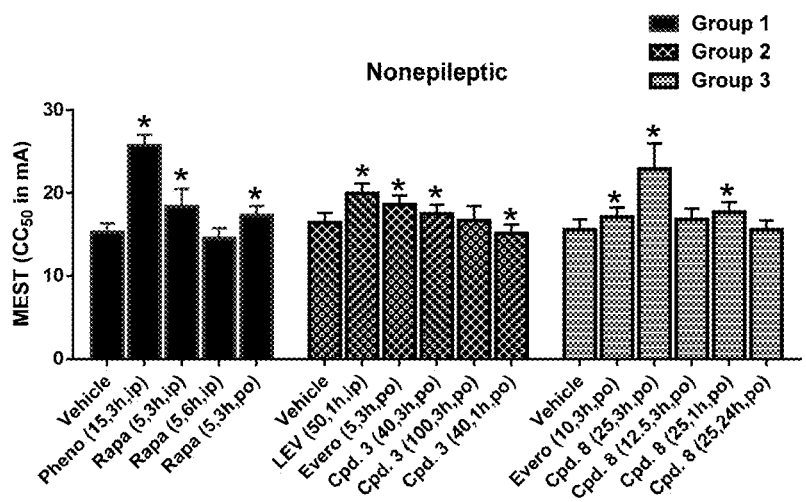
FIG. 4A, B: MEST of naïve mice.
Figure 4B:
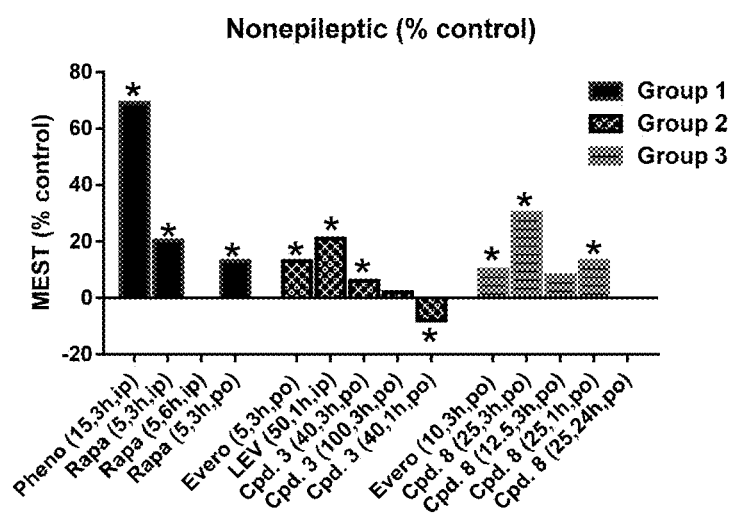
FIG. 4: After treatment of epileptic and nonepileptic mice with mTOR inhibitors, Phenobarbital or Levetiracetam maximal electroshock seizure threshold test (MEST) was performed. Antiepileptic effect of inhibitors was observed.
Figure 4C:
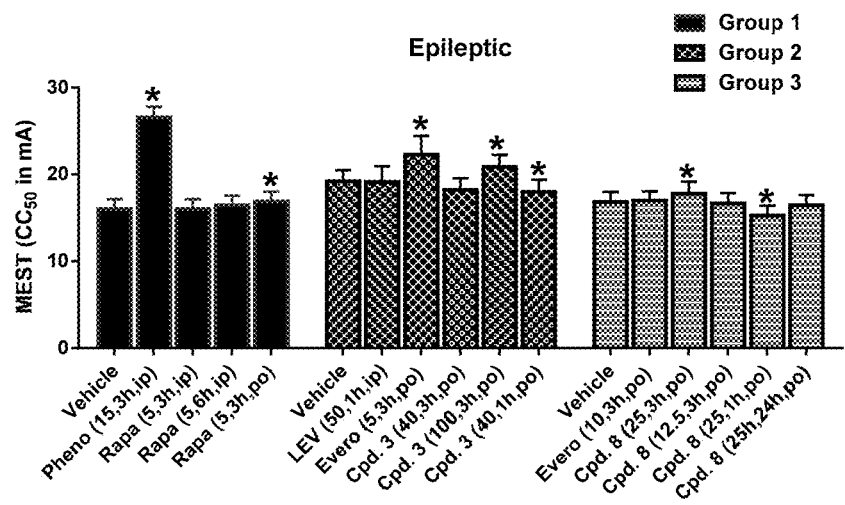
Figure 4D:
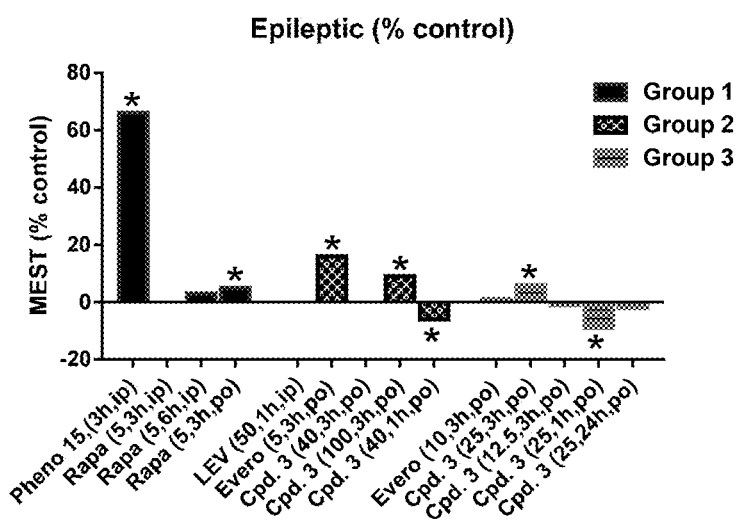
Figure 5A:
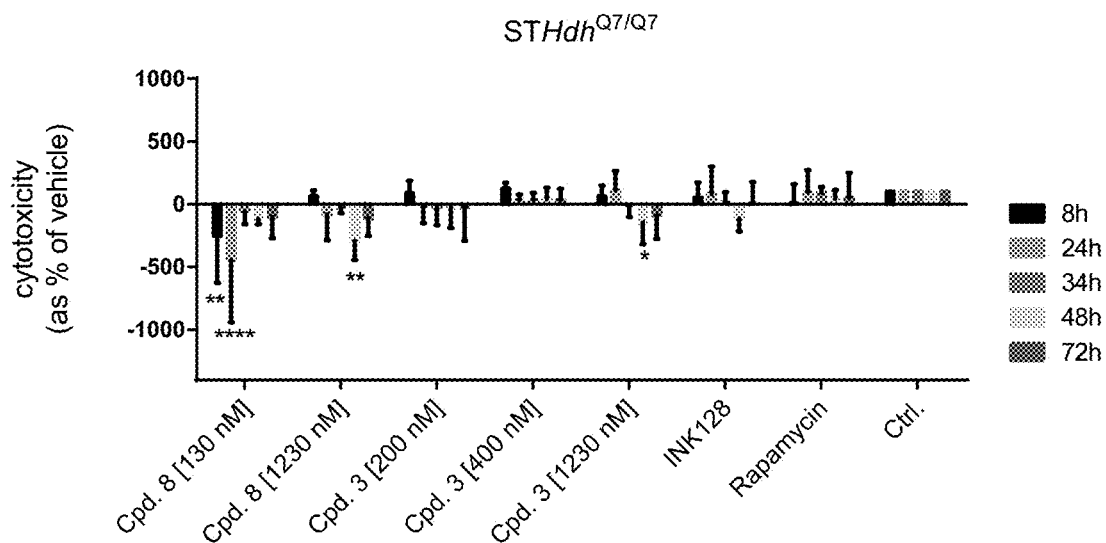
FIG. 5: Cell viability and protein synthesis of immortalized striatal cells derived from a knock-in mouse model expressing full-length HTT with 7 (STHdh$^{Q7/Q7}$) or 111 CAG-repeats (STHdh$^{Q111/Q111}$) after incubation with different concentrations of Cpd. 3 and Cpd. 8 and the mTORC1/2 inhibitor INK 128 (Sapanisertib) (100 nM) and rapamycin (400 nM).
Figure 5B:
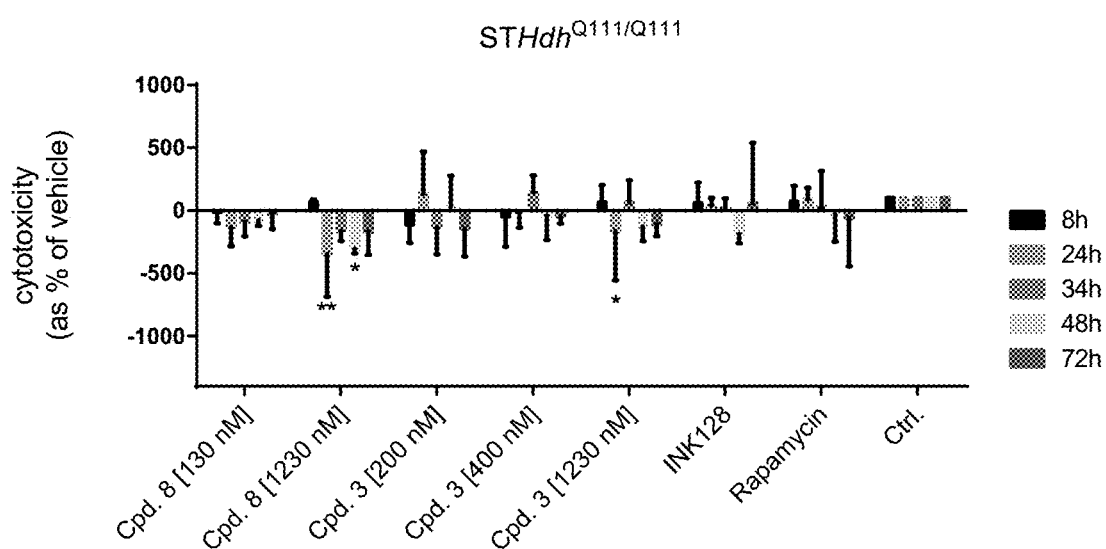
Figure 5C:
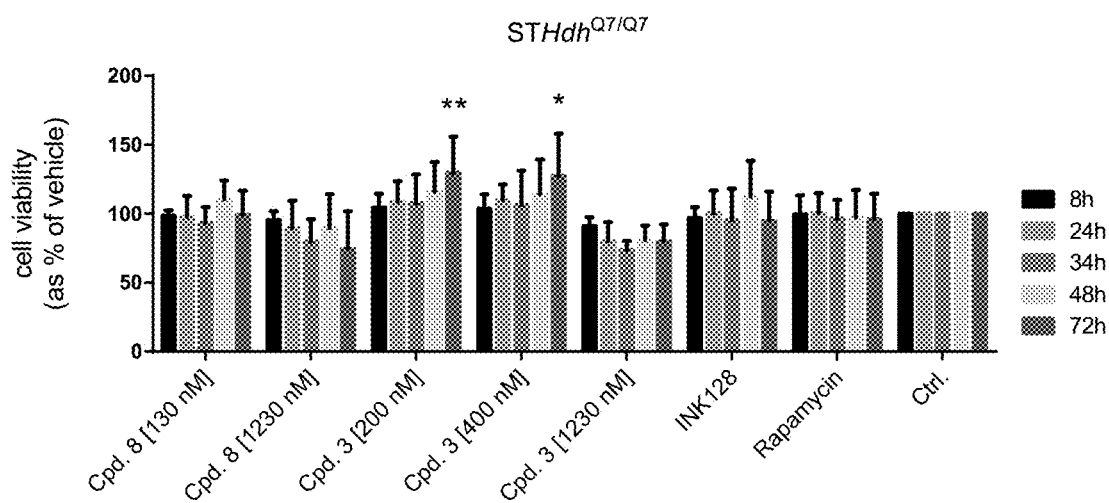
Figure 5D:
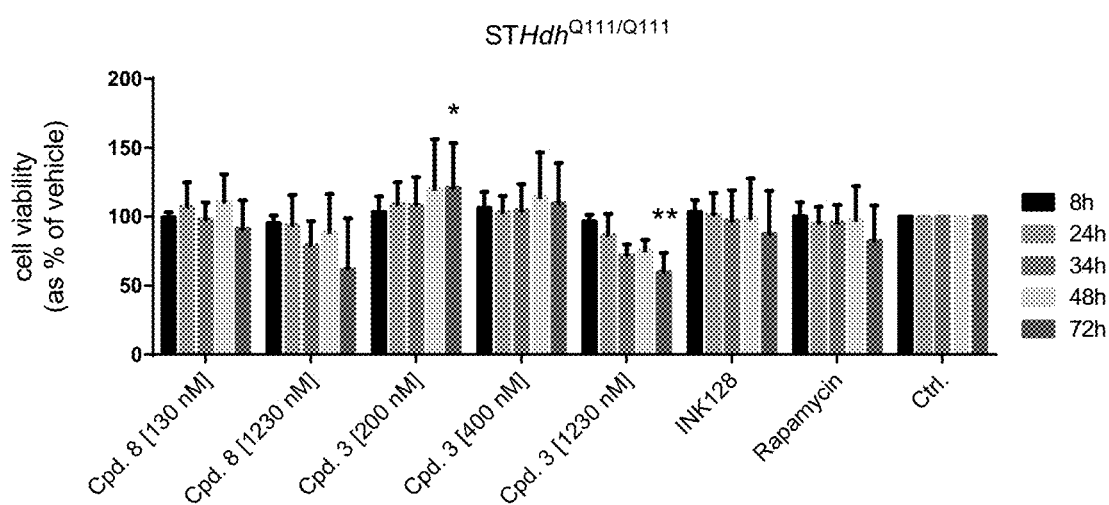

In both, naïve mice and epileptic mice, S6 phosphorylation (S235/236) was significantly decreased versus control by Cpd. 3 (4.6 fold; 4.3 fold, respectively) Cpd. 8 (10.9 fold; 2.8 fold, respectively)(FIG. 3B). No significant changes in mTOR signaling were observed in everolimus treated mice indicating that both, Cpd. 3 and Cpd. 8 penetrate into the brain at effective doses and inhibit mTOR signaling in brain tissue in epileptic as well as in naïve mice. Everolimus does seem not reach effective concentrations in the brain under the conditions used as mTOR signaling is not inhibited by the compound.

Example 7

Cpd. 3 and Cpd. 8 Inhibit Seizures in the Maximal Electroshock Seizure Threshold Test (MEST)

The antiepileptic effect of Cpd. 3 and Cpd. 8 was tested using the maximal electroshock seizure threshold test (MEST), a mouse epilepsy model. It has been shown before, that rapamycin increases the seizure threshold in this model (Macias, M., et al., PLoS One, 2013. 8(5): p. e64455.).

A total of 166 adult female NMRI mice were used obtained from Charles River (Sulzfeld, Germany) at a weight range of 21-25 g (mice). Animals were kept under the following conditions: Housing: Animals were housed in groups of max. 8 mice under controlled conditions (temperature: 22±1° C.; humidity: 50% 60%/), under a 12-h light-dark cycle (lights on at 6:00 a.m.). Feeding: Standard laboratory chow (Altromin 1324 standard diet, Altromin Spezialfutter GmbH, Lage, Germany) was provided ad libitum. Drinking water: Tap water was provided ad libitum.

Epilepsy was induced in half of the animals by pilocarpine administration (see EXAMPLE 4). The MEST determines a population seizure threshold in groups of ~20 animals and not the threshold for an individual animal. In the present study, the MEST was determined by a staircase procedure as previously described. A stimulator (BMT Medizintechnik, Berlin, Germany) that delivered a constant current (adjustable from 1-200 mA regardless of the impedance of the animal) with sinusoidal pulses (50/sec) for 0.2 sec was used.

Current administration was performed via bilateral transcorneal stimulation (using copper electrodes). Before transcorneal stimulation, a drop of tetracaine solution (2%) was administered to the eyes of the mouse for local anesthesia. Two minutes later, the mouse was restrained by hand to press the copper electrodes on both corneas while the stimulus was applied by stepping on a foot pedal switch connected with the stimulator. Electrodes were covered with soft leather and soaked with saline before each current application. Directly after stimulation, the mouse was released from restraint in order to permit observation of seizures exhibited. The stimulus intensity was varied by an up-and-down method in which the current was lowered or raised by 0.06 mA log intervals according to whether the preceding mouse did or did not exert a tonic hindlimb extension. The first stimulation was started with a current near to the control threshold.

Drug solutions were prepared freshly before every experiment:
Phenobarbital (sodium salt): 15 mg in 10 ml distilled water
Levetiracetam: 50 mg in 10 ml distilled water
Rapamycin: 5 mg in 10 ml vehicle (4% ethanol (100%), then 5% PEG 400 and 5% Tween 80)
Everolimus: 5/10 mg in 10 ml vehicle (8% ethanol, 10% PEG400, and 10% Tween 80)
Cpd. 3 (HCl): 40/100 mg in 10 ml (Suspension; 5% PEG 400 and 2% Tween 80, HPBCD (10%6))
Cpd. 8 (HCl): 12.5/25 mg in 10 ml (5% PEG 400 and 2% Tween 80, HPBCD (10%))

The data generated from groups of 20-22 nonepileptic control (sham-SE) and 20-25 epileptic mice (pilo-SE) were used to calculate the CC50 (convulsant current that induces a tonic hindlimb seizure in 50% of the mice per group with confidence limits for 95% probability). Statistical analysis were calculated using Student's t-test. All tests were used two-sided; a P<0.05 was considered significant.

Experiments were performed in groups of 20-25 mice. Average CC50 control values (without vehicle injection) were 15.8 t 0.36 mA in nonepileptic mice (mean f SEM of 5 threshold determinations in 3 different groups of mice) and 15.6±0.45 mA in epileptic mice (mean±SEM of 5 threshold determinations in 3 different groups of mice). Phenobarbital produced the most pronounced anticonvulsant effect of the compounds tested in this study. The CC50 was 25.7 mA in nonepileptic and 26.56 mA in epileptic mice which is a threshold increase of 69% and 66%, respectively. There was no significant difference between nonepileptic and epileptic mice (FIG. 4). Levetiracetam (50 mg/kg) significantly increased the CC50 in nonepileptic mice by 21% while there was no effect in epileptic mice (Table 2, FIG. 4).

5 mg/kg rapamycin significantly increased the seizure threshold in MEST by 13% in nonepileptic and only by 5% in epileptic mice (FIG. 4) as shown before by Hartman et al. [25]. After intraperitoneal injections rapamycin increased the threshold only in nonepileptic mice by 20%, while there was no effect in epileptic mice (FIG. 4). 10 mg/kg and 5 mg/kg everolimus significantly increased the CC50 by 10% and 13% in nonepileptic mice, respectively. In epileptic mice, only the lower dose increased the CC50 by 16% while 10 mg/kg was not effective (Table 3 and FIG. 4).

When 40 mg/kg Cpd. 3 was applied only 1 h before threshold determination, CC50 was significantly decreased in both, epileptic and nonepileptic mice. When pretreatment time was prolonged to 3 h, CC50 was significantly increased by 6% only in nonepileptic mice while CC50 in epileptic mice was no longer decreased but remained on control level. Application of a higher dose (100 mg/kg) led to a significant increase of the CC50 by 9% in epileptic but not in nonepileptic mice (Tab. 2 and FIG. 4).

Overall, Cpd. 3 exhibited a slight but inconsistent anticonvulsant effect with the parameters tested in this study. It seems that prolongation of the pretreatment time has a favourable effect. The use of a suspension could account for the marginal effect and the apparent inconsistency of the data.

Cpd. 8 exhibited a pronounced dose-dependent anticonvulsant effect in nonepileptic mice. CC50 was increased by 30% (25 mg/kg) and 8% (12.5 mg/kg). This is comparable to the anticonvulsant effect of levetiracetam. Reduction of the pretreatment time to 1 h reduced the anticonvulsant effect. When the pretreatment time was increased to 24 h the anticonvulsant effect vanished (Tab. 3 and FIG. 4). In epileptic mice Cpd. 8 did not exert an anticonvulsant effect with any dose or pretreatment time tested. When the pretreatment time was reduced to 1 h, Cpd. 8 decreased the CC50 by 9% similar to Cpd. 3 (Tab. 3 and FIG. 4 A-D).

We performed no special tests for the determination of adverse effects. Mice were observed about 30 min after injection in their home cages for obvious sedation or reduction of wellbeing. Five minutes before electrical stimulation mice were again observed in their home cages and two minutes before stimulation during handling procedure for treatment with local anaesthesia. Every obvious variation from normal behavior was noted. Only phenobarbital induced noticeable sedation which lasted for more than 60 min. All other test drugs (including vehicle solutions) were tolerated without any obvious adverse effects.

TABLE 2

Seizure thresholds of the Cpd. 3 versus everolimus/levetiracetam. For every threshold the current necessary to induce a seizure with full hindlimb tonus in 50% of the mice of the respective group (CC50) and the standard deviation is indicated. Further, the threshold change of the drug tests in percent in relation to the vehicle threshold and the threshold difference of the nonepileptic and epileptic mice in percent for each test are shown.

|  | 5 mg/kg everolimus p.o. pretreatment 3 h | Vehicle p.o. 10% HP-β-CD 5% PEG400 2.5% Tween80 | 40 mg/kg Cpd. 3 p.o. pretreatment 3 h | 100 mg/kg Cpd. 3 p.o. pretreatment 3 h | 40 mg/kg Cpd. 3 p.o. pretreatment 1 h | 50 mg/kg Levetiracetam i.p. pretreatment 1 h |
|---|---|---|---|---|---|---|
| Interval to SE induction | 9 weeks after SE | 10 weeks after SE | 13 weeks after SE | 14 weeks | 15 weeks | 16 weeks after SE |
| CC50 Sham-SE (nonepileptic) [mA] | 18.62 ± 1.1* | 16.44 ± 1.17 | 17.49 ± 1.20* | 16.72 ± 1.72 | 15.14 ± 1.06* | 19.95 ± 1.22* |
| CC50 Pilo-SE (epileptic) [mA] | 22.28 ± 2.16* | 19.20 ± 1.28 | 18.20 ± 1.35 | 20.85 ± 1.38* | 17.99 ± 1.39* | 19.15 ± 1.79 |
| Threshold difference between nonepileptic and epileptic [%] | 20% | 17% | 4% | 25% | 19% | −4% |
| Threshold difference between vehicle and drug threshold [%] nonepileptic | 13% |  | 6% | 2% | −8% | 21% |
| Threshold difference between vehicle and drug threshold [%] epileptic | 16% |  | 5% | 9% | −6% | 0% |

*$p < 0.05$; ANOVA + post hoc Dunnett's test always compared to vehicle group (yellow).
Significant differences between nonepileptic and epileptic mice are not indicated.

TABLE 3

Seizure thresholds of the Cpd. 8 versus everolimus. For every threshold the current necessary to induce a seizure with full hindlimb tonus in 50% of the mice of the respective group (CC50) and the standard deviation is indicated. Further, the threshold change of the drug tests in percent in relation to the vehicle threshold and the threshold difference of the nonepileptic and epileptic mice in percent for each test are shown.

|  | 25 mg/kg Cpd. 8 p.o. pretreatment 3 h | Vehicle p.o. 10% HP-β-CD 5% PEG400 2.5% Tween80 | 12.5 mg/kg Cpd. 8 p.o. pretreatment 3 h | 25 mg/kg Cpd. 8 p.o. pretreatment 1 h | 10 mg/kg everolimus p.o. pretreatment 3 h | 25 mg/kg Cpd. 8 p.o. pretreatment 24 h |
|---|---|---|---|---|---|---|
| Interval to SE induction | 9 weeks after SE | 10 weeks | 11 weeks | 12 weeks | 13 weeks after SE | 14 weeks |
| CC50 Sham-SE (nonepileptic) [mA] | 22.91 ± 3.08* | 15.62 ± 1.19 | 16.84 ± 1.29 | 17.71 ± 1.20* | 17.14 ± 1.11* | 15.62 ± 1.10 |
| CC50 Pilo-SE (epileptic) [mA] | 17.78 ± 1.38 | 16.84 ± 1.14 | 16.67 ± 1.19 | 15.25 ± 1.17* | 16.98 ± 1.06* | 16.47 ± 1.14 |
| Threshold difference between nonepileptic and epileptic [%] | −22% | 8% | −1% | −14% | 1% | 5% |

TABLE 3-continued

Seizure thresholds of the Cpd. 8 versus everolimus. For every threshold the current necessary to induce a seizure with full hindlimb tonus in 50% of the mice of the respective group (CC50) and the standard deviation is indicated.
Further, the threshold change of the drug tests in percent in relation to the vehicle threshold and the threshold difference of the nonepileptic and epileptic mice in percent for each test are shown.

| | | 25 mg/kg Cpd. 8 p.o. pretreatment 3 h | Vehicle p.o. 10% HP-β-CD 5% PEG400 2.5% Tween80 | 12.5 mg/kg Cpd. 8 p.o. pretreatment 3 h | 25 mg/kg Cpd. 8 p.o. pretreatment 1 h | 10 mg/kg everolimus p.o. pretreatment 3 h | 25 mg/kg Cpd. 8 p.o. pretreatment 24 h |
|---|---|---|---|---|---|---|---|
| Threshold difference between vehicle and drug threshold [%] | Nonepileptic epileptic | 30% 6% | | 8% −1% | 13% −9% | 10% 1% | 0% −2% |

*p < 0.05; ANOVA + post hoc Dunnett's test always compared to vehicle group (yellow).
Significant differences between nonepileptic and epileptic mice are not indicated.

Example 8

Viability and Protein Synthesis of STHdh Cells Treated with mTOR Inhibitors

STHdh cells are immortalized striatal cells derived from a knock-in mouse model expressing full-length HTT with 111 CAG-repeats (STHdh$^{Q111/Q111}$). Control STHdh$^{Q7/Q7}$ cells were generated from wildtype mouse embryos. Cells can be differentiated into neuronal cells with a dopamine containing cocktail.

A. LDH Assay

LDH is a cytoplasmic enzyme that is excreted upon damage to the plasma membrane, e.g. during apoptosis. Cytotoxicity of test compounds was measured using the lactate dehydrogenase (LDH) assay from Roche, Switzerland according to the manufacturer's instructions.

STHdh$^{Q111/Q111}$ and STHdh$^{Q7/Q7}$ (Coriell Institute for Medical Research, USA) were cultured in DMEM (Invitrogen, USA) supplemented with FBS (Invitrogen, USA) 10%, Geniticine (G418, Biochrom, Germany)) 1% und antibiotic antimycotic (Invitrogen, USA) 1% in a humidified incubator at 37° C. and 5% CO2. For all examples described for this invention, STHdh cells were differentiated at the time of compound addition using a final concentration of 50 μM Forskolin, 750 μM IBMX, 200 nM TPA, 10 μM dopamine, 10 μg/μl α-FGF in culture media. $10^4$ STHdh$^{Q7/Q7}$ and STHdh$^{Q111/Q111}$ cells per well were seeded in a 96 well plate incubated with Cpd. 3 (130 nM, 1230 nM), Cpd. 8 (400 nM and 1230 nM), INK128 (100 nM) and rapamycin (400 nM) and LDH was measured after 8 h, 24 h, 34 h, 48 h and 72 h (FIG. 5 A, B).

None of the compounds tested induced increased LDH activity in the media indicating that no cytotoxicity was induced by the mTOR inhibitors. At higher concentrations of Cpd. 3 and Cpd. 8 the LDH activity was decreased compared to control. mTOR inhibitors were well tolerated by STHdh cells and the number of apoptotic cells was not increased by cell treatment of up to 72 hours. In conclusion, compounds of this invention are suitable for assessment in these cell lines and, furthermore, compounds do not appear to have a direct effect on general the metabolic activity of neuronal cells in general.

B. PrestoBlue Assay

Cell viability/metabolic activity was detected using the PrestoBlue viability reagent (Invitrogen, USA) according to the manufacturer's instructions. $110^4$ STHdh$^{Q7/Q7}$ and STHdh$^{Q111/Q111}$ cells per well were seeded in a 96 well plate incubated with Cpd. 3 (130 nM, 1230 nM), Cpd. 8 (400 nM and 1230 nM), INK128 (100 nM) and rapamycin (400 nM) and PrestoBlue was measured after 8 h, 24 h, 34 h, 48 h and 72 h. Non-toxic concentrations determined were transferred to primary neurons used later on in this study. Cells did not show changes in metabolic activity at 8 h, 24 h, 34 h and 48 h for each of the compounds tested (FIG. 5 C, D). At lower concentration of Cpd. 3 and Cpd. 8 even a slight increase in mitochondrial activity could be detected. At 72 hours decreased metabolic activity was detected after treatment with 1230 nM of Cpd. 3 and (not significantly) also Cpd. 8 in STHdh$^{Q111/Q111}$. This effect has not been observed in STHdh$^{Q7/Q7}$ cells indicating that 1. Wild type cells are less sensitive to mTOR inhibition and 2. Compounds are well tolerated and therefore suitable for testing as autophagy-inducers in these cell lines.

Example 9

Cpd. 3 and Cpd. 8 Inhibit mTOR Signaling in STHdh$^{Q7/Q7}$ and STHdh$^{Q111/Q111}$ Cells In order to test whether Cpd. 3 and Cpd. 8 inhibit mTOR signaling and induce autophagy in neuronal cell models of HD, treatment of STHdh$^{Q111/Q111}$ and STHdh$^{Q7/Q7}$ cells was employed. STHdh$^{Q111/Q111}$ and STHdh$^{Q7/Q7}$ cells were maintained as described under EXAMPLE 6. Cells were seeded in 10 cm dishes. When cells were about 80% confluent, cells were differentiated and treated with compounds at the same time. Cells were treated with Cpd. 3 (200 nM, 400 nM, 1230 nM), Cpd. 8 (130 nM, 1230 nM), INK128 (100 nM), rapamycin (400 nM) or DMSO control for 4 hours. At the end of incubation time cells were washed with cold PBS buffer and lysed with 200 μl of RIPA buffer supplemented with 4% Complete protease inhibitor (Roche, Switzerland) and 10% PhosStop (Roche, Switzerland). After 30 min of incubation on ice, lysates were vortexed, centrifuged (20 min, 4° C., 16000 rpm) and supernatants were collected. Protein concentration was determined as described above. 30 µg of protein per sample was analyzed by western blot as described above using the following primary antibodies:

| | |
|---|---|
| 4E-PB1 (1:1000), P-4E-BP1 (T37/46) (1:1000), mTOR (1:1000), P-mTOR(S2448) (1:1000), S6rP (1:1000), P-S6rP (S235/236) (1:1000) | Cell Signaling, UK |
| beta-actin (1:50000) | Sigma-Aldrich, USA |
| LC3 (1:200) | Nanotools, Germany |

Figure 6A:
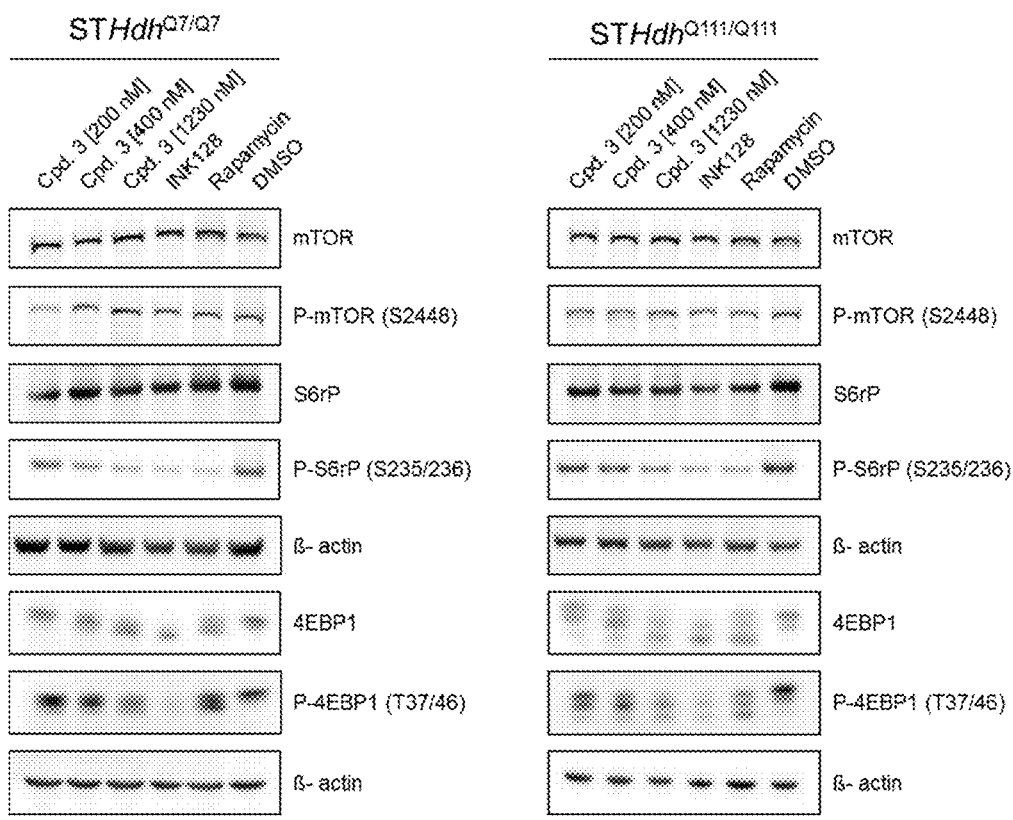
FIG. 6A+B: Decrease in phosphorylation of mTOR signaling molecules mTOR, S6rp and 4E-PB is concentration dependent. n=3
Figure 6B:
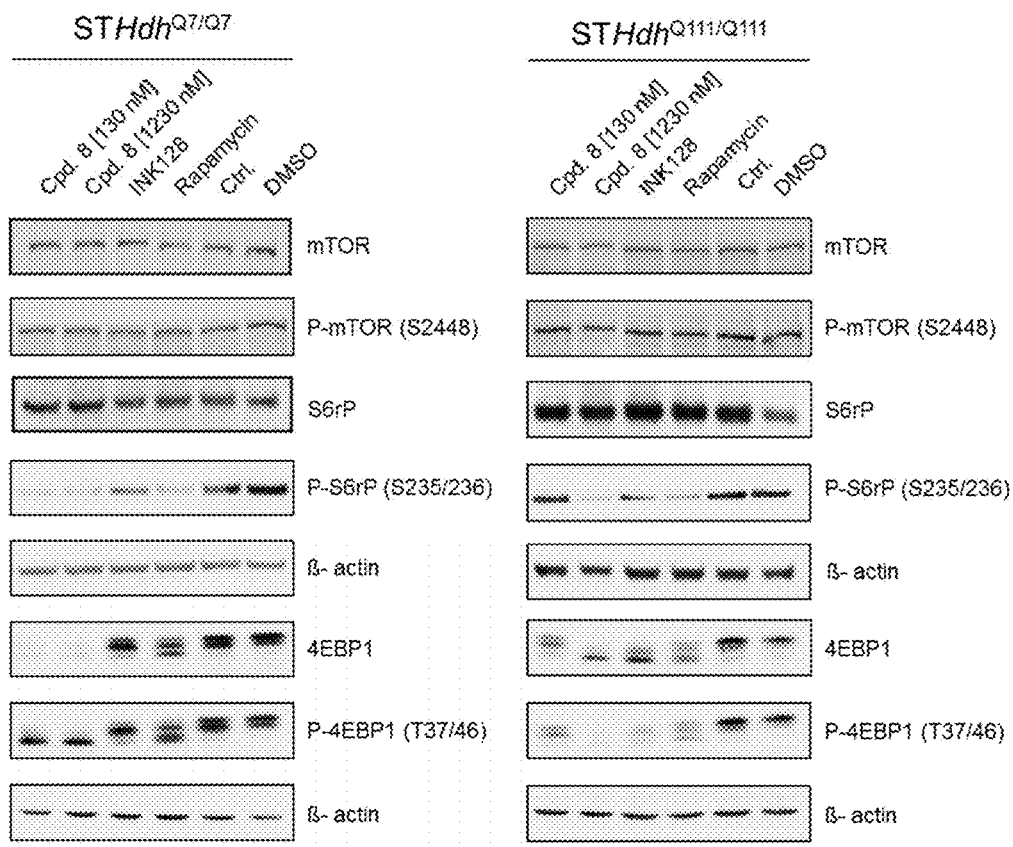
FIG. 6: Inhibition of the mTOR signaling pathway and induction of autophagy in STHdh$^{Q7/Q7}$ and STHdh$^{Q111/Q111}$ cells after treatment with Cpd. 3 (200 nM, 400 nM, 1230 nM), Cpd. 8 (130 nM, 1230 nM), INK 128 (100 nM), rapamycin (400 nM) or DMSO control for 4 hours. Western blot analysis of cell lysates.

Cpd. 3 inhibited mTOR signaling as indicated by reduced S6rP phosphorylation and 4E-BP phosphorylation in both, STHdh$^{Q111/Q111}$ and STHdh$^{Q7/Q7}$ cells in a concentration dependent manner. Reference compounds/positive controls INK128 and rapamycin showed a similar degree of pathway inhibition (FIG. 6A). Cpd. 8 also inhibited mTOR signaling. An effect could be observed already at a low concentration of 130 nM in STHdh$^{Q7/Q7}$ cells (FIG. 6B).

Figure 6C:
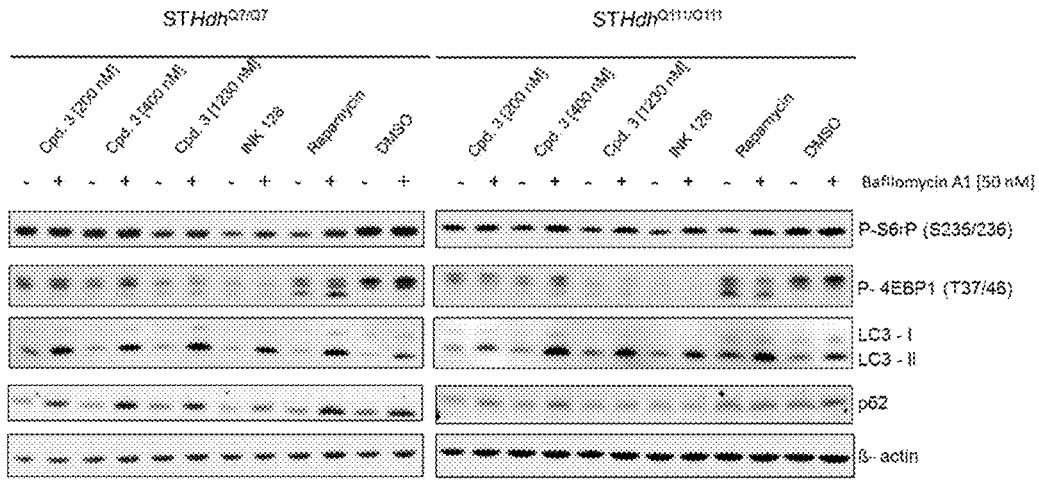
Figure 6C:
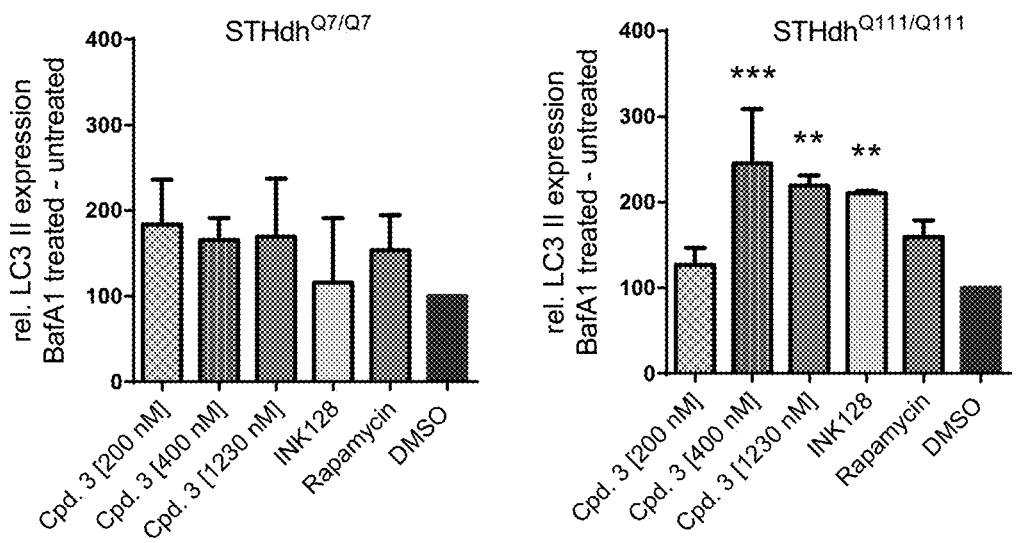
Figure 6D:
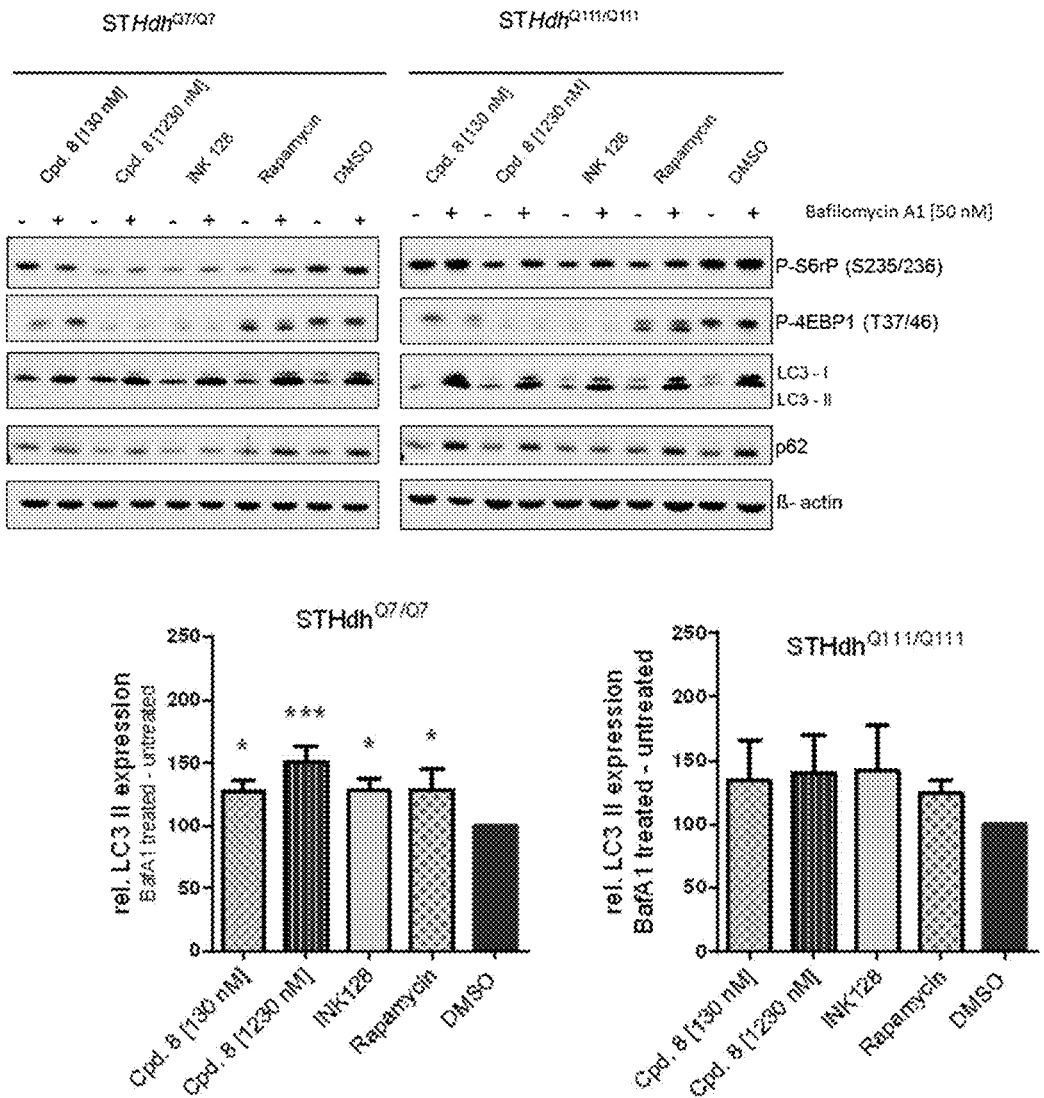

In order to detect levels of LC3-II, an autophagy marker in autophagosomes, cell treatment was performed in the presence and absence of Bafilomycin A, an inhibitor of autophagosome degradation. Thus compounds lead to accumulation of LC3-II levels when autophagy is induced. Cpd. 3 (FIG. 6C) and Cpd. 8 (FIG. 6D) induced autophagy in striatal cells. For Cpd. 3 a stronger effect on autophagy was observed in STHdh$^{Q111/Q111}$ cells. Autophagy induction was not significant in the non-mutHTT counterpart, but signs of LC3II-elevation were observed in these cells as well. Cpd. 8 also induced autophagy in striatal cell lines. in a level comparable to INK 128.

Data indicate that Cpd. 3 and Cpd. 8 inhibit mTOR signaling in striatal cell lines that carry mutHTT or unmutated-Q7 extended huntingtin. Inhibition of the mTOR pathway leads to induction of autophagy. The basic mechanism for huntingtin aggregate clearance via macroautophagy was induced by the mTOR or PI3K/mTOR inhibitor Cpd. 3 and Cpd. 8 in a neuronal environment.

Example 10

Cpd. 3 and Cpd. 8 Inhibit Aggregate Formation in HEK Cells Expressing Exon1 of mutHTT HEK cells (DSMZ, Germany) were maintained in DMEM/Glutamax (Invitrogen, USA), 1% Antibiotic/Antimycotic (Invitrogen, USA), 10% FBS in a humidified incubator at 37° C. and 5% CO2. HEK cells were transiently transfected with pcDNA3.1/V5-His vector from Clontech (Mountain View, USA) containing the expression sequence for Exon1 of HTT with a 19Q (no aggregation) or 51Q extension and enhanced green fluorescent protein (eGFP) tag using Attractene Transfection Reagent (Qiagen, Netherlands). 1×10$^6$ cells were seeded in a 6 well plate. On the next day 2 µg DNA were mixed with 95.5 µl transfection media and 4.5 µl transfection reagent. After an incubation time of 15 min the mixture was added to the cells. After 72 hours cells were harvested or fixed for analysis.

Figure 7A:
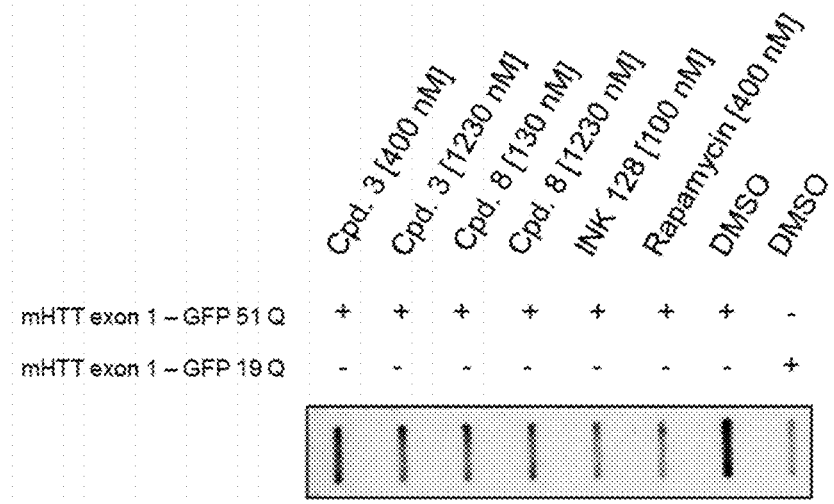
FIG. 7: Reduction of mHTT aggregate formation on human embryonic kidney cells (HEK293) cells transfected with exon 1 of mHTT with a Q51 or Q19 extension, respectively.
Figure 7B:
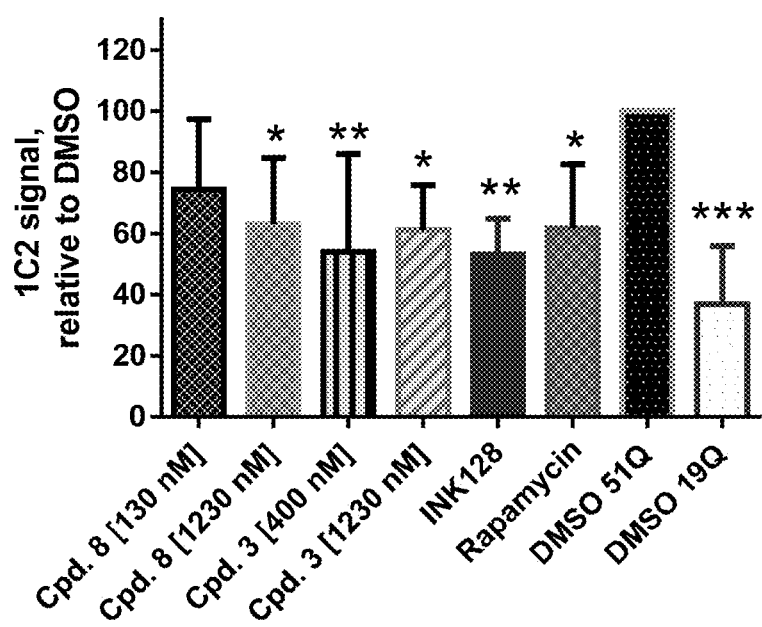

A. Cod. 3 and Cpd. 8 Reduce Aggregate Formation in Transfected HEK Cells Shown in a Filter Trap Assay HEK cells transfected with 19Q- or 51Q-HTT-Exon1-eGFP were treated with DMSO control. 51Q-HTT-Exon I-eGFP HEK cells form aggregates. These cells were treated with Cpd. 3 (400, 1230 nM), Cpd. 8 (130, 1230 nM), INK128 (100 nM) or Rapamycin (400 nM) for 8 hours and then lysed with RIPA buffer. After 30 min incubation on ice, cells were homogenized (Dounce Homogenizer, Thermo Fisher, USA). 50 µg of protein solution in PBS was supplemented with 2% SDS (Roth, Germany). Samples were sucked through a nitrocellulose membrane (0.45 µm) and washed twice with PBS buffer. Aggregated proteins do not dissolve in SDS solution and bind to the membrane. mutHTT was detected on the membrane using a ployQ antibody (1C2, Millipore, Germany) diluted 1:1000 in TBST supplemented with 5% milk powder and a HRP conjugated secondary anti-mouse antibody (FIGS. 7A, B) Bands were quantified with the Odyssey LI-CORE system (Li-Core, USA) (FIG. 7B).

Data demonstrates that treatment of 51Q-HTT-Exon1 HEK cells with mTOR inhibitors (Cpd. 3, Cpd.8, INK128 and Rapamycin) leads to significant reduction of cytotoxic mutHTT aggregates in these cells. 130 nM of Cpd. 8 was not sufficient to induce significant aggregate reduction. Aggregate clearance led to a reduction of aggregates that did not reach total clearance (compared to 19Q-HTT). As induction of autophagy has been demonstrated before, it can be assumed that aggregate clearance is performed by macroautophagy.

Figure 7C:
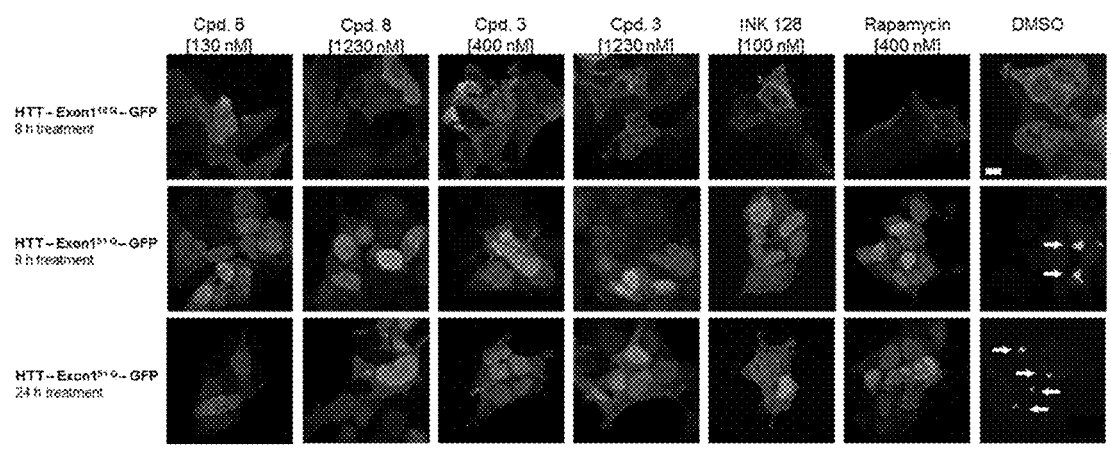
Figure 7D:
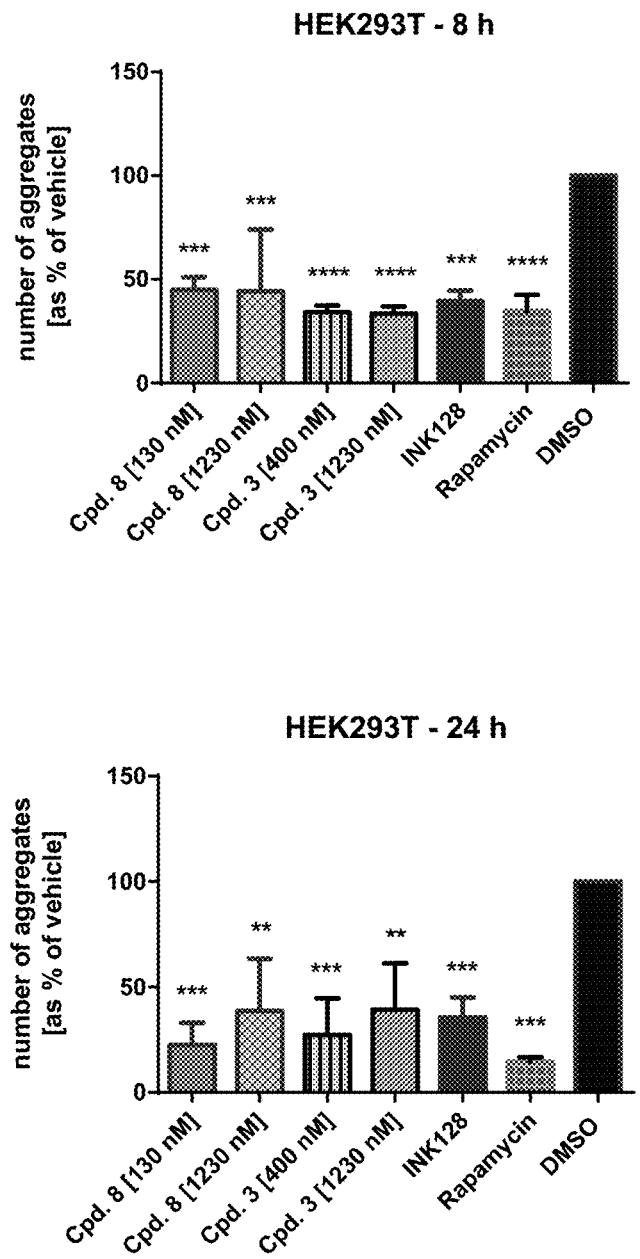
Figure 8A:
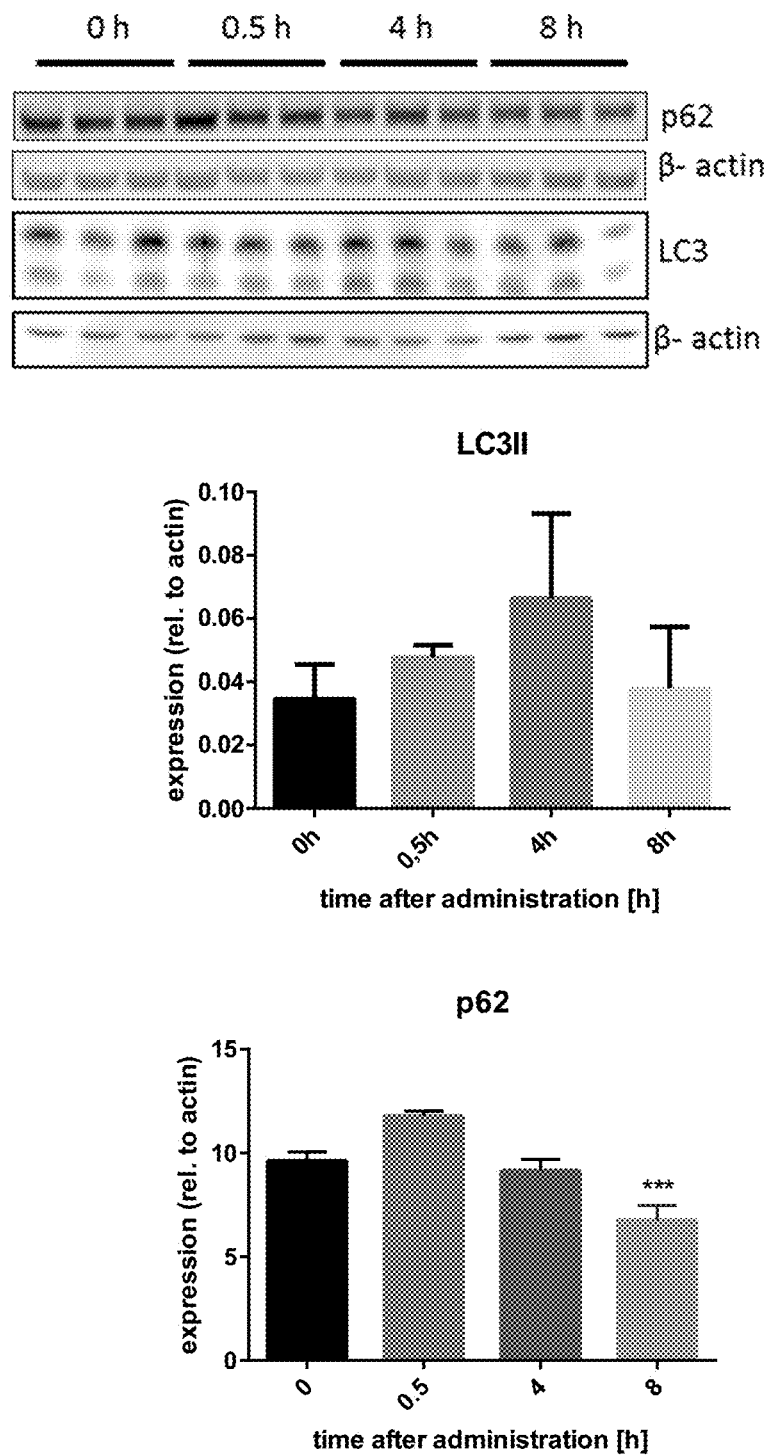
FIG. 8A: Induction of autophagy in brains of BALB/C mice 0.5 h, 4 h, 8 h, respectively, after a single, oral administration of Cpd. 3, 50 mg/kg. Brain lysates were analyzed by western blot. Autophagic markers $LC_3$-II and p62 were altered at time points between 30 minutes and 8 hours. Quantification of western blot bands shows induction of autophagy. n=3, ANOVA, * p<0.0005,  p<0.005, * p<0.05
Figure 8B:
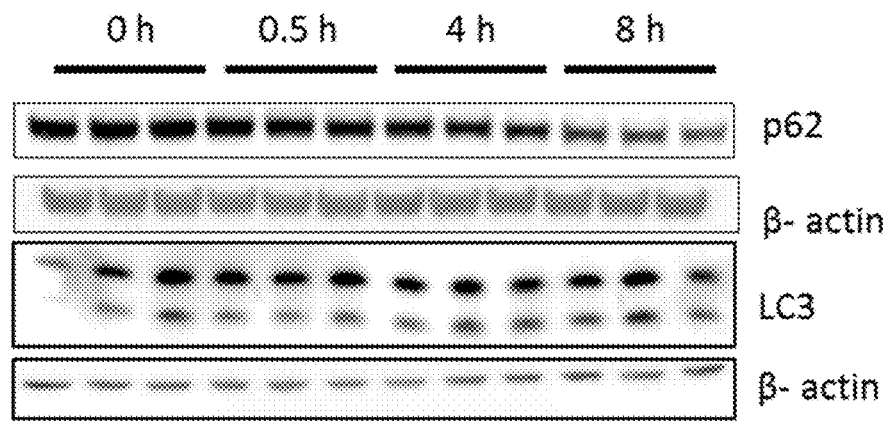
FIG. 8B: Induction of autophagy in brains of BALB/C mice after a single, oral administration of Cpd. 8, 50 mg/kg. Brain lysates were analyzed by western blot. Autophagic markers $LC_3$-II and p62 were altered at time points between 30 minutes and 8 hours. Quantification of western blot bands shows induction of autophagy. n=3, ANOVA, * p<0.0005,  p<0.005, * p<0.05.
Figure 8B:
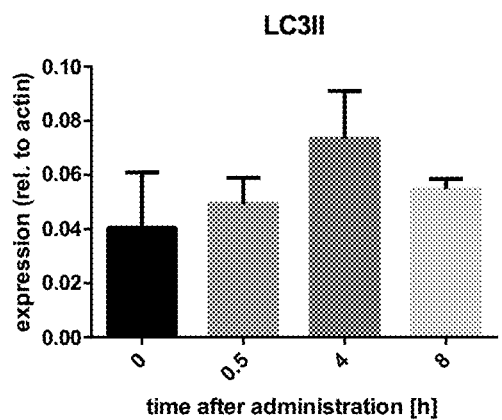
Figure 8B:
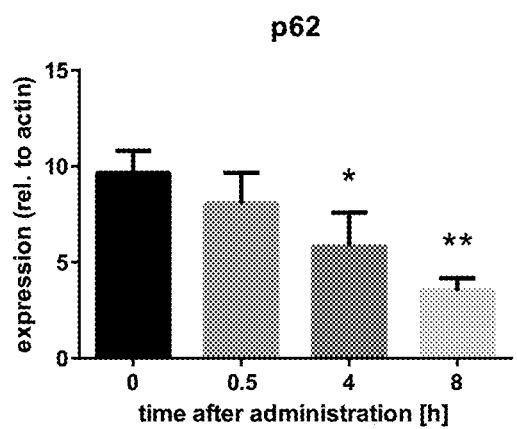

B. Cpd. 3 and Cpd. 8 Reduce Aggregate Formation in Transfected HEK Cells Shown by Immune Cytochemistry HEK cells were seeded in poly-L-lysine (Sigma-Aldrich, USA) coated coverslips in 24 well plates at 10$^4$ cells per well and transiently transfected with 19Q- or 51Q-HTT-Exon1-eGFP. Cells were treated with Compounds as described under A for 8 or 24 hours. This incubation ended 72 hours after transfection. Cells were fixed with 4% (para-formaldehyde) PFA. Coverslips were fixed glass slides using mounting media that contained 4',6-Diamidin-2-phenylindol (DAPI) (FIG. 7C). Nuclei and aggregates containing HTT-Exon1-eGFP were counted manually. 10 000 cells were counted per sample (FIG. 7D).

Since the fluorescence of eGFP labeled HTT is very bright, samples treated with DMSO appear darker overall. mTOR inhibitor reduced number of mutHTT aggregates in HEK cells by macroautophagy indicating that this mechanism might also clear huntingtin aggregates in neurons of animal models or patients. The effect was more pronounced after 24 hours (77% reduction, Cpd. 8, 130 nM; 73% reduction, Cpd. 3, 400 nM) as compared to 8 hours (55% reduction Cpd. 8, 130 nM; 66% reduction Cpd. 3, 400 nM) of treatment. In terms of dose finding, lower concentrations of Cpd. 3 (400 nM) and Cpd. 8 (130 nM) appear to be at least as efficient as high concentrations. So it might be possible to treat patients at lower, non-toxic doses.

Example 11

Cpd. 3 and Cpd. 8 Induce Autophagy in Brain of Wt Mice

In order to investigate whether mTOR inhibition by Cpd. 3 and Cpd. 8 induces autophagy—the essential mechanism for huntingtin aggregate clearance-in the brain, BALB/c nude mice were treated with Cpd. 3 and Cpd. 8 as described in sample 5.

Brain lysates were analyzed by western blot as described in example 5 using a LC3 antibody (1:20, Nanotools, Germany) and a p62 antibody (SQTS1/p62 1:1000, Cell Signaling, USA) and the according secondary HRP-coupled antibodies (FIG. 8 A, B).

Autophagy induction was proven by time-dependent increase in the autophagic marker LC3II (upper band) and decrease in the autophagic marker p62 after a single oral administration of both, Cpd. 3 and Cpd. 8. Data indicate that concentration of compounds in the brain is sufficient to induce autophagy in neuronal cells. As induction of autophagy has been shown to lead to clearance of huntingtin aggregates in cell models, Cpd. 3 and Cpd. 3 as well as other mTOR inhibitors are likely to induce autophagic reduction of mutHTT aggregates in animals or humans.

Example 12

Effect of Chronic Treatment of Cpd. 3 and Cpd.8 on Electrographic Seizures in TSC1GFAP Ko Mice This study was done to test the effect of Cpd. 3, Cpd. 8 and a reference compound (Cpd. R, CAS-No 1225037-39-7) on spontaneous seizures and mortality as compared to vehicle treatment in Tsc1GFAP knockout mice. Tsc1 ($Tsc1^{flox/flox}$-GFAP-Cre ($Tsc1^{GFAP}$ conditional knockout) is a mouse model of TSC with conditional inactivation of the Tsc1 gene in GFAP-positive cells (Tsc1GFAPCKO mice), which develops progressive epilepsy, encephalopathy, and premature death, as well as cellular and molecular brain abnormalities likely contributing to epileptogenesis.

A: Animals and Treatment

Tsc1 mice belonging to either sex were acclimated to the environment, examined, handled, and weighed prior to initiation of the study to assure adequate health and suitability and to minimize non-specific stress associated with human handling. During the course of the study, 12/12 light/dark cycles were maintained. The room temperature was maintained between 20 and 23° C. with a relative humidity maintained around 50%. Food and water were provided ad libitum for the duration of the study. Each mouse was randomly assigned to designated treatment groups. The dosing was performed during the animals' light cycle phase.

Aseptic technique was used throughout the surgical procedures described below. Mice were anesthetized with isoflurane (3% for induction and 1-2% for maintenance with oxygen as a carrier gas; approximate flow rate, 1 liter per minute) and placed on a homeostatic heating pad to maintain the core temperature at 37±1° C. Adequate plane of anesthesia was insured by the lack of a withdrawal response to toe pinch and a visible change in the breathing rate. The mouse head was immobilized in a stereotaxic frame with a nose piece that supplied the anesthetic continuously. Ophthalmic ointment was applied to the eyes to prevent drying of the cornea. The area for surgical incision was identified and scrubbed with chlorhexidine followed by an alcohol scrub. A dorsal skin incision was made on the head in a rostro-caudal direction and the skin was reflected to reveal the skull. Subcutaneous tissues were blunt dissected away with a sterile cotton-tipped applicator and saline. The skull was cleaned to reveal bregma. Using a dental drill or a 20-23 gauge needle, a small hole was made to allow implantation of the indwelling electrode wire or skull screws. An 8201-EEG head mount (Pinnacle Technology, Inc., Lawrence, KS) with bi-hemispheric leads in the frontal and parietal cortices and an indwelling local field potential electrode targeting the region above the CA1 were used. Initial fixation of this mount to the skull was done by super glue. The headmount was then cemented onto the skull with dental acrylic. The headmount and screws were covered with dental cement. Application of the dental cement also serves to close the wound. Typically, the skin is pulled taught around the implant/headmount and only skin caudal to the implant remains unopposed. Once the dental acrylic cured, isoflurane was turned off and the animal was removed from the stereotaxic apparatus.

After surgery, the animal was placed in a clean recovery cage placed on a heated warm water circulating heating pad under half of the cage until it is ambulatory. Before, during, and after surgery, animals were administered fluids, nutrition, antibiotics, and analgesics as required/recommended by the Program of Veterinary Care (PVC) team and IACUC, in concert with the Attending Veterinarian and/or according to IACUC Guidelines. Animals were checked daily by Animal Care staff and during the 7 day post-op period. Only animals that were fully recovered from surgery (healthy-looking and displaying normal behaviors such as eating, grooming, exploring and nesting) were used in experiments. Post-surgery, mice were single-housed. Animals were housed individually to prevent other animals from contaminating the surgery site or damaging the implant. Mice were implanted with electrodes at the age of P22 to P27 and allowed to recover for up to 4 weeks of age (P35). A total of 56 mice were implanted to yield four groups of ~10 mice for the study.

EEG was recorded continuously using the Pinnacle Technology 8206 data conditioning and acquisition system (DCAS), which performs secondary amplification and filtering before sending data to Pinnacle's Sirenia® Acquisition software for collection via a USB connection. EEG was recorded using 10× or 100× gain pre-amplifiers. For seizure activity, which elicits large spikes in amplitude the 10× gain is typically optimal. The pre-amplified tether was connected to a low-torque commutator mounted above the cage and allows for unencumbered freedom of movement and reduced movement artifacts. Real-time visualization of all EEG channels from all mice was observed using Sirenia or PAL-8400 software. Synchronized video recordings were collected for the duration of the EEG recordings.

Compounds were dissolved in vehicle consisting of 20% Dexolve-7 (Davos Pharma, Liberty, MO, USA) in water, pH 3. Mice in the study were randomly assigned to one of the following treatment groups: vehicle 10 ml/kg (group D; post natal day (PND) 21-53; p.o. q.d.), Cpd. R 50 mg/kg (group C; PND21-53; p.o. q.d.), Cpd. 8 25 mg/kg (group A; PND21-53; p.o. q.d.), Cpd. 3 100 mg/kg (group B; PND21-53; p.o. q.d.).

B: Electroencephalographic Recording and Analysis

After postoperative recovery was complete, mice were tethered to the pinnacle recording system individually in their home cages and spontaneous EEG was recorded for the following two weeks (PND 35-48; weeks 6 and 7). Simultaneously, videographic recording was made through this period to provide a data stream for behavioral evaluation of the mice as needed. After the recording period was completed, individual EEG traces were evaluated for aberrant EEG activity. Electrographic seizures were identified by their characteristic pattern of discrete periods of rhythmic spike discharges that evolved in frequency and amplitude lasting at least 10 seconds, typically ending with repetitive burst discharges and voltage suppression. These were defined as having very stereotypical beginning, end, and evolution in the middle, starting with low amplitude fast activity and high frequency spikes (tonic), which gradually evolved into a slower, bursting (clonic) phase followed by a severe voltage suppression often with rhythmic artifact superimposed, which represents respirations and is picked up clearly because the EEG itself is suppressed. Most typical seizures in the TS mice last at least 30-40 seconds. Note that these mice have abnormal EEG patterns often featuring frequent runs of interictal spikes, which can also be called spike trains, but we did not consider them seizures based on the above criteria (usually there is no stereotypical evolution). Seizure incidence was tabulated for each mouse and summarized for each treatment group for week 6 (PND36), week 7, and week 8 (PND55).

Data were analyzed by analysis of variance (ANOVA). If one or more of these factors were significant (P<0.05), further post-tests (Dunnet's or Wilcoxon) were done to identify which specific contrasts (i.e. Vehicle v. Cpd. R for week 6) were significant. P values were adjusted for multiple comparisons and a p<0.05 was deemed significant. Summary data are reported as group mean±standard error of the mean (SEM).

Body Weight

Figure 9A:
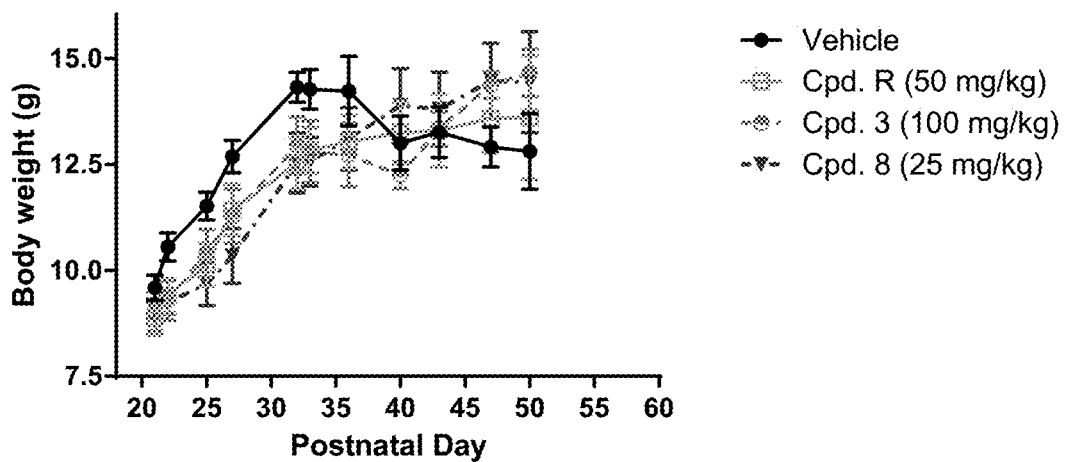
FIG. 9A: Body weight of TSC1 GFAP mice treated with vehicle, Cpd. R, Cpd. 3 and Cpd. 8 at different postnatal days before (P21) and during (P22-P50) treatment. Mean±SEM. As some animals died during observation period n varied between 6 and 14.

The body weight of individual subjects assigned to different treatment groups prior to any treatment is shown in FIG. 9A. A one-way ANOVA revealed no statistical difference between groups. Body weight of animals treated with Cpd. 3 and Cpd. 8 was higher towards the end of the study. At this time the normal life span of TSC mice is close to the end. They will lose more weight and die. As treated animals show higher weight they appear to have improved health status and therefore might have an extended life span.

Electrographic Seizures and Mortality

Figure 9B:
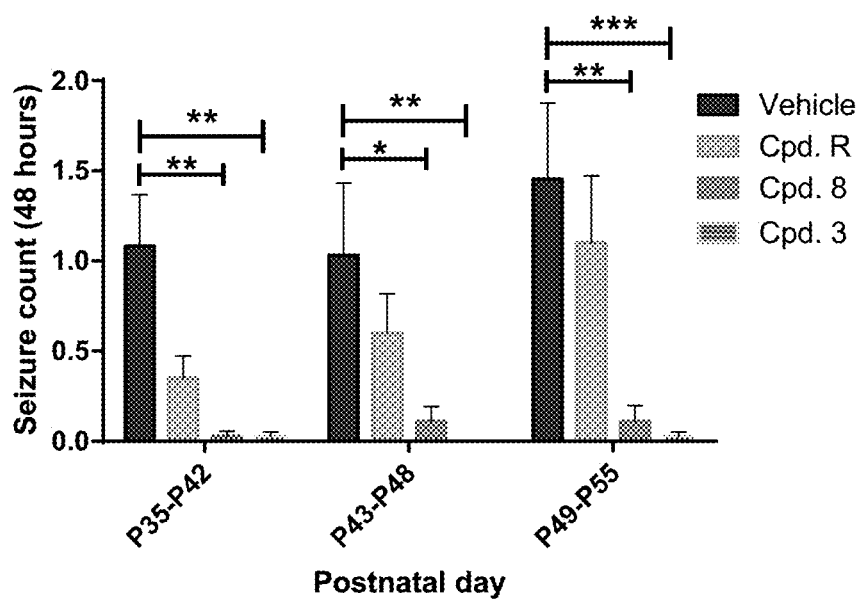
FIG. 9B: Effects of specific treatment regimens on spontaneous electrographic seizures in Tsc1 GFAP mice. Cpd. 3 and Cpd. 8 strongly reduce spontaneous seizures while the reference molecule Cpd. R had a weaker effect. Data are presented as mean±SEM (N=27-48 recordings/group) for each week of testing. Statistical significance is marked by a multiplicity-adjusted p<0.05 with vehicle as a comparator (Wilcoxon non-parametrical test).

Whereas Tsc1 genotype mice treated with vehicle daily from PND21-55 suffered robust electrographic seizures (n=150), mice treated with 25 mg/kg Cpd. 8 from PND21-53 showed significantly lower numbers of seizures (n=8) and mice treated with 100 mg/kg Cpd. 3 from PND21-53 showed significantly lower numbers of seizures (n=2) over the same period. A reference group that received Cpd. R from PND21-55 showed a modest reduction in the number of seizures (n=76) that was significantly different from vehicle when across all time points. Pairwise Wilcoxon tests were conducted to identify which specific contrasts were significant (FIG. 9B). The incidence in seizures was significantly different between vehicle and Cpd. 8/Cpd. 8 at weeks 6 (PND35-42; p=0.0009 and p=0.0005 respectfully), at weeks 7 (PND43-48; p=0.0427 and p=0.0023), and at weeks 8 (PND49-55; p=0.0017 and p=0.0002) (FIG. 9B).

The protective effect of Cpd. 3 and Cpd. 8 against seizures in the Tsc1 GFAP conditional knockout mice could be shown. Cpd. R has a weaker seizure-suppressive effect than the new compounds tested. Likely, this can be explained by the shorter half-life of Cpd. R (1 1 hour) compared to Cpd. 3 (5 hours) and Cpd. 8 (5 hours).

Example 13

Treatment of R6/2 Mice and zQ175 Mice

R6/2 mice are a B6CBA-Tg(HDexon1)62Gbp/1J mouse model expressing exon 1 of the human huntingtin gene with an extension of 160±5 CAG repeats. Mice have a severe phenotype that develops between 4 and 12 weeks. A PK/PD study in R6/2 mice is being performed in order to determine a dose that is as low as possible and still engages the target in different brain regions (striatum, cortex, cerebellum). R6/2 mice and their wt counterparts are treated in the following treatment groups consisting of 19 animals: 1. Wt, vehicle; 2. R6/2 vehicle; 3. R6/2 Cpd. 3; 4. R6/2 Cpd.8. Per oral dosing is performed for 5 days with a following drug holiday of 2 days for a total of 8 weeks. After 4 and 8 weeks animals are tested in two phenotypic tests: LabMaster and Rotarod. Consecutively, mice are sacrificed and brains are analyzed for mTOR signaling and induction of autophagy using western blot analysis as well as for levels of soluble and aggregated mHTT using TR-FRET assays.

zQ175 knock-in (KI) mice exhibit extensive behavioral, histopathological, and molecular phenotypes reminiscent of human disease. These mice exhibit age-associated increase in mHTT inclusions from 2-12 months of age in the striatum and cortex. 10 mice per group will be treated with 1. Vehicle; 2. Cpd. 3; 3. Cpd. 8 from 3 months to 5 months of age. Mice will be given peroral dosing of compounds or vehicle for 5 consecutive days followed by 2 days of drug holiday. Key readouts are 1) Determine mHTT aggregate formation in homogenate from striatum and muscle quadriceps using Singulex (central versus peripheral effects).

Compound levels in plasma, brain and quadriceps muscle on the last day of dosing (2 h post dose) from experimental animals. Satellite animals will be used on day one of study to determine PK and basal HTT levels.

Example 14

Treatment of R6/2 Mice in an In Vivo Model of Huntington's Disease

An in vivo model of Huntington's disease was used to evaluate the efficacy of Cpd. 3 and cpd. 8 in reducing mutHTT aggregate formation in the striatum. R6/2 mice are a B6CBA-Tg(HDexon1)62Gbp/3J Huntington's disease mouse model expressing exon 1 of the human huntingtin gene with an extension of 160 f 5 CAG repeats. Mice have a severe phenotype that develops between 4 and 12 weeks. As the animals are extremely fragile, doses had to be reduced to 65% of the doses used in more robust animal models.

B6CBA-Tg(HDexon1)62Gpb/3J (R6/2) mice were obtained from 40 breeding pairs of wildtype males with ovarian transplant females purchased from Charles River (Charles River Laboratories, Sulzfeld, Germany). The pups were transgenic for the human N-terminal fragment of the HTT gene. For this study male mice were used and were kept in separate cages to reduce the stress of hierarchy fights from weaning on. Standard cages with a 12 hours light/dark cycle were used. Standard chow and water were supplied ad libitum.

R6/2 Pharmacokinetics

In order to test exposure of brain areas, R6/2 mice were treated with a single oral dose of Cpd. 3 (75 mg/kg, 50 mg/kg, 25 mg/kg) or Cpd. 8 (25 mg/kg, 16 mg/kg, 8 mg/kg), 3 animals per group. After one hour plasma was collected and animals were sacrificed. Striatum, cerebellum and cortex was separately snap frozen and analyzed for compound concentration using LC/MS/MS.

Figure 10:
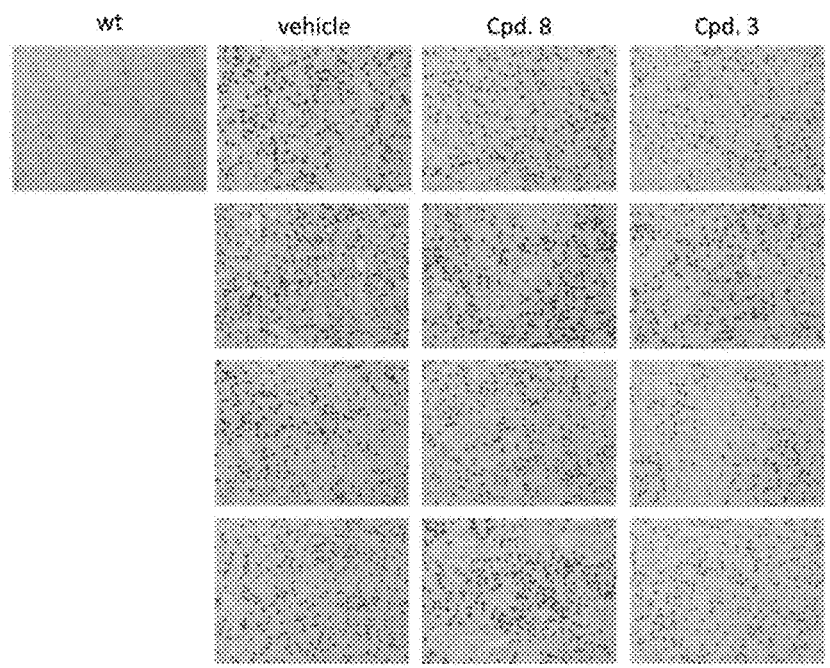
Figure 10:
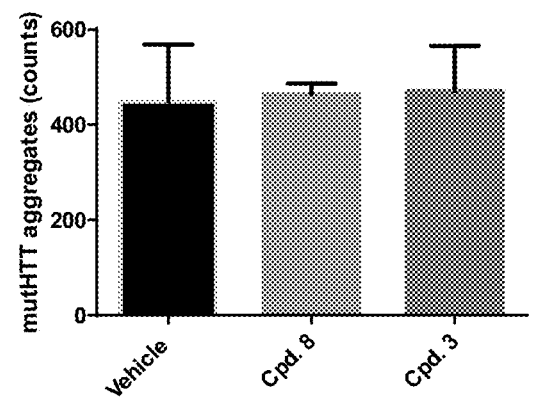
Figure 10:
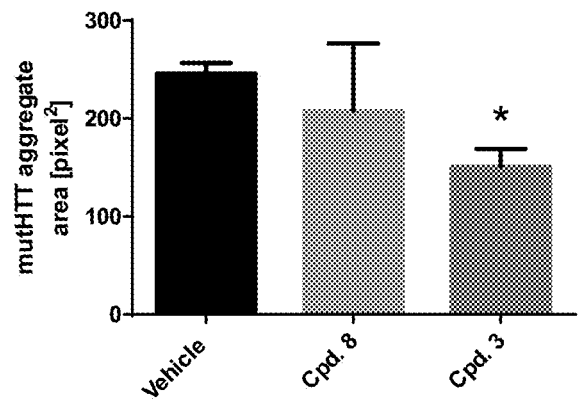

Tissue concentrations reached were well in the efficacious range for all Cpd. 3 concentrations. For Cpd. 8 sufficient levels were reached at all concentrations, although 8 mg/kg might give a slightly too short target coverage (FIG. 10A).

Compound Longterm Treatment of R6/2 Mice

Treatment groups were established from genotype and measurement of weight, rotarod performance and litter. They were distributed equally over the four groups, each group contained 12 animals. R6/2 mice and their wt counterparts were dosed in the following treatment groups: 1. Wt, vehicle (20% SBECD in water, pH 3); 2. R6/2 vehicle (20% SBECD in water, pH 3); 3. R6/2 Cpd. 3 (65 mg/kg); 4. R6/2 Cpd.8 (16.25 mg/kg). Per oral dosing was performed for 6 days with a following drug holiday of 1 day for a total of 11.5 weeks.

Immunohistochemistry

To detect mutHTT aggregates, immunostaining of striata was performed. Brains were fixed in 4% paraformaldehyde (SAV LP GmbH, Flintsbach am Inn, Germany). Before embedding in O.C.T (Sakura Finetek Germany GmbH, Staufen im Breisgau, Germany)), whole brains were soaked in sucrose solution (30% w/v) for 3 days and cut serially into 25 μm coronal sections on a cryostat (Leica CM-3050-S, Leica Biosystems Nussloch GmbH, Germany). Sections were stored in PBS, supplemented with 0.03% sodium acetate at 4° C. For free-floating staining, striatal sections were placed into fresh PBS. All steps were performed at room temperature. Blocking was performed in 0.5% sodium borohydride in PBS for 30 minutes and followed by washing. Primary antibody incubation with EM48 (MAB5374; Merck Chemicals GmbH, Darmstadt, Germany) diluted 1:1000 was performed overnight. On the following day sections were washed with TBST and incubated with biotinylated goat anti-mouse IG-G (Vecta BA9200, Vector Laboratories, Burlingame, Ca) at a 1:1000 dilution for 2 hours. Avidin-biotin complex (Vectastain® Elite ABC Kit, Vector Laboratories, Burlingame, Ca) was used at a 1:400 dilution. Incubation time was 1 hour. To further enhance the signal, ABC incubation was repeated after biotinylated tyramine, supplemented with 0.001% H2O2 was administered for 8 minutes. For color development, sections were incubated for 4 minutes in a nickel-DAB-H2O2 containing buffer (0.6% nickel, 0.01% DAB and 0.001% H2O2 in 0.05 M Tris, 0.05 M imidazole). Reaction was stopped by placing the sections in TI buffer (0.05 M Tris, 0.05 M imidazole) and mounted in water, free floating. Sections were dehydrated by ethanol and xylol dilution row and sealed under coverslips with mounting medium (CV, Leica).

Images were acquired using a Zeiss Axioplan microscope (Plan-NEOFLUAR×40/0.75 objective, AxioCam MRc) and Axiovision 4.8 software (Carl Zeiss Microscopy GmbH, Jena, Germany). Per animal three subsequent sections of the striatum were analyzed, 4 animals were analysed The EM48 positive structures were analyzed with the ImageJ built in particle analysis, with a fixed threshold for all pictures (ImageJ 1.47v; NIH, Bethesda, MD, USA). Statistical analysis was performed with GraphPad Prism 6 (GraphPad Software Inc., La Jolla, CA, USA). One-way ANOVA was performed with multiple comparisons to the placebo group and Dunnet's correction method.

Image analysis of stained striata showed specificity of staining as no aggregates were detected in wt animals (FIG. 10B). Furthermore, the number of aggregates counted was not changed in Cpd. 3 or Cpd. 8 treated R6/2 mice versus vehicle controls. But the seize of mutHTT aggregates was slightly (although not significantly) reduced in Cpd. 8 treated animals and decreased by 40% in Cpd. 3 treated animals (FIG. 10B). This reduction in aggregates could influence disease progression in HD patients.

The invention claimed is:

1. A method of preventing or treating a neurological disorder in a subject comprising administering an effective amount of a compound of formula (I) to said subject,

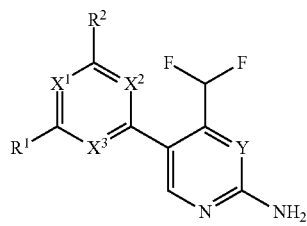

(I)

wherein $X^1$, $X^2$ and $X^3$ are, independently of each other, N or CH; with the proviso that at least two of $X^1$, $X^2$ and $X^3$ are N;

Y is N or CH;

$R^1$ and $R^2$ are independently of each other (i) a morpholinyl of formula (II)

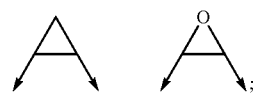

(II)

wherein the arrow denotes the bond in formula (I); and wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxy$C_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —$CH_2$—O—$CH_2$—, —$CH_2$—NH—$CH_2$—, or any of the structures

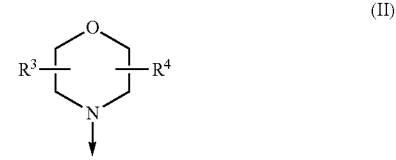

wherein the arrows denote the bonds in formula (II); or (ii) a saturated 6-membered heterocyclic ring Z selected from thiomorpholinyl and piperazinyl, optionally substituted by 1 to 3 $R^7$; wherein $R^7$ is independently at each occurrence $C_1$-$C_3$alkyl optionally substituted with one or two OH, $C_1$-$C_2$fluoroalkyl, $C_1$-$C_2$alkoxy$C_1$-$C_3$alkyl, $C_3$-$C_6$cycloalkyl; or two $R^7$ substituents form together a bivalent residue —$R^8R^9$— selected from $C_1$-$C_3$alkylene optionally substituted with 1 to 4 F, —$CH_2$—O—$CH_2$— or —O—$CH_2CH_2$—O—;

with the proviso that at least one of $R^1$ and $R^2$ is a morpholinyl of formula II;

and prodrugs, metabolites, tautomers, solvates and pharmaceutically acceptable salts thereof.

2. The method according to claim 1, wherein said $R^1$ and said $R^2$ are independently of each other selected from

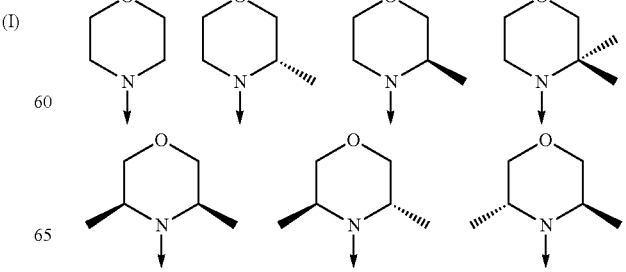

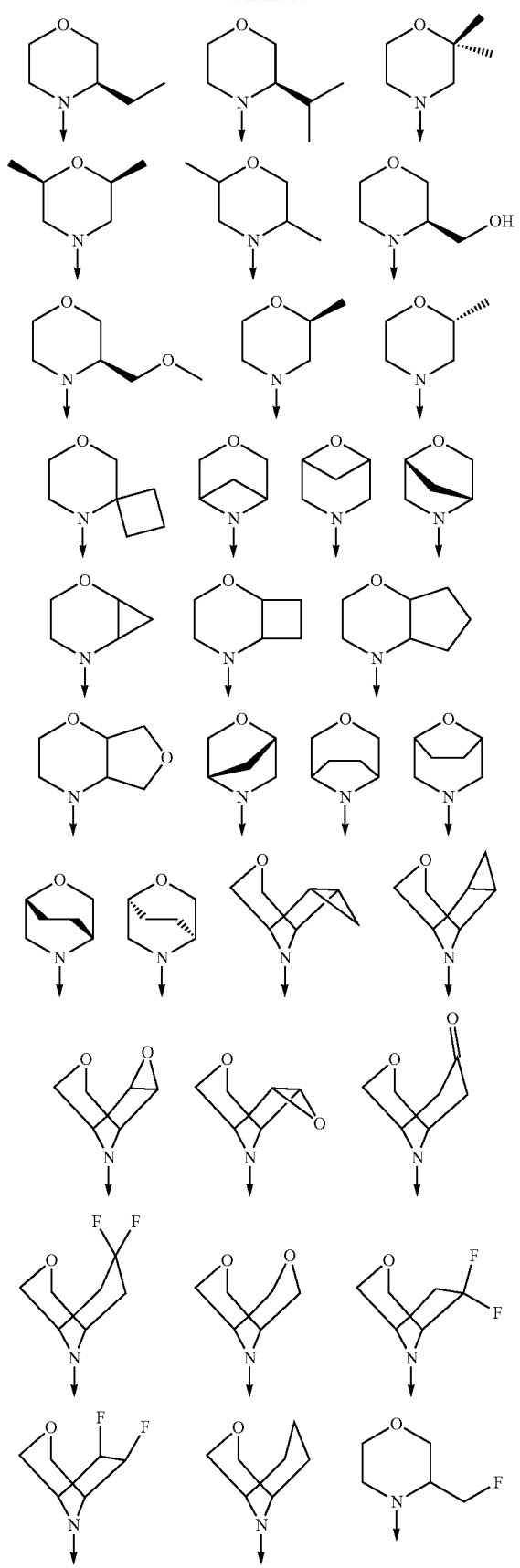

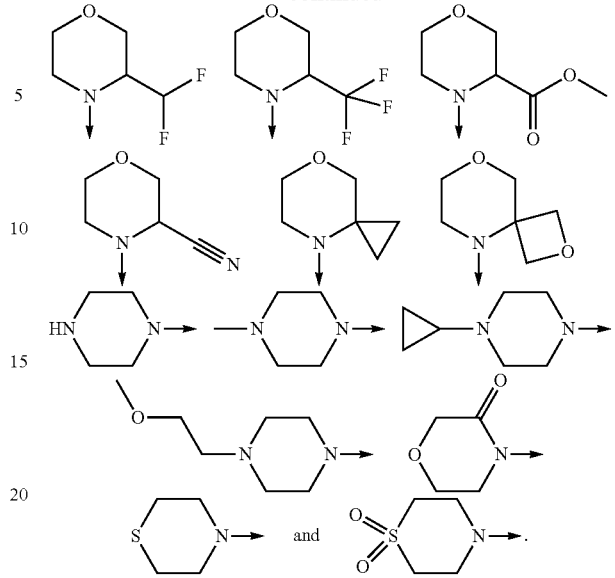

3. The method according to claim 1, wherein $R^1$ and $R^2$ are independently of each other selected from

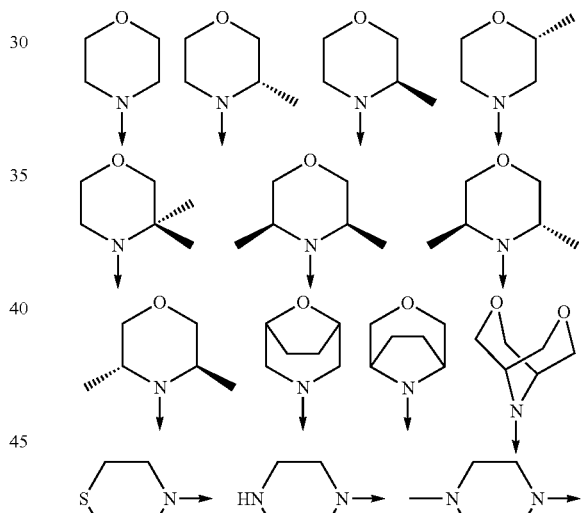

4. The method according to claim 1, wherein said compound is selected from
4-(difluoromethyl)-5-(4,6-dimorpholino-1,3,5-triazin-2-yl)pyridin-2-amine;
4-(difluoromethyl)-5-(4,6-dimorpholino-1,3,5-triazin-2-yl)pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
5-(4-(3-oxa-8-azabicyclo[3.2.1]octan-8-yl)-6-morpholino-1,3,5-triazin-2-yl)-4-(difluoromethyl)pyridin-2-amine;
5-(4-(3-oxa-8-azabicyclo[3.2.1]octan-8-yl)-6-morpholino-1,3,5-triazin-2-yl)-4-(difluoromethyl)pyrimidin-2-amine;
5-(4,6-bis((S)-3-methylmorpholino)-1,3,5-triazin-2-yl)-4-(difluoromethyl)pyridin-2-amine;

5-(4,6-bis((S)-3-methylmorpholino)-1,3,5-triazin-2-yl)-4-(difluoromethyl)pyrimidin-2-amine;
(S)-4-(difluoromethyl)-5-(4-(3-methylmorpholino)-6-morpholino-1,3,5-triazin-2-yl)pyridin-2-amine;
(S)-4-(difluoromethyl)-5-(4-(3-methylmorpholino)-6-morpholino-1,3,5-triazin-2-yl)pyrimidin-2-amine;
5-(4-(3-oxa-8-azabicyclo[3.2.1]octan-8-yl)-6-((S)-3-methylmorpholino)-1,3,5-triazin-2-yl)-4-(difluoromethyl)pyridin-2-amine;
5-(4-(3-oxa-8-azabicyclo[3.2.1]octan-8-yl)-6-((S)-3-methylmorpholino)-1,3,5-triazin-2-yl)-4-(difluoromethyl)pyrimidin-2-amine;
4-(difluoromethyl)-5-(4-morpholino-6-(piperazin-1-yl)-1,3,5-triazin-2-yl)pyridin-2-amine;
4-(difluoromethyl)-5-(4-morpholino-6-(piperazin-1-yl)-1,3,5-triazin-2-yl)pyridin-2-amine;
(S)-4-(difluoromethyl)-5-(4-(3-methylmorpholino)-6-(piperazin-1-yl)-1,3,5-triazin-2-yl)pyridin-2-amine;
(S)-4-(difluoromethyl)-5-(4-(3-methylmorpholino)-6-(piperazin-1-yl)-1,3,5-triazin-2-yl)pyrimidin-2-amine;
4-(difluoromethyl)-5-(2,6-dimorpholinopyrimidin-4-yl)pyridin-2-amine;
4'-(difluoromethyl)-2,6-dimorpholino-[4,5'-bipyrimidin]-2'-amine;
4-(difluoromethyl)-5-(4,6-dimorpholinopyrimidin-2-yl)pyridin-2-amine;
4'-(difluoromethyl)-4,6-dimorpholino-[2,5'-bipyrimidin]-2'-amine;
4-(difluoromethyl)-5-(4-morpholino-6-thiomorpholino-1,3,5-triazin-2-yl)pyridin-2-amine;
4-(difluoromethyl)-5-(4-morpholino-6-thiomorpholino-1,3,5-triazin-2-yl)pyrimidin-2-amine;
5-(6-(3-oxa-8-azabicyclo[3.2.1]octan-8-yl)-2-(3-oxa-8-azabicyclo[3.2.1]octan-8-yl)pyrimidin-4-yl)-4-(difluoromethyl)pyridin-2-amine;
5-(2-(3-oxa-8-azabicyclo[3.2.1]octan-8-yl)-6-morpholinopyrimidin-4-yl)-4-(difluoromethyl)pyridin-2-amine;
2-(3-oxa-8-azabicyclo[3.2.1]octan-8-yl)-4'-(difluoromethyl)-6-morpholino-[4,5'-bipyrimidin]-2'-amine;
5-(2,6-bis((S)-3-methylmorpholino)pyrimidin-4-yl)-4-(difluoromethyl)pyridin-2-amine;
4'-(difluoromethyl)-2,6-bis((S)-3-methylmorpholino)-[4,5'-bipyrimidin]-2'-amine;
(S)-4-(difluoromethyl)-5-(6-(3-methylmorpholino)-2-morpholinopyrimidin-4-yl)pyridin-2-amine;
(S)-4'-(difluoromethyl)-6-(3-methylmorpholino)-2-morpholino-[4,5'-bipyrimidin]-2'-amine;
5-(4-(8-Oxa-3-azabicyclo[3.2.1]octan-3-yl)-6-(8-oxa-3-azabicyclo[3.2.1]octan-3-yl)-1,3,5-triazin-2-yl)-4-(difluoromethyl)pyridin-2-amine;
5-[4,6-bis(2,2-dimethylmorpholin-4-yl)-1,3,5-triazin-2-yl]-4-(difluoromethyl)pyridin-2-amine;
(S)-4-(difluoromethyl)-5-(2-(3-methylmorpholino)-6-morpholinopyrimidin-4-yl)pyridin-2-amine;
(S)-4'-(difluoromethyl)-2-(3-methylmorpholino)-6-morpholino-[4,5'-bipyrimidin]-2'-amine;
4-(difluoromethyl)-5-[4-[(2S,6R)-2,6-dimethylmorpholin-4-yl]-6-[(3R)-3-methylmorpholin-4-yl]-1,3,5-triazin-2-yl]pyridin-2-amine;
5-[4,6-bis[(2R,6S)-2,6-dimethylmorpholin-4-yl]-1,3,5-triazin-2-yl]-4-(difluoromethyl)pyridin-2-amine;
5-[4,6-bis(3,7-dioxa-9-azabicyclo[3.3.1]nonan-9-yl)-1,3,5-triazin-2-yl]-4-(difluoromethyl)pyridin-2-amine;
4-(difluoromethyl)-5-[4-(3,7-dioxa-9-azabicyclo[3.3.1]nonan-9-yl)-6-(3-oxa-8-azabicyclo[3.2.1]octan-8-yl)-1,3,5-triazin-2-yl]pyridin-2-amine;
5-[4,6-bis(3,3-dimethylmorpholin-4-yl)-1,3,5-triazin-2-yl]-4-(difluoromethyl)pyridin-2-amine;
5-[4,6-bis[(3R,5S)-3,5-dimethylmorpholin-4-yl]-1,3,5-triazin-2-yl]-4-(difluoromethyl)pyridin-2-amine;
5-[4,6-bis[(3R)-3-methylmorpholin-4-yl]-1,3,5-triazin-2-yl]-4-(difluoromethyl)pyridin-2-amine;
4-(difluoromethyl)-5-[4-(3,3-dimethylmorpholin-4-yl)-6-morpholino-1,3,5-triazin-2-yl]pyridin-2-amine;
4-(difluoromethyl)-5-[4-[(3R,5S)-3,5-dimethylmorpholin-4-yl]-6-[(3R)-3-methylmorpholin-4-yl]-1,3,5-triazin-2-yl]pyridin-2-amine;
4-(difluoromethyl)-5-[4-(3,3-dimethylmorpholin-4-yl)-6-[(3R)-3-methylmorpholin-4-yl]-1,3,5-triazin-2-yl]pyridin-2-amine;
4-(difluoromethyl)-5-[4-[(3R)-3-(methoxymethyl)morpholin-4-yl]-6-[(3R)-3-methylmorpholin-4-yl]-1,3,5-triazin-2-yl]pyridin-2-amine;
4-(difluoromethyl)-5-[4-(3,7-dioxa-9-azabicyclo[3.3.1]nonan-9-yl)-6-[(3R)-3-methylmorpholin-4-yl]-1,3,5-triazin-2-yl]pyridin-2-amine;
4-(difluoromethyl)-5-[4-[(3R)-3-methylmorpholin-4-yl]-6-(3-oxa-6-azabicyclo[3.1.1]heptan-6-yl)-1,3,5-triazin-2-yl]pyridin-2-amine;
4-(difluoromethyl)-5-[4-[(3R)-3-methylmorpholin-4-yl]-6-(6-oxa-3-azabicyclo[3.1.1]heptan-3-yl)-1,3,5-triazin-2-yl]pyridin-2-amine;
4-(difluoromethyl)-5-[4-[(3R)-3-methylmorpholin-4-yl]-6-[(1R,4R)-2-oxa-5-azabicyclo[2.2.1]heptan-5-yl]-1,3,5-triazin-2-yl]pyridin-2-amine;
4-(difluoromethyl)-5-[4-[(3R)-3-methylmorpholin-4-yl]-6-[(1S,4S)-2-oxa-5-azabicyclo[2.2.1]heptan-5-yl]-1,3,5-triazin-2-yl]pyridin-2-amine;
5-[4,6-bis[(3R)-3-ethylmorpholin-4-yl]-1,3,5-triazin-2-yl]-4-(difluoromethyl)pyridin-2-amine;
5-[4,6-bis(8-oxa-5-azaspiro[3.5]nonan-5-yl)-1,3,5-triazin-2-yl]-4-(difluoromethyl)pyridin-2-amine;
5-[4,6-bis[(3R)-3-isopropylmorpholin-4-yl]-1,3,5-triazin-2-yl]-4-(difluoromethyl)pyridin-2-amine 4-(difluoromethyl)-5-[4-(3,3-dimethylmorpholin-4-yl)-6-[(3R,5S)-3,5-dimethylmorpholin-4-yl]-1,3,5-triazin-2-yl]pyridin-2-amine;
4-(difluoromethyl)-5-[4-(3,3-dimethylmorpholin-4-yl)-6-[(3R)-3-(methoxymethyl)morpholin-4-yl]-1,3,5-triazin-2-yl]pyridin-2-amine;
[(3R)-4-[4-[6-amino-4-(difluoromethyl)-3-pyridyl]-6-(3,3-dimethylmorpholin-4-yl)-1,3,5-triazin-2-yl]morpholin-3-yl]methanol;
4-(difluoromethyl)-5-[4-(3,3-dimethylmorpholin-4-yl)-6-(3,7-dioxa-9-azabicyclo[3.3.1]nonan-9-yl)-1,3,5-triazin-2-yl]pyridin-2-amine;
5-[4-(4-cyclopropylpiperazin-1-yl)-6-(3,3-dimethylmorpholin-4-yl)-1,3,5-triazin-2-yl]-4-(difluoromethyl)pyridin-2-amine;
4-(difluoromethyl)-5-[4-(3,3-dimethylmorpholin-4-yl)-6-[4-(2-methoxyethyl)piperazin-1-yl]-1,3,5-triazin-2-yl]pyridin-2-amine;
[(3R)-4-[4-[6-amino-4-(difluoromethyl)-3-pyridyl]-6-[(3R)-3-methylmorpholin-4-yl]-1,3,5-triazin-2-yl]morpholin-3-yl]methanol;
4-(difluoromethyl)-5-[4-[(3R,5R)-3,5-dimethylmorpholin-4-yl]-6-[(3R)-3-methylmorpholin-4-yl]-1,3,5-triazin-2-yl]pyridin-2-amine;
4-(difluoromethyl)-5-[4-[(3S,5S)-3,5-dimethylmorpholin-4-yl]-6-[(3R)-3-methylmorpholin-4-yl]-1,3,5-triazin-2-yl]pyridin-2-amine;

4-(difluoromethyl)-5-[4-morpholino-6-(3-oxa-9-azabicyclo[3.3.1]nonan-9-yl)-1,3,5-triazin-2-yl]pyridin-2-amine;

4-(difluoromethyl)-5-[4-(3,7-dioxa-9-azabicyclo[3.3.1]nonan-9-yl)-6-(3-oxa-9-azabicyclo[3.3.1]nonan-9-yl)-1,3,5-triazin-2-yl]pyridin-2-amine;

5-[4,6-bis[(3S,5S)-3,5-dimethylmorpholin-4-yl]-1,3,5-triazin-2-yl]-4-(difluoromethyl)pyridin-2-amine;

4-(difluoromethyl)-5-[4-(3,7-dioxa-9-azabicyclo[3.3.1]nonan-9-yl)-6-morpholino-1,3,5-triazin-2-yl]pyridin-2-amine;

4-(difluoromethyl)-5-[4-[(3S)-3-ethylmorpholin-4-yl]-6-[(3R)-3-methylmorpholin-4-yl]-1,3,5-triazin-2-yl]pyridin-2-amine;

4-(difluoromethyl)-5-[4-[(3R)-3-ethylmorpholin-4-yl]-6-[(3R)-3-methylmorpholin-4-yl]-1,3,5-triazin-2-yl]pyridin-2-amine;

4-(difluoromethyl)-5-[4-[(3R)-3-methylmorpholin-4-yl]-6-(8-oxa-5-azaspiro[3.5]nonan-5-yl)-1,3,5-triazin-2-yl]pyridin-2-amine;

and tautomers, solvates and pharmaceutically acceptable salts thereof.

6. The method according to claim 1, wherein said compound is selected from 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; and (S)-4-(difluoromethyl)-5-(4-(3-methylmorpholino)-6-morpholino-1,3,5-triazin-2-yl)pyridin-2-amine;

and tautomers, solvates and pharmaceutically acceptable salts thereof.

7. The method according to claim 1, wherein $R^1$ and $R^2$ are independently of each other a morpholinyl of formula (II).

8. The method according to claim 7, wherein $R^1$ is equal to $R^2$.

9. The method according to claim 7, wherein $R^1$ is not equal to $R^2$.

10. The method according to claim 1, wherein the neurological disorder is epilepsy or a neurodegenerative disease.

11. The method according to claim 1, wherein the neurological disorder is a neurodegenerative disease, and wherein the neurodegenerative disease is selected from the group consisting of Huntington's disease, spinocerebellar ataxias, Parkinson's disease, morbus Alzheimer, amyotrophic lateral sclerosis (ALS), cystic fibrosis, familial amyloidotic polyneuropathy, spongiform encephalopathies, dementia with Lewy bodies, frontotemporal dementia with Parkinsonism, spinocerebellar ataxias, spinal and bulbar muscular atrophy, hereditary dentatorubral-pallidoluysian atrophy, familial British dementia, familial Danish dementia and prion disease.

12. The method according to claim 11, wherein the neurodegenerative disease is Huntington's disease.

13. The method according to claim 1, wherein the neurological disorder is epilepsy.

14. The method according to claim 13, wherein the epilepsy is symptomatic epilepsy, and wherein said symptomatic epilepsy is caused by brain injury, brain tumor, brain infection, adrenoleukodystrophy, Rasmussen's syndrome, Sturge-Weber syndrome, megalencephaly, polyhydramnios, tuberous sclerosis complex (TSC), symptomatic epilepsy syndrome, PMSE, PTEN mutations or focal cortical dysplasia (FCD).

15. The method according to claim 13, wherein the epilepsy is symptomatic epilepsy, wherein said symptomatic epilepsy is due to a disease characterized by upregulation of mTOR ("TORopathy").

5. The method according to claim 1, wherein said compound is selected from the group consisting of 4-(difluoromethyl)-5-(4,6-dimorpholino-1,3,5-triazin-2-yl)pyrimidin-2-amine;

5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;

5-(4-(3-oxa-8-azabicyclo[3.2.1]octan-8-yl)-6-morpholino-1,3,5-triazin-2-yl)-4-(difluoromethyl)pyridin-2-amine;

5-(4,6-bis((S)-3-methylmorpholino)-1,3,5-triazin-2-yl)-4-(difluoromethyl)pyrimidin-2-amine;

(S)-4-(difluoromethyl)-5-(4-(3-methylmorpholino)-6-morpholino-1,3,5-triazin-2-yl)pyridin-2-amine;

4-(difluoromethyl)-5-(4-morpholino-6-(piperazin-1-yl)-1,3,5-triazin-2-yl)pyrimidin-2-amine;

4-(difluoromethyl)-5-(4,6-dimorpholino-1,3,5-triazin-2-yl)pyridin-2-amine; and (S)-4-(difluoromethyl)-5-(4-(3-methylmorpholino)-6-morpholino-1,3,5-triazin-2-yl)pyrimidin-2-amine;

5-[4,6-bis(3,7-dioxa-9-azabicyclo[3.3.1]nonan-9-yl)-1,3,5-triazin-2-yl]-4-(difluoromethyl)pyridin-2-amine;

4-(difluoromethyl)-5-[4-(3,7-dioxa-9-azabicyclo[3.3.1]nonan-9-yl)-6-(3-oxa-8-azabicyclo[3.2.1]octan-8-yl)-1,3,5-triazin-2-yl]pyridin-2-amine;

5-[4,6-bis(3,3-dimethylmorpholin-4-yl)-1,3,5-triazin-2-yl]-4-(difluoromethyl)pyridin-2-amine;

5-[4,6-bis[(3R,5S)-3,5-dimethylmorpholin-4-yl]-1,3,5-triazin-2-yl]-4-(difluoromethyl)pyridin-2-amine;

5-[4,6-bis[(3R)-3-methylmorpholin-4-yl]-1,3,5-triazin-2-yl]-4-(difluoromethyl)pyridin-2-amine;

4-(difluoromethyl)-5-[4-(3,3-dimethylmorpholin-4-yl)-6-morpholino-1,3,5-triazin-2-yl]pyridin-2-amine;

4-(difluoromethyl)-5-[4-[(3R,5S)-3,5-dimethylmorpholin-4-yl]-6-[(3R)-3-methylmorpholin-4-yl]-1,3,5-triazin-2-yl]pyridin-2-amine;

4-(difluoromethyl)-5-[4-(3,3-dimethylmorpholin-4-yl)-6-[(3R)-3-methylmorpholin-4-yl]-1,3,5-triazin-2-yl]pyridin-2-amine;

4-(difluoromethyl)-5-[4-[(3R)-3-(methoxymethyl)morpholin-4-yl]-6-[(3R)-3-methylmorpholin-4-yl]-1,3,5-triazin-2-yl]pyridin-2-amine;

4-(difluoromethyl)-5-[4-(3,7-dioxa-9-azabicyclo[3.3.1]nonan-9-yl)-6-[(3R)-3-methylmorpholin-4-yl]-1,3,5-triazin-2-yl]pyridin-2-amine;

16. The method according to claim 2, wherein the neurological disorder is epilepsy or a neurodegenerative disease.

17. The method according to claim 2, wherein the neurological disorder is a neurodegenerative disease, wherein said neurodegenerative disease is Huntington's disease.

18. The method according to claim 2, wherein the neurological disorder is epilepsy.

19. The method according to claim 15, wherein said TORopathy is selected from the group consisting of TSC, polyhydramnios, megalencephaly, symptomatic epilepsy syndrome, PMSE, focal cortical dysplasia (FCD) and a TORopathy associated with PTEN mutations.

20. The method according to claim 13, wherein the epilepsy is idiopathic epilepsy, and wherein said idiopathic epilepsy is selected from the group consisting of Doose syndrome (myoclonic astatic epilepsy of childhood), West syndrome, benign Rolandic epilepsy, Lennox-Gastaut syndrome, Landau-Kleffner syndrome, symptomatic epilepsy syndrome, PMSE and juvenile myoclonic epilepsy.

* * * * *